US006521814B1

(12) United States Patent
Chambon et al.

(10) Patent No.: US 6,521,814 B1
(45) Date of Patent: Feb. 18, 2003

(54) USE OF LIGANDS FOR TREATMENT OF DISEASES RESPONSIVE TO RETINOIDS

(75) Inventors: Pierre Chambon, Blaesheim (FR);
Emiliana Borrelli, Strasbourg (FR);
Norbert B. Ghyselinck, Strasbourg (FR); Valérie Dupé, London (GB);
Manuel Mark, Morchwiller (FR);
Daniel Metzger, Strasbourg (FR)

(73) Assignees: Institut National de la Santa et de la Recherche Medicale, Paris (FR);
Centre National de la Recherche Scientifique, Paris (FR); Universite Louis Pasteur, Strasbourg (FR);
Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/218,446

(22) Filed: Dec. 22, 1998

Related U.S. Application Data
(60) Provisional application No. 60/068,471, filed on Dec. 22, 1997.

(51) Int. Cl.[7] .................. G01N 33/00; G01N 33/53; A01K 67/00; A01K 67/027; C12Q 1/68
(52) U.S. Cl. .................. 800/3; 800/8; 800/18; 435/6; 435/7.1; 435/7.2; 435/325
(58) Field of Search .................. 800/81, 3, 18; 435/7.1, 7.2, 325, 354, 6

(56) References Cited

U.S. PATENT DOCUMENTS

| 5,399,586 A | 3/1995 | Davies et al. ............ 514/448 |
| 5,780,676 A | 7/1998 | Boehm et al. ............ 562/490 |
| 6,030,794 A | * 2/2000 | Chambon et al. ........... 435/7.2 |

FOREIGN PATENT DOCUMENTS

| EP | 0 325 849 B1 | 8/1989 |
| EP | 0 479 916 B1 | 4/1992 |
| WO | WO 94/26100 | 11/1994 |

OTHER PUBLICATIONS

Bradley, A., et al., Modifying the mouse: design and desire, (May 1992), Biotechnology, vol. 10, pp. 534–539.*
Fassler, R., et al., Knockout Mice: How to make them and why. The immunological approach, (1995), Int. Arch Allergy Immunol 1995: 323–334.*
Accili, D. and Taylor, S.I., "Targeted inactivation of the insulin receptor gene in mouse 3T3–L1 fibroblasts via homologous recombination," *Proc. Natl. Acad. Sci. USA* 88:4708–4712 (1991).
Allenby, G. et al., "Retinoic acid receptors and retinoid X receptors: Interactions with endogenous retinoic acids," *Proc. Natl. Acad. Sci. USA* 90:30–34 (1993).
Baik, J.–H. et al., "Parkinsonian–like locomotor impairment in mice lacking dopamine D2 receptors," *Nature* 377:424–428 (1995).

Boylan, J.F. et al., "Loss of retinoic acid receptor γ function in F9 cells by gene disruption results in aberrant Hoxa–1 expression and differentiation upon retinoic acid treatment," *Proc. Natl. Acad. Sci. USA* 90:9601–9605 (1993).
Boylan, J.F. et al., "Targeted Disruption of Retinoic Acid Receptor α (RARα) and RARγ Results in Receptor–Specific Alterations in Retinoic Acid–Mediated Differentiation and Retinoic Acid Metabolism," *Mol. Cell. Biol.* 15:843–851 (1995).
Bradley, D.J. et al., "Differential expression of α and β thyroid hormone receptor genes in rat brain and pituitary," *Proc. Natl. Acad. Sci. USA* 86:7250–7254 (1989).
Bugge, T.H. et al., "RXRα, a promiscuous partner of retinoic acid and thyroid hormone receptors," *EMBO J.* 11:1409–1418 (1992).
Callahan, P.M. et al., "Dopamine $D_1$ and $D_2$ mediation of the discriminative stimulus properties of d–amphetamine and cocaine," *Psychopharmacology* 103:50–55 (1991).
Capecchi, M.R., "The New Mouse Genetics: Altering the Genome by Gene Targeting," *Trends in Genetics* 5:70–76 (1989).
Capecchi, M.R., "Altering the Genome by Homologous Recombination," *Science* 244:1288–1292 (1989).
Chambon, P., "The retinoid signaling pathway: molecular and genetic analyses," *Cell Biol.* 5:115–125 (1994).
Chen, J.–Y., "Two distinct actions of retinoid–receptor ligands," *Nature* 382:819–822 (1996).
Chiba, H. et al., "Distinct Retinoid X Receptor–Retinoic Acid Receptor Heterodimers Are Differentially Involved in the Control of Expression of Retinoid Target Genes in F9 Embryonal Carcinoma Cells," *Mol. Cell. Biol.* 17:3013–3020 (Jun. 1997).
Civelli, O. et al., "Molecular biology of the dopamine receptors," *Eur. J. Pharm. Mol. Pharm. Sec.* 207:277–286 (1991).
Chambon, P., "A decade of molecular biology of retinoic acid receptors," *FASEB J.* 10:940–954 (1996).
Chiba, H. et al., "Specific and Redundant Functions of Retinoid X Receptor/Retinoic Acid Receptor Heterodimers in Differentiation, Proliferation, and Apoptosis of F9 Embryonal Carcinoma Cells," *J. Cell Biol.* 139:735–747 (Nov. 1997).

(List continued on next page.)

Primary Examiner—Deborah J. Reynolds
Assistant Examiner—Eleanor Sorbello
(74) Attorney, Agent, or Firm—Sterne, Kessler Goldstein & Fox

(57) ABSTRACT

The invention relates to methods for treatment of neurological disease by administering an agent which interacts with a retinoid receptor associated with the neurological disease. The invention is also related to a method of modulating dopamine receptor synthesis by introducing an agent that interacts with a retinoid receptor associated with the dopamine receptor synthesis. The invention is further related to a transgenic animal, e.g., mouse, and mammalian cell line, which is deficient in the normal synthesis of one or more receptors of RARα, β, γ and RXR, and cell line thereof.

73 Claims, 51 Drawing Sheets

(1 of 51 Drawing Sheet(s) Filed in Color)

OTHER PUBLICATIONS

Clifford, J. et al., "RXRα–null F9 embryonal carcinoma cells are resistant to the differentiation, anti–proliferative and apoptic effects of retinoids," *EMBO J. 15:*4142–4155 (1996).

Dal Toso, R. et al., "The dopamine D2 receptor: two molecular forms generated by alternative splicing," *EMBO J 8(13):*4025–4034 (1989).

Dollé, P. et al., "Differential expression of genes encoding α, β and γ retinoic acid receptors and CRABP in the developing limbs of the mouse," *Nature 342:*702–705 (1989).

Dollé, P. et al., "Retinoic acid receptors and cellular retinoid binding proteins. I. A systematic study of their differential pattern of transcription during mouse organogenesis," *Devel. 110:*1133–1151 (1990).

Dollé, P. et al., "Developmental expression of murine retinoid X receptor (RXR) genes," *Mechan. Devel. 45:*91–104 (1994).

Durand, B. et al., "All–Trans and 9–Cis Retinoic Acid Induction of CRABPII Transcription Is Mediated by RAR–RXR Heterodimers Bound to DR1 and DR2 Repeated Motifs," *Cell 71:*73–85 (1992).

Espeseth, A.S. et al., "Retinoic acid receptor expression vector inhibits differentiation of F9 embryonal carcinoma cells," *Genes & Devel. 3:*1647–1656 (1989).

Everitt, B.J., "Sexual Motivation: A Neural and Behavioural Analysis of the Mechanisms Underlying Appetitive and Copulatory Responses of Male Rats," *Neurosci. & Biobehav. Rev. 14:*217–232 (1990).

Farooqui, S.M., "Induction of Adenylate Cyclase Sensitive Dopamine D2–Receptors in Retinoic Acid Induced Differentiated Human Neuroblastoma SHSY–5Y Cells," *Life Sci. 55:*1887–1893 (1994).

Feil, R. et al., "Ligand–activated site-specific recombination in mice," *Proc. Natl. Acad. Sci. USA 93:*10887–10890 (1996).

Folkers, G.E. et al., "The Retinoic Acid Receptor–β2 Contains Two Separate Cell–Specific Transactivation Domains, at the N–Terminus and in the Ligand–Binding Domain," *Mol. Endocrin. 7:*616–627 (1993).

Ghyselinck, N.B. et al., "Role of the retinoic acid receptor beta (RARβ) during mouse development," *Int J. Dev. Biol. 41:*425–447 (Jun. 1997).

Giguere, V. et al., "Identification of a receptor for the morphogen retinoic acid," *Nature 330:*624–629 (1987).

Gingrich, J.A. and Caron, M.G., "Recent Advances in the Molecular Biology of Dopamine Receptors," *Annu. Rev. Neurosci. 16:*299–321 (1993).

Giros, B. et al., "Hyperlocomotion and indifference to cocaine and amphetamine in mice lacking the dopamine transporter," *Nature 379:*606–612 (1996).

Green, S., "Promiscuous liaisons," *Nature 361:*590–591 (1993).

Grondona, J.M. et al., "Retinal dysplasia and degeneration in RARβ2/RARγ2 compound mutant mice," *Devel. 122:*2173–2188 (1996).

Guiramand, J. et al., "Alternative Splicing of the Dopamine D2 Receptor Directs Specificity of Coupling to G–proteins," *J. Biol. Chem. 270:*7354–7358 (1995).

Hodgson, J., "Carbohydrate–based Therapeutics," *Bio/Tech. 9:*609–613 (1991).

Jackson, D.M. and Westlind–Danielsson, A., "Dopamine Receptors: Molecular Biology, Biochemistry and Behavioural Aspects," *Pharmac. Ther. 64:*291–369 (1994).

Jiang, H. et al., "Modulation of limb bud chondrogenesis by retinoic acid and retinoic acid receptors," *Int. J. Dev. Biol. 39:*617–627 (1995).

Kastner, P. et al., "Role of Nuclear Retinoic Acid Receptors in the Regulation of Gene Expression," in *Vitamin A in Health and Disease,* Blomhoff, R., ed., Marcel Dekker, Inc., New York, NY, pp. 189–238 (1994).

Kastner, P. et al., "Genetic Analysis of RXRα Developmental Function: Convergence of RXR and RAR Signaling Pathways in Heart and Eye Morphogenesis," *Cell 78:*987–1003 (1994).

Kastner, P. et al., "Nonsteroid Nuclear Receptors: What Are Genetic Studies Telling Us about Their Role in Real Life?" *Cell 83:*859–869 (1995).

Kastner, P. et al., "Abnormal spermatogenesis in RXRβ mutant mice," *Genes & Devel. 10:*80–92 (1996).

Kastner, P. et al., "Genetic evidence that the retinoid signal is transduced by heterodimeric RXR/RAR functional units during mouse development," *Devel. 124:*313–326 (Jan. 1997).

Kliewer, S.A. et al., "Retinoid X receptor interacts with nuclear receptors in retinoic acid, thyroid hormone and vitamin $D_3$ signalling," *Nature 355:*446–449 (1992).

Koob, G.F. et al., "Effects of 6–Hydroxydopamine Lesions of the Nucleus Accumbens Septi and Olfactory Tubercle on Feeding, Locomotor activity, and Amphetamine Anorexia in the Rat," *J. Comp. Physiol. Psychol. 92(5):*917–927 (1978).

Krężel, W. et al., "RXRγ null mice are apparently normal and compound $RXR\alpha^{+/-}/RXR\beta^{-/-}RXR\gamma^{-/-}$ mutant mice are viable," *Proc. Natl. Acad. Sci. USA 93:*9010–9014 (1996).

Krężel, W. et al., "Impaired Locomotion and Dopamine Signaling in Retinoid Receptor Mutant Mice," *Science 279:*863–867 (Feb. 1998).

Laudet, V. and Stehelin, D., "Flexible friends. Nuclear receptors of the thyroid hormone receptor and retinoic acid receptor subfamily bind some DNA response elements in combination with auxiliary proteins, which turn out to be also nuclear receptors." *Curr. Biol. 2:*293–295 (1992).

Leid, M. et al., "Purification, Cloning, and RXR Identity of the HeLa Cell Factor with Which RAR or TR Heterodimerizes to Bind Target Sequences Efficiently," *Cell 68:*377–395 (1992).

Leid, M. et al., "Multiplicity generates diversity in the retinoic acid signalling pathways," *TIBS 17:*427–433 (1992).

Linney, E., "Retinoic Acid Receptors: Transcription Factors Modulating Gene Regulation, Development, and Differentiation," *Curr. Topics Devel. Biol. 27:*309–350 (1992).

Liu, Q. and Linney, E., "The Mouse Retinoid–X Receptor–γ Gene: Genomic Organization and Evidence for Functional Isoforms," *Mol. Endo. 7:*651–658 (1993).

Lohnes, D. et al., "Function of Retinoic Acid Receptor γ in the Mouse," *Cell 73:*643–658 (1993).

Lohnes, D. et al., "Function of the retinoic acid receptors (RARs) during development. (I) Craniofacial and skeletal abnormalities in RAR double mutants," *Devel. 120:*2723–2748 (1994).

Lufkin, T. et al., "High postnatal lethality and testis degeneration in retinoic acid receptor α mutant mice," *Proc. Natl. Acad. Sci. USA 90:*7225–7229 (1993).

Luo, J. et al., "Mice lacking all isoforms of retinoic acid receptor β develop normally and are susceptible to the teratogenic effects of retinoic acid," *Mech. Devel. 53:*61–71 (1995).

Luo, J. et al., "Compound mutants for retinoic acid receptor (RAR)β and RARα1 reveal developmental functions for multiple RARβ isoforms," *Mech. Devel.* 55:33–44 (1996).

Mader, S. et al., "Multiple Parameters Control the Selectivity of Nuclear Receptors for Their Response Elements," *J. Biol. Chem.* 268:591–600 (1993).

Mangelsdorf, D.J. et al., "Nuclear receptor that identifies a novel retinoic acid response pathway," *Nature* 345:224–229 (1990).

Mangelsdorf, D.J. et al., "Characterization of three RXR genes that mediate the action of 9–cis retinoic acid," *Genes & Devel.* 6:329–344 (1992).

Mangelsdorf, D.J. and Evans, M.R., "The RXR Heterodimers and Orphan Receptors," *Cell* 83:841–850 (1995).

Marks, M.S. et al., "H–2RIIBP (RXRβ) heterodimerization provides a mechanism for combinatorial diversity in the regulation of retinoic acid and thyroid hormone responsive genes," *EMBO J.* 11:1419–1435 (1992).

McCaffery, P. and Dräger, U.C., "High levels of a retinoic acid–generating dehydrogenase in the meso–telencephalic dopamine system," *Proc. Natl. Acad. Sci. USA* 91:7772–7776 (1994).

Mendelsohn, C. et al., "Developmental analysis of the retinoic acid–inducible RAR–β2 promoter in transgenic animals," *Devel.* 113:723–734 (1991).

Mendelsohn, C. et al., "RARβ isoforms: distinct transcriptional control by retinoic acid and specific spatial patterns of promoter activity during mouse embryonic development," *Mech. Devel.* 45:227–241 (1994).

Mendelsohn, C. et al., "Function of the retinoic acid receptors (RARs) during development (II) Multiple abnormalities at various stages of organogenesis in RAR double mutants," *Devel.* 120:2749–2771 (1994).

Mendelsohn, C. et al., "Retinoic Acid Receptor β2 (RARβ2) Null Mutant Mice Appear Normal," *Developmen. Biol.* 166:246–258 (1994).

Metzger, D. et al., "Conditional site–specific recombination in mammalian cells using a ligand–dependent chimeric Cre recombinase," *Proc. Natl. Acad. Sci. USA* 92:6992–6995 (1995).

Minowa, T. et al., "Analysis of the Promoter Region of the Rat $D_2$ Dopamine Receptor Gene," *Biochem.* 31:8389–8396 (1992).

Minowa, T. et al., "Negative Modulator of the Rat $D_2$ Dopamine Receptor Gene," *J. Biol. Chem.* 269:11656–11662 (1994).

Mullins, L.J. and Mullins, J.J., "Transgenesis in the Rat and Larger Mammals," *J. Clin. Invest.* 97:1557–1560 (1996).

Nagata, T. et al., "The mouse Rxrb gene encoding RXRβ: genomic organization and two mRNA isoforms generated by alternative splicing of transcripts initiated from CpG island promoters," *Gene* 142:183–189 (1994).

Nagpal, S. et al., "RAR–β4, a retinoic acid receptor isoform is generated from RAR–β2 by alternative splicing and usage of a CUG initiator codon," *Proc. Natl. Acad. Sci. USA* 89:2718–2722 (1992).

Nagpal, S. et al., "Promoter Context– and Response Element–Dependent Specificity of the Transcriptional Activation and Modulating Functions of Retinoic Acid Receptors," *Cell* 70:1007–1019 (1992).

Nagpal, S. et al., "RARs and RXRs: evidence for two autonomous transactivation functions (AF–1 and AF–2) and heterodimerization in vivo," *EMBO J.* 12:2349–2360 (1993).

Nestler, E.J., "Hard Target: Understanding Dopaminergic Neurotransmission," *Cell* 79:923–926 (1994).

Pedersen, W.A. et al., "All–trans– and 9–cis–Retinoic Acid Enhance the Cholinergic Properties of a Murine Septal Cell Line: Evidence that the Effects Are Mediated by Activation of Retinoic Acid Receptor–α," *J. Neurochem.* 65:50–58 (1995).

Petkovich, M. et al., "A human retinoic acid receptor which belongs to the family of nuclear receptors," *Nature* 330:444–450 (1987).

Renaud, J.–P. et al., "Crystal structure of the RAR–γ ligand–binding domain bound to all–trans retinoic acid," *Nature* 378:681–689 (1995).

Robbins, T.W. and Everitt, B.J., "Functions of dopamine in the dorsal and ventral striatum," *Sem. Neurosci.* 4:119–127 (1992).

Roy, B. et al., "Synergistic Activation of Retinoic Acid (RA)–Responsive Genes and Induction of Embryonal Carcinoma Cell Differentiation by an RA Receptor α (RARα)–, RARβ–, or RARγ–Selective Ligand in Combination with a Retinoid X Receptor–Specific Ligand," *Mol. Cell. Biol.* 15:6481–6487 (1995).

Ruberte, E. et al., "Retinoic acid receptors and cellular retinoid binding proteins II, Their differential pattern of transcription during early morphogenesis in mouse embryos," *Devel.* 111:45–60 (1991).

Ruberte, E. et al., "Retinoic acid receptors and cellular retinoid binding proteins III. Their differential transcript distribution during mouse nervous system development," *Devel.* 118:267–282 (1993).

Saiardi, A. et al., "Antiproliferative Role of Dopamine: Loss of $D_2$ Receptors Causes Hormonal Dysfunction and Pituitary Hyperplasia," *Neuron* 19:115–126 (Jul. 1997).

Samad, T.A. et al., "Regulation of dopaminergic pathways by retinoids: Activation of the D2 receptor promoter by members of the retinoic acid receptor–retinoid X receptor family," *Proc. Natl. Acad. Sci. USA* 94:14349–14354 (Dec. 23, 1997).

Sucov, H.M. et al., "RXRα mutant mice establish a genetic basis for vitamin A signaling in heart morphogenesis," *Genes & Devel.* 8:1007–1018 (1994).

Sugawara, A. et al., "Isoform–Specific Retinoid–X Receptor (RXR) Antibodies Detect Differential Expression of RXR Proteins in the Pituitary Gland," *Endocrin.* 136:1766–1774 (1995).

Taneja, R. et al., "Reexpression of retinoic acid receptor (RAR)γ or overexpression of RARα or RARβ in RARγ–null F9 cells reveals a partial functional redundancy between the three RAR types," *Proc. Natl. Acad. Sci. USA* 92:7854–7858 (1995).

Taneja, R. et al., "Cell–type and promoter–context dependent retinoic acid receptor (RAR) redundancies for RARβ2 and Hoxa–1 activation in F9 and P19 cells can be artefactually generated by gene knockouts," *Proc. Natl. Acad. Sci. USA* 93:6197–6202 (1996).

Thomas, J.H., "Thinking about genetic redundancy," *Trends in Genetics* 9:395–399 (1993).

Thomas, K.R. and Capecchi, M.R., "Site–Directed Mutagenesis by Gene Targeting in Mouse Embryo–Derived Stem Cells," *Cell* 51:503–512 (1987).

Tsien, J.Z. et al., "Subregion– and Cell Type–Restricted Gene Knockout in Mouse Brain," *Cell* 87:1317–1326 (1996).

Valdenaire, O. et al., "Transcription of the rat dopamine–D2–receptor gene from two promoters," *Eur. J. Biochem.* 220:577–584 (1994).

van der Leede, B.M. et al., "Genomic Organization of the Human Retinoic Acid Receptor β2," *Biochem. Biophys. Res. Comm.* 188:695–702 (1992).

Wan, Y.–J.Y. et al., "The Expression of Retinoid X Receptor Genes Is Regulated by All–trans– and 9–cis–Retinoic Acid in F9 Teratocarcinoma Cells," *Experimen. Cell Res.* 210:56–61 (1994).

Xu, M. et al., "Elimination of Cocaine–Induced Hyperactivity and Dopamine–Mediated Neurophysiological Effects in Dopamine D1 Receptor Mutant Mice," *Cell* 79:945–955 (1994).

Yu, V.C. et al., "RXRβ: A Coregulator That Enhances Binding of Retinoic Acid, Thyroid Hormone, and Vitamin D Receptors to Their Cognate Response Elements," *Cell* 67:1251–1266 (1991).

Yu, V.C. et al., "Transcriptional regulation by the nuclear receptor superfamily," *Curr. Opin. Biotech.* 3:597–602 (1992).

Zelent, A. et al., "Differentially expressed isoforms of the mouse retinoic acid receptor β are generated by usage of two promoters and alternative splicing," *EMBO J.* 10:71–81 (1991).

Zetterström, R.H. et al., "Dopamine Neuron Agenesis in Nurr1–Deficient Mice," *Science* 276:248–250 (Apr. 1997).

Zhang, X. et al., "Retinoid X receptor is an auxiliary protein for thyroid hormone and retinoic acid receptors," *Nature* 355:441–446 (1992).

\* cited by examiner

RARE D2    5'-AGCTTCCTCGTGGCCAGGGTGACCCCGCG-3'

D2 m1      5'-AGCTTCCTCGGTGCGAGGGGTACGCCGCG-3'

D2 m2      5'-AGCTTCCTCGTGACCAGGGTGACCCCGCG-3'

RAREβ 2    5'-GGGTAGGGTTCACCGAAAGTTCACTG-3'

FIG.7A

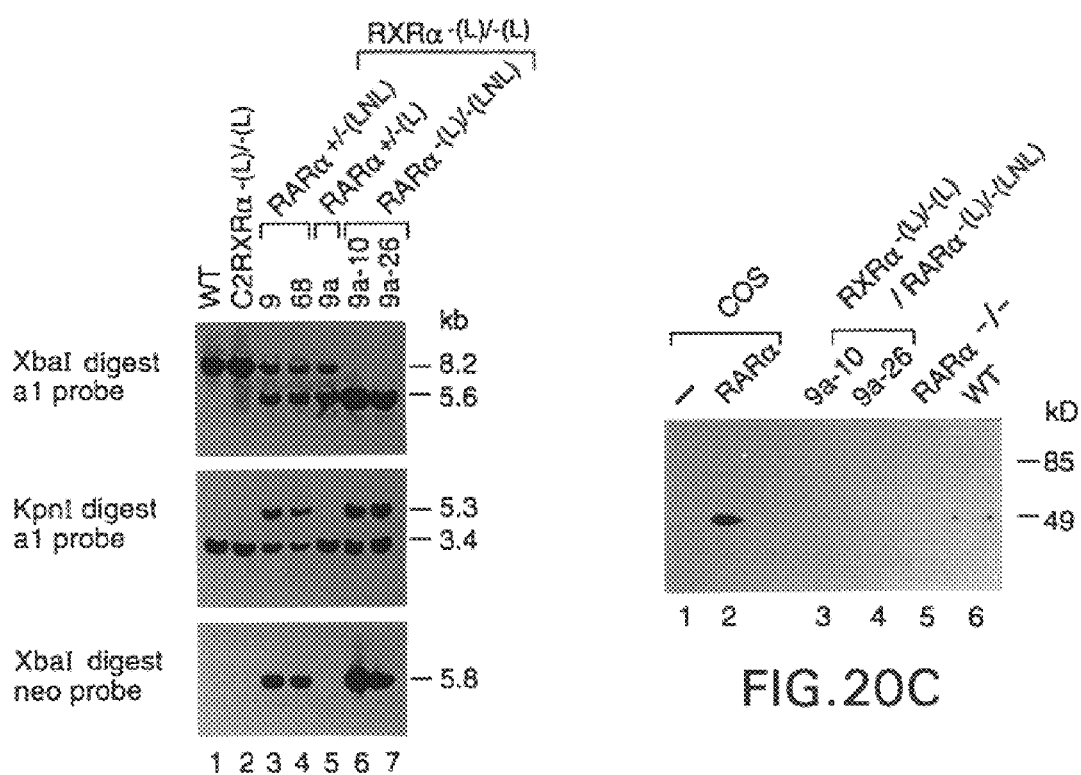

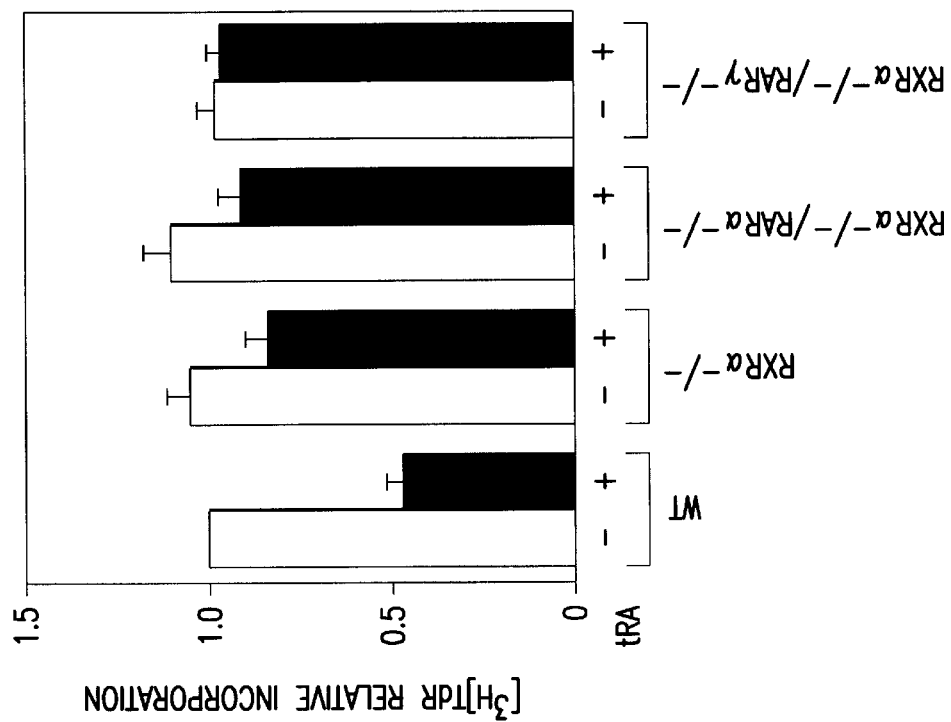
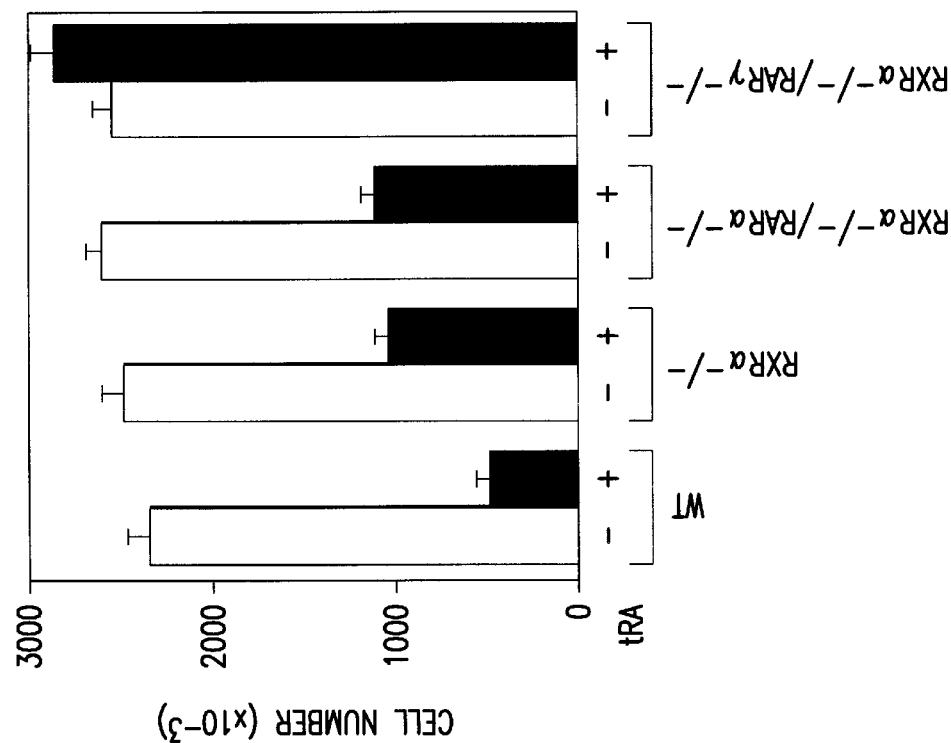
FIG. 24A
FIG. 24B

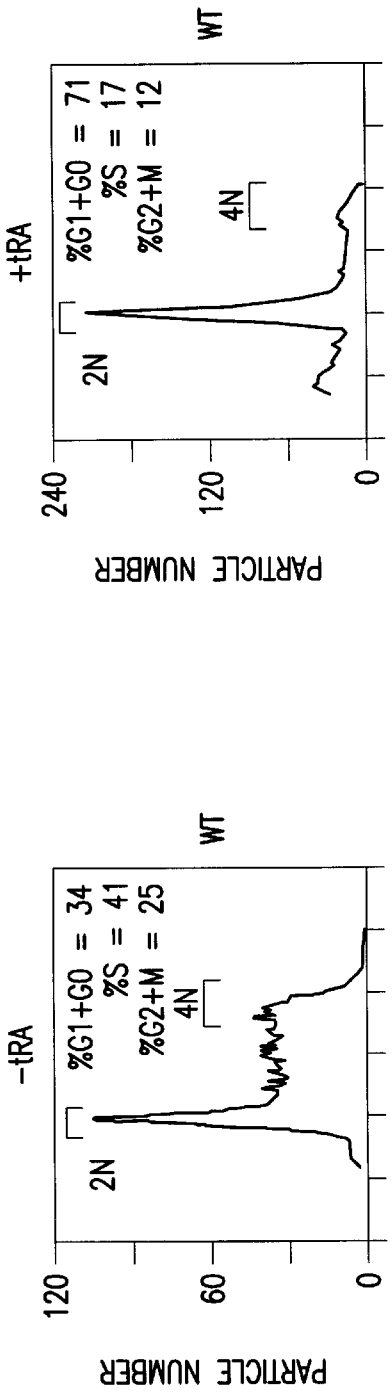
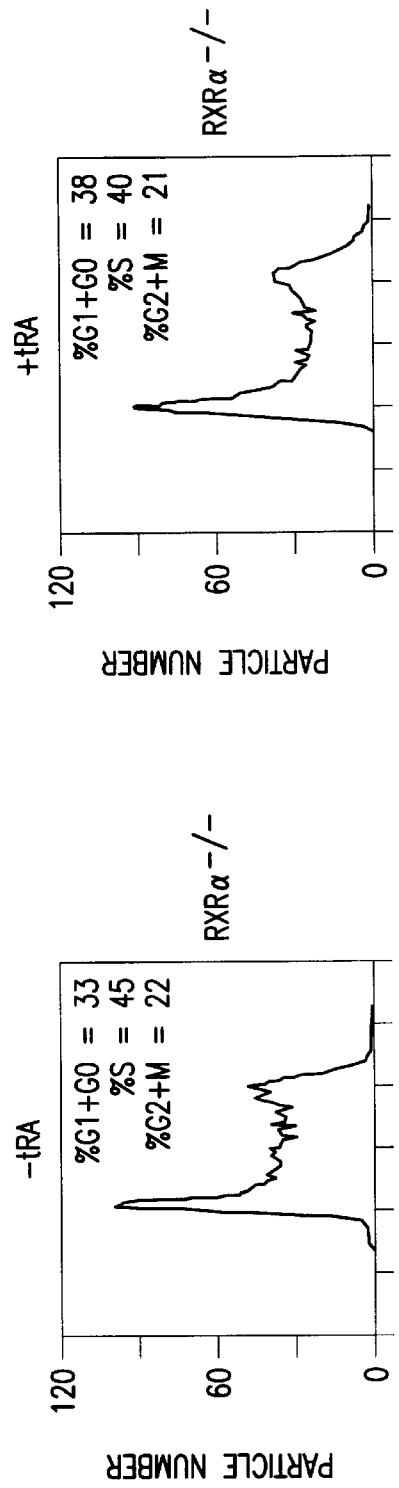
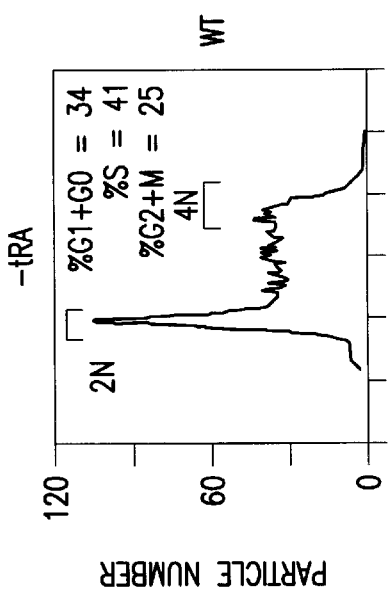
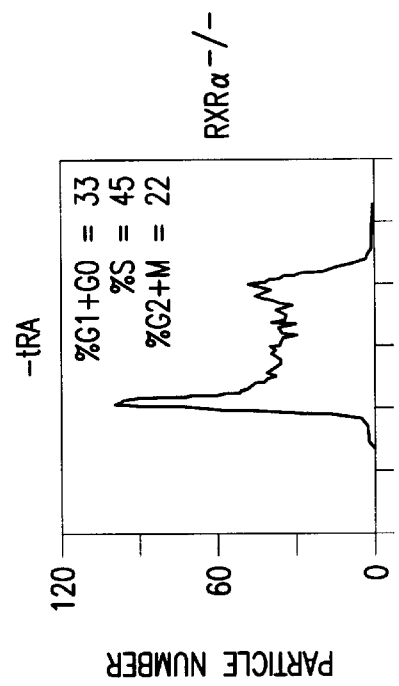
FIG. 24C-A
FIG. 24C-B
FIG. 24C-C
FIG. 24C-D

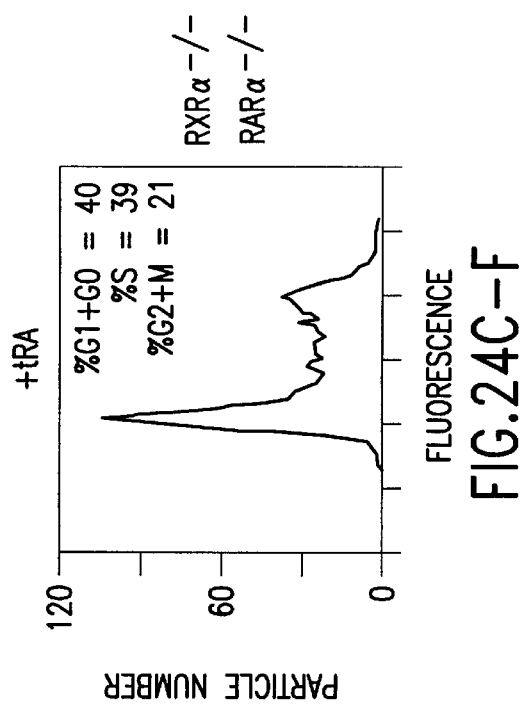
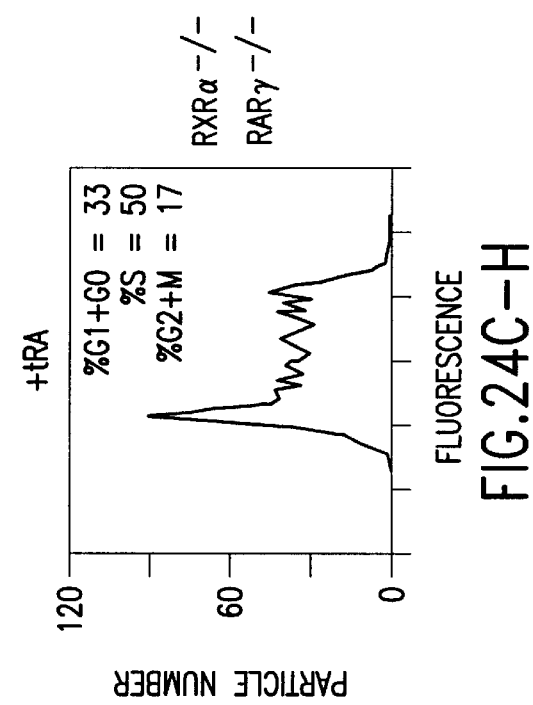
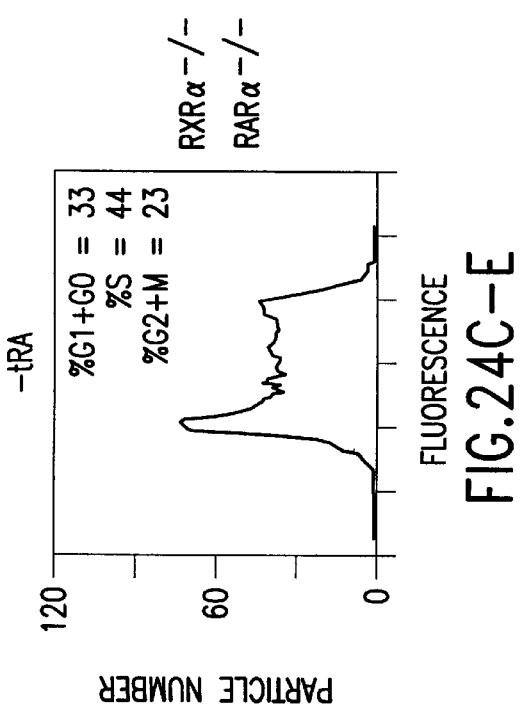
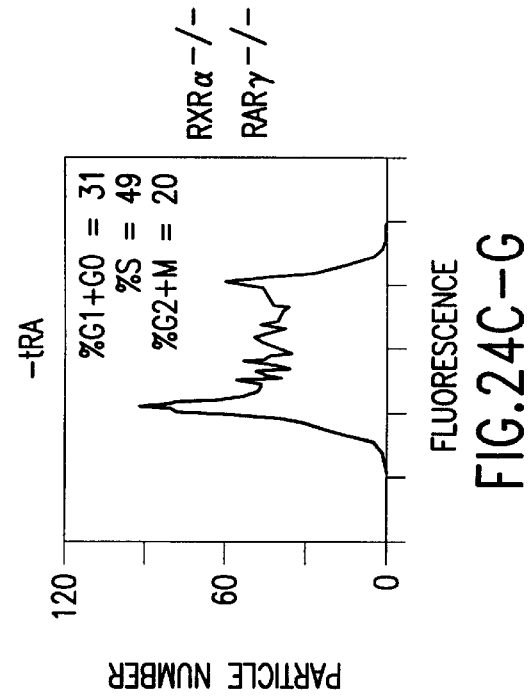

SEQUENCE LISTING

<160> NUMBER OF SEQ ID NOS: 8

<210> SEQ ID NO 1
<211> LENGTH: 540
<212> TYPE: DNA
<213> ORGANISM: Rattus sp.

<400> SEQUENCE: 1

| | | | | | |
|---|---|---|---|---|---|
| gatctgctct | gcccaagtct | tcctctcaga | aagcacaaca | gcagaacgaa | ctgctgtgat | 60 |
| tttcagacct | gaggtctgta | caccgactct | ggatatcctt | ccggaatcta | tttctccttt | 120 |
| aaagacttga | tgtaccacat | gtagtgcttc | agctagccct | tggccctgac | tcctcaaagg | 180 |
| aggggatcga | cccgctggtg | ttgtgattgc | tagaccagag | taggtttgga | tgggcagagt | 240 |
| gttacttaaa | aagtatagga | tgacaccggc | gagcagtccg | gagcacaggc | tatccccact | 300 |
| caaagccaga | gatggattct | cggtctcagc | tctcaaggtt | ccttccccag | gccccacagt | 360 |
| gcagagatag | ttctggggcc | ctgggtgggt | ggggcctctg | tacaagggc | ggggttcccg | 420 |
| ggcgcctcgt | ggccagggtg | accccgcccc | ctcctcctgc | gcagcgctct | gattccgcgg | 480 |
| agctgtccag | cctcagtgcc | ggagctggtc | gcctcttgtg | cgcagcgcct | cctgcccgcc | 540 |

<210> SEQ ID NO 2
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 2
agcttcctcg tggccagggt gaccccgcg                                    29

<210> SEQ ID NO 3
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 3
agcttcctcg gtgcgagggg tacgccgcg                                    29

<210> SEQ ID NO 4
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 4
agcttcctcg tgaccagggt gaccccgcg                                    29

<210> SEQ ID NO 5
<211> LENGTH: 26
<212> TYPE: DNA
<213> ORGANISM: Artificial Sequence
<220> FEATURE:
<223> OTHER INFORMATION: Oligonucleotide primer -continued

<400> SEQUENCE: 5
gggtagggtt caccgaaagt tcactg                                    26

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (7)..(9)
<223> OTHER INFORMATION: May be any nucleotide

<400> SEQUENCE: 6
gggtcannnt ggtca                                                15

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 7
ccccgggtag gtagatagcg tac                                       23

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 8
gctatctacc tacccgggggg tac                                      23

USE OF LIGANDS FOR TREATMENT OF DISEASES RESPONSIVE TO RETINOIDS

The present application claims benefit of the filing date of U.S. application Ser. No. 60/068,471, filed Dec. 22, 1997, which disclosure is herein incorporated by reference.

BACKGROUND OF THE INVENTION

1. Field of the Invention

The invention relates to methods for treatment of neurological disease by administering an agent which interacts with a retinoid receptor associated with the neurological disease. The invention also relates to a method of modulating dopamine receptor synthesis by introducing an agent that interacts with a retinoid receptor associated with the dopamine receptor synthesis. The invention further relates to a transgenic mouse which is deficient in the normal synthesis of one or more receptors of RARα, β, γ and RXR, and cell line thereof.

2. Related Art

Retinoids

A number of studies have demonstrated that retinoids (vitamin A derivatives) are essential for normal growth, vision, tissue homeostasis, reproduction and overall survival (for reviews and references, see Sporn et al., *The Retinoids,* Vols. 1 and 2, Spom et al., eds., Academic Press, Orlando, Fla. (1984)). Retinoids are also apparently crucial during embryogenesis, since offspring of dams with vitamin A deficiency (VAD) exhibit a number of developmental defects (Wilson, J. G., et al., *Am. J. Anat.* 92:189–217 (1953)). With the exceptions of vision (Wald, G., et al., *Science* 162:230–239 (1968)) and spermatogenesis in mammals (van Pelt, H. M. M., and De Rooij, D. G., *Endocrinology* 128:697–704 (1991)), most of the effects generated by VAD in animals and their fetuses can be prevented and/or reversed by retinoic acid (RA) administration (Wilson, J. G., et al., *Am. J. Anat.* 92:189–217 (1953); Thompson et al., *Proc. Royal Soc.* 159:510–535 (1964)). The dramatic teratogenic effects of maternal RA administration on mammalian embryos (Shenefelt, R. E., *Teratology* 5, 103–108 (1972); Kessel, M., *Development* 115:487–501 (1992); Creech Kraft, J., In *Retinoids in Normal Development and Teratogenesis,* G. M. Morriss-Kay, ed., Oxford University Press, Oxford, UK, pp. 267–280 (1992)), and the marked effects of topical administration of retinoids on embryonic development of vertebrates and limb regeneration in amphibians (Mohanty-Hejmadi et al., *Nature* 355:352–353 (1992); Tabin, C. J., *Cell* 66:199–217 (1991)), have contributed to the notion that RA may have critical roles in morphogenesis and organogenesis.

Retinoid Receptors

Except for those involved in visual perception (Wald, G. et al., *Science* 162:230–239 (1968)), the molecular mechanisms underlying the highly diverse effects of retinoids have until recently remained obscure. The discovery of nuclear receptors for RA (Petkovich et al., *Nature* 330:444–450 (1987); Giguère et al., *Nature* 330:624–629 (1987)) has greatly advanced the understanding of how the retinoids may exert their pleiotropic effects (Leid, M., et al., *TIBS* 17:427–433 (1992); Linney, E., *Current Topics in Dev. Biol.* 27:309–350 (1992)). It is thought that the effects of the RA signal are mediated through two families of receptors—the RAR family and the RXR family—which belong to the superfamily of ligand-inducible transcriptional regulatory factors that include steroid/thyroid hormone and vitamin D3 receptors (for reviews, see Leid, M., et al., *TIBS* 17:427–433 (1992); Chambon, P., Semin. *Cell Biol.* 5:115–125 (1994); Chambon, P., *FASEB J.* 10:940–954 (1996); Giguere, V., *Endocrinol. Rev.* 15:61–79 (1994); Mangelsdorf, D. J., and Evans, R. M., *Cell* 83:841–850 (1995); Gronemeyer, H., and Laudet, V., *Protein Profile* 2:1173–1236 (1995)).

RAR Receptors

Receptors belonging to the RAR family (RARα, β and γ and their isoforms) are activated by both all-trans- and 9-cis-RA (Leid, M., et al., *TIBS* 17:427–433 (1992); Chambon, P., Semin. *Cell Biol.* 5:115–125 (1994); Dollé, P., et al., *Mech. Dev.* 45:91–104 (1994)). Within a given species, the DNA binding (C) and the ligand binding (E) domains of the three RAR subtypes are highly similar, whereas the C-terminal domain F and the middle domain D exhibit no or little similarity. The amino acid sequences of the three RAR subtypes are also notably different in their B regions, and their main isoforms (α1 and α2, β1 to β4, and γ1 and γ2) further differ in their N-terminal A regions (Leid, M., et al, *TIBS* 17:427–433 (1992)). Amino acid sequence comparisons have revealed that the interspecies conservation of a given RAR subtype is greater than the similarity found between the three RAR subtypes within a given species (Leid, M., et al., *TIBS* 17:427–433 (1992)). This interspecies conservation is particularly striking in the N-terminal A regions of the various RARα, β and γ isoforms, whose A region amino acid sequences are quite divergent. Taken together with the distinct spatio-temporal expression patterns observed for the transcripts of each RAR and RXR subtype in the developing embryo and in various adult mouse tissues (Zelent, A., et al., *Nature* 339:714–717 (1989); Dollé, P., et al., Nature 342:702–705 (1989); Dollé et al., *Development* 110:1133–1151 (1990); Ruberte et al., *Development* 108:213–222 (1990); Ruberte et al., *Development* 111:45–60 (1991); Mangelsdorf et al., *Genes & Dev.* 6:329–344 (1992)), this interspecies conservation has suggested that each RAR subtype (and isoform) may perform unique functions. This hypothesis is further supported by the finding that the various RAR isoforms contain two transcriptional activation functions (AFs) located in the N-terminal A/B region (AF-1) and in the C-terminal E region (AF-2), which can synergistically, and to some extent differentially, activate various RA-responsive promoters (Leid, M., et al., *TIBS* 1 7:427–433 (1992); Nagpal, S., et al., *Cell* 70:1007–1019 (1992); Nagpal, S., et al., *EMBO J.* 12:2349–2360 (1993)). Knock-outs of RARα, β and γ have also provided some insight into the physiological functions of these receptors (see, WO 94/26100; Ghyselinck et al., *Intl. J. Dev. Biol.* 41:425–447 (1997)).

RXR Receptors

Unlike the RARs, members of the retinoid X receptor family (RXRα, β and γ) are activated exclusively by 9-cis-RA (Chambon, P., *Semin. Cell Biol.* 5:115–125 (1994); Dollé, P., et al., *Mech. Dev.* 45:91–104 (1994); Linney, E., *Current Topics in Dev. Biol.* 27:309–350 (1992); Leid, M., et al., *TIBS* 1 7:427–433 (1992); Kastner et al., in *Vitamin A in Health and Disease,* R. Blomhoff, ed., Marcel Dekker, New York (1993)). However, the RXRs characterized to date are similar to the RARs in that the different RXR subtypes also differ markedly in their N-terminal A/B regions (Leid, M., et al., *TIBS* 17:427–433 (1992); Leid, M., et al., *Cell* 68:377–395 (1992); Mangelsdorf et al., *Genes & Dev.* 6:329–344 (1992)), and contain the same transcriptional activation functions in their N-terminal A/B region and C-terminal E region (Leid, M., et al., *TIBS* 1 7:427–433 (1992); Nagpal, S., et al., *Cell* 70:1007–1019 (1992); Nagpal, S., et al., *EMBO J.* 12:2349–2360 (1993)).

It is currently unclear whether all the molecular properties of RXRs characterized in vitro are relevant for their physiological functions in vivo. In particular, it is unknown under what conditions these receptors act as 9-cis-RA-dependent transcriptional regulators (Chambon, P., Semin. Cell Biol. 5:115–125 (1994)). The knock-outs of RXRα and RXRβ in the mouse have provided some insight into the physiological functions of these receptors. For example, the ocular and cardiac malformations observed in RXRα$^{-/-}$ fetuses (Kastner, P., et al., Cell 78:987–1003 (1994); Sucov, H. M., et al., Genes & Dev. 8:1007–1018 (1994)) are similar to those found in the fetal VAD syndrome, thus suggesting an important function of RXRα in the transduction of a retinoid signal during development. The involvement of RXRs in retinoid signaling is further supported by studies of compound RXRα/RAR mutants, which reveal defects that are either absent or less severe in the single mutants (Kastner, P., et al., Cell 78:987–1003 (1994); Kastner, P., et al., Cell 83:859–869 (1995); Chiba, H., et al., J. Cell Biol. 139:735–747 (1997)). Moreover, it has been shown that activation of RA-responsive promoters likely occurs through RAR/RXR heterodimers rather than through homodimers (Yu, V. C. et al., Cell 67:1251–1266 (1991); Leid, M., et al., Cell 68:377–395 (1992b); Durand et al., Cell 71:73–85 (1992); Nagpal, S., et al., Cell 70:1007–1019 (1992); Zhang, X. K., et al., Nature 355, 441–446 (1992); Kliewer et al., Nature 355:446–449 (1992); Bugge et al., EMBO J. 11: 1409–1418 (1992); Marks et al., EMBO J. 11:1419–1435 (1992); Yu, V. C. et al., Cur. Op. Biotech. 3:597–602 (1992); Leid, M., et al., TIBS 17:427–433 (1992); Laudet and Stehelin, Curr. Biol. 2:293–295 (1992); Green, S., Nature 361:590–591 (1993)). These results strongly suggest that RAR/RXR heterodimers are indeed functional units that transduce the RA signal in vivo, although it is unclear whether all of the suggested heterodimeric combinations occur in vivo (Chambon, P., Semin. Cell Biol. 5:115–125 (1994)). Thus, the basis for the highly pleiotropic effect of retinoids may reside, at least in part, in the control of different subsets of retinoid-responsive promoters by cell-specifically expressed heterodimeric combinations of RAR/RXR subtypes (and isoforms), whose activity may be in turn regulated by cell-specific levels of all-trans- and 9-cis-RA (Leid, M., et al., TIBS 17:427–433 (1992)).

Retinoid Signaling Through RAR/RXR Heterodimers

Nuclear receptors (NRs) are members of a superfamily of ligand-inducible transcriptional regulatory factors that include receptors for steroid hormones, thyroid hormones, vitamin D3 and retinoids (Leid, M., et al., Trends Biochem. Sci. 17:427–433 (1992); Leid, M., et al., Cell 68:377–395 (1992); and Linney, E. Curr. Top. Dev. Biol., 27:309–350 (1992)). NRs exhibit a modular structure which reflects the existence of several autonomous functional domains. Based on amino acid sequence similarity between the chicken estrogen receptor, the human estrogen and glucocorticoid receptors, and the v-erb-A oncogene Krust, A., et al. (EMBO J. 5:891–897 (1986)) defined six regions—A, B, C, D, E and F—which display different degrees of evolutionary conservation amongst various members of the nuclear receptor superfamily. The highly conserved region C contains two zinc fingers and corresponds to the core of the DNA-binding domain (DBD), which is responsible for specific recognition of the cognate response elements. Region E is functionally complex, since in addition to the ligand-binding domain (LBD), it contains a ligand-dependent activation function (AF-2) and a dimerization interface. An autonomous transcriptional activation function (AF-1) is present in the non-conserved N-terminal A/B regions of the steroid receptors. Interestingly, both AF-1 and AF-2 of steroid receptors exhibit differential transcriptional activation properties which appear to be both cell type and promoter context specific (Gronemeyer, H. Annu. Rev. Genet. 25:89–123 (1991)).

As described above, the all-trans (T-RA) and 9-cis (9C-RA) retinoic acid signals are transduced by two families of nuclear receptors, RAR α, β and γ (and their isoforms) are activated by both T-RA and 9C-RA, whereas RXR α, β and γ are exclusively activated by 9C-RA (Allenby, G., et al., Proc. Natl. Acad. Sci. USA 90:30–34 (1993)). The three RAR subtypes differ in their B regions, and their main isoforms (α1 and α2, β1–4, and γ1 and γ2) have different N-terminal A regions (Leid, M., et al., Trends Biochem. Sci. 17:427–433 (1992)). Similarly, the RXR subtypes differ in their A/B regions (Mangelsdorf, D. J. et al, Genes & Dev. 6:329–344 (1992)).

The E-region of RARs and RXRs has also been shown to contain a dimerization interface (Yu, V. C., et al., Curr. Opin. Biotechnol. 3:597–602 (1992)). Most interestingly, it was demonstrated that RAR/RXR heterodimers bind much more efficiently in vitro than homodimers of either receptor to a number of RA response elements (RAREs) (Yu, V. C., et al., Cell 67:1251–1266 (1991); Berrodin, T. J., et al., Mol. Endocrinol 6:1468–1478 (1992); Bugge, T. H., et al, EMBO J. 11:1409–1418 (1992); Hall, R. K., et al, Mol. Cell. Biol. 12: 5527–5535 (1992); Hallenbeck, P. L., et al., Proc. Natl. Acad. Sci. USA 89:5572–5576 (1992); Husmann, M., et al., Biochem. Biophys. Res. Commun. 187:1558–1564 (1992); Kliewer, S. A., et al., Nature 355:446–449 (1992); Leid, M., et al., Cell 68:377–395 (1992); Marks, M. S., et al., EMBO J. 11:1419–1435 (1992); Zhang, X. K., et al., Nature 355:441–446 (1992)). RAR and RXR heterodimers are also preferentially formed in solution in vitro (Yu, V. C., et al., Cell 67:1251–1266 (1991); Leid, M., et al., Cell 68:377–395 (1992); Marks, M. S., et al., EMBO J. 11:1419–1435 (1992)), although the addition of 9C-RA appears to enhance the formation of RXR homodimers in vitro (Lehman, J. M., et al., Science 258:1944–1946(1992); Zhang, X. K., et al., Nature 358:587–591(1992)).

It has been shown that activation of RA-responsive promoters likely occurs through RAR/RXR heterodimers rather than through homodimers (Yu, V. C., et al., Cell 67:1251–1266(1991); Leid, M., et al., Cell 68:377–395 (1992b); Durand et al., Cell 71:73–85 (1992); Nagpal, S., et al., Cell 70:1007–1019 (1992); Zhang, X. K., et al., Nature 355, 441–446 (1992); Kliewer et al., Nature 355:446–449 (1992); Bugge et al., EMBO J. 11:1409–1418 (1992); Marks et al., EMBO J. 11:1419–1435 (1992); Yu, V. C. et al., Cur. Op. Biotech. 3:597–602 (1992); Leid, M., et al., TIBS 17:427–433 (1992); Laudet and Stehelin, Curr. Biol. 2:293–295 (1992); Green, S., Nature 361:590–591 (1993)). The RXR portion of these heterodimers has been proposed to be silent in retinoid-induced signaling (Kurokawa, R., et al., Nature 371:528–531 (1994); Forman, B. M., et al., Cell 81:541–550 (1995); Mangelsdorf, D. J., and Evans, R. M., Cell 83:835–850 (1995)), although conflicting results have been reported on this issue (Apfel, C. M., et al., J. Biol. Chem. 270(51):30765–30772 (1995); see Chambon, P., FASEB J. 10:940–954 (1996) for review). The results of these studies strongly suggest that RAR/RXR heterodimers are indeed functional units that transduce the RA signal in vivo (Chambon, P., Semin. Cell Biol. 5:115–125 (1994)). Thus, the basis for the highly pleiotropic effect of retinoids may reside, at least in part, in the control of different subsets of retinoid-responsive promoters by cell-specifically expressed heterodimeric combinations of RAR:RXR subtypes (and isoforms), whose activity may be in turn regulated by cell-specific levels of all-trans- and 9-cis-RA (Leid, M., et al., TIBS 17:427–433 (1992)).

The RXR receptors may also be involved in RA-independent signaling. For example, the observation of aberrant lipid metabolism in the Sertoli cells of RXRβ$^{-/-}$ mutant animals suggests that functional interactions may also occur between RXRβ and the peroxisomal proliferator-activated receptor signaling pathway (WO 94/26100; Kastner, P., et al., *Genes & Dev.* 10:80–92 (1996)).

Therapeutic Uses of Retinoids

Overview

As retinoic acid is known to regulate the proliferative and differentiative capacities of several mammalian cell types (Gudas, L. J., et al., *In The Retinoids*, 2nd ed., Sporn, M. B., et al., eds., New York: Raven Press, pp. 443–520 (1994)), retinoids are used in a variety of chemopreventive and chemotherapeutic settings.

The prevention of oral, skin and head and neck cancers in patients at risk for these tumors has been reported (Hong, W. K., et al., *N. Engl. J. Med.* 315:1501–1505 (1986); Hong, W. K., et al., *N. Engl. J. Med* 323:795–801 (1990); Kraemer, K. H., et al., *N. Engl. J. Med.* 318:1633–1637 (1988); Bollag, W., et al., *Ann. Oncol.* 3:513–526 (1992); Chiesa, F., et al., *Eur. J. Cancer B. Oral Oncol.* 28:97–102 (1992); Costa, A., et al., *Cancer Res.* 54:Supp. 7, 2032–2037 (1994)). Retinoids have also been used to treat squamous cell carcinoma of the cervix and the skin (Verma, A. K., *Cancer Res.* 47:5097–5101 (1987); Lippman S. M., et al., *J. Natl Cancer Inst.* 84:235–241 (1992); Lippman S. M., et al., *J. Natl Cancer Inst.* 84:241–245 (1992)) and Kaposi's sarcoma (Bonhomme, L., et al., *Ann. Oncol.* 2:234–235 (1991)), and have found significant use in the therapy of acute promyelocytic leukemia (Huang, M. E., et al., *Blood* 72:567–572 (1988); Castaigne, S., et al., *Blood* 76:1704–1709 (1990); Chomienne, C., et al., *Blood* 76:1710–1717 (1990); Chomienne, C., et al., *J. Clin. Invest.* 88:2150–2154 (1991); Chen Z., et al., *Leukemia* 5:288–292 (1991); Lo Coco, F., et al., *Blood* 77:1657–1659 (1991); Warrell, R. P., et al., *N. Engl. J. Med* 324:1385–1393 (1991); Chomienne, C., et al., *FASEB J.* 10: 1025–1030 (1996)).

Acute Promyelocytic Leukemia (APL)

A balanced chromosomal translocation, t(15;17), has been identified in most acute promyelocytic leukemia (APL) cells (Larson, A. R., et al., *Am. J. Med.* 76:827–841 (1984)). The breakpoint for this translocation occurs within the second intron of the RARα gene (Alcalay, M. D., et al., *Proc. Natl. Acad. Sci. USA* 88:1977–1981 (1991); Chang, K. S., et al., *Leukemia* 5:200–204 (1991); Chen, S., et al., *Blood* 78:2696–2701 (1991) and within two loci of the gene encoding the putative zinc finger transcription factor PML (Goddard, A., et al., *Science* 254:1371–1374 (1991)). This reciprocal t(15;17) translocation leads to the generation of a PML-RARα fusion protein which is co-expressed with PML and RARα in APL cells (see Warrell, R. P., et al., *N. Engl. J. Med.* 329:177–189 (1993); Grignani, F., et al., *Blood* 83:10–25 (1994); Lavau, C., and Dejean, A., *Leukemia* 8:1615–1621 (1994); de Thé, H., *FASEB J.* 10:955–960 (1996)). The PML-RARα fusion is apparently responsible for the differentiation block at the promyelocytic stage, since (i) it is observed in nearly all APL patients (Warrell, R. P., et al., *N. Engl. J. Med* 329:177–189 (1993); Grignani, F., et al., *Blood* 83:10–25 (1994); Lavau, C., and Dejean, A., *Leukemia* 8:1615–1621 (1994)), (ii) it inhibits myeloid differentiation when overexpressed in U937 or HL60 myeloblastic leukemia cells (Grignani, F., et al., *Cell* 74:423–431 (1993)), and (iii) complete clinical remission due to differentiation of the leukemic cells to mature granulocytes upon treatment with all-trans retinoic acid (T-RA) is tightly linked to PML-RARA expression (Warrell, R. P., et al., *N. Engl. J. Med.* 324:1385–1393 (1991); Lo Coco, R., et al., *Blood* 77:1657–1659 (1991); Chomienne, C., et al., *FASEB J.* 10:1025–1030 (1996)). Multiple studies have addressed the possible impact of PML-RARα fusion protein formation on cell proliferation (Mu, X. M., et al., *Mol. Cell . Biol.* 14:6858–6867 (1994)) and apoptosis (Grignani, F., et al., *Cell* 74:423–431 (1993)), AP1 transrepression (Doucas, V., et al., *Proc. Natl. Acad. Sci. USA* 90:9345–9349 (1993)), and vitamin D3 signaling (Perez, A., et al., *EMBO J.* 12:3171–3182 (1993)), but the mechanism(s) by which PML-RARα blocks myeloid cell maturation has remained elusive. Consistent with the aberrant nuclear compartmentalization of PML-RARα , which adopts the "PML-type" location upon RA treatment (Dyck, J. A., et al., *Cell* 76:333–343 (1994); Weis, K., et al., *Cell* 76:345–358 (1994); Koken, M. H., et al., *EMBO J.* 13:1073–1083 (1994)), the currently prevailing hypothesis is that PML-RARα possesses altered transcriptional properties compared to PML or RARα and/or may act in a dominant-negative manner (Perez, A., et al., *EMBO J.* 12:3171–3182 (1993); de Thé, H., et al., *Cell* 66:675–684 (1991); Kastner, P., et al., *EMBO J.* 11:629–642 (1992)).

Disorders of the Dopamine Signaling Pathway

Dopamine (DA) is one of the major neuromodulators in the central nervous system (CNS), controlling key physiological functions, from coordination of movements to hormone synthesis and secretion. DA functions are exerted through the interaction with five distinct membrane receptors (DA D1, D2, D3, D4 and D5 receptors (D1R, D2R, D3R, D4R and D5R, respectively)) which belong to the family of seven transmembrane domain G-protein-coupled receptors (Gingrich, J. A. & Caron, M. G., *Annu. Rev. Neurosci.* 16:299–321 (1993)). The DA D2 receptor (D2R) is highly expressed in the CNS and in the pituitary gland. There are two isoforms of this receptor, D2L and D2S, which are generated by alternative splicing from the same gene (Dal Toso, R., et al., *EMBO J.* 8:4025–4034 (1989)). Both isoforms are expressed in the same tissues and present a similar pharmacological profile (Jackson, D. M. & Weslind-Danielsson, A., *Pharmac. Ther.* 64:291–369 (1994)). However, they couple to different G-proteins (Montmayeur, J. P. & Borrelli, E., *Proc. Natl. Acad. Sci. U.S.A.* 88:3135–3139 (1991); Montmayeur, J. P., et al., *Mol. Endocrinol.* 7:161–170 (1993); Guiramand, J., et al., *J. Biol. Chem.* 270:7354–7358 (1995)). In contrast to the wide expression of dopaminergic receptors throughout the CNS, DA is synthesized in a small group of mesencephalic neurons located in the substantia nigra and ventral tegmental area. Interestingly, D2Rs are located both pre- and post-synaptically (Civelli, O., et al., *Eur. J. Pharmacol.* 19:277–286 (1991)), indicating a key role not only in mediating events in the target cells of dopaminergic neurons, but also in controlling the release of DA.

Knock-out of the D2R gene results in a locomotor Parkinsonian-like phenotype and in pituitary tumors in the mouse (Baik, J. H., et al., *Nature* 377:424–428 (1995); Saiardi, A., et al., *Neuron* 19:115–126 (1997)). These results underline the importance of the expression of this gene in the control of different physiological functions, while alterations of its expression might be the basis of some human pathologies. Sequence analysis of the D2R promoter has revealed features of a housekeeping promoter (Minowa, T., et al., *Biochemistry* 31:8389–8396 (1992); Valdenaire, O., et al., *Eur. J Biochem.* 220:577–584 (1994)). The D2R promoter lacks TATA and CAAT boxes, while multiple Sp1 binding sites are present. Thus, the control of the expression of the D2R gene must involve cell-specific transcription factors.

Given that retinoids have important roles in development, it would be of interest to determine if retinoids have a role in neurological diseases.

SUMMARY OF THE INVENTION

The present invention provides a method of treating a neurological disease in a subject, the method comprising administering to the subject an effective amount of an agent which interacts with a retinoid receptor associated with the neurological disease. The present invention also provides a method of treating a neurological disease in a subject comprising administering to a subject an effective amount of an agent that is a retinoid agonist or antagonist. The agonist or antagonist may, but is not required to, bind to a retinoid receptor. The neurological disease may be caused by a disorder of the dopamine signaling pathway. The disorder may be due to hyperactivity of the dopamine signaling pathway, for example, schizophrenia. The disorder may be due to hypoactivity of the dopamine signaling pathway, for example, Parkinson's disease.

The present invention also provides for a method of treating a neurological disease such as, for example, schizophrenia, Parkinson's disease, anxiety, depression, drug addiction, disorders of cognition, emesis, eating disorders, pituitary tumor, attention deficit-hyperactivity disorder, Tourette's Syndrome, Huntington's disease, tardive dyskinesia, Lesch-Nyhan disease and Rett syndrome.

In the present invention, the agent for effecting treatment of the neurological disease may be an agonist or antagonist of said retinoid receptor. The retinoid receptor associated with the neurological disease is selected from RARα, RARβ, RARγ, and RXR. RXR includes RXRα, RXRβ and RXRγ. The agent may interact with one or more, or a combination of two or more receptors selected from the group consisting of RARα, RARβ, RARγ, RXRα, RXRβ and RXRγ. The agent may interact with RARα/RXRγ, RARβ/RXRβ, RARβ/RXRγ, or RXRβ/RXRγ.

The present invention further provides a method of modulating dopamine receptor synthesis in a subject, the method comprising introducing to the subject, an agent that interacts with a receptor selected from the group consisting of RARα, RARβ, RARγ and RXR. The dopamine receptor may be selected from the group consisting of D1R, D2R, D3R, D4R and D5R. The present invention provides for a method of increasing dopamine receptor synthesis in a subject, the method comprising introducing to the subject, an agent that is an agonist of a receptor selected from the group consisting of RARα, RARβ, RARγ and RXR. The invention further provides for a method of decreasing dopamine receptor synthesis in a subject, the method comprising introducing to the subject, an agent that is an antagonist of a receptor selected from the group consisting of RARα, RARβ, RARγ and RXR.

The present invention additionally provides a method of treating a neurological disease or neurological state linked to a dysfunction of dopaminergic systems by providing an effective amount of a retinoid agonist. An example of a neurological disease linked to a dysfunction of dopaminergic systems is Parkinson's disease.

In addition, the invention provides a method of treating a neurological disease or neurological state that results in hyperlocomotion by providing an effective amount of a retinoid antagonist. In particular embodiments of this invention, a neurological disease or a neurological state that results in hyperlocomotion is drug abuse, e.g., use of cocaine or its derivatives. In more particular embodiments of the invention, the neurological disease or neurological state is cocaine abuse.

The invention further provides for a transgenic non-human animal, such as a rodent, which has been genetically altered such that the animal is deficient in the normal synthesis of one or more, or two or more receptors selected from the group consisting of RARβ, RARγ, RXRβ and RXRγ. The animal may not synthesize detectable levels of one or more receptors selected from the group consisting of RARβ, RARγ, RXRβ, and RXRγ. The animal may not synthesize one or more functional receptors selected from the group consisting of RARβ, RARγ, RXRβ, and RXRγ. The animal may be heterozygous or homozygous for a deficiency in the normal synthesis of one or more receptors selected from the group consisting of RARβ, RXRγ, RARβ/RXRβ, RARβ/RXRγ and RXRβ/RXRγ. In a particular embodiment of this invention, the transgenic animal is a transgenic mouse.

The invention is also directed to a transgenic non-human animal, such as a rodent, which has been genetically altered such that the animal is heterozygous or homozygous for a deficiency in the normal synthesis of a combination of two receptors selected from the group consisting of RARα/RARβ, RARβ/RARγ, RARα/RXRα, RARγ/RXRα and RARα/RXRγ.

The above mentioned transgenic animal may contain a heterozygous or homozygous disruption in the endogenous gene encoding the above mentioned retinoid receptor, wherein the disruption comprises the insertion of a selectable marker sequence, and wherein the disruption results in the lack of expression of the receptor and confers a phenotype.

Also provided in the present invention is a mammalian cell line which is heterozygous or homozygous for a deficiency in the normal synthesis of one or more, or two or more receptors selected from the group consisting of RARβ, RARγ, RXRβ, and RXRγ. In one embodiment of the invention, the cell line does not synthesize detectable levels of one or more receptors selected from the group consisting of RARβ, RARγ, RXRβ, and RXRγ. In another embodiment, the cell line does not synthesize one or more functional receptors selected from the group consisting of RARβ, RARγ, RXRβ, and RXRγ. The invention further provides for a cell line that is deficient in the normal synthesis of one or more receptors selected from the group consisting of RARβ, RXRγ, RARβ/RXRβ, RARβ/RXRγ and RXRβ/RXRγ. The cell line may be derived from a pluripotent cell line having the ATCC designation CRL 11632.

The invention is also directed to a mammalian cell line, which has been genetically altered such that the mammalian cell line is heterozygous or homozygous for a deficiency in the normal synthesis of a combination of two receptors selected from the group consisting of RARα/RARβ, RARβ/RARγ, RARα/RXRα, RARγ/RXRα and RARα/RXRγ.

The above mentioned mammalian cell line may contain a heterozygous or homozygous disruption in the endogenous gene encoding the above mentioned retinoid receptor, wherein the disruption comprises the insertion of a selectable marker sequence, and wherein the disruption results in the lack of expression of the receptor.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 2. Quantification of D1R and D2R transcripts in the striata of wild-type and mutant mice.

FIG. 7. DNA binding analysis of RARα and RXRα to the D2R RARE. FIG. 7A. Nucleotide sequences of the D2R RARE (RARE D2) (SEQ ID NO:2) and the two mutants D2m1 (SEQ ID NO:3) and D2m2 (SEQ ID NO:4) oligonucleotides. RARE D2 (SEQ ID NO:2) contains the native RARE-like element of the D2R promoter, highlighted in bold. The mutated bp are underlined. RARβ2 oligonucleotide (SEQ ID NO:5) containing the DR5 RARE present in the promoter of RARβ2 gene is also represented.

FIG. 10. Targeted disruption of the RARE gene.

FIG. 12. Persistent hyperplastic primary vitreous body (PHPV or retrolenticular membrane), cataracts and congenital fold of the retina in Aβ null mutants. FIG. 12E, FIG. 12F: ×70 and FIG. 12G: ×140.

FIG. 14. Cranial and cervico-occipital skeletal defects in E18.5 RAR null mutants (genotypes as indicated). in FIG. 14A–14G, FIG. 14H and 14I, FIG. 14J and 14K: ×12; FIG. 14L and 14M: ×38.

FIG. 15. Immunohistochemical localization of RARα, RARβ and RARγ (as indicated) in E13.5 limbs (FIGS. 15A–15C) and newborn (FIGS. 15D and 15E) and adult (FIGS. 15F and 15G) brain. All the tissues are from WT mice except (FIG. 15G) where the anti-RARβ antibody was applied on a brain section from an Aβ mutant. A, accumbens nucleus; AC, anterior commisure; C, cerebral cortex; CP, caudate-putamen; CR, precartilaginous anlagen of the carpal bones; D, digit; E, ectoderm; EC, external capsule; ED, epidermis; EY, eye; IC, internal capsule; ID, interdigital mesenchyme; LV, lateral ventricle; OT, olfactory tubercle; SZ, subventricular zone. Magnifications.

FIG. 16. Comparison of the cranial nerves and brain of WT and Aβ mutants. FIGS. 16D–16E: ×15.

FIG. 17. Eye defects in double null mutants of RARβ and RARγ. Frontal histological sections from E14.5 (FIGS. 17A–17D), E16.5 (FIGS. 17E, FIG. 17F) and E18.5 (FIG. 17G, FIG. 17J) WT (FIGS. 17A, 17C, 17E, 17G and 17I) and Aβ/Aγ mutants (FIGS. 17B, 17D, 17F, 17H and 17J). A, anterior chamber; C, cornea; CA, cartilage; CS, corneal stroma; CV, an example of cavity in the neural retina; D, dorsal retina; E, eyelids; GCL, ganglion cell layer; H, hyaloid vessels; IE, epithelial portion of the iris; IS, stroma of the iris; INL, inner neuroblastic layer; IPL, anlage of the inner plexiform layer; J, conjunctival sac; L, lens; M, undifferentiated mesenchyme; O, optic nerve; ONL, outer neuroblastic layer; R, retrolenticular membrane; RP, retinal pigment epithelium; S, sclera; SV, secondary vitreous; T, vascular capsule of the lens (tunica vasculosa lentis); V, ventral retina; VA, vacuoles. The thin arrows, double arrows and thick arrows in (FIG. 17C) and (FIG. 17D) point to normal mitotic figures, ectopic mitotic figures and to macrophage-like cells, respectively. The brackets in (FIG. 17H) encompass the optic nerve coloboma and the squared brackets in (FIGS. 17E and 17I) the equatorial region of the lens. The asterisks indicate artefactual detachments generated during tissue processing. Magnifications.

FIG. 18B: ×26; ×18 (FIG. 18E; E14.5) and ×13 (FIG. 18E; E15.5 and 16.5).

FIG. 19. Distribution of RARα, RARβ and RARγ transcripts in the ocular (FIGS. 19A–19C) and nasal (FIG. 19B) regions of WT fetuses. C, cornea; E, lower (ventral) eyelid; EI, rostral ethmoturbinate; GCL, ganglion cell layer; H, epithelial portion of the Harderian gland; L, lens; MS, maxillary sinus; N, nasal septum; NA, nasal capsule; OF, olfactory epithelium; ONL, outer nuclear layer; PC, perichondrium; PO, periocular mesenchyme; R, primary vitreous body; RE, retina; RS, respiratory epithelium; UM, first upper molar; V, secondary vitreous body. The in situ hybridization signal is shown in false colors after computer processing of a bright-field view (showing the histology) and of a dark field view (revealing the autoradiography silver grain signal) of the same section. The threshold levels for false colors have been selected in order to eliminate the isolated (background) silver grains, but to reveal all significant labeling (yellow) as well as more intensely labeled areas (red). Magnification.

FIG. 20. Disruption of both alleles of the RARα gene by HR in a RXRα$^{-(L)/-(L)}$ cell line. (FIG. 20B) Southern blot analysis indicating the targeting of the RARα gene in a RXRα$^{-(L)/-(L)}$ cell line. The genotypes of different cell lines (e.g., 9) and their subclones (9a, etc.) are indicated at the top of each lane, and correspond to all three panels. (FIG. 20C) Western blot analysis indicating the absence of RARα protein in RXRα$^{-(L)/-(L)}$/RARα$^{-(L)/-(LNL)}$ cell lines. Lanes 1 and 2 contain 2 μg of whole cell extracts from COS cells transfected with either the pSG5 (Green, S., et al., *Nucl. Acids Res.* 16:369 (1988)) or mRARαø expression construct (Zelent, A., et al., *Nature* 339:714–717 (1989)), and lanes 3–6 contain 60 μg of whole cell extracts from WT and mutant F9 cells, as indicated. RARα protein was detected using the rabbit polyclonal antibody RPα(F), followed by chemiluminescence detection. Mol wt is shown in kD.

FIG. 21. Disruption of both alleles of the RARγ gene by HR in a RXRα$^{-(L)/-(L)}$ cell line.

FIG. 22. RXRα$^{-/-}$/RARγ$^{-/-}$ F9 cells do not differentiate into primitive and parietal endodermlike cells.

FIG. 23. RXRα$^{-/-}$/RARγ$^{-/-}$ F9 cells are defective for tRA-induced differentiation into VE-like cells.

FIG. 24. The antiproliferative response to tRA is impaired in RXRα$^{-/-}$ and RXRα$^{-/-}$/RARα$^{-/-}$ cells, and is abolished in RXRα$^{-/-}$/RARγ$^{-/-}$ F9 cells. (FIG. 24A) The number of cells after 6 d of culture in the presence (black bars) or absence (white bars) of 1 μM tRA are indicated for WT and mutant cells. The bars represent the mean ±SEM for triplicate cultures within the same experiment. (FIG. 24B) Cells were cultured for 4 d with or without 1 μM tRA, followed by 2 h of [$^3$H]thymidine ([$^3$H]TdR) labelling. The bars represent the mean ±SEM for three different experiments, setting the amount of [$^3$H]TdR incorporation per 1000 cells equal to one, for WT control cells. (FIG. 24C) Subconfluent cultures of WT (FIGS. 24C-A and 24C-B), RXRα$^{-/-}$ (FIGS. 24C-C and 24C-D), RXRα$^{-/-}$/RARα$^{-/-}$ (FIGS. 24C-E and 24C-F), and RXRα$^{-/-}$/RARγ$^{-/-}$ (FIGS. 24C-G and 24C-H) cells were grown for 5 d in the presence (FIGS. 24C-B, 24C-D, 24C-F and 24C-H) or absence (FIGS. 24C-A, 24C-C, 24C-E and 24C-G) of 1 μM tRA, and analyzed by FACS®. The X axis indicates the integrated fluorescence intensity and the Y axis the particle number. Approximately 20,000 particles are represented in each histogram. The percentage of cells in G1+G0, S, and G2+M phases are indicated. The arrow highlights the sub-2N size, DNA-containing particles corresponding to "apoptotic bodies."

Figure 1A:
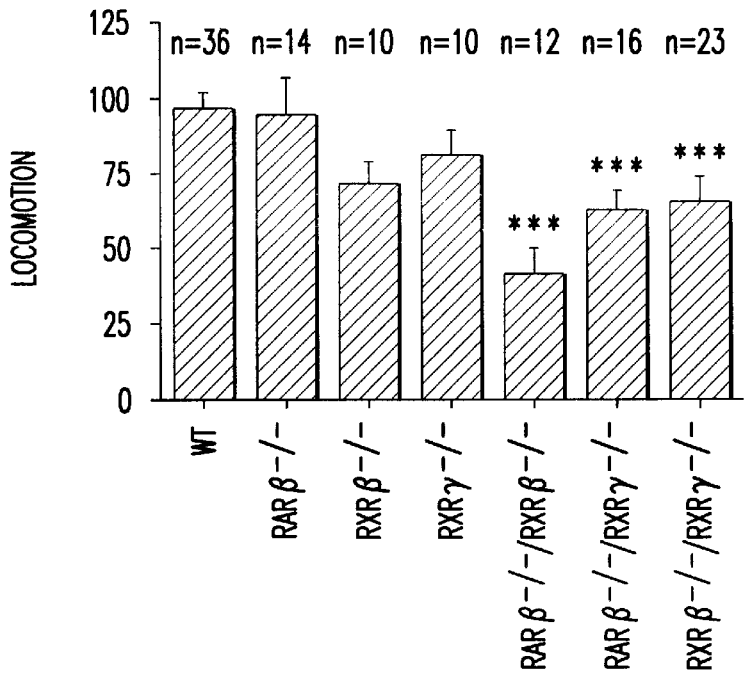
FIG. 1. Locomotor activity of $RAR\beta^{-/-}$, $RXR\beta^{-/-}$, $RXR\gamma^{-/-}$, $RAR\beta^{-/-}//RXR\beta^{-1-}$, $RAR\beta^{-/-}/RXR\gamma^{-/-}$ and RXRβ−/−/RXRγ−/− null mutant animals. In the open field test forward locomotion (FIG. 1A, number of squares crossed) and the number of rearings (FIG. 1B) were scored during a 5 min test period. Rotarod performance (FIG. 1C) was determined as the time spend on the rotating rod. To avoid the possible effects of a mixed genetic background, large numbers (n) of animals were used in these tests. Data were expressed as means ±S.E.M. and groups were compared by one-way analysis of variance (ANOVA), with Welch correction ($F_{locomotion}[6,37]=8.36$; $F_{rearings}[6,39]=12.92$; $F_{latency}[6,59]=1262$). Post hoc analysis were performed using Bonferroni multiple t test with all possible 21 comparisons (BMDP; Dixon, W. J., in DMDP statistical software manual (Berkeley: University of California Press, 1988)); *P<0.001, P<0.01, *P<0.05 relative to WT littermates; #P<0.1, relative to RARβ−/−RXRγ−/− group.

instead block the transactivation caused by other agonists, are examples of "antagonists." Agents to be used in the methods of the present invention can be, but are not limited to, peptides, carbohydrates, steroids and vitamin derivatives, which may each be natural or synthetic (prepared, for example, using methods of synthetic organic and inorganic chemistry that are well-known in the art).

By agents that are "specific" for a retinoid receptor are intended agents that only bind to a particular tetinoid receptor. By agents that are "selective" for a retinoid receptor are intended agents that preferably bind to a particular retinoid receptor over others by a magnitude of approximately five-fold or greater than to other retinoid receptors, preferably eight-fold or greater, more preferably, ten-fold or greater.

Standard retinoids known in the art a RAR agonists include the the following:

Candidate RARγ agonists include, but are not limited to,

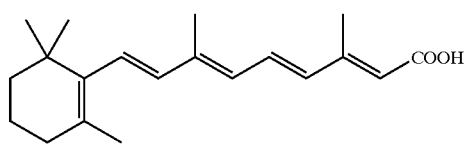

All-trans-retinoic acid

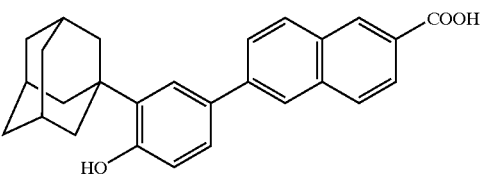

CD-437

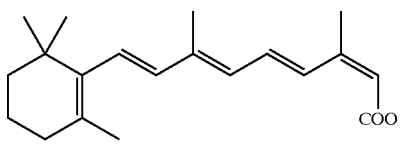

13-cis-retinoic acid (see, Schadendorf, D., et al., *Intl. J. Oncol.* 5:1325–1331 (1994)); and

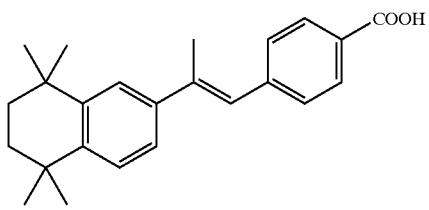

"Arotinoid"

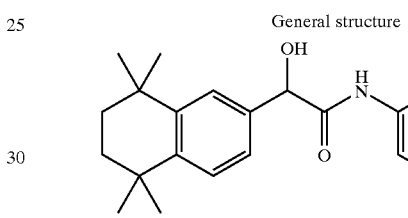

General structure

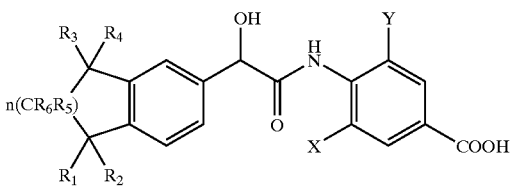

Specific example

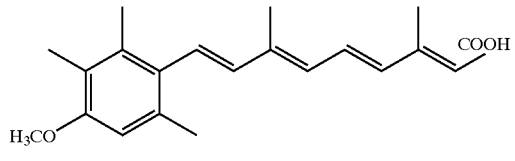

Acetretin

Candidate RARγ,β-selective agonists include, but are not limited to, (see, Swann, R. T., et al., EP 747,347).

Candidate RAR agonists include, but are not limited to,

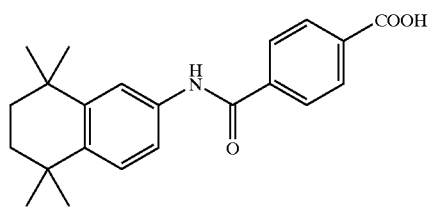

AM-80

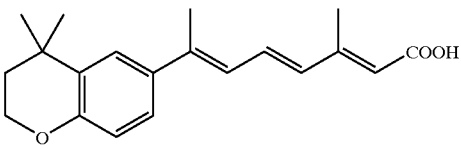

(see Takeuchi, M., et al., *Brit. J. Haematol.* 97:137–140 (1997)).

(see, Benbrook, D. M., et al., *J. Med. Chem.* 40:3567–3583 (1997));

Candidate RARβ,γ-selective agonist include, but are not limited to,

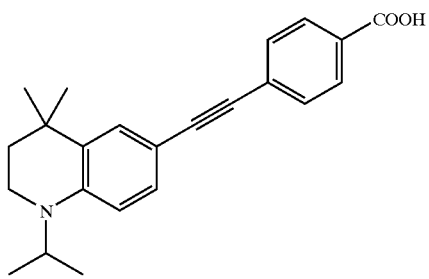

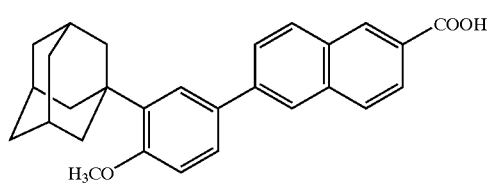

Adapalene (see, shroot, B. and Michel, S., *J. Amer. Acad. Dermatol.* 36:S96–S103 (1997)).

(see, Beard, R. L., et al., *Bioorg. Med. Chem. Lett.* 7:2372–2378 (1997)); and

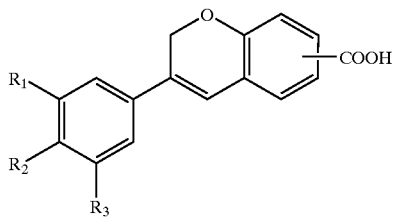

(see, Diaz, P., et al., *Bioorg. Med. Chem. Lett.* 7:2289–2294 (1997)).

Candidate RARA antagonists include, but are not limited to,

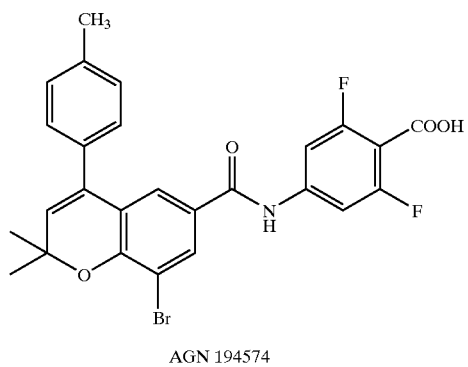

AGN 194574

(see, Teng, M., et al., *J. Med. Chem.* 40:2445–2451 (1997)).

Candidate RARα,β antagonists include, but are not limited to,

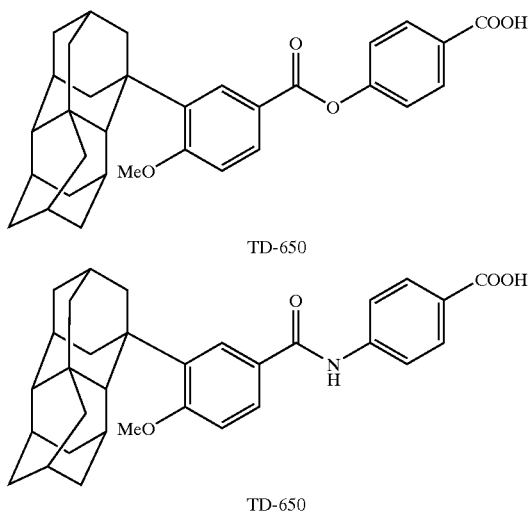

TD-650

TD-650

(see, Kaneko, S., et al., *Med. Chem. Res.* 1:220–225 (1991)).

Candidate RAR antagonists include, but are not limited to,

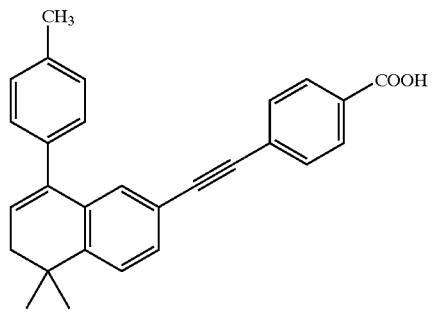

AGN 193109

(see, Agarwal, C., et al., *J. Biol. Chem.* 271:12209–12212 (1996); Johnson, A. T., et al., *J. Med. Chem.* 38:4764 (1995); Klein, E., et al., WO 97/09,297).

Further, RARα specific or selective agonists and antagonists may contain an amide group. RARγ specific or selective agonists may contain a hydroxy group. RARβ specific or selective agonists may be characterized by the absence of a hydroxy and amide groups. Moreover, it has been determined that RARβ specific agonists may be characterized by a dihydronaphthalene nucleus bearing a 2-thienyl group at C8 (see, U.S. Pat. No. 5,559,248; Johnson, A. T., et al., *J. Med. Chem.* 39:5029–5030 (1996)).

Candidate RXR antagonists include, but are not limited to,

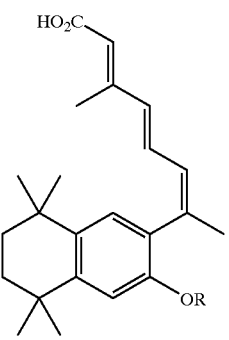

R = n-Propyl
LG100754

(see, Canan Koch, S. S., et al., *J. Med. Chem.* 39:3229–3234 (1996); and

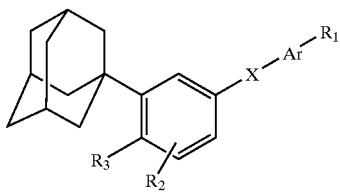

General structure

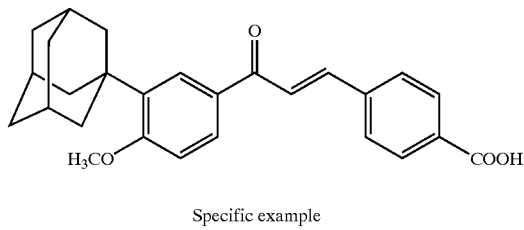

Specific example (see, Bernardon, J. M. and B. Charpentier, EP 776,881).

General RXR agonists include, but are not limited to,

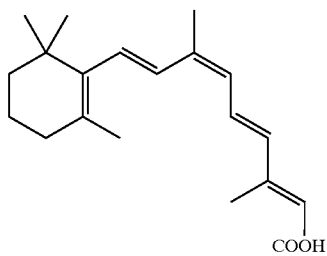

9-cis-Retinoic acid

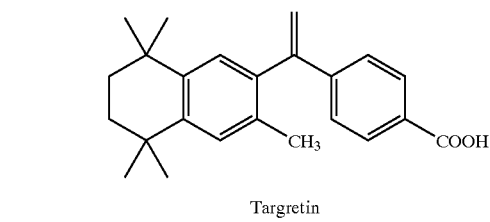

Targretin

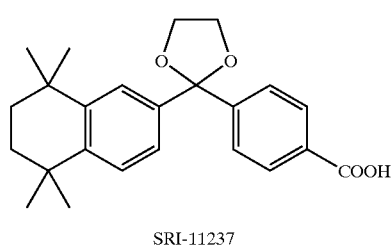

SRI-11237

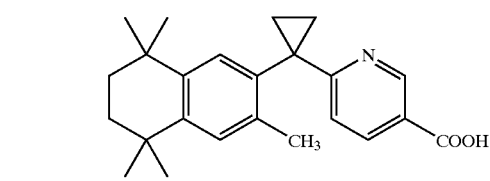

Additional candidate RXR agonists include, but are not limited to,

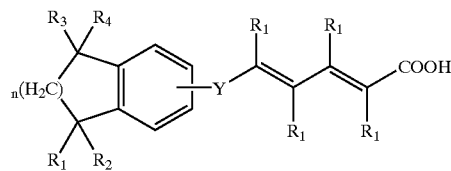

General structure

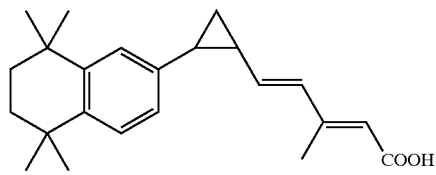

Specific example (see, Vuligonda, V. And R. A. Chandraratna, U.S. Pat. No. 5,675,033);

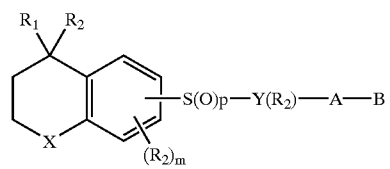

General structure

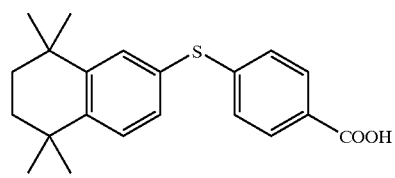

Specific example (see, Beard, R. L., et al., WO 97/16,422);

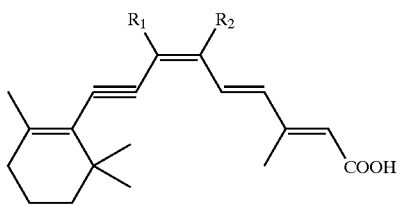

General structure

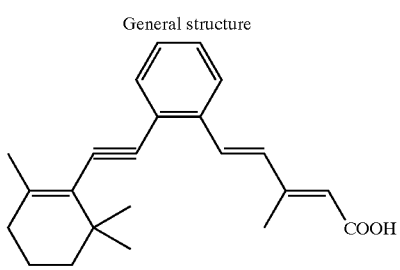

Specific example (see, Klaus, M., et al., EP 728,742);

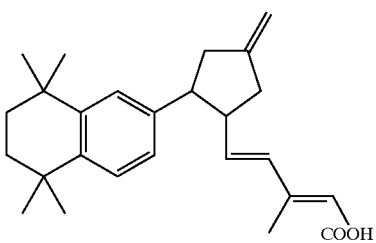

(see, Farmer, L. J., et al., *Bioorg. Med. Chem. Lett.* 7:2393–2398 (1997)); and

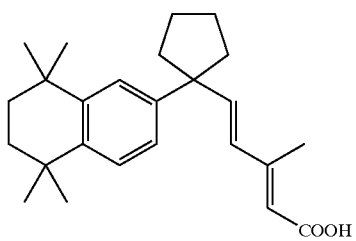

(see, Farmer, L. J., et al., *Bioorg. Med. Chem. Lett.* 7:2747–2752 (1997)).

Candidate RAR or RXR agonists include, but are not limited to,

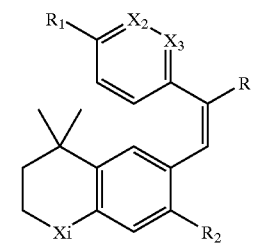

General structure

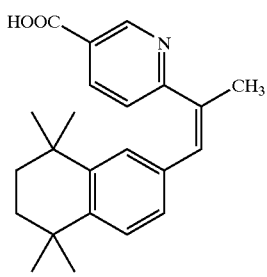

Specific example (Leblond, B., WO 97/26,237).

Other RXR agonists, with a variety of structures, are disclosed in Boehm, M. F., et al., *J. Med. Chem.* 38:3146–3155 (1995). Further, a number of retinoids of diverse structure types which are triple RAR agonists, selective RARα agonists, selective RARβ agonists, selective RARγ agonists, selective RARβ,γ agonists, selective RXR agonists and RXR/RAR pan-agonists are described in Sun, S. Y., et al., *Cancer Res.* 57:4931–4939 (1997). The invention can also be carried out with the RXR agonist LG1069, the structure and preparation of which are described in Boehm et al., *J. Med. Chem.* 37:2930–2941 (1994). Other useful RXR agonists are also described in, for example, Lehmann et al., *Science* 258:1944–1946 (1992).

Other candidate RAR and/or RXR antagonists and agonists include, but are not limited to,

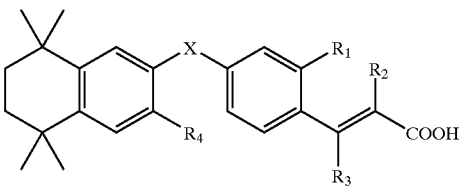

General structure

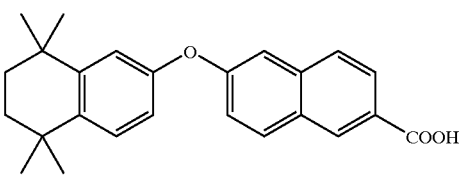

Specific example (see, Bernardon, J. M., EP 722,928);

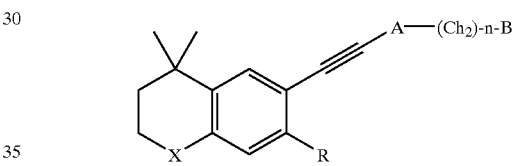

General structure

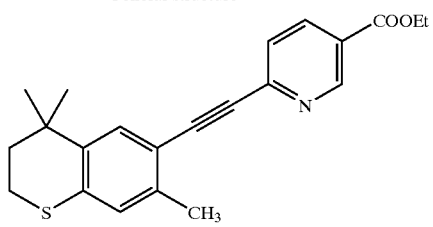

Specific example (see, Chandraratna, R., WO 96/11,686; and *Drugs of the Future* 22:249–255 (1997));

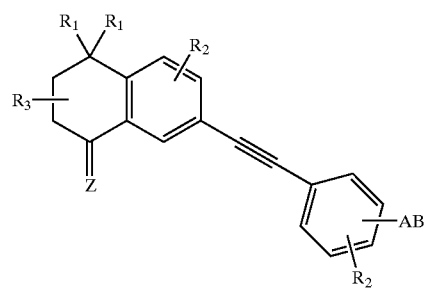

General structure

-continued

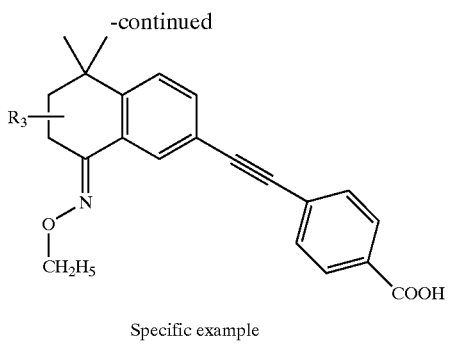

Specific example (see, Vuligonda, S., et al., U.S. Pat. No. 5,599,967);

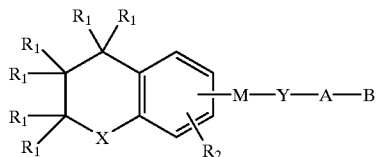

General structure

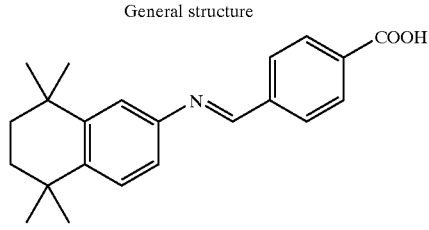

Specific example (see, Chandraratna, R. A. and M. Teng, WO 96/06,070);

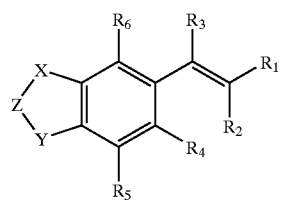

General structure

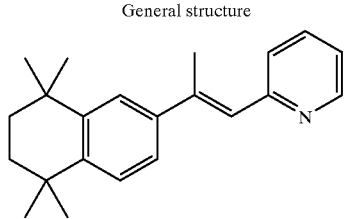

Specific example (see, Klaus, M. and E. Weis, EP 253,302);

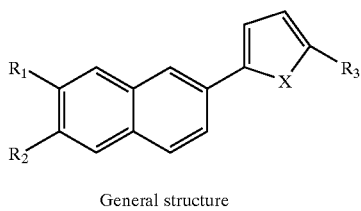

General structure

-continued

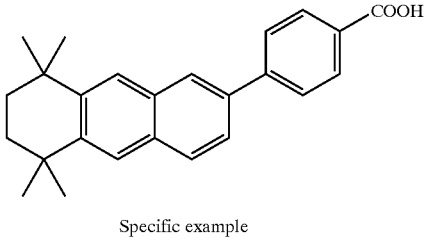

Specific example (see, Shroot, B. V., et al., EP 210,929); and

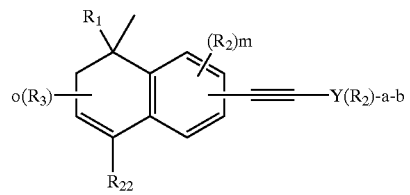

General structure

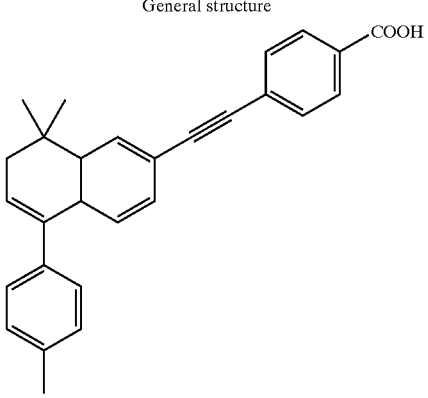

Specific example (see, Johnson, A. T., et al., U.S. Pat. No. 5,648,514).

Other RAR antagonists and RXR agonists suitable for use in the present invention may be prepared by the above-cited methods and others routine to those of ordinary skill in the art.

Screening Methods

A number of methods for screening candidate RAR and RXR agonists and antagonists are well-known in the art, and will allow one of ordinary skill to determine if a compound is useful in the present invention.

The agent can be selected and screened at random, or can be rationally selected or rationally designed using protein modeling techniques.

For random screening, agents such as, but not limited to, peptides, carbohydrates, steroids or vitamin derivatives (e.g., derivatives of retinoic acid) are selected at random and are assayed, using direct or indirect methods that are routine in the art, for their ability to bind to a retinoid receptor or a functional retinoid receptor heterodimer that is present in mice or cell lines described in the present invention. Alternatively, agents can be assayed for retinoic acid agonist or antagonist activity.

Agents may be rationally selected. As used herein, an agent is said to be "rationally selected" when the agent is chosen based on the physical structure of a known ligand of a retinoid receptor or a functional heterodimeric retinoid receptor. For example, assaying compounds possessing a retinol-like structure would be considered a rational selection since retinol-like compounds are known to bind to a variety of retinoid receptor heterodimers.

Since highly purified RAR and RXR proteins are now available, X-ray crystallography and NMR-imaging techniques can be used to identify the structure of the ligand binding site present on these proteins and, by extension, that which is specifically present on the retinoid receptors. Utilizing such information, computer modeling systems are now available that allows one to "rationally design" an agent capable of binding to such a defined structure (Hodgson, *Biotechnology* 8:1245–1247 (1990)), Hodgson, *Biotechnology* 9:609–613 (1991)).

As used herein, an agent is said to be "rationally designed" if it is selected based on a computer model of the ligand binding site of one or more retinoid receptor(s).

For example, in Chen, J.-Y. et al., *EMBO J.* 14(6): 1187–1197 (1995), three "reporter" cell lines have been used to characterize a number of RARα-, RARβ-, or RARγ-specific dissociating synthetic retinoids that selectively induce the AF-2 activation function present in the LBD of RARβ (βAF-2). These cell lines stably express chimeric proteins containing the DNA binding domain of the yeast transactivator GAL4 fused to the EF regions (which contain the LBD and AF-2 activation function) of RARα (GAL-RARα), RARβ (GAL-RARβ) or RARγ (GAL-RARγ), and a luciferase reporter gene driven by a pentamer of the GAL4 recognition sequence ("17m") in front of the β-globin promoter ((17m)5-GAL-Luc). In these cell lines, the RAR ligands thus induce luciferase activity that can be measured in the intact cells using a single-photon-counting camera. This reporter system is insensitive to endogenous receptors which cannot recognize the GAL4 binding site. Using analogous screening assays, these synthetic retinoids, like RA, have been reported to inhibit the anchorage-independent growth of oncogene-transformed 3T3 cells, while the promoter of the human interleukin-6 (IL-6) gene, whose product is involved in the regulation of hematopoiesis, immune responses and inflammation (Kishimoto, T., et al., *Science* 258:593–597 (1992)) has been shown to be induced by RA but not by the synthetic dissociating retinoids which repressed its activity.

In a similar manner, RXR agonists have been identified using cell lines that express a RXR receptor linked to a TREpal-tk reporter gene which is activated by both RAR/RXR heterodimers and RXR homodimers (Lehmann, J. M., et al., *Science* 258:1944–1946 (1992)). Thus, reporter cell lines that are easily constructed, by methods routine to one of ordinary skill, may be used to distinguish not only the specific RAR or RXR types to which a candidate ligand will bind, but also whether that binding induces an activating (i.e., agonistic) or repressive (i.e., antagonistic) effect. Although the above-referenced reporter cell lines comprised the luciferase or thymidine kinase genes as reporters, other reporters such as Neo, CAT, β-galactosidase or Green Fluorescent Protein are well known in the art and may be used in a similar fashion to carry out the present invention. For example, references disclosing reporter plasmids containing a reporter gene and expression vectors encoding a LBD of a nuclear receptor include Meyer et al., *Cell* 57:433–442 (1989); Meyer et al., *EMBO J.* 9(12):3923–3932 (1990); Tasset et al., *Cell* 62:1177–1187 (1990); Gronemeyer, H., and Laudet, V., *Protein Profile* 2:1173–1308 (1995); Webster et al., *Cell* 54:199–207 (1988); Strädle et al., *EMBO J.* 7:3389–3395 (1988); Seipel et al., *EMBO J.* 11:4961–4968 (1992); and Nagpal, S., et al., *EMBO J.* 12:2349–2360 (1993).

Other routine assays have been used to screen compounds for their agonistic or antagonistic properties on functions of other nuclear receptors, such as steroid receptors. For example, a transient expression/gel retardation system has been used to study the effects of the synthetic steroids RU486 and R5020 on glucocorticoid and progesterone receptor function (Meyer, M.-E., et al., *EMBO J.* 9: 3923–3932 (1990)). Similar assays have been used to show that tamoxifen competitively inhibits estradiol-induced ERAP 160 binding to the estrogen receptor, suggesting a mechanism for its growth-inhibitory effects in breast cancer (Halachimi, S., et al., *Science* 264:1455–1458 (1994)). Since the RAR and RXR receptors are apparently structurally similar to other nuclear receptors such as the steroid receptors (as reviewed in Chambon, P., *FASEB J.* 10:940–954 (1996)), routine assays of this type may be useful in assessing compounds for their agonistic or antagonistic activities on RAR and/or RXR receptors.

As an alternative routine method, the effect of a candidate agonist or antagonist on the binding of the ligand-dependent AF-2 modulator TIF1 to a RAR or RXR LBD can be studied using glutathione-S-transferase (GST) interaction assays by tagging the LBDs with GST as described in detail in Le Douarin et al., *EMBO J.* 14:2020–2033 (1995).

In another screening assay, transgenic animals, e.g., mice, and cell lines, that are altered in their expression of one or more of RAR and RXR receptors may be made as described previously (Krezel, W., et al., *Proc. Natl. Acad. Sci. USA* 93:9010–9014 (1996)) and may be used to identify agonists and antagonists of specific members of the RAR/RXR class of receptors using methods described previously (WO 94/26100). In such an assay, the agent which is to be tested will be incubated with one or more of the transgenic cell lines or mice or tissues derived therefrom. The level of binding of the agent is then determined, or the effect the agent has on biological effect or gene expression is monitored, by techniques that are routine to those of ordinary skill. As used herein, the term "incubate" is defined as contacting the compound or agent under investigation with the appropriate cell or tissue, or administering the agent or compound to the appropriate animal, e.g., transgenic mouse, via any one of the well-known routes of administration including enteral, intravenous, subcutaneous, and intramuscular.

Other assays may also be used to determine the agonistic or antagonistic effects of RAR and RXR ligands. For example, certain agonistic retinoids will induce the association of endogenous PML/PML-RARα fusion protein with nuclear bodies in cells from APL patients (Dyck, J. A., et al., *Cell* 76:333–343 (1994); Weis, K., et al., *Cell* 76:345–356 (1994); Koken, M. H. M., et al., *EMBO J.* 13:1073–1083 (1994)) or in related established cell lines such as NB4 (Lanotte, M., et al., *Blood* 77:1080–1086 (1991)). These effects of RAR or RXR agonists or antagonists may be determined, for example, by various immunological techniques such as immunofluorescent or immunoelectron microscopy, using antibodies specific for PML, RAR and/or PML-RARα fusion proteins. RAR or RXR agonists or antagonists may also be identified by their abilities to induce the in vitro differentiation (maturation) of certain established cell lines such as HL-60 myeloblastic leukemia cells (Nagy, L., et al., *Mol. Cell. Biol.* 15:3540–3551 (1995)), NB4 promyelocytic cells (Lanotte, M., et al., *Blood* 77:1080–1086 (1991), P19 or F9 embryonic carcinoma cells (Roy, B., et al., *Mol. Cell. Biol.* 15:6481–6487 (1995); Horn, V., et al., *FASEB J.* 10:1071–1077 (1996)), or ras-transformed 3T3 cells (Chen et al., *EMBO J.* 14:1187–1197 (1995)). Ligand-induced differentiation in these and other cell lines may be determined by assaying ligand-treated or -untreated cells for the expression of a variety of well-known markers of differentiation as generally described in the above references.

Similarly, the candidate antagonists or agonists may be screened by measuring their abilities to induce apoptosis (programmed cell death) in, for example, HL-60 cells (Nagy, L., et al., *Mol. Cell. Biol.* 15:3540–3551 (1995)) or P19 cells (Horn, V., et al., *FASEB J.* 10:1071–1077 (1996)), or in other primary cells or established cell lines. Apoptosis is typically assessed by measurement of ligand-induced DNA fragmentation, which is accomplished by methods such as gel electrophoresis (appearance of smaller molecular weight bands), microscopy (changes in plasma membrane morphology such as formation of surface protruberances ("blebbing") or in nuclear morphology such as pycnosis or fragmentation) or expression of the putative apoptosis suppressive protein BCL-2 (decreased in apoptotic cells); for general methods and discussions of these assays as they pertain to RAR and RXR biology, see Nagy, L., et al., *Mol. Cell. Biol.* 15:3540–3551 (1995); Horn, V., et al., *FASEB J.* 10:1071–1077 (1996)). Other methods for assaying ligand-induced apoptosis in primary cells and established cell lines, such as flow cytometry or particle analysis (appearance of smaller particles with different light scatter and/or DNA content profiles), are well-known in the art (Telford, W. G., et al., *J. Immunol. Meth.* 1 72:1–16 (1994); Campana, D., et al., *Cytometry* 18:68–74 (1994); Sgonc, R. and Wick, G., *Int. Arch. Allergy Immunol* 105:327–332 (1994); Fraker, P. J., et al., *Meth. Cell Biol.* 46:57–76 (1995); Sherwood, S. W., and Schimke, R. T., *Meth. Cell Biol.* 46:77–97 (1995); Carbonari, M., et al., *Cytometry* 22:161–167 (1995); Mastrangelo, A. J. and Betenbaugh, M. J., *Curr. Opin. Biotechnol.* 6:198–202 (1995)).

Screening of agonists or antagonists may be accomplished by an assay known as "in vivo footprinting" (Mueller, P. R., and Wold, B., *Science* 246:780–786 (1989); Garrity, P. A., and Wold, B. J., *Proc. Natl. Acad. Sci. USA* 89:1021–1025 (1992)), which has proven useful for analysis of RA-induced transcription of RARβ2 (Dey, A., et al., *Mol. Cell. Biol.* 14:8191–8201 (1994)).

Other methods for determining the agonistic or antagonistic activities of a candidate ligand which are routine in the art may also be used in carrying out the present invention. In performing such assays, one skilled in the art will be able to determine which RAR or RXR receptor subtype an agent binds to, what specific receptor(s) are utilized by a given compound, and whether the agent is an agonist or antagonist of the given receptor(s).

The agents screened can be, but are not limited to peptides, carbohydrates, steroids and vitamin derivatives.

Clinical Indications

A retinoid-responsive disease may be due to, but is not limited to, an aberration of a gene encoding a retinoid receptor; the aberration may be due to point mutation, deletion, insertion, inversion, frameshift, and/or translocation of a portion of a gene encoding the retinoid receptor and a portion of a second gene, wherein the expression of the second gene is not ordinarily subject to regulation by the retinoid which binds to the retinoid receptor.

Dopamine is a neuromodulator involved in the control of key physiological functions. Dopamine-dependent signal transduction is activated through the interaction with membrane receptors of the seven transmembrane domain G-proteins coupled family. Among them, dopamine D2 receptor is highly expressed in the striatum and the pituitary gland as well as by mesencephalic dopaminergic neurons. Lack of D2 receptors in mice leads to a locomotor Parkinsonian-like phenotype and to pituitary tumors. The D2 receptor promoter (SEQ ID NO:1) has characteristics of a house-keeping gene. However, the restricted expression of this gene to particular neurons and cells points to a strict regulation of its expression by cell specific transcription factors. Analysis of retinoid acid receptor-null mice shows that in these animals D2 receptor expression is reduced. It is also shown herein that the transcription of the D2R gene is induced upon treatment of pituitary cells with retinoids. In the invention, a promoter fragment which is responsible for RA-inducibility in transfected cells has been defined (SEQ ID NO:1). A functional RA-response element (RARE) is present in the D2R promoter (SEQ ID NO:1) which readily binds retinoic acid receptor/retinoid X receptor (RAR/RXR) heterodimers. Importantly, D2R transcripts are reduced in striatal tissue from certain RAR- and RXR-null mice, thus revealing a novel role for retinoids in the regulation of CNS functions.

In the invention, significant locomotor defects were found in RARβ, RXRβ and RXRγ single and compound mutants. Several of these mutants also exhibited reduction in striatal D1R and D2R transcripts compared to wild-type controls (see Examples, infra). Thus, RAR and/or RXR agonists and antagonists may be used for treating neurological diseases caused by disorders of the dopamine signaling pathway. The disorder may be due to hyperactivity or hypoactivity of the dopamine signaling pathway. Neurological diseases include, but are not limited to, schizophrenia, Parkinson's disease, anxiety, depression, drug addiction, disorders of cognition, emesis, eating disorders, pituitary tumor, attention deficit-hyperactivity disorder, Tourette's Syndrome, Huntington's disease, tardive dyskinesia, Lesch-Nyhan disease and Rett syndrome. See, Jackson, D. M., and A. Westlind-Danielsson, in: *Pharmac. Ther.* 64:291–369 (1994); Kruk, Z. L., and Pycock, C. J., Neurotransmitters and Drugs, 3d (1991); Eadie, M. J., Drug Therapy in Neurology (1992); Kozikowski, A. P., Drug Design for Neuroscience (1993). In the invention, decreased expression of the dopamine receptor (D1R, D2R, D3R, D4R or D5R) may be desired to treat, e.g., schizophrenia or substance abuse by administering a RAR or RXR antagonist. Alternatively, increased expression of the dopamine receptor (D1R, D2R, D3R, D4R or D5R) may be desired to treat, e.g., Parkinson's disease or depression by administering a RAR or RXR agonist.

Formulation and Methods of Administration

As indicated above, RAR- and RXR-selective ligands are known to elicit a wide array of cellular responses, several of which have clinical applications in treating a patient. The term "patient" as used herein is intended an animal, preferably a mammal, including a human. As used herein, "an effective amount of a RAR (or RXR) antagonist or agonist" is intended an amount effective to elicit a cellular response that is clinically significant, without excessive levels of side effects, in cells which express a RAR (or RXR) receptor.

Pharmaceutical compositions are thus provided comprising at least one RAR or RXR antagonist or agonist (such as those described above), and a pharmaceutically acceptable carrier or excipient, which may be administered orally, rectally, parenterally, intrasystemically, intravaginally, intraperitoneally, topically (as by powders, ointments, drops or transdermal patch), bucally, or as an oral or nasal spray. By "pharmaceutically acceptable carrier" is intended, but not limited to, a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as, but not limited to, preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drugs, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 $\mu$m in diameter. Suitable inert carriers include sugars such as lactose. Desirably, at least 95% by weight of the particles of the active ingredient have an effective particle size in the range of 0.01 to 10 $\mu$m.

Alternatively, the composition may be pressurized and contain a compressed gas, such as nitrogen or a liquefied gas propellant. The liquefied propellant medium and indeed the total composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye. The RAR and RXR antagonists and agonists are delivered in a pharmaceutically acceptable ophthalmic vehicle, such that the compounds are maintained in contact with the ocular surface for a sufficient time period to allow the compounds to penetrate the corneal and internal regions of the eye, for example, the anterior chamber, posterior chamber, vitreous body, aqueous humor, vitreous humor, cornea, iris/cilary, lens, choroid/retina and sclera. The pharmaceutically acceptable ophthalmic vehicle may be, for example, an ointment, vegetable oil or an encapsulating material.

Compositions for rectal or vaginal administration are preferably suppositories which can be prepared by mixing the RAR or RXR antagonist or agonist with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the RAR or RXR antagonist or agonist, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 et seq (1976)).

Dosaging

One of ordinary skill will appreciate that effective amounts of a RAR or RXR antagonist or agonist can be determined empirically and may be employed in pure form or, where such forms exist, in pharmaceutically acceptable salt, ester or prodrug form. The RAR and RXR antagonists and agonists may be administered to a patient in need thereof as pharmaceutical compositions in combination with one or more pharmaceutically acceptable excipients. It will be understood that, when administered to a human patient, the total daily usage of the compounds and compositions of the present invention will be decided by the attending physician within the scope of sound medical judgement. The specific therapeutically effective dose level for any particular patient will depend upon a variety of factors: the type and degree of the cellular response to be achieved; activity of the specific RAR or RXR antagonist or agonist employed; the specific composition employed; the age, body weight, general health, sex and diet of the patient; the time of administration, route of administration, and rate of excretion of the RAR or RXR antagonist or agonist; the duration of the treatment; drugs used in combination or coincidental with the specific RAR or RXR antagonist or agonist; and like factors well known in the medical arts. For example, it is well within the skill of the art to start doses of RAR and RXR antagonists and agonists at levels lower than those required to achieve the desired therapeutic effect and to gradually increase the dosages until the desired effect is achieved.

For example, satisfactory results are obtained by oral administration of a RAR or RXR antagonist or agonist at dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v. Dosaging of the RAR antagonist may be arranged as described in EP 0 661 259 A1, which is incorporated herein by reference in its entirety.

Dosaging may also be arranged in a patient specific manner to provide a predetermined concentration of a RAR or RXR antagonist or agonist in the blood, as determined by techniques accepted and routine in the art (HPLC is preferred). Thus patient dosaging may be adjusted to achieve regular on-going blood levels, as measured by HPLC, on the order of from 50 to 1000 ng/ml, preferably 150 to 500 ng/ml.

It will be readily apparent to one of ordinary skill in the relevant arts that other suitable modifications and adaptations to the methods and applications described herein may be made without departing from the scope of the invention or any embodiment thereof.

Transgenic Mice and Cell Lines

The present invention uses the technique of homologous recombination, as disclosed in WO 94/26100, U.S. application Ser. No. 08/580,713, filed Dec. 29, 1995, and U.S. application Ser. No. 08/914,256, filed Aug. 19, 1997 (each of which are incorporated by reference herein in its entirety), to replace two or more of the sequences encoding retinoid receptors (hereby intending a combination selected from RARα, β, γ, RXRα, β, and γ) with a sequence(s) which either prevents expression of all of the isoforms, or of a specific isoform, of retinoid receptor, or with a sequence(s) which encodes an altered form of the receptor. It has previously been demonstrated that gene replacement techniques can be used to knock out or alter the expression of the RXRα and RAR family of receptors (see WO 94/26100).

In one embodiment, the present invention provides mice and cell lines which have been altered to contain a sequence which confers a deficiency in the normal expression of two or more retinoid receptors. The mice and cell lines of the present invention can be heterozygous or homozygous for the desired trait, provided that the mice or cell lines contain the altered retinoid receptor(s) coding sequence(s). The mice and cell lines may contain a homozygous or heterozygous disruption in the endogenous gene encoding RARα, RARβ, RARγ, RXRα, RXRβ, or RXRγ, or combinations thereof, wherein the disruption comprises the insertion of a selectable marker sequence, wherein the disruption results in lack of expression of the receptor. The disruption may confer a locomotor defect phenotype or other phenotypes as described in the Examples, infra. The heterozygous mice may be used to, but not limited to, generate homozygous mice. The cell lines may be used to, but not limited to, generate heterozyous and homozyous mice.

As used herein, a mouse or cell line is said to be genetically altered to contain a sequence which conveys a deficiency in the normal expression of retinoid receptor if recombinant techniques are utilized to insert, delete, replace or otherwise disrupt sequences encoding, or directing the expression of, one or more or all isoforms of the retinoid receptor. The insertion, deletion, replacement or disruption within such sequences has the effect of altering the normal level of expression of the given sequence or altering the activity of the protein which is expressed.

Mice can be altered such that the mouse expresses a lower level of the protein when compared to a non-altered mouse. In some instances, where a mouse is altered such that a target gene is deleted or a large exogenous DNA sequence is inserted within the target sequence, the mouse will not produce detectable levels of the given receptor. However, in some instances it may be possible for extremely low quantities of the given receptor to be produced, although such product may, in itself, be inoperative or nonfunctional in its usual physiological actions.

As used herein, "wild-type" refers to an animal or cell line that has not been genetically altered.

As used herein, "normal expression" is defined as the level of expression which is present in a wild-type animal or cell line. Accordingly, as used herein a mouse or cell line is said to be "deficient in normal expression" if the mouse or cell line expresses lower levels (including the total absence thereof) of a functional retinoid receptor when compared to that which is present in a wild-type animal or cell line. A variety of techniques known in the art can be used to quantitate the level at which a given protein is expressed. These include, but are not limited to immunological techniques such as ELISA, RIA, western blot or flow cytometry/FACS, or quantitative analytical techniques such as spectroscopy or chromatographic methods including HPLC, FPLC, affinity or flame chromatography.

Alternatively the mice of the present invention can be altered so as to express an altered form of the given protein. For example, mice can be altered such that a specific mutation is introduced into a given region of a specific isoforn of RXRγ. Alternatively, mice can be altered such that the specific isoform of RXRγ is altered (for example, the sequence encoding RXRγ1 can be replaced with sequence encoding RXRγ2) and the subsequent effects observed. Such alterations may be generated in other retinoid receptors.

As used herein, a "subtype" or "isotype" of a retinoid receptor, for example, an RAR receptor, is identified by the presence of a subtype specific sequence which occurs within the A, B D and/or E regions of the receptor. All isoforms from a given organism of a specific RAR subtype, for example all isoforms of human RARα, possess a conserved sequence within one of these regions which defines the subtype.

As used herein, an "isoform" of RARα is identified by sequence heterogeneity which is present in the A region of the RARα receptor. The various isoforms of RARα (e.g., RARα1, RARα2) from a given organism will possess differing A region sequences.

The mice and cell lines of the present invention are preferably obtained by a method known in the art as homologous recombination (HR). This method has been used in lower eukaryotes (e.g., yeast), and has also been described for the mouse (for review, see Capecchi, M., *Trends Gen.* 5(3) :70–76 (1989)). For example, HR has also proven useful for the construction of mice and cell lines that are genetically altered with respect to expression of various subtypes and isoforms of RAR receptors and isoforms of RXRα (WO 94/26100). In one embodiment, the cell line is derived from a pluripotent cell line, which was deposited on May 6, 1994 with the American Type Culture Collection, which is located at 10801 University Boulevard, Manassas, Va. 20110-2209, U.S.A., having ATCC accession number CRL 11632.

HR essentially comprises isolating genomic sequences containing the target gene, employing known genetic engineering techniques to mutate or otherwise disable (i.e., "knock out") or modify the gene, and then reintroducing the gene into the relevant species. This is achieved by preparing a culture of pluripotent, or totipotent, cells, typically taken from animal embryos (embryonic stem or "ES" cells). The advantage of ES cells is that they can be successfully cultured for a large number of generations under conditions in which they will not differentiate, allowing the introduction of exogenous DNA into somatic and/or germline cells of embryonic animals. Following introduction of the foreign DNA, the ES cells are removed from their differentiation block and then can be reintroduced into recipient embryos, where they differentiate into mature somatic or germline cells carrying the exogenous DNA (or "transgene").

A variety of methods may be used to introduce foreign DNA into recipient cells, including calcium phosphate precipitation, microinjection, lipofection, viral transduction or electroporation. In carrying out the present invention, the technique of electroporation is typically used to render the ES cells capable of taking up exogenous DNA. The modified gene is then introduced, in a suitable manner, to these cells. Once taken up, the exogenous DNA is often incorporated into the genome of the recipient cells via non-homologous recombination (random integration), although incorporation may alternatively proceed by homologous recombination.

To select cells in which a recombination event has taken place, a selectable marker sequence, many of which are well-known in the art, may be used. For example, the use of the bacterial Neo gene to confer resistance to neomycin, or an analogue thereof such as G418, is routine. The marker gene may be inserted in the gene to be modified, thereby disabling the target gene, while providing a positive selectable marker. Clones which are Neo$^+$ (i.e., which are resistant to neomycin and therefore capable of growth in neomycin- or G418-containing media) have integrated the vector by homologous or non-homologous recombination.

To select for homologous recombinants, the ends of the modified gene may have other markers inserted, such as the Herpes Simplex Virus thymidine kinase (HSVTK) gene. In a HR event, only those sequences homologous to the target gene will be recombined; thus, the HSVTK genes will not be recombined, and the marker will not be transferred into the target sequence. Therefore, the desired homologous recombinant will be resistant to, for example, ganciclovir, which is converted into a toxic metabolite when the HSVTK gene product is present (as would occur following a non-homologous recombination event).

Correct clones may be identified by the techniques of PCR or by genomic Southern blotting, which are routine to those of ordinary skill in the art. When a suitable clone has been identified, the ES cells may be injected into early-stage embryos (blastocysts) and reintroduced into a pseudopregnant female. Chimeric animals will generally result from at least some of these reimplanted embryos, their tissues deriving in part from the selected clone. In these animals, in addition to the somatic cells the germline cells (spermatozoa or ova) may also be chimeric, containing the modified gene. Progeny deriving from such germ cells will be heterozygous for the gene or will be wild type, following the expected Mendelian inheritance frequencies.

The heterozygous progeny can be cross-bred to yield homozygous animals, which should occur with predicted Mendelian inheritance. Confirmation of the allelic structure of the mice (i.e., heterozygous, homozygous or wild type) can be ascertained by a variety of routine methods (e.g., Southern blotting).

The mice and cell lines of the present invention may also be deficient in the expression of other genes, and thus provide the opportunity to study the interactions of a retinoid receptor protein with other proteins, or the effects these proteins have on retinoid-dependent gene expression. For example, in addition to animals deficient in RARβ, the present invention provides mice that are further deficient in one or more additional RXR subtypes. To this end, an RARβ mutation can be introduced onto RXRβ and/or RXRγ mutant genetic backgrounds. Furthermore, using these same methods animals or cell lines may be created which comprise combinations of mutations affecting RARβ together with mutations of either another retinoid receptor subtype, thyroid hormone receptor α or thyroid hormone receptor β. These latter combinations may be of particular interest since these genes are co-expressed with RXRγ in a number of tissues (Dollé, P., et al., Mech. Dev. 45:91–104 (1994); Bradley, D. J., et al., Proc. Natl. Acad Sci. USA 86:7250–7254 (1989)).

The present invention also envisages cell lines suitable for generating mice of the invention, and techniques for generating such lines and mice.

Thus, to obtain mice according to the present invention, one skilled in the art can use the strategy of homologous recombination (HR) in embryonic stem cells (ES cells) to replace the wild-type sequences encoding two or more retinoid receptors with an altered sequence.

The absence of retinoid receptors in a cell line or animal allows one skilled in the art to screen for genes and agents which can restore the altered mice to a wild-type phenotype, as well as to screen for agents which act as agonists or antagonists of retinoid receptors, using methods described for similar studies of the RAR family of receptors and for RXRβ (WO 94/26100).

The mice and cell lines of the present invention allow the investigation, at the cellular level as well as at the in vivo level, of a system which lacks one or more specific retinoid receptors. This capability will allow the establishment of the importance of each retinoid receptor, and its various isoforms, in animal development and physiology.

Thus, it will be appreciated that there are many uses to which the mice and cell lines of the present invention may be put. They are particularly useful in studying any aspect of retinoic acid mediated gene expression and tissue specific expression of various retinoid receptors. In addition, the mice and cell lines of the present invention may be used to identify agonists and antagonists of specific members of the RAR/RXR class of receptors using methods described previously (WO 94/26100).

To assay an agent for its possible agonistic or antagonistic activity, in general the agent which is to be tested will be incubated with one or more of the cell lines or mice of the present invention or tissues derived therefrom. The level of binding of the agent is then determined, or the effect the agent has on development or gene expression is monitored, by techniques that are routine to those of ordinary skill.

As used herein, the term "incubate" is defined as contacting the compound or agent under investigation with the appropriate cell or tissue of the invention, or administering the agent or compound to the appropriate mouse of the invention via any one of the well-known routes of administration including enteral, intravenous, subcutaneous, and intramuscular.

For example, the cell lines and transgenic animals, e.g., mice, of the present invention, or tissues derived therefrom, can be used in an assay system comprising the steps of: (a) incubating an agent with one or more of the cell lines or mice of the present invention, or cells or tissues derived therefrom; (b) determining whether the agent binds to the cells, tissues, or mice, or determining the effects the agent has on pathologies linked to dysfunction of dopaminergic systems exhibited by the transgenic animals or gene expression; and (c) comparing the binding of the agent to, or the effects of the agent on, the cells, tissues or transgenic animals of the present invention to the binding of the agent to, and/or effects of the agent on, cells, tissues or transgenic animals that express normal levels of a functional retinoid receptor. In a particular example, the effects of the agent on locomotor defects exhibited by the transgenic animals, e.g., mice, are determined. In another particular example, the effects of the agent on D2R gene expression are determined.

In performing such an assay, one skilled in the art will be able to determine which retinoid receptor an agent binds to, and hence determine what specific receptor(s) are utilized by a given compound. Additionally, one can determine in which tissues a given retinoid receptor is active.

In one aspect of the above-described assay, the cell line or mouse, in addition to being altered in the expression of two or more retinoid receptors, is altered such that it contains a marker sequence such as luciferase, beta galactosidase, green fluorescent protein or chloramphenicol acyltransferase, operably linked to a response element (RARE or RXRE). The agent which is to be tested is incubated with the altered cell or mouse, or tissues derived therefrom, and the expression of the reporter sequence is assayed. In this fashion, agents can be identified which are capable of either stimulating or inhibiting the expression of a DNA sequence which is controlled by a specific RARE or RXRE.

As described herein, by "a" or "an" is intended one or more.

The following Examples serve only to illustrate the invention, and are not to be construed as in any way limiting on the invention.

EXAMPLE 1

Figure 1B:
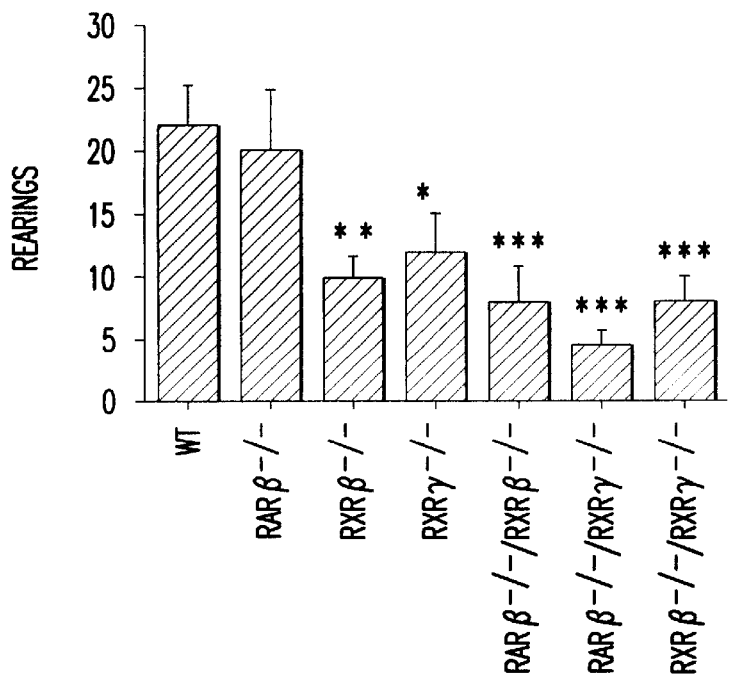
Figure 1C:
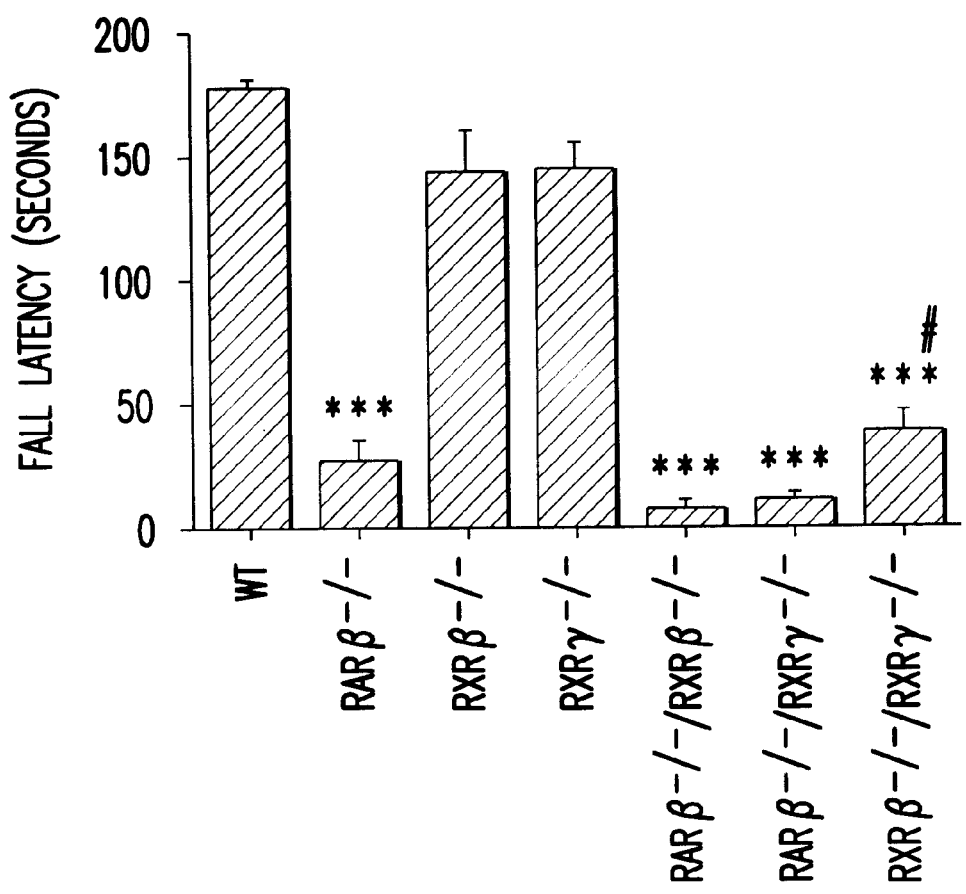
Figures 3A, 3B, 3C, 3D:
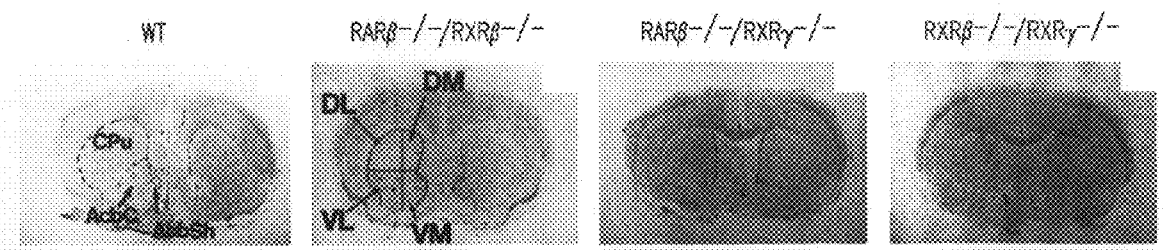
FIG. 3. Analysis of D1R, D2R and enkephalin expression in wild-type and mutant brains. The views of selected section planes are presented for histological identification (FIGS. 3A–3D). In situ hybridization (ISH) using antisense RNA probes corresponding to D1R (FIGS. 3E–3H), D2R (FIGS. 3I–3L) and Enk (FIGS. 3Q–3T) were carried out as described (Cryostat sections (7 μm) were prepared on gelatin-coated slides. The antisense RNA probes were prepared using T3 (D2R) and Sp6 (D1R) polymerases and α-$^{35}$S-labeled CTP (Amersham). The D1R and D2R probes were synthesized from 384 bp (linearized by Bsu36I) and 1680 bp long (linearized by EcoRI) mouse cDNA templates, respectively. Hybridization conditions and preparation of probes for retinoid receptors were as described (Dollé, P., et al., Development 110:1133 (1990)). All slides were exposed to Kodak NTB-2 autoradiography emulsion for 2 weeks, with wild type (WT) and RARβ−/−/RXRβ−/−, RARβ−/−/RXRγ−/− and RXRβ−/−/RXRγ−/− mutant sections. In situ binding (ISB) of the D2R specific antagonist I$^{125}$-Sulpride (FIGS. 3M–3P) was performed as described (Baik, J. H., et al., Nature 377:424 (1995)). Each experiment was performed with at least three animals with similar results. The expression pattern of RARβ, RARγ, RXRβ and RXRγ transcripts in the striatum of WT mice is shown as indicated (FIGS. 3U–3X). Sense probes did not give any signal in any of these experiments. Note that although the RXRβ transcript signal in panel W was very weak, the RXRβ protein was readily immunohistochemically detected in the whole striatum (Dollé, P., et al., Mech. Dev. 45:91 (1994)). CPu, caudate-putamen; AcbC, core of the nucleus accumbens; AcbSh, shell of the nucleus accumbens; DL, dorsolateral striatum; DM, dorsomedial striatum; VL, ventrolateral striatum; VD, ventrodorsal striatum.
Figures 3E, 3F, 3G, 3H:
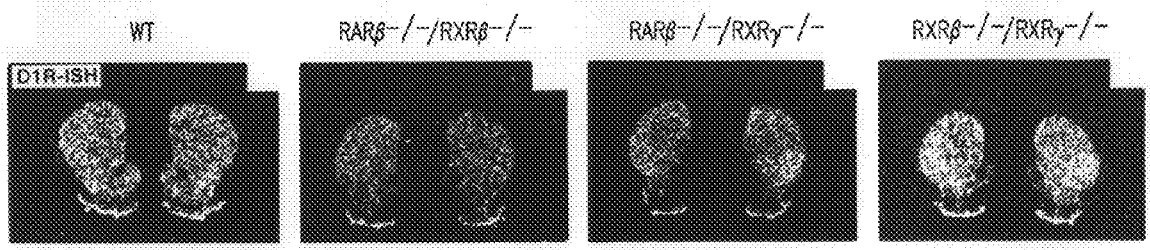
Figures 3I, 3J, 3K, 3L:
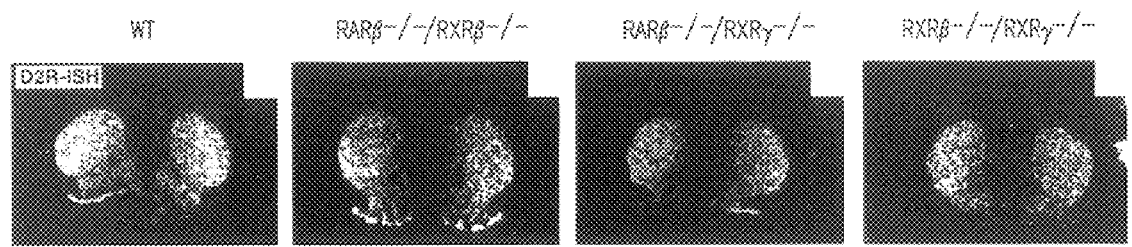
Figures 3M, 3N, 3O, 3P:
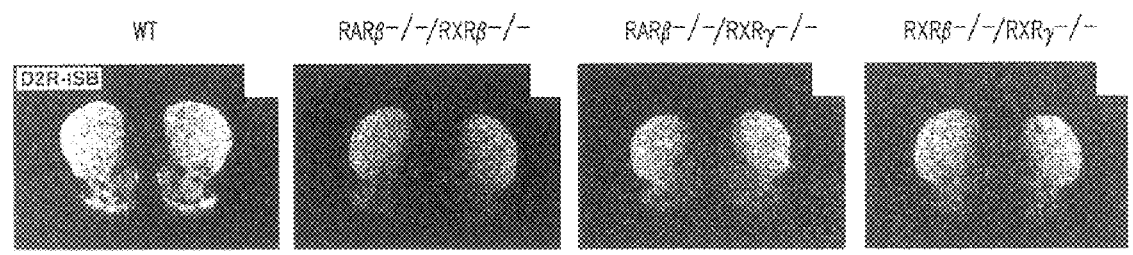
Figures 3Q, 3R, 3S, 3T:
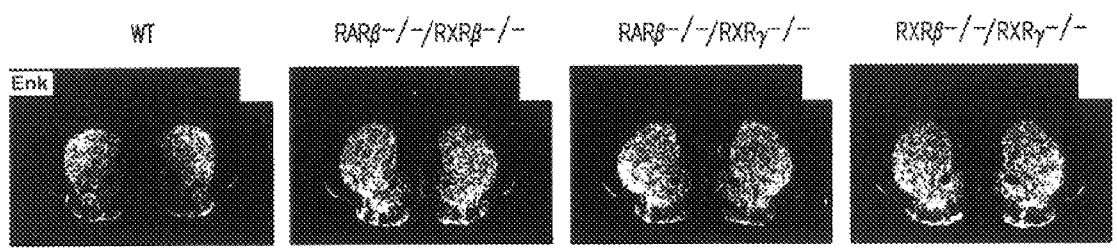
Figures 3U, 3V, 3W, 3X:
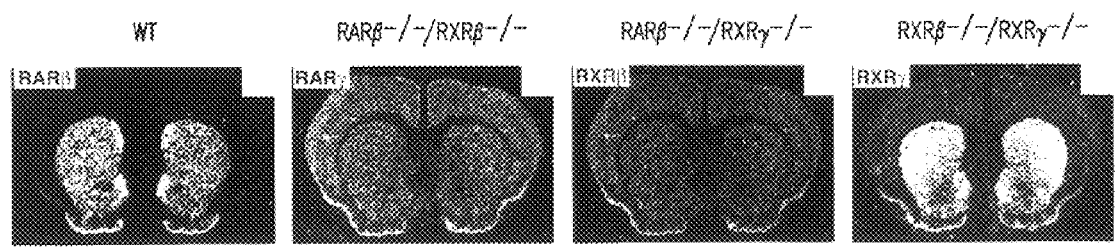

Retinoid Receptor Mutant Mice Exhibit Impaired Locomotion and Dopamine Signaling Results The retinoic acid (RA) signal is transduced by two nuclear receptor families, the RARs (α, β, γ) and the RXRs (α, β, γ), which function as RAR/RXR heterodimers and play important roles during mouse development and post-natal life (Chambon, P., FASEB. J. 10:940 (1996); Mangelsdorf, D. J. and Evans, R. M, Cell 83:841 (1995); Kastner, P., et al., Cell 83:859 (1995); Kastner, P., et al., Development 1124:313 (1997); Ghyselinck, N. B., et al., Int. J. Dev. Biol. 41:425 (1997)); and references cited therein). The high levels of expression of retinoid receptors in the brain and spinal cord (Dollé, P., et al., Mech. Dev. 45:91 (1994)), together with the RA responsiveness of various neurotransmitter pathways in vitro (Farooqui, S. M., Life. Sci. 55:1886 (994); Pedersen, W. A., et al., J. Neurochem. 65:50 (1995)), suggest that retinoid signaling might be involved in the regulation of neural functions. The locomotor skills of knockout mice for RARβ, RARγ, RXRβ and RXRγ, which are all expressed in the striatum (Dollé, P., et al., Mech. Dev. 45:91 (1994); see also FIG. 3U-3X), were analyzed using open field and rotarod behavioral tests. The open field test revealed that RARβ/RXRβ, RARβ/RXRγ, RXRβ/RXRγ double null mutants, but not the corresponding single mutants, exhibited statistically significant reductions in forward locomotion when compared to WT littermates (FIG. 1A). Furthermore, 40% of RARβ/RXRβ null mutants also showed backwards locomotion. The frequency of rearings was significantly diminished in all double null mutants, as well as in RXRβ$^{-/-}$ and RXRγ$^{-/-}$ single mutants (FIG. 1B). When the rotarod test was used to measure motor coordination, the fall latency was highly increased in RARβ, RARβ/RXRβ and RARβ/RXRγ null mutants (FIG. 1C), as most of these mutants fell shortly after the beginning of the rotation. Interestingly, the performance of RXRβ/RXRγ mutants, in spite of their normal RARβ gene expression, was also impaired. In contrast, RARα and RARγ null mice, as well as RARα/RXRγ or RARγ/RXRγ double null mutants did not show any defects in these locomotor tests, even though both RARα and RARγ transcripts were expressed in the striatum (FIG. 3V).

Thus, RARβ, RXRβ and RXRγ appear to be involved specifically in the control of locomotor behaviors, although to different extent. The observation that the defects exhibited by RARβ/RXRβ, RARβ/RXRγ and RXRβ/RXRγ double mutants were similar, suggests that: (i) heterodimers (Chambon, P., *FASEB. J.* 10:940 (1996); Mangelsdorf, D. J., and Evans, R. M, *Cell* 83:841 (1995); Kastner, P., et al, *Cell* 83:859 (1995)) of RARβ with either RXRβ or RXRγ are the functional receptor units involved in control of locomotion; and (ii) RXRβ and RXRγ are functionally redundant. Note that the above locomotor defects reveal a physiological function for RXRγ, as no obvious developmental nor post-natal abnormalities could be ascribed to its knockout in single and compound mutants (Kastner, P., et al., *Development* 124:313 (1997); Krezel, W., et al., *Proc. Natl. Acad. Sci. USA* 93:9010 (1990)).

RARβ, RXRβ and RXRγ are expressed in skeletal muscles, peripheral nervous system (PNS) and central nervous system (CNS) (Dollé, P., et al., *Mech. Dev.* 45:91 (1994); Ruberte, E., et al., *Development* 118:267 (1993)). Thus, defects in these structures could be at the origin of locomotor defects. The morphology and histology of skeletal muscles of all double null mutants appeared normal and no abnormalities were detected in the post-natal development of fast- and slow-twitch muscle fibers. The PNS of these mutants appeared anatomically normal during development (10.5 day post-coitum [dpc] embryos stained with an anti-neurofilament antibody) and postnatal life (morphological observations of sciatic and facial nerves in aged animals). Furthermore, muscle and PNS functions of RARβ, RXRβ, RXRγ single and double mutants were indistinguishable from those of WT littermates with respect to compound muscle action potentials, motor unit number and absence of spontaneous activity in the gastrocnemius muscle. In addition, all of these mutant animals had normal balance reflexes and no gross anatomical nor histological abnormalities could be detected in their spinal cords. Thus, the muscle or PNS deficiencies are unlikely to account for the locomotor impairment, which may instead reflect a CNS dysfunction.

Figure 2A:
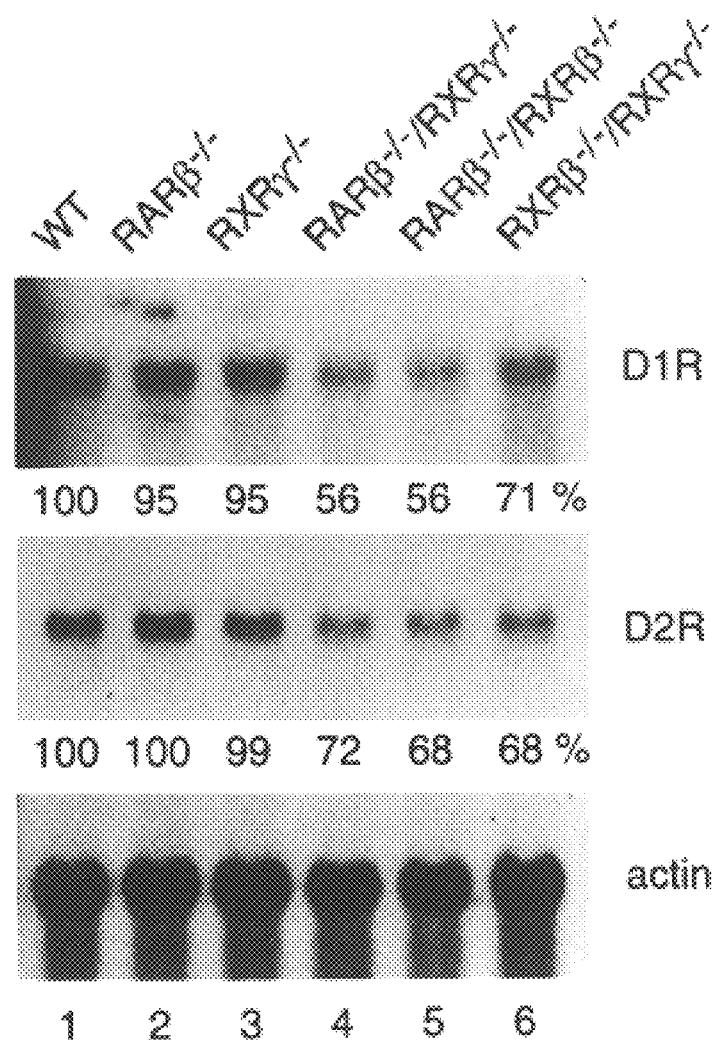
FIG. 2A. For Northern blot analysis, 20 mg of whole-striatal RNA was electrophoresed, transferred and hybridized to D1R and D2R full-length cDNA probes as described (Ausubel, F.M., et al., Current Protocols in Molecular Biology (Wiley, New York, 1987)). A β-actin probe was used to correct for variations in RNA content of the loaded samples. Transcript levels were quantified by phosphoimager (Fuji). After correction for variation in p-actin transcript levels, D1R and D2R transcript levels in RARβ−/−, RXRγ−/−, RARβ−/−/RXRβ−/−, RARβ−/−/RXRγ−/− and RXRβ−/− mutants (lanes 2–6) were expressed relative to WT mice (lane 1). The values given below the lanes represent the mean of at least three independent experiments which did not differ by more than 10%.

Dopamine signaling, which is predominantly mediated by D1 and D2 dopamine receptors (D1R and D2R) in the striatum, is involved in the control of motor planning (voluntary movements) (Jackson, D. M., and Westlind-Danielsson, A., *Pharmacol. Ther.* 64:291 (1994); Xu, M., et al., *Cell* 79:945 (1994); Nestler, E., *Cell* 79:923 (1994); Baik, J. H., et al., *Nature* 377:424 (1995)). The strong striatal expression of RARβ and RXRγ (Dollé, P., et al., *Mech. Dev.* 45:91 (1994); FIG. 3, U and X), the similarity between the present locomotor defects and those of D2R knockout mice (Baik, J. H., et al., *Nature* 377:424 (1995)), and the responsiveness of D2R to RA in cultured cells (Farooqui, S. M., *Life. Sci.* 55:1886 (1994); Samad, A., et al., *Proc. Natl. Acad. Sci. USA* 94:14349–14354(1997)), prompted us to analyze the expression of D1 R and D2R (the most abundant dopamine receptors in the striatum) in our mutants. RARβ/RXRP, RARβ/RXRγ and RXRβ/RXRγ double null mutants, but not RARβ or RXRγ single mutants reproducibly exhibited 40% and 30% reduction in whole-striatal D1R and D2R transcripts, respectively, when compared to WT controls (FIG. 2A). This reduction of D1R and D2R transcripts and receptor proteins was particularly marked in the medioventral regions of the striatum, including the shell and the core of the nucleus accumbens, and the mediodorsal part of the caudate putamen (FIG. 3, E–P).

Figure 2B:
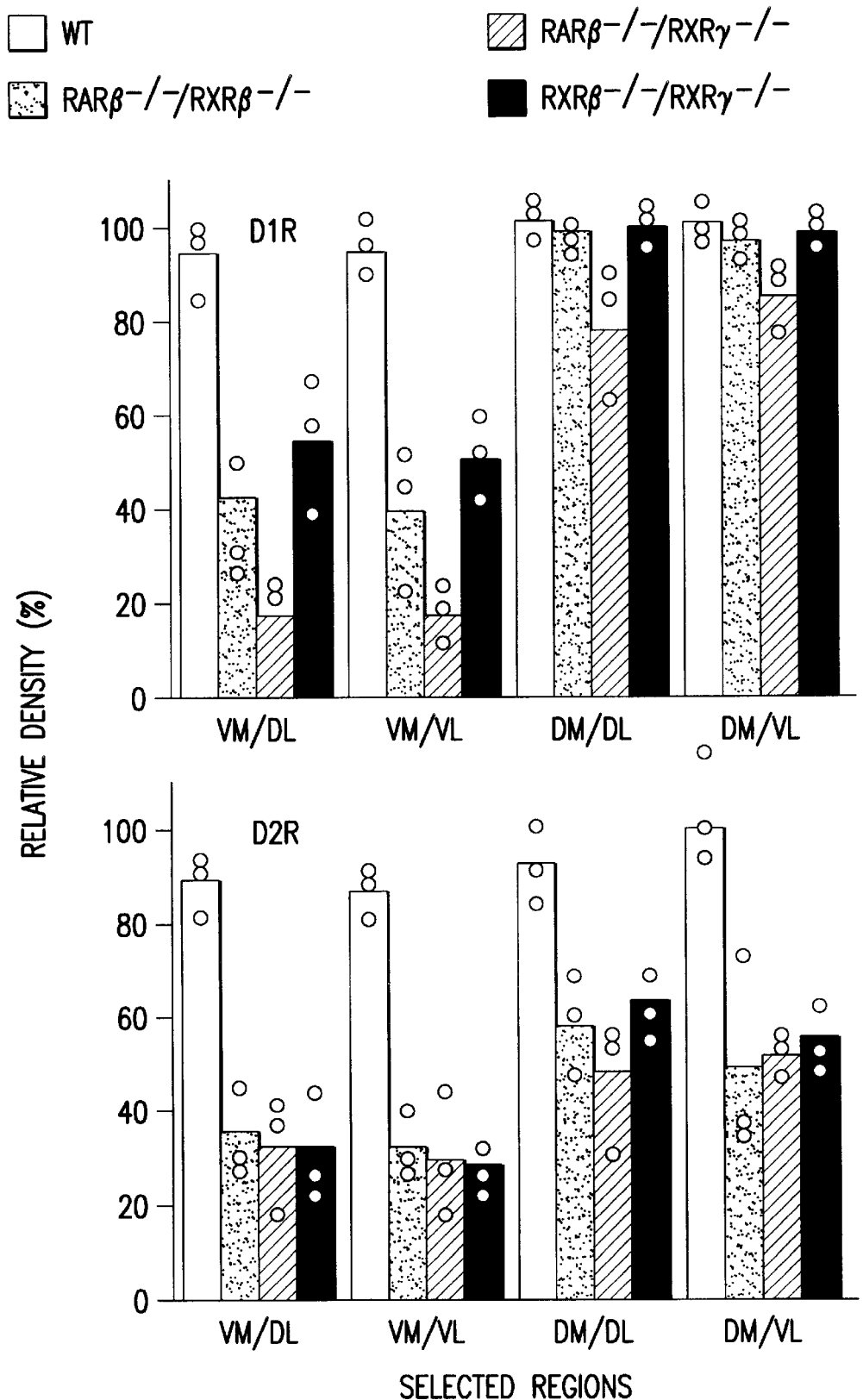
FIG. 2B. Regional changes in D1R and D2R transcript expression (as revealed by in situ hybridization) were quantified densitometrically in selected striatal regions (see FIG. 3B). Data represent the ratios between the signal intensities measured in the different areas in individual WT and mutant animals, as indicated. In each case, the vertical bars correspond to mean values obtained from three animals, each animal being represented by a dot. VM/DL, VM/VL, DM/DL and DM/VL, ratios of signal intensities in the various areas as defined in FIG. 3B; for each animal the area exhibiting the strongest signal intensity was taken as 100%.

In contrast, expression of these receptors persisted, with no significant variations in ventrolateral and dorsolateral striatal regions (compare FIG. 3E to FIGS. 3F–3H, FIG. 3I to FIGS. 3J–3L and FIG. 3M to FIGS. 3N–3P). The reduction of D1R and D2R transcripts in the ventromedial vs ventrolateral striatal region in each animal ranged from 50 to 80% depending on the type of tested double mutants (FIG. 2B). To investigate whether the reduction of dopaminergic receptor expression could reflect the absence of the cells expressing them, expression of enkephalin, a known marker of D2R-containing neurons, was tested. The expected increase (Baik, J. H., et al., *Nature* 377:424 (1995)) in enkephalin expression was observed in the nucleus accumbens region where D2R expression was reduced (FIGS. 3Q–3T), thus indicating that the neurons which normally express the D2R were present. Furthermore, the histology of the mutant striata appeared normal (FIGS. 3A–3D) and no increase in apoptosis could be detected. Thus, the reduced levels of D1R and D2R transcripts appear to result from an altered control of their expression, and the lack of retinoid receptors does not seem to affect the development of striatal neurons. The characterization of a putative RA response element (RARE) in the D2R promoter (Samad, A., et al., *Proc. Natl. Acad. Sci. USA* 94:14349–14354 (1997)) suggests that its expression could be altered at the transcriptional level. Moreover, the simultaneous reduction of both D1R and D2R transcripts in the same brain area indicates that the expression of these two genes could be, at least partially, similarly controlled.

The ventral striatum belongs to the mesolimbic dopaminergic system, whose neurons project from the ventral tegmental area to the nucleus accumbens and the olfactory tubercule. Dysfunction of dopamine signaling in the ventral striatum, induced by lesions or infusions of D2 receptor antagonists, reduces motor activity in rats and delays the initiation of the execution of some stereotyped behaviors (Koob, G. F., et al.,*J. Comp. Physiol. Psychol.* 5:917 (1978); Everitt, B. J.,*Neurosci. Behav. Rev.* 14:217 (1990); Robbins, T. W. and Everitt, B. J., *Sem. Neurosci.* 4:119 (1992)). Thus, the reduction of D1R and D2R expression in this area could generate the behavioral abnormalities observed in the retinoid receptor mutants. On the other hand, it is unlikely that these abnormalities could be due to reduced dopamine levels because: i) with the exception of RXRβ transcripts, the present retinoid receptors are not expressed in the mesencephalic regions (substantia nigra and ventral tegmental area) where dopaminergic neurons arise (Dollé, P., et al., *Mech. Dev.* 45:91 (1994); ii) the expression of tyrosine hydroxylase (the limiting enzyme in catecholamine synthesis) is apparently not altered in these areas; and iii) the expression of D2R, which in these regions controls dopamine release, is also not affected.

Figure 4A:
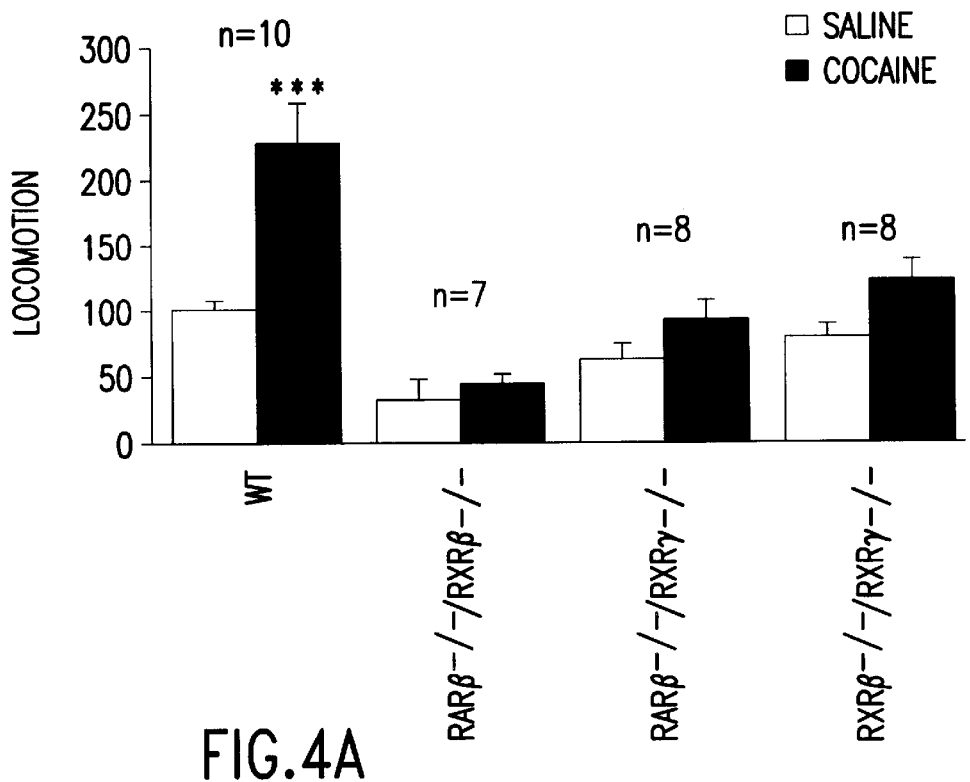
FIG. 4. Effects of cocaine on motor behavior of RARβ−/−RXRβ−/−, RARβ−/−/RXRγ−/− and RXRβ−/−RXRγ−/− mice. The locomotion (FIG. 4A, number of squares crossed) and rearing behaviors (FIG. 4B) of wild-type and double mutant males treated with saline or cocaine were examined in the open field test (For cocaine-induced behavior analysis, animals of each genotype were divided into two groups treated with intraperitoneal injection of either cocaine (20 mg/kg), or an equivalent volume of saline. The open field test was carried out for 5 min, 25 min. after the injection. Locomotion and stereotyped behaviors were scored as above. Each animal was tested only once (n, corresponds to the number of animals in each group). Data were analyzed in two-way analyses of variance (ANOVA) with Brown-Forsythe correction, since the variances were not equal ($F_{locomotion}[3,26]=6.47$, P<0.005; $F_{rearings}[3,29]=7.85$, P<0.001). The effects of the cocaine treatments were then compared in post hoc analysis using Bonferroni multiple t test with alpha adjusted for 16 comparisons (i.e., 4 comparisons of saline and cocaine treated groups within each genotype; 6 comparisons between each saline treated and 6 comparisons between each cocaine treated group (BMDP; Dixon, W. J., in DMDP statistical software manual (Berkeley: University of California Press, 1988));***P<0.001 relative to saline treated animals of the same genotype.
Figure 4B:
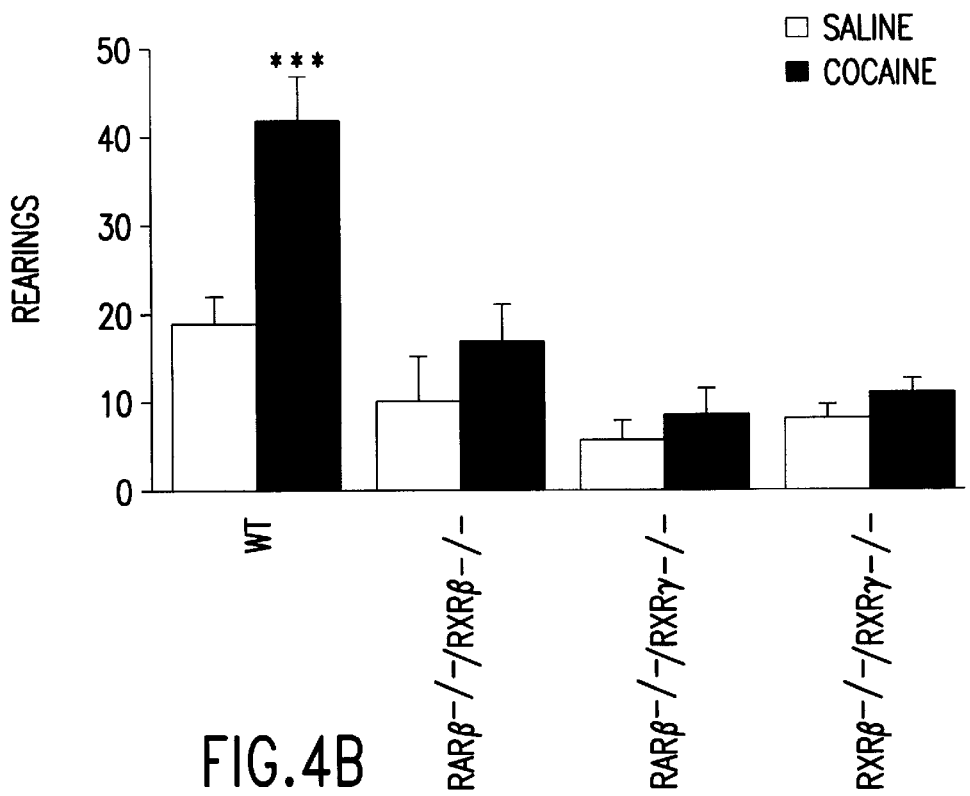

Cocaine-induced hyperlocomotor activity was used to assess the dopaminergic pathway integrity in the mesolimbic system (Xu, M., et al., *Cell* 79:945 (1994); Nestler, E., *Cell* 79:923 (1994); Giros, B., et al., *Nature* 379:606 (1996)). Cocaine interferes with the dopamine signaling through its binding to the dopamine transporter (Callahan, P. M., et al., *Psychopharmacol.* (Berl.) 103:50 (1991)). In the presence of cocaine, the uptake of released dopamine is blocked. This leads to increased dopamine concentration in synapses, which results in hyperlocomotion (Giros, B., et al., *Nature* 379:606 (1996)). No statistically significant cocaine-mediated increase of locomotion or rearings was observed in the RARβ/RXRβ, RARβ/RXRγ and RARβ/RXRγ null mutants, when compared to the corresponding saline treated animals (FIGS. 4A and 4B). Thus, these mutants exhibit a lack of cocaine locomotor-activating effects similar to those found in D1R-null mice (Xu, M., et al., *Cell* 79:945 (1994); Nestler, E., *Cell* 79:923 (1994)). In view of the existing synergism between D1R and D2R in these effects (Xu, M., et al., *Cell* 79:945 (1994); Nestler, E., *Cell* 79:923 (1994)), the concomitant decrease of these receptors in the ventromedial area of the striatum may lead to a phenotype that resembles that of D1R-null mice.

Taken together, the decrease of D1R and D2R expression in the ventral striatum of RARβ/RXRβ, RARβ/RXRγ and RXRβ/RXRγ null mutants and the impaired response of these mutants to cocaine, provide strong evidence that retinoids are involved in controlling the function of the dopaminergic mesolimbic pathway. The reduction of D1R and D2R expression occurred preferentially in the ventral striatum, indicating that additional factors are involved in the control of D1R and D2R expression in the dorsal striatum, as RARβ, RXRβ and RXRγ are expressed in entire caudate-putamen and nucleus accumbens structures (Dollé, P., et al., *Mech. Dev.* 45:91 (1994); see also legend to FIG. 3, U–X). It should also be noted that some locomotor defects in RARβ/RXRβ null mutants (backwards locomotion) were more severe than expected from the level of reduction in D1R and D2R transcripts, when compared with RARβ/RXRγ null mice. Thus, besides D1R and D2R, additional dopamine receptor(s) (e.g., D3R, Jackson, D. M., and Westlind-Danielsson, A., *Pharmacol. Ther.* 64:291 (1994)) and neurotransmitter pathways might also be affected in the retinoid receptor mutants.

The present findings, together with the localization of a RA synthesizing enzyme in mesostriatal dopaminergic neurons (McCaffery, P. and Drager, U. C., *Proc. Natl. Acad. Sci. USA* 91:7772 (1994)), raise the possibility that altered vitamin A signaling could be implicated in the etiology of pathologies (for example, Parkinson's disease and schizophrenia), which have been linked to dysfunction of dopaminergic systems. Moreover, the orphan nuclear receptor Nurr1, a putative heterodimerization partner of RXRs, appears to be required for the formation of dopamine-producing neurons (Xetterstrom, R. H., et al., *Science* 276:248(1997)). As retinoid receptors are broadly distributed in the CNS (Dollé, P., et al., *Mech. Dev.* 45:9 (1994)), additional brain functions might be modulated by retinoid signaling. Because many RXR/RAR double mutants exhibit highly -a pleiotropic defects and die in utero or at birth (Kastner, P., et al., *Cell* 83:859 (1995); Kastner, P., et al., *Development* 124:313 (1997)), spatio-temporally controlled somaticmutations in the CNS (Tsien, J. X., et al., *Cell* 87:1317 (1996); Feil, R., et al., *Proc. Natl. Acad. Sci. USA* 93:10887 (1996)) are required to further investigate the functions of retinoid signaling in the brain.

Materials and Methods

Behavioral tests. RARβ, RXRβ, RXRγ mutant mice (original 129/SVxC57/B6 genetic background with several subsequent back-crosses with 129/SV -animals) were generated as described (Ghyselinck, N. B., et al., *Int. J. Dev. Biol.* 41:425–447 (1997); Krezel, W., et al., *Proc. Natl. Acad. Sci. USA* 93:9010–9014 (1996); and Kastner, P., et al., *Genes. Dev.* 10.80–92 (1996) In the RXRγ mutant mice, exons 3 and 4 encoding for the DNA binding domain are replaced. In the RXRβ mutant mice, the DNA binding domain (3' region of exons 3 and 4) are replaced.). Double null mutants were obtained by crossing double heterozygotes. WT and single mutant mice were littermates of the double mutants. Animals were bred and maintained in standard animal housing conditions. Food and water were freely available in a room with constant temperature and humidity with 12 hr light/dark cycle. All of the tested animals were males, which at the age of 3–4 months were isolated for at least 7 days prior to each test. Tests were always carried out between 4 and 7 p.m. For the open field test, each mouse was placed in the middle of a 30 cm enclosure, the floor of which was partitioned into 12 squares of equal surface area. The locomotion (number of squares crossed) and rearings were counted for 5 min (Baik, J. H., et al., *Nature* 377.424–428 (1995)). For the rotarod test, mice were placed on the 6-cm-diameter rod and after 30 s of habituation period, the rod was set in motion (3 turns per minute). Each mouse was given a maximum of five trials, each of 180 seconds. The best performance (i.e., the longest time spent on the rod without falling) was kept for analysis (Janssen, P. A., et al., *Psychopharmacol.* 1:389 (1960); Wolffgramm, J., et al., *Pharmacol. Biochem. Behav.* 36:907 (1990)).

For cocaine-induced behavior analysis, animals of each genotype were divided into two groups treated with intraperitoneal injection of either cocaine (20 mg/kg), or an equivalent volume of saline. The open field test was carried out for 5 min, 25 min after the injection. Locomotion and stereotyped behaviors were scored as above. Each animal was tested only once.

In situ hybridization. Cryostat sections (7 µm) were prepared on gelatine coated slides and hybridized with the specific probes, as described (Dollé, P., et al., *Development* 110:1133–1151 (1990)). The antisense RNA probes were prepared using T3 (D2R) and Sp6 (D1R) polymerases and α-$^3$S-labeled CTP (Amersham). The D1R and D2R probes were synthesized from 384 bp (linearized by Bsu36I) and 1680 bp long (linearized by EcoRI) mouse cDNA templates, respectively. Slides were exposed to Kodak NTB-2 autoradiography emulsion for 2 weeks.

EXAMPLE 2

Figure 5A:
FIG. 5A. Nucleotide sequence (SEQ ID NO: 1) of the rat D2 receptor gene promoter. Nucleotides are numbered according to the transcription initiation site (+1), indicated by the arrow. Putative response elements for AP1, AP2, Sp1, and GATA factors are underlined. A putative retinoic acid/vitamin D receptor response element (RARE) is in bold and underlined.

Regulation of Dopaminergic Pathways by Retinoids: Activation of the D2 Receptor Promoter by Members of the Retinoic Acid Receptor-Retinoid X Receptor Family Results The D2R Gene Promoter is Induced by Retinoids. Despite the specific expression of the dopamine D2 receptor (D2R), which is restricted to certain neurons of the central nervous system and cells of the pituitary gland, the D2R gene promoter (SEQ ID NO:1) has house-keeping characteristics and does not contain functional TATA and CAAT boxes. However, the presence of a positive cis-acting element located between nucleotides −75 and −30, and of two negative cis-acting elements, between nucleotides −116 and −76 and −160 and −135, has been reported (Minowa, T., et al., *Biochemistry* 31:8389–8396 (1992); Minowa, M. T., et al., *J. Biol. Chem.* 269:11656–11662 (1994)). In addition, putative consensus target sequences for Sp1, AP1, AP2, and GATA transcription factors can be identified (FIG. 5A). The analysis of the D2R promoter sequence (SEQ ID NO:1) revealed the presence of a putative retinoic acid response element (RARE) centered at position −68. This led us to investigate whether retinoic acid (RA) might play a role in the control of the D2R gene expression.

Figure 5B:
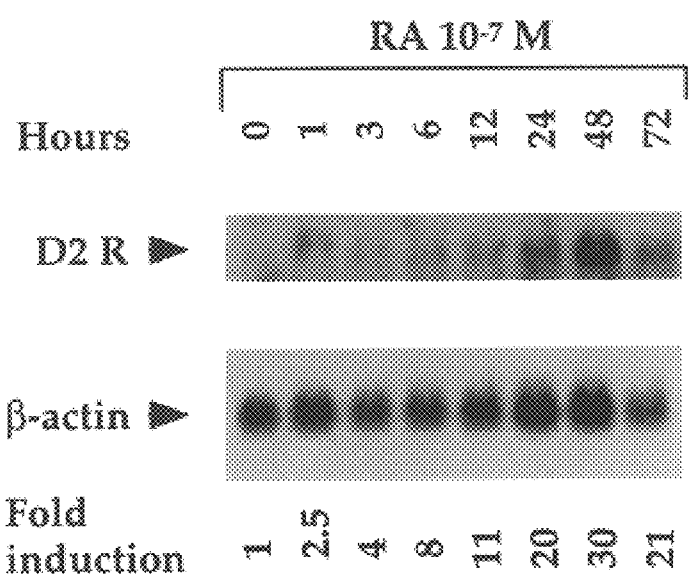
FIG. 5B. Time course analysis of D2R transcripts from MMQ cells after induction with 10$^{-7}$ M t-RA and 9-cis RA. Induction periods are represented in hours. D2R and β-actin transcripts are indicated. The increase in D2R messenger is represented as fold induction with respect to the transcript level in the absence of RA treatment, after normalization for β-actin mRNA levels.

We took advantage of the availability of a pituitary cell line (MMQ) expressing D2Rs (Judd, A. M., et al., *Endocrinology* 123:2341–2350 (1988)) to test whether RA treatment of these cells would result in an increased expression of the D2R gene. Northern blot analysis of RNA extracted from these cells after treatment with t-RA and 9-cis RA ($10^{-7}$M) showed a two-fold increase in D2R mRNA after 1 hour of treatment with a peak of 30-fold induction after 48 hours (FIG. 5B). The increase in D2R mRNA while reduced was still significant after 72 hours of induction (FIG. 5B). These data suggested that retinoids might be involved in the regulation of D2R gene expression at the transcriptional level.

Retinoids Induce the Activity of the D2R Promoter in Transfected Cells. A plasmid was constructed in which a 750 bp fragment (C1), spanning the 5' flanking region of the gene (Valdenaire, O., et al., *Eur. J Biochem.* 220:577–584 (1994)), drives the expression of the CAT reporter gene (FIG. 6A). COS-1 cells, which do not express endogenously the D2R gene, were transfected with this reporter plasmid together with vectors expressing retinoid receptors (FIG. 6A). Two families of nuclear retinoid receptors, binding as heterodimers to RARβ s have been described (RAR and RXR), which bind t-RA and 9-cis-RA with different affinities (Leid, M., et al., *Trends Biochem. Sci.* 17:427–433 (1992); Mangelsdorf, D. J., et al., *Genes & Dev.* 6:329–344 (1992); Chambon, P., *FASEB J.* 10:940–954 (1996)). Each of these families comprises three members: α, β and γ. The ability of RARs and RXRs to induce transcription from the D2R promoter was assessed either when transfected alone or in combinations, in the presence or absence of RA.

The basal activity of the D2R promoter (SEQ ID NO:1) was undetectable (FIG. 6A, lane 1). Similarly, no significant changes in CAT activity were observed after treatment of C1 reporter-transfected cells with $10^{31\ 7}$ M of either t-RA or 9-cis-RA (FIG. 6A, lanes 2 and 3). Cotransfection of the C1 reporter with an RARα expression vector in cells treated with t-RA resulted into a 16-fold increase of CAT activity (FIG. 6A, lane 5). Similar results were obtained with RARβ or RARγ. Cotransfection of RXRγ (similar results were obtained with RXRα and RXRβ) with the C1 reporter led to a 9-fold increase in CAT activity in the presence of 9-cis-RA (FIG. 6A, lane 7), whereas cotransfection of RARα and RXRγ resulted in a 45-fold synergistic activation in the presence of t-RA and 9-cis-RA (FIG. 6A, lane 9). Other combinations of RAR and RXR isotypes yielded similar synergistic activities. The basal activation of transfected RAR and RXR in the absence of ligand, observed in FIG. 6A, lanes 4, 6 and 8, is most likely due to endogenous RA in the culture media.

Figure 6B:
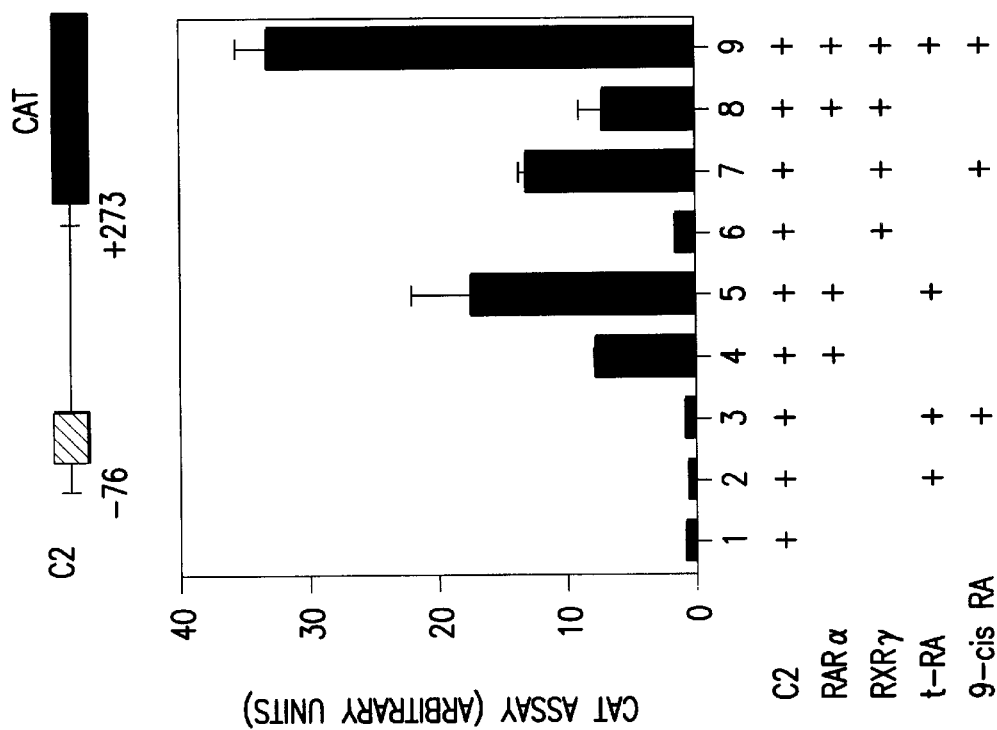
FIG. 6. Analyses of transcriptional activation by RARα, RXRγ and RARα/RXRγ on the D2R promoter reporter constructs. Reporter constructs are schematically represented at the top of each figure. The striped box (▨) corresponds to the RARE-like sequence (RARE D2) of the D2R promoter and the black box (■) to the Chloramphenicol Acetyl Transferase gene (CAT). The striped box (▨) in the C4 reporter construct represents the mutated sequence of the RARE-like site D2 m1 (see FIG. 7A). COS-1 cells were cotransfected with the indicated expression vectors and the C1reporter (FIG. 6A), the C2 reporter (FIG. 6B), or the C3 or C4 reporter (FIG. 6C) constructs. t-RA and 9-cis RA were used at 10 M$^{-7}$ and added as indicated. Bars represent the mean of several independent experiments and standard deviations are indicated.
Figure 6A:
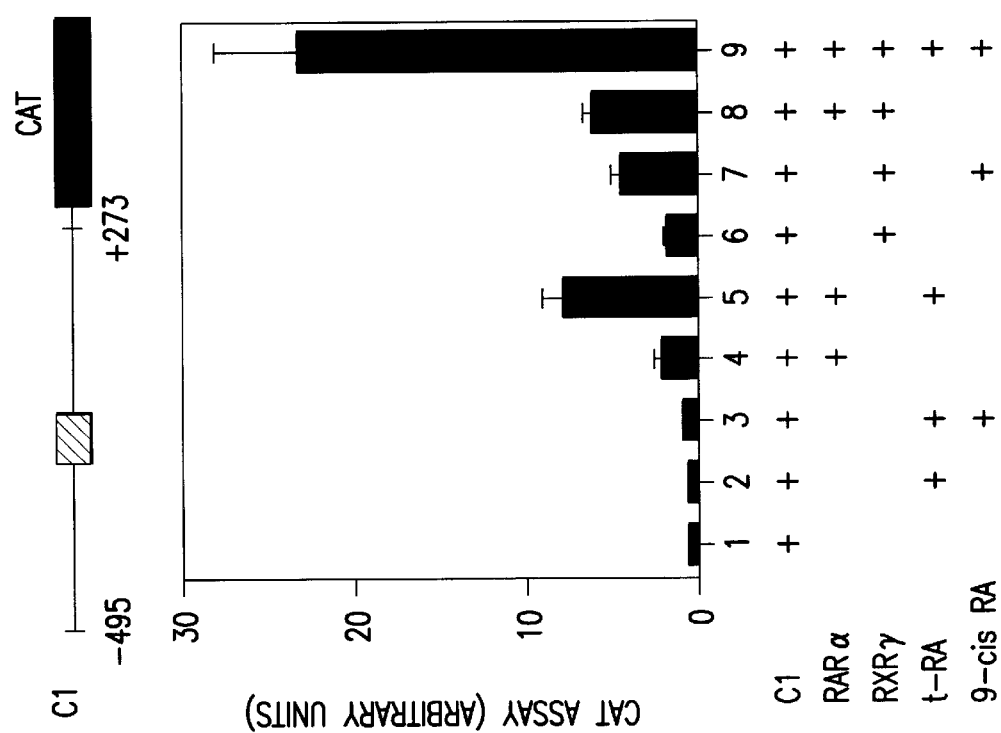
Figure 6C:
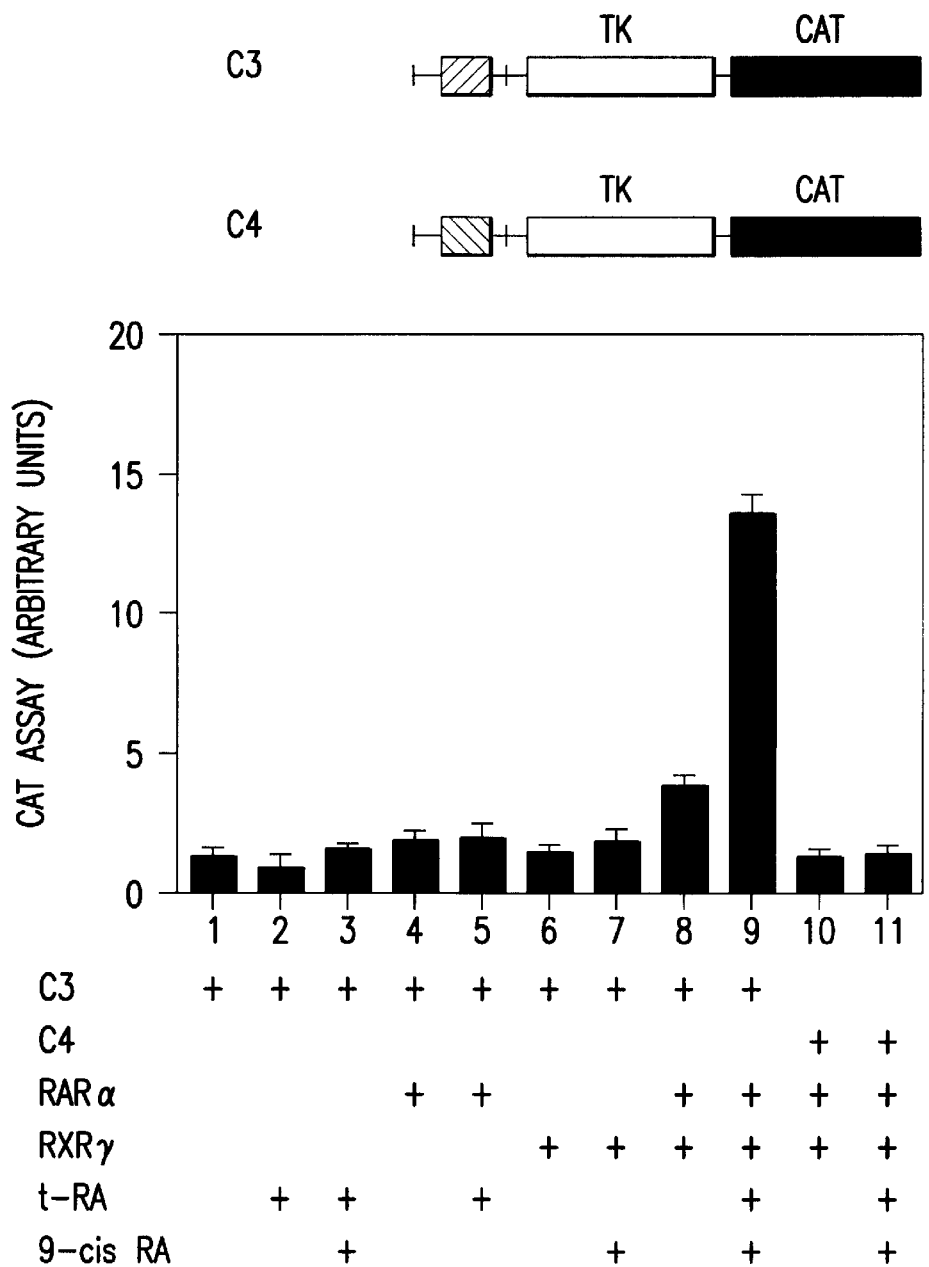

To establish whether the RARE-like element found in the D2R promoter (SEQ ID NO:1) might be the RA response element, the C2 and C3 reporters were constructed (FIGS. 6B and 6C). In the C2 reporter, the region 5' to the putative RARE site was deleted. This region has also been reported to contain a negative regulator of the D2R promoter in the neuroblastoma cell line NB41A3 (Minowa, T., et al., *Biochemistry* 31:8389–8396 (1992)). In C3, a single copy of a synthetic oligonucleotide (RARE D2) (SEQ ID NO:2) containing the putative D2R RARE was cloned upstream of a heterologous promoter, the herpes simplex I TK promoter, at position −110 of the pBL2TK-CAT reporter vector. The C2 reporter had no detectable basal activity in COS-1 cells, indicating that deletion of the previously described negative element contained in the D2R promoter (SEQ ID NO:1) does not lead to an increased promoter activity in these cells (FIG. 6B, lanes 1 to 3). However, cotransfection of the C2 reporter with a RARα expression vector leads to 35-fold increase of CAT activity after induction with t-RA (FIG. 6B, lane 5). Cotransfection of RXRγ with C2 and induction with 9-cis-RA led to 21-fold increase in CAT activity (FIG. 6B, lane 7). Similarly to the C1 reporter, coexpression of RARα/RXRγ resulted in a 66-fold increase of CAT activity in the presence of t-RA and 9-cis-RA (FIG. 6B, lane 9), as compared to control (FIG. 6B, lane 3). As for the C1 reporter, CAT activity observed in the absence of ligand in FIG. 6B, lanes 4, 6 and 8, is most probably due to endogenous RA.

To demonstrate that the putative RARE was involved in the increase of reporter activity by liganded RAR/RXR, we used the reporter C3. This construct has a constitutive basal activity when transfected in COS-1 cells probably due to the TK promoter (FIG. 6C, lane 1). Cotransfection of the C3 reporter with either RARα or RXRγ, both in the presence or in the absence of the related ligands, did not result in detectable induction (FIG. 6C, lanes 2 to 7). This suggests that the D2R RARE is sensitive to its promoter flanking sequences which might be required for its full activity. In contrast, cotransfection of the C3 reporter with RARα/RXRγ expression vectors, in the presence of t-RA and 9-cis-RA, resulted in an 11 -fold increase of CAT activity as compared to the basal TK activity in the absence of ligands (FIG. 6C, lanes 1 and 9).

These results indicate that the RARE-like site present in the D2R promoter (SEQ ID NO:1) responds to the presence of RA, through the binding of RAR/RXR heterodimers, with no apparent significant preference for particular RAR isotypes. In agreement with this conclusion, mutations in the D2R RARE sequence in the reporter construct lead to the absence of induction of CAT activity by RAR/RXR. Indeed, when the C4 reporter was used, in which the D2R RARE was replaced by the mutant D2 m1 (SEQ ID NO:3) which carries 6-bp conversions within the site (FIG. 7A), no detectable CAT activity was observed upon cotransfection with RAR/RXR in the presence of t-RA and 9-cis-RA (FIG. 6C, lanes 10 and 11).

Figures 7B, 7C:
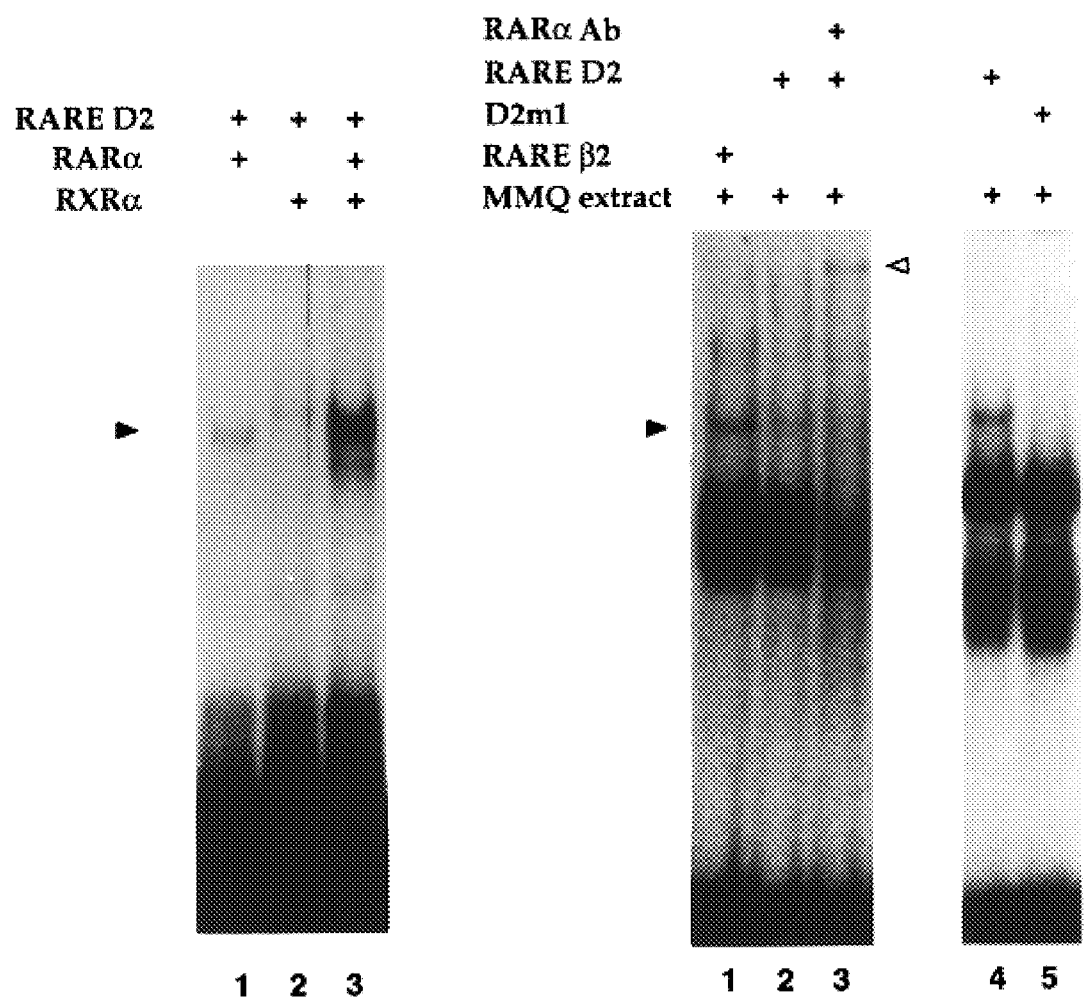
FIG. 7B. Experiments were performed using a labeled RARE D2 oligonucleotide (SEQ ID NO:2) as probe, in the presence of recombinant retinoid receptors RARα and/or RXRα as indicated. The shifted complexes are indicated by the arrowhead.
FIG. 7C. Gel shift analysis performed using RAREβ2 (SEQ ID NO:5) or RARE D2 (SEQ ID NO:2) as labeled probe together with 6 μg of MMQ cell nuclear extracts. The nature of the DNA-protein complex obtained with RARE D2 (SEQ ID NO:2) was verified by supershift experiments using a monoclonal antibody against RARα. The open arrowhead indicates the supershifted complex.

The D2R Promoter Contains a RARE. Experiments were performed to establish whether the putative RARE present in the D2R promoter (SEQ ID NO:1) could bind RARs and RXRs in vitro. A $^{32}$P-labeled oligonucleotide corresponding to the RARE-like site (RARE D2) (SEQ ID NO:2) present in the D2R promoter (SEQ ID NO:1) was synthesized (FIG. 7A). The binding ability of this oligonucleotide was assessed in gel shift assays using either recombinant RAR proteins or nuclear extracts from MMQ cells. FIG. 7B shows that RARα and RXRα individually bind poorly to the D2R RARE (SEQ ID NO:2), whereas the presence of both receptors greatly enhances D2R RARE (SEQ ID NO:2) binding because of the higher affinity of RAR/RXR heterodimers to a RARE (Mader, S., et al, *J. Biol. Chem.* 268:591–600 (1993); Kliewer, S. A., et al., *Nature* 355:446–449 (1992)). Furthermore, the D2R RARE (SEQ ID NO:2) was able to form a complex with endogenous proteins present in MMQ cell nuclear extracts, similarly to the RAREβ2 (SEQ ID NO:5) (FIG. 7C, lanes 1 and 2). Analysis of mRNA extracted from these cells revealed the presence of transcripts for RARα, RXRα and RXRβ. To confirm the presence of the retinoid receptors in the retarded complex, gel shift analysis were performed in the presence of a monoclonal antibody directed against RARα. The results clearly show that RARα antibody supershifted the binding complex (FIG. 7C, lane 3). When antibodies against RARα and RXRs were used in the same reaction, a similar supershift pattern of the retarded complex was observed. The complex observed with MMQ extracts is specific as demonstrated by the absence of the retarded complex when the mutant D2 m1 oligonucleotide (SEQ ID NO:3) was used instead of D2R RARE (SEQ ID NO:2) (FIG. 7C, lanes 4 and 5).

Figure 8:
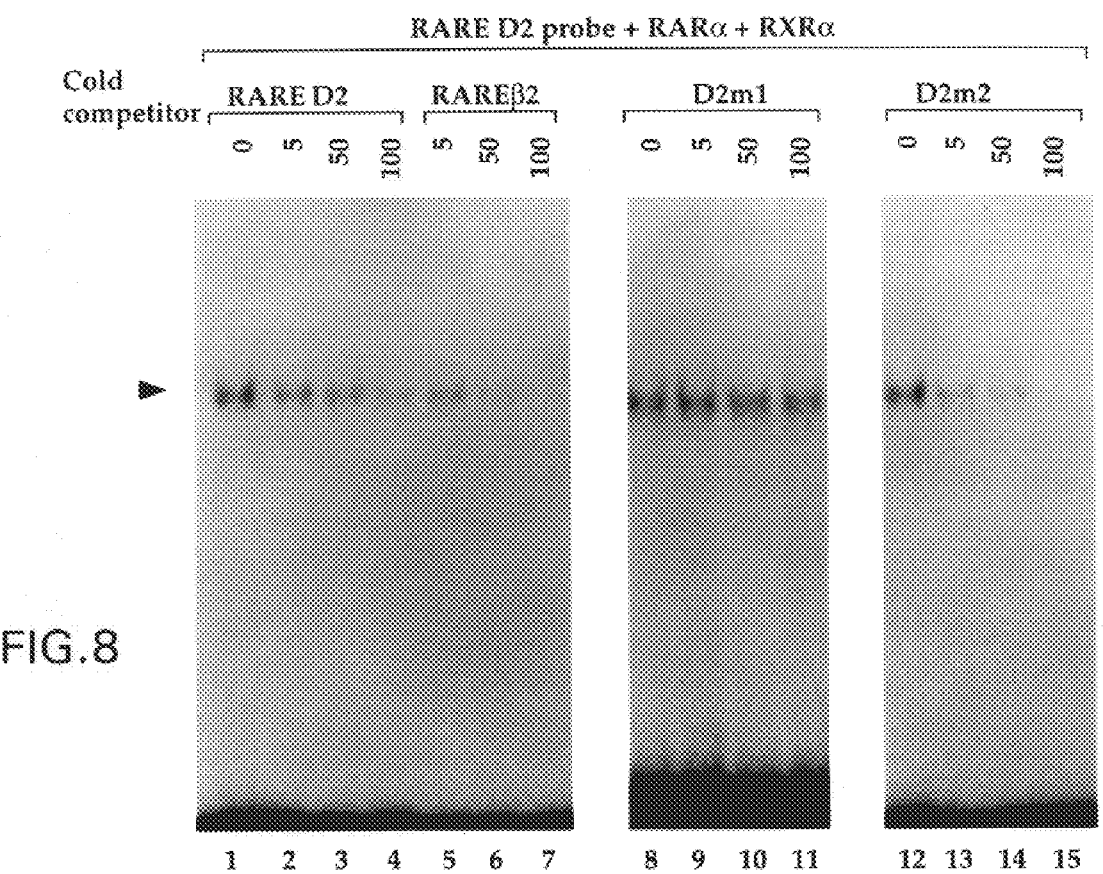
FIG. 8. DNA binding competition assays. Gel shift analysis using labeled RARE D2 (SEQ ID NO:2) and recombinant RARα and RXRα as indicated. As competitors, RARE D2 (SEQ ID NO:2), RAREβ2 (SEQ ID NO:5) and the mutant D2m1 and D2m1 cold oligonucleotides (SEQ ID NO:3) were used as indicated at 5, 50- and 100-fold molar excess. The black arrowhead indicates the shifted complex.

To characterize the specificity of binding, competition assays were performed using recombinant RARα and RXRα receptors in the presence of 5-, 50-, and 100-fold excess of D2R RARE oligonucleotides (SEQ ID NO:2) (FIG. 8). Binding was efficiently blocked by competition with a 50-fold excess of unlabeled D2R RARE oligonucleotide (SEQ ID NO:2) and almost disappeared in the presence of 100-fold excess (FIG. 8, lanes 1 to 4). When the RARβ2 oligonucleotide (SEQ ID NO:5) (FIG. 7A) was used as a competitor, a drastic decrease of the labeled complex was already observed using a 5-fold excess of unlabeled RARβ2 (SEQ ID NO:5), and was complete at 50-fold excess (FIG. 8, lanes 1 and 5 to 7). The higher competing capacity of the RARβ2 oligonucleotide (SEQ ID NO:5) is keeping with the presence of a direct repeat spaced by five nucleotides (DR5) in contrast to the D2R RARE which, instead, contains a direct repeat spaced by three nucleotides (DR3) (Leid, M., et al., *Trends Biochem. Sci.* 17:427–433 (1992); Chambon, P., *FASEB J.* 10:940–954 (1996); Mangelsdorf, D. J., et al., *Cell* 83:835–839 (1995)).

To further characterize the D2R RARE element and its binding affinity to retinoid receptors, mutations were introduced into this sequence generating D2 ml (SEQ ID NO:3) and D2 m2 (SEQ ID NO:4) (FIG. 7A). These mutated oligonucleotides were used for competition in gel-shift assays (FIG. 8). The unlabeled D2 ml oligonucleotide (SEQ ID NO:3) in which the D2R RARE was drastically altered, failed to compete with the labeled oligonucleotide to bind the RAR/RXR heterodimer even after addition of 100-fold excess of the competitor (FIG. 8, lanes 8 to 11). In contrast the mutant D2 m2 (SEQ ID NO:4) (FIG. 7A), which converts the D2R RARE into a perfect DR3 element (GGGTCANNNTGGTCA (SEQ ID NO :6)), was more efficient at competing than the native site (compare in FIG. 8, lanes 12–15 to lanes 1–4).

The above data further support the conclusion that the retarded complex formed by the binding of the heterodimer RARα/RXRα on the D2R RARE is specific.

Altered Expression of the D2R gene in Mice Mutants for RARs and RXRs. The results strongly suggest that RARs regulate D2R gene transcription. Thus, the absence of one of these transcription factors in vivo may alter the levels of D2R messenger RNA. Thus in vivo studies were performed by analyzing the level of expression of D2R in mice in which the expression of one or more retinoid acid receptors has been knocked out by homologous recombination.

Interestingly, dopaminergic neurons of the nigrostriatal pathway have been found to synthesize RA (McCaffery, P. & Dräger, U. C., *Proc. Natl. Acad. Sci. USA* 91:7772–7776 (1994)). In addition, whereas RARα is uniformly expressed in the mouse brain, RARβ, RXRβ and RXRγ receptors are more abundantly expressed in certain brain regions, such as caudate putamen and nucleus accumbens, both striatal regions that highly express D2R.

Figure 9:
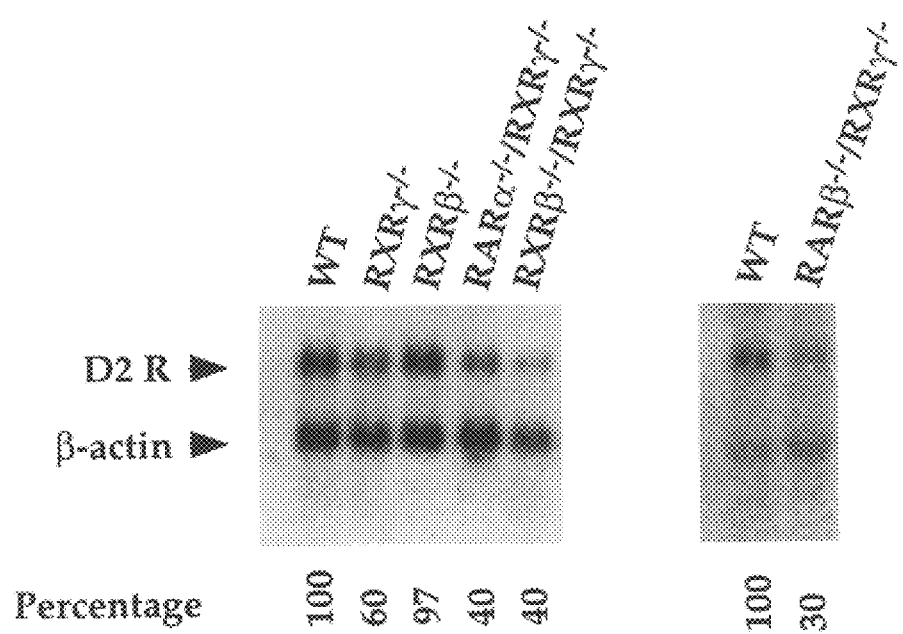
FIG. 9. Northern blot analysis of D2R mRNA expression in the striatum of wild-type and mutant mice. Genotypes are indicated on the top of each lane. Arrowheads indicate the bands corresponding to D2R and β-actin mRNAs. The expression level of D2R mRNA in wild-type mice was arbitrarily set at 100%.

D2R mRNA expression was analyzed in RXRβ$^{-/-}$ and RXRγ$^{-/-}$ single mutants (Kastner, P., et al., *Genes & Dev.* 10:80–92 (1996); Krezel, W., et al., *Proc. Natl. Acad. Sci. USA* 93:9010–9014 (1996)). Ten mg of total RNA from striatal tissues of these mice was analyzed by Northern blotting, using a mouse D2R-specific probe. D2R expression in mutants was compared to the expression in wild-type littermates. In support to the in vitro data, a 40% reduction of D2R mRNA expression in the striatum of RXRγ$^{-/-}$ mice (FIG. 9) was found, whereas no reduction of D2R mRNA was observed in the same tissue of RXRβ-deficient mice (FIG. 9).

Next, the following double mutants were analyzed: RARα$^{-/-}$/RXRγ$^{-/-}$, RXRγ$^{-/-}$/RXRβ$^{-/-}$ and RARβ$^{-/-}$/ RXRγ$^{-/-}$. Interestingly, these mice showed a more severe decrease in the striatal D2R gene expression (FIG. 9). The D2R mRNA level in the striatum of RARα$^{-/-}$/RXRγ$^{-/-}$ and RXRγ$^{-/-}$/RXRβ$^{-/-}$ mutant mice was decreased by 60% as compared to wild-type littermates, and by 70% in the RARβ/RXRγ deficient mice.

These data indicate that RARα, RARβ, RXRβ and RXRγ are likely to be involved in the regulation of the expression of the D2R gene in vivo. Note that the expression pattern of two retinoid receptors, RARβ and RXRγ, correlates with the reduction of the striatal D2R mRNA levels in the mice lacking these receptors.

Materials and Methods

Expression Vectors. The C1 reporter construct was obtained by subcloning the HindIII fragment spanning the 5' promoter region of the D2R gene (positions −495 to +273), in the reporter plasmid pBLCAT3 (Luckow, B. & Schütz, G., *Nucleic Acids Res.* 15:5490 (1987)). The C2 reporter plasmid was constructed by subcloning the SmaI-XhoI fragment (positions −76 to +273) in the same position. The C3 and C4 reporters were generated by cloning a 29 bp synthetic oligonucleotide corresponding, respectively, to the natural rat D2R RARE sequence and the mutated one into pBL-CAT2 (Luckow, B. & Schütz, G., *Nucleic Acids Res.* 15:5490 (1987)). The polylinker in pBLCAT2 is located upstream of the herpes simplex virus 1 (HSV1) thymidine kinase (TK) promoter, from position −105 to +51. To measure transfection efficiency the plasmid pCH110 carrying the β-galactosidase gene (Pharmacia) was used. Mouse RARβ, β and γ, as well as mouse RXRα, β and γ expression vectors were derived from the parental pSG5 vector (Green, S., et al., *Nucleic Acids Res.* 16:369 (1988)).

Cell Culture and Transient Expression Assay. MMQ, a rat pituitary cell line (Judd, A. M., et al., *Endocrinology* 123:2341–2350 (1988); Forget, H., et al., *Mol. Cell. Endocrinol.* 93:125–133 (1993)), was grown in RPMI medium supplemented with 10% fetal calf serum (FCS) and 5% horse serum (HS). Time course induction assays with all-trans-RA (t-RA) and 9-cis RA at 0.1 μM were performed in RPMI medium 1640 supplemented with charcoal-treated serum.

COS-1 cells were used for transient transfection assays. Cells were grown in Dulbecco's modified Eagle's medium supplemented with 5% fetal calf serum.

Several hours before transfection, the medium was replaced with fresh medium containing 5% charcoal-treated FCS. Cells ($10^6$ per 10 cm plate) were transfected by the calcium phosphate method using 2 μg of the reporter plasmid, 0.1 μg of retinoid acid receptor expression vectors and 0.5 μg of pCH110. In all transfection assays, the Bluescript (SK$^-$) plasmid was used as a carrier to reach 20 μg of total transfected DNA per plate. Twenty-four hours after transfection, cells were washed, and the medium was replaced for an additional twenty-four hours either in the presence or absence of t-RA or 9-cis RA ligand (0.1 μM). Before CAT assays, extracts were normalized for β-galactosidase activity (Petkovich, M., et al., *Nature* 330:444–450 (1987)).

DNA Binding Assays. A 29-bp synthetic oligonucleotide (SEQ ID NO:2) corresponding to the RARE region in the D2R promoter (SEQ ID NO:1) (from positions −76 to −49), in addition to two mutated oligonucleotides (SEQ ID NOs:3 and 4) (FIG. 7A) were used in gel retardation assays. A synthetic oligonucleotide corresponding to the RARE-β2 (SEQ ID NO:5) (Mader, S., et al., *J. Biol. Chem.* 268:591–600 (1993)) was used as positive control. Bacterially-expressed purified mouse RARα (ΔAB) and RXRα (ΔAB) proteins were kindly provided by H. Gronemeyer. Nuclear extracts from MMQ cells were prepared by lysing the cells in extraction buffer (20 mM Tris-HCl (pH 8.0), 2 mM dithiothreitol, 400 mM KCl, 20% glycerol) by three cycles of freeze-thawing (Kumar, V. & Chambon, P., Cell 55:145–156 (1988)). Gel retardation assays were performed as described (Nicholson, R. C., et al., EMBO J. 9:1986–1989 (1990)). For competition reactions, unlabeled double-stranded oligonucleotides were added to the binding reaction 20 min before RAR-RXR or the MMQ extracts. Supershift assay was performed by adding the mouse RARα monoclonal antibody (Gaub, M. P., et al., Exp. Cell. Res. 201.335–346 (1992)) to the binding reaction 20 min prior to labeled D2R RARE oligonucleotides (SEQ ID NO:2).

RNA Analysis. Total RNA from MMQ cells and striatal tissues was prepared using the urea/LiCl procedure (Auffray, C. & Rougeon, F., Eur. J. Biochem. 107:303–314 (1980)). Northern blot analysis was performed using 7 μg of total RNA. Restriction fragments derived from the mouse D2R cDNA (360-bp AccI fragment) and β-actin cDNA (700-bp HindIII-EcoRI fragment) were used to generate $^{32}$P-labeled probes by random priming. Hybridizations were performed under standard conditions in 50% formamide at 42° C., followed by washes in 0.3M NaCl/30 mM sodium citrate/ 0.1% SDS at 50° C.

The intensity of bands on X-Ray autoradiographs was quantified using an imaging densitometer (Bio-Rad Laboratories).

Discussion

Dopamine controls a wide variety of physiological functions through the activation of membrane receptors. Alterations in the dopaminergic system in humans result in mental diseases such as schizophrenia and Parkinson's disease. It has been shown herein that deletion of the D2R gene in knockout mice results in an impaired locomotor phenotype with analogies with Parkinson's disease and in pituitary tumors (Baik, J. H., et al., Nature 377:424–428 (1995); Saiardi, A., et al., Neuron 19:115–126 (1997)). These observations suggest that gene regulation of dopamine receptors, and in particular of the D2R, is a key element in the normal function of the dopaminergic system. In this respect, it is interesting to note that the two major dopamine receptors, D1 and D2, are thought to possess promoters with house keeping characteristics (Minowa, T., et al., Biochemistry 31:8389–8396 (1992); Valdenaire, O., et al., Eur. J. Biochem. 220:577–584 (1994)). Thus, specificity in the expression pattern of these receptors must be temporally and spatially dictated by cell specific transcription factors.

A RARE element has been characterized herein which is located in the 5' flanking region of the dopamine D2 receptor gene at position −68. The described D2R RARE is made up of repeated motifs closely related to the core motif 5'-PuG (G/T)TCA-3'. The two motifs are spaced by three bp, a spacing which has been described to favor the binding of vitamin D3 receptor (Leid, M., et al., Trends Biochem. Sci. 17:427–433 (1992); Chambon, P., FASEB J. 10:940–954 (1996); Mangelsdorf, D. J., et al., Cell 83:835–839 (1995)). It has been demonstrated herein that RAR/RXR heterodimers bind to this motif and activate transcription from the D2R promoter (SEQ ID NO:1).

The non-consensus response elements present in D2R and some other natural promoters may result in lower binding affinities for retinoid receptors, as observed here in gel shift competition assays using D2R RARE (SEQ ID NO:2), D2m2 (SEQ ID NO:4) and RARβ2 oligonucleotides (SEQ ID NO:5) (FIG. 8). This might correspond to a regulatory mechanism aimed at attenuating the response to specific ligands in vivo. It is also possible that transcription factors recognizing nonconsensus motifs may be subject to cooperative interactions with other factors binding to nearby or adjacent sites (Day, R. N., et al., Mol. Endocrinol. 4:1964–1971 (1990); Rhodes, S. J., et al., Genes & Dev. 7:913–932 (1993)). The presence of these cooperative interactions could determine the strength and cellular specificity of the transcriptional response. In the case of the D2R promoter (SEQ ID NO:1), the close vicinity of the D2R RARE and the Sp 1 sites might represent an example of such cooperativity.

It should be pointed out that the D2R is expressed in different regions of the brain and in particular by the dopaminergic cells in mesencephalic neurons and by the dopaminergic neuron targets, such as the medium spiny neurons in the striatum, but also by cortical and hypothalamic cells. In addition, outside the brain the D2R is highly expressed in the pituitary gland by two cell types, melanotrophs and lactotrophs. It is thus conceivable that the D2R promoter (SEQ ID NO:1) might be controlled by different combinations of members of the thyroid hormone/RA and vitamin D3 receptor families in different cell types.

However, the results point to an important role of members of RAR and RXR families in the control of D2R expression in the striatum. This control is dependent on the binding of RAR/RXR heterodimers as demonstrated by the stronger decrease of D2R expression in RAR/RXR double mutants as compared to single mutants. This suggests that absence of one retinoid receptor might be partially compensated by other members of the RAR/RXR family in simple mutants. These results strongly support the in vitro data and identify these receptors as specific transcription factors required for full expression of the D2R gene in the striatum.

The data indicate an involvement of RA in adult CNS functions, as the absence of retinoid receptors results in a reduced expression of the DA D2 receptor. It has been previously shown that, in mice, altered expression of this receptor results in a Parkinsonian phenotype (Baik, J. H., et al., Nature 3 77:424–428 (1995)) and pituitary tumors (Saiardi, A., et al., Neuron 19:115–126 (1997)). It is well established that Parkinson's disease is generated by a strong reduction of DA levels. The data raise the possibility that aberrant control of dopaminergic receptors expression might also lead to neurological disorders.

EXAMPLE 3

Role of the Retinoic Acid Receptor Beta (RARβ) During Mouse Development

Introduction

Retinoids, the biologically active derivatives of vitamin A, have been implicated in many aspects of vertebrate physiology and homeostasis (Wolbach, S. B. and Howe, P. R., J. Exp. Med. 42:753–777 (1925); Blomhoff, R., Vitamin A in Health and Disease, Marcel Dekker, New York, (1994); Underwood, B. A. and Arthur, P., FASEB J. 10:1040–1048 (1996) for reviews and references). In addition, they appear to play essential roles in organogenesis, as inferred from the large spectrum of developmental abnormalities displayed by vitamin A deficient (VAD) fetuses (reviewed in Wilson, J. G., et al., Am. J. Anat. 92:189–217 (1953)). During the past decade, the characterization of two families of nuclear receptors for retinoids, the RARs (RARα, β, and γ, activated by all natural forms retinoic acids—RA) and the RXRs (RXRα, β and γ, activated only by 9-cis RA) has revealed the complexity of the molecular machinery transducing the retinoid signal. An additional level of complexity was brought to light by the finding that RXRs not only form homodimers, but can also heterodimerize with a variety of other nuclear receptors. Most notably, it was demonstrated that RXRs represent the nuclear factors required by RARs to bind tightly to a variety of cognate response elements in vitro and to transactivate in transfected cells (Mangelsdorf, D. J. and Evans, R. M., *Cell* 83:841–850 (1995); Chambon, P., *FASEB J.* 10:940–954 (1996) and references therein). Furthermore, a clear convergence between the RXRα and RAR signaling pathways has been revealed in cultured cells and in the mouse (Kastner, P., et al., *Cell* 83:859–869 (1995) and Kastner, P., et al., *Development* 124:313–326 (1997); Chambon, P. *FASEB J.* 10:940–954 (1996) and references therein).

Genetic analysis of the functions of the various RARs in the mouse, has clearly shown that they mediate the developmental functions of retinoids since, altogether, RARβ2 single null mutants (Mendelsohn, C., et al., *Dev. Biol.* 166:246–258 (1994); Grondona, J. M., et al., *Development* 122:2173–2188 (1996)), RARα1$^{-/-}$/RARβ2$^{-/-}$, RARα$^{-/-}$/RARβ2$^{-/-}$, RARβ2$^{-/-}$/RARγ$^{-/-}$, RARα$^{-/-}$/RARγ$^{-/-}$ and RARα1$^{-/-}$/RARβ$^{-/-}$ double mutants (Lohnes, D., et al., *Development* 120:2723–2748 (1994); Mendelsohn, C., et al., *Development* 120:2749–2771 (1994); Luo, J., et al., *Mech. Dev.* 55:33–44 (1996)) recapitulated almost all of the VAD-induced developmental defects (i.e., the fetal VAD syndrome). In addition to establishing the involvement of RA and RARs in the known functions of vitamin A during organogenesis, the analysis of RAR-deficient mice has revealed numerous abnormalities that had not previously been associated with an impaired vitamin A function, most notably neural tube defects, vertebral homeotic transformations, cranial and limb skeletal deficiencies and glandular abnormalities (reviewed in Kastner, P., et al., *Cell* 83:859–869 (1995)).

In the case of the RARβ isotype, four isoforms (RARβ1 to RARβ4) have been characterized, each exhibiting a specific expression pattern in adult tissues (Zelent, A., et al., *EMBO J.* 10:71–81 (1991); Nagpal, S., et al., *Proc. Natl. Acad. Sci USA* 89:2718–2722 (1992)). The distribution of RARβ isoforms in embryonic tissues has not been analyzed, although differential activity of the two RARβ promoters was reported (Mendelsohn, C., et al., *Development* 113:723–734 (1991), Mendelsohn, C., et al., *Mech. Dev.* 45:227–241 (1994)). Nevertheless, in situ hybridization data suggested that RARβ could play unique roles in the differentiation of the tracheal, intestinal and genital tract epithelia, as well as in the ontogenesis of the limbs and nervous system (Dollé, P., et al., *Development* 110:1133–1151 (1990); Ruberte, E., et al., *Development* 111:45–60 (1991)). Previous analyses of mice lacking either the RARβ2 and β4 isoforms or all RARβ isoforms (RARβ 'total') revealed only two types of abnormalities: a mass of pigmented tissue behind the lens (retrolenticular membrane) observed only in RARβ2/β4 mutants (Grondona, J. M., et al, *Development* 122:2173–2188 (1996)), and a fusion of cranial nerves IX and X observed only in RARβ 'total' mutants (Luo, J., et al, *Mech. Dev.* 53:61–71 (1995)). With the aim of understanding these apparent discrepancies between the two phenotypes and to uncover the possible specific function(s) of the RARβ1 and β3 isoforms, we have now generated our own mice lacking all RARβ isoforms. Our analysis indicates that RARβ 'total' mutants indeed display a retrolenticular membrane and that this abnormality represents a congenital defect. Additionally, our RARβ mutants are growth-deficient and exhibit vertebral homeotic transformations. In contrast, abnormalities of cranial nerves IX and X do not appear to be specific features of the RARβ 'total' mutant phenotype. We also report the congenital defects observed by introducing the RARβ 'total' mutation in RARα or RARγ null genetic backgrounds.

Results

A. Targeted disruption of the RARβ gene

Figure 10A:
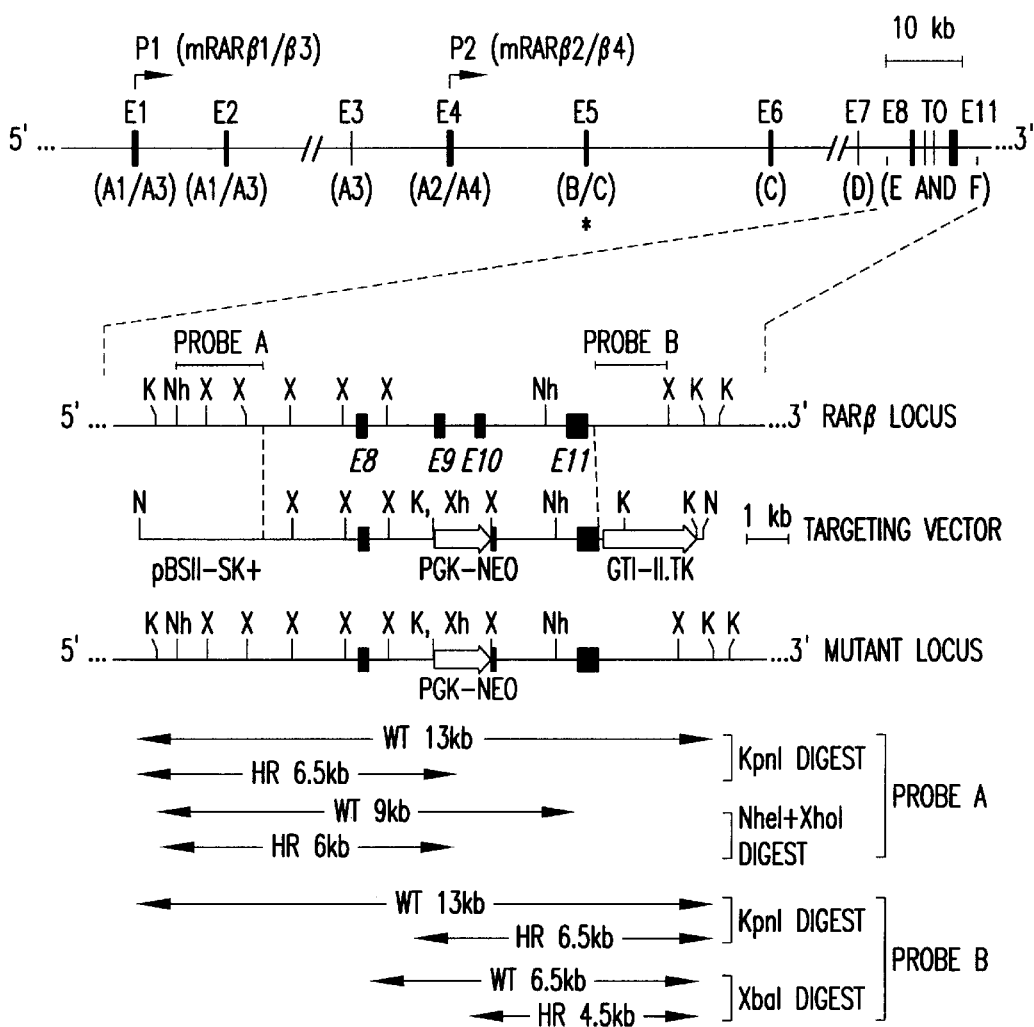
(FIG. 10A) A schematic drawing of the RARβ locus is shown at the top. The eleven exons are presented as solid boxes on the genomic DNA. As indicated below the exons, E1 to E4 are specific for RARβ isoforms, while E5 to E11 are used to compose the B to F region of all four isoforms. The alternative promoters (P1 and P2) are indicated by broken arrows. The asterisk points to the exon mutated by Luo, J., et al., *Mech. Dev.* 53:61–71 (1995)). The enlargement represents exons E8 to E11 containing the ligand binding domain common to all isoforms. The RARβ targeting vector and the expected structure of the recombinant mutant allele are shown at the bottom. The predicted genomic fragments detected with the probes following KpnI, NheI-XhoI or XbaI digestion are indicated for both the wild type (WT) and the recombinant allele (HR). Restriction sites are: K, KpnI; N, NotI; Nh, NheI; X, XbaI; Xh, XhoI.
Figure 10B:
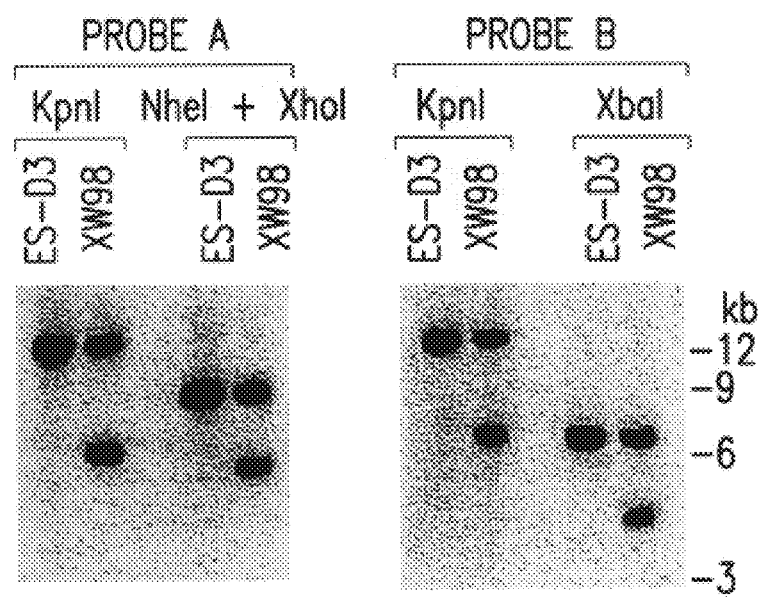
(FIG. 10B) Genomic DNA from D3 ES cells and targeted ES cells (XW98) were digested with KpnI, NheI-XhoI or XbaI, as indicated, blotted and hybridized with the 5' external probe (probe A, left side) or the 3' external probe (probe B, right side). DNA size is indicated to the left of the figure in kilobases (kb).
Figure 10C:
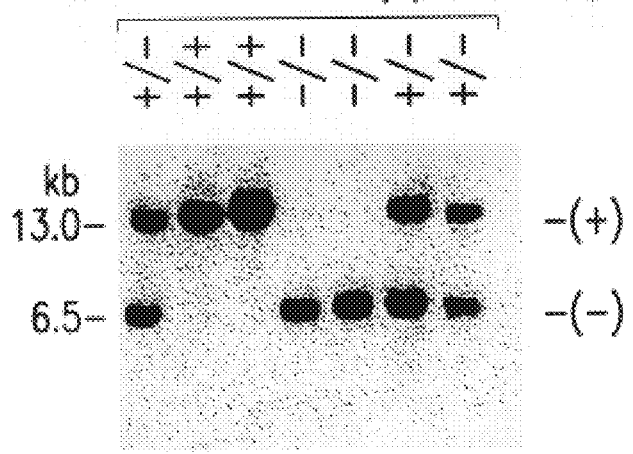
(FIG. 10C) Southern blot of DNA derived from 2-week-old offspring of heterozygous RARβ+/− intercrosses showing the presence of homozygous (−/−, containing the 6.5 kb KpnI fragment only), heterozygous (+/−, containing both the 6.5 and 13.0 kb KpnI fragments) and wild type (+/+, containing the 13 kb KpnI fragment only) alleles.

Genomic clones were isolated from a genomic DNA library derived from the 129/Sv strain. Exon mapping of these clones showed that the RARβ gene extended over 120 kb (FIG. 10*a,* top) and that its exonic organization was similar to that of the human RARβ gene (van der Leede, B. J., et al., *Biochem. Biophys. Res. Commun.* 188:695–702 (1992)). Although we successfully disrupted the RARβ2 isoform at exon E4 in ES cells without too much difficulty (Mendelsohn, C., et al., *Dev. Biol.* 166:246–258 (1994)), the disruption of the RARβ gene (all isoforms) proved to be much more difficult. We had to 'move along' the RARβ gene before finding a region which could be targeted. For unknown reasons, several attempts to target at the level of exon E5 (B domain of RARβ) and exon E6 (C domain of RARβ) were unsuccessfull in our hands. In contrast, Luo, J., et al., *Mech. Dev.* 53:33–44 (1995), succeeded in disrupting the RARβ gene by replacing exon E5 (asterisk in FIG. 10*a*) by a neomycin resistance gene (Neo). We finally isolated one ES cell clone exhibiting a targeted RARβ allele at the level of exons E9 and E10. The replacement-type targeting vector (Capecchi, M. R., *Science* 244:1288–1292 (1989)) used to obtain this clone contains about 7 kb of mouse genomic DNA in which the sequences encoding the ligand binding domain (LBD—common to all RARβ isoforms), between amino acids number 263 and 369 (numbering of the RARβ2 isoform), were replaced with a Neo cassette (FIG. 10*a,* bottom). The resulting protein should be truncated in helix H5 of the LBD just prior to isoleucine 263, one of the specific ligand-binding pocket residues (Renaud, J. P., et al., *Nature* 378:681–689 (1995)). This deletion, encompassing most of the LBD and the entire F region, was shown to completely abolish both the ligand-inducible transactivation functions of RARβ (Folkers, G. E., et al., *Mol. Endocrinol.* 7:616–627 (1993), the dimerization properties and the binding to a RA-response element. The linearized targeting vector was electroporated into D3 ES cells and 1 targeted clone out of 130 colonies was identified by Southern blot analysis using a probe (probe A) located immediately 5' to the replacement construct (FIG. 10*b*). The structure of the targeted allele was further characterized in this clone (XW98). DNA was digested with several enzymes and hybridized with either the 5' or a 3' probe (probe B). Duplications or rearrangements were not detected (FIG. 10*b*). In addition, Southern blots hybridized with a Neo probe showed the pattern expected for a single targeting event, indicating that no non-homologous recombination event had occurred in this ES cell line. The clone XW98 was injected into C57BL/6 blastocysts to create chimeric mice, out of which 4 males transmitted the mutation to their offspring (FIG. 10*c*).

Figure 10D:
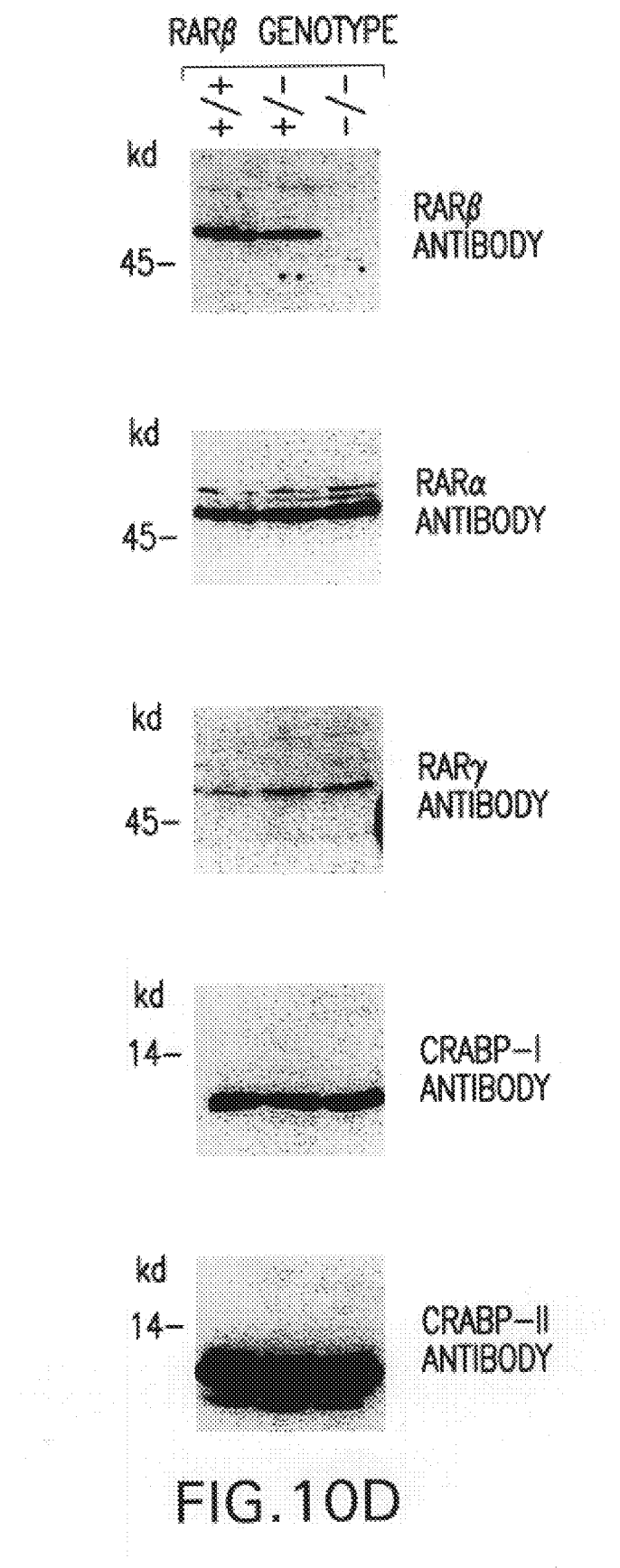
(FIG. 10D) Western blot analysis showing expression of RARβ, RARα, RARγ, CRABP-I and CRABP-II in RARβ mutant. About 80 ug of nuclear extracts or 20 ug of cytosolic extracts from E10.5 WT (+/+), RARβ heterozygous (+/−) and RARE homozygous (−/−) embryos were subjected to SDS-PAGE and immunostaining. The nuclear extracts were immunoprobed with the RARβ specific antiserum. Note the absence of the 55 kDa RARβ signal in the mutant embryo. After stripping, the same blot was subsequently probed with the RARα and the RARγ specific antisera. The hazy bands upper from the RARγ-specific band is a nonspecific signal and is independent of the RARβ genotype. The cytosolic extracts were first probed with the CRABP-I monoclonal antibody and then with the CRABP-II monoclonal antibody.
Figure 10E:
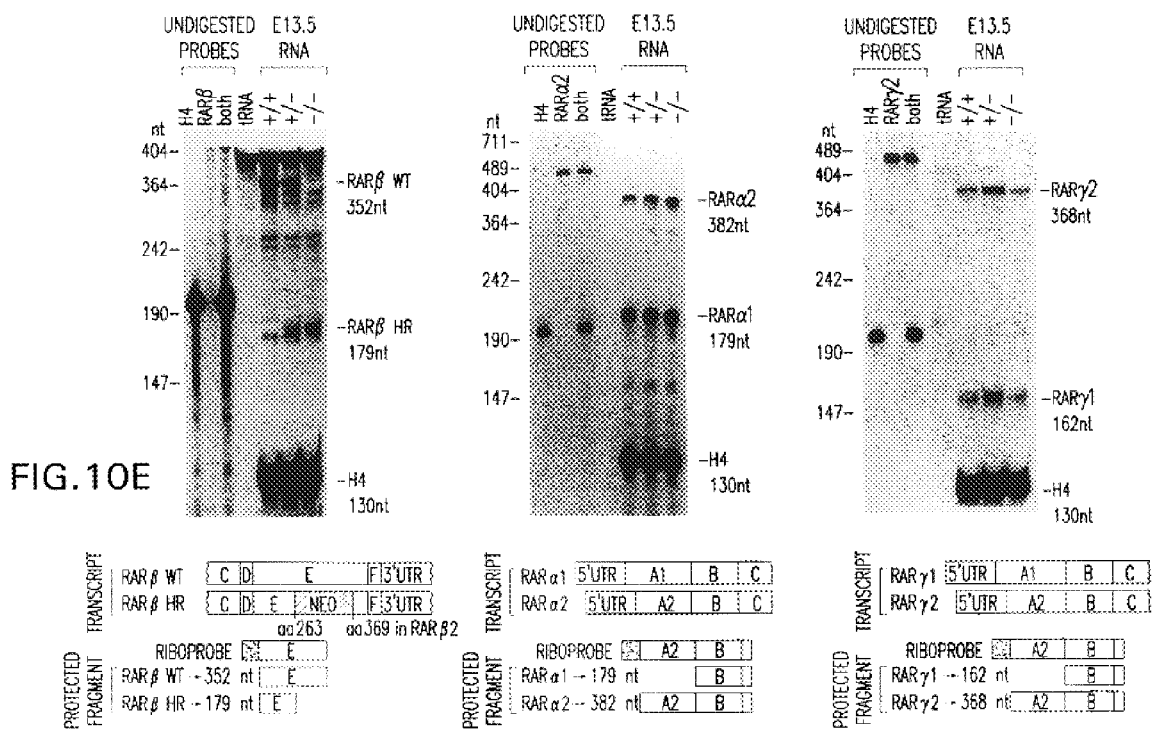
(FIG. 10E) RNAse protection analysis showing RARβ (left panel), RARα (middle panel) and RARγ (right panel) transcripts in E13.5 WT (+/+), heterozygous (+/−) and homozygous (−/−) embryos for RARE disruption. The representation of the strategy for RNAse protection analysis, with the probes used and the expected protected fragments, is illustrated in the lower part of the figure. RARβ wildtype transcripts are represented at the top of the diagram, with the predicted RARβ mutated transcripts shown immediately below. Neo indicates the position of the neomycin resistance gene (not to scale), resulting from targeting of the cognate allele. The amino acid numbers delineating the deletion are relative to the RARβ2 isoform. The riboprobe used is shown in the middle of the diagram, followed by the protected fragments for both wild type (WT) and mutated (HR) RARβ RNA, as indicated on the left. In each case the identity of the protected fragments with their size are indicated to the right of the gel. A tRNA sample was used as negative control and the histone H4 (probe is a gift of R. Grosschedl) protection was included as an internal control for the quantitation and integrity of the RNA samples. Note that the increase in RARγ levels is artifactual since H4 RNA levels are also increased in this experiment.

Western blot analysis was used to verify that the RARβ gene was functionally disrupted. Antibodies directed against the F region common to all RARβ isoforms readily detected the receptor in extracts from 10.5 day post-coitum (i.e., embryonic day 10.5: E10.5) wild type (WT) and heterozygous embryos, whereas no receptor was detected in RARβ mutant homozygotes (FIG. 10*d*). Immunoblotting with antibodies directed against RARα, RARγ, CRABPI and CRABPII (FIG. 10*d*) did not reveal any significant variation (within the sensitivity of the assay) among the same protein extracts. RNAse protection assays were also carried out using RNA from E13.5 fetuses (a time at which RARβ RNA is abundantly expressed, (Zelent, A., et al., *EMBO J.* 10:71–81 (1991)). WT embryos and heterozygous embryos for the RARβ mutation expressed the RARβ RNA as evidenced by the 352 nt long protected fragment (RARβ WT, FIG. 10e, left panel). Additionally, the heterozygous embryos expressed the mutant RARβ RNA, as evidenced by the presence of a 179 nt long protected fragment (RARβ HR, FIG. 10e, left panel). In the RARβ$^{-/-}$ homozygotes, only the mutant form of RARβ RNA was present. Note that the level of expression of the mutant RNA was much lower than that of the WT form, presumably due to a decreased stability of the truncated mRNA. We cannot exclude that some RARβ peptides could be translated from the mutant mRNA. Nevertheless, these peptides would be terminated prematurely and lack both the LBD and the F region. Using a RARα probe, similar levels of the RARα2 and RARα1 transcripts were detected in WT, heterozygote or homozygote E13.5 embryos (FIG. 10e, middle panel). Additionally, there was no detectable change in the levels of RNAs encoding the RARγ1 and γ2 isoforms in the embryos lacking RARβ (FIG. 10e, right panel). These results indicate that RARβ does not play a unique role in controlling RARα and RARγ expression, and that no global compensatory increase of any of these isoforms occurred.

It is unlikely that the abnormalities observed in the present RARβ 'total' mutants could result from a dominant effect of the putative truncated peptides which could be translated from the lower level of mutant mRNAs for at least two reasons. Firstly, it was demonstrated that RARβ truncated at the level of the LBD does not exhibit any dominant negative effect on either DNA binding or transactivation by RARβ (Shen, S., et al., *Mech. Dev.* 40:177–189 (1993)). Secondly, heterozygous animals never displayed any defects. Thus, the present disruption of the RARβ gene most probably corresponds to a null mutation.

B. RARβ$^{-/-}$ (Aβ Mutants Are Growth Deficient

To simplify the nomenclature, RAR isotype mutants for both alleles will be designated hereafter as Aα, Aβ and Aγ and the "$^{-/-}$" indicating homozygocity will be omitted. For example, RARβ$^{-/-}$, RARα$^{-/-}$/RARβ$^{-/-}$ and RARα$^{-/-}$/RARβ$^{+/-}$ mutants will be referred to as Aβ, Aα/Aβ and Aα/Aβ$^{+/-}$ mutants, respectively.

Figure 11B:
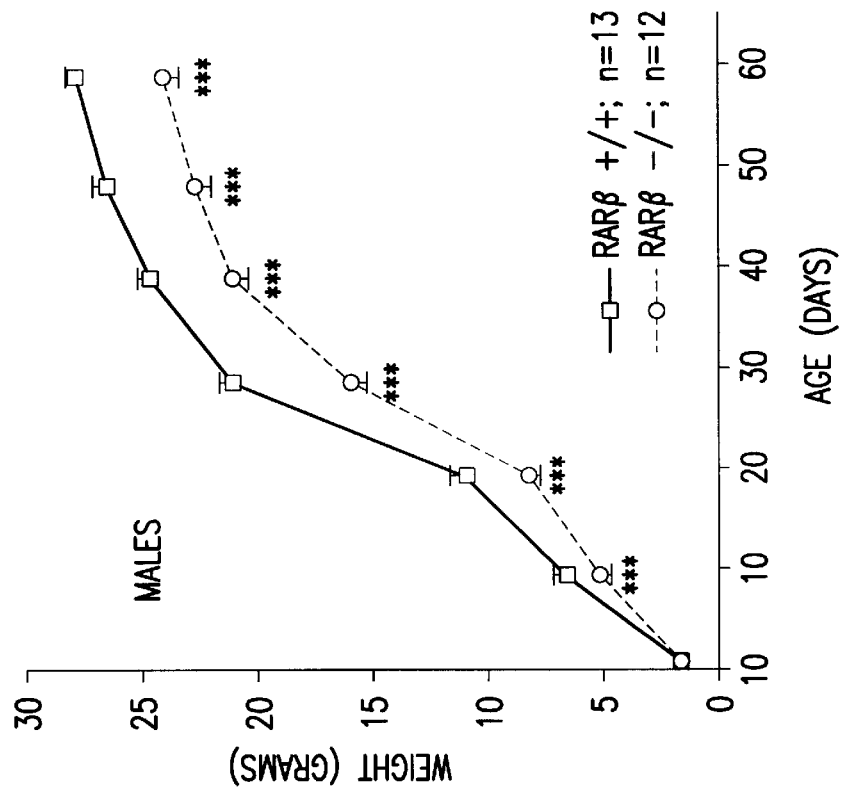
FIG. 11. Weight of females (FIG. 11A) and males (FIG. 11B) mice wild-type (+/+) and homozygous (+/−) for the RARβ null mutation. Offspring (130) derived from intercrosses between RARβ+/− mice were weighed every 10 days from birth until 2 months of age. The numbers of animals in each group is indicated. Means of weights are presented with standard errors. After testing for normality and variance homogeneity, results obtained for unpaired values were subjected to Student's t-test between groups of mice for each genotype. The 0.05 level was selected as the point of minimal statistic significance. Asterisks indicate the level of significance for the observed differences between +/+ and −/− mice ($*p<0.05$; $p<0.0$ and $*p<0.001$).
Figure 11A:
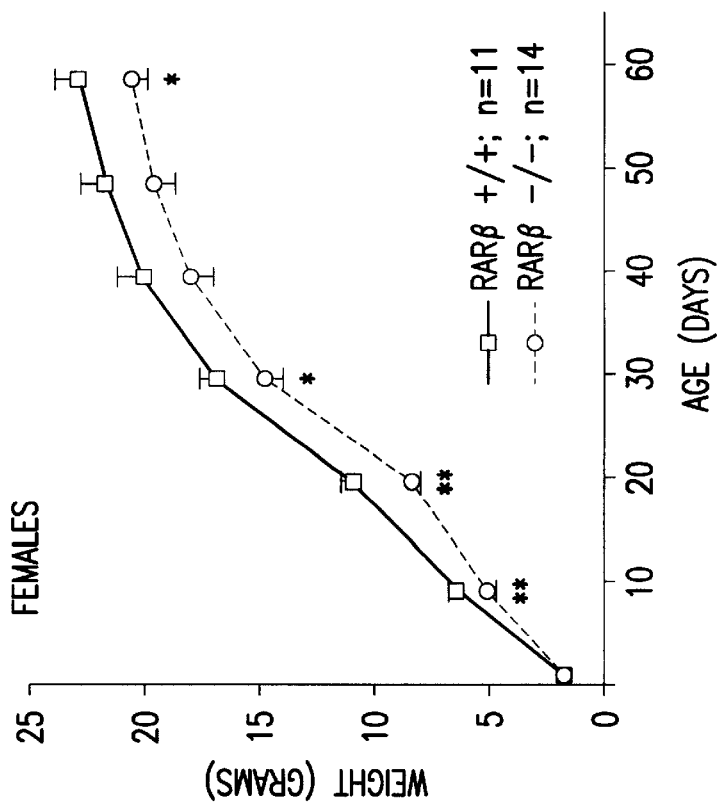

Aβ homozygotes were generated at the expected Mendelian frequency from intercrosses of Aβ$^{+/+}$ heterozygotes (Table 1), indicating that the RARβ mutation is not lethal during embryogenesis or post-natal development. Both Aβ males and females were fertile (Table 1) and lived as long as their WT littermates (at least 2 years). The weight of Aβ mutants was normal at birth but a weight decrease of ~20% in the female and of ~25% in the males was measured for the whole body, the liver and one of the leg muscles at post-natal day 20 (P20; FIG. 11). Similarly, a reduction (~10%) in the length of the tibia, fibula, femur and humerus was evidenced in AP mice as compared to WT. This harmonious post-natal growth retardation syndrome might reflect a decrease of growth hormone production (Bedo, G., et al., *Nature* 339:231–234 (1989)).

TABLE 1

Viability and Fertility of RARβ Mutant Mice

| | Genotype of offspring | | |
|---|---|---|---|
| Intercrosses | +/+ | +/− | −/− |
| Male Aβ+/− × Female Aβ+/− | 44 (1.0) | 110 (2.5) | 52 (1.2) |
| Male Aβ × Female Aβ+/− | — | 30 (1.0) | 35 (1.2) |
| Male Aβ+/− × Female Aβ | — | 35 (1.0) | 33 (0.9) |

The number of wild type offspring was arbitrarily assigned a value of 1.0 and the relative ratio of heterozygote and homozygote animals was calculated accordingly (numbers in parentheses).

Figure 12A:
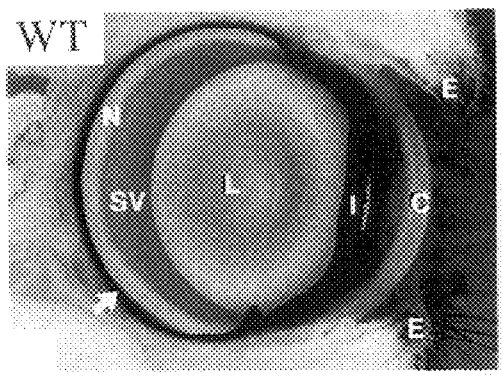
(FIGS. 12A–12D) Comparison of adult (6 month-old) WT and Aβ mutant eyes.
Figure 12B:
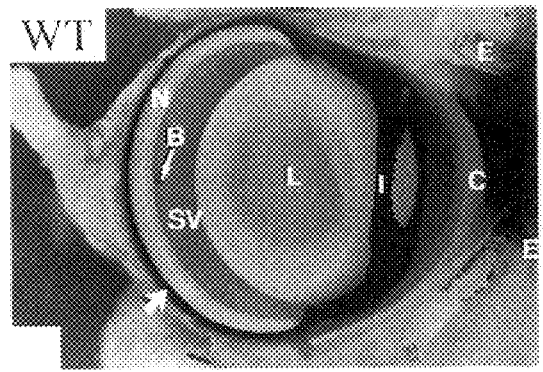
Figure 12C:
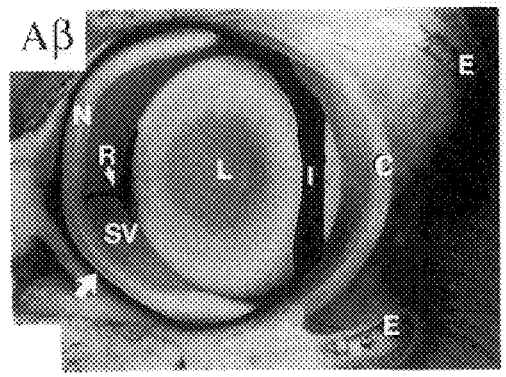
Figure 12D:
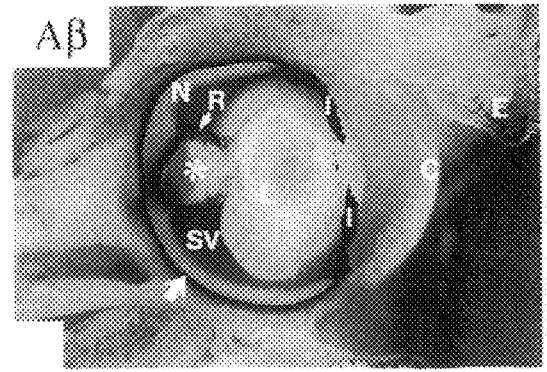
Figure 12E:
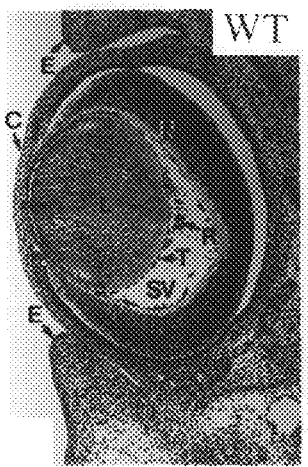
(FIGS. 12E and 12F) Comparison of frontal histological sections from E14.5 WT and Aβ mutant eyes.
Figure 12F:
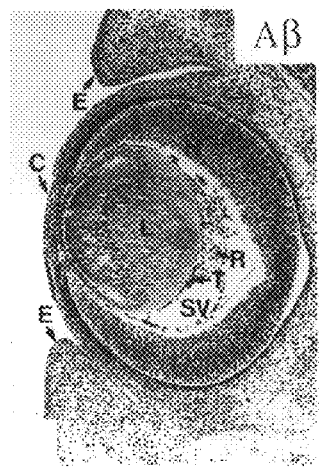
Figure 12G:
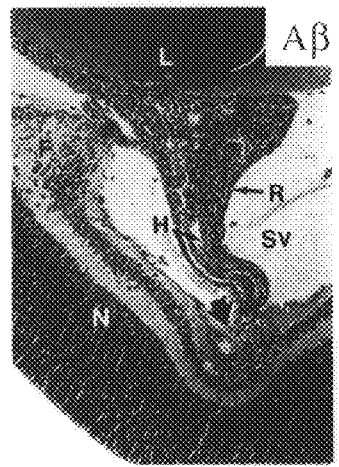
(FIG. 12G) Histological section through the PHPV at P4B, Bergmeister's papilla; C, cornea; E, eyelids; F, congenital retinal fold; H, hyaloid artery and vein; I, iris; L, lens; N, neural retina; R, primary vitreous body (E14.5) or retrolenticular membrane (P4 and adults); SV, secondary vitreous body; T, vascular capsule of the lens. The large white arrow points to the choroid and retinal pigment epithelium which are indistinguishable from one another on macroscopical specimens. The large black arrow points toward the optic papilla. The asterisk indicates the cataract. Same magnifications in FIG. 12A–12D.

C. RARβ$^{-/-}$ (Aβ) Mutants Display Congenital Defects in the Ocular Region and in the Axial Skeleton 1. Ocular defects Examination of eye sections from adult (3 to 8 month-old) Aβ eyes revealed in ~85% of the cases the presence within the vitreous body of an abnormal retrolenticular mass of pigmented tissue (R, FIGS. 12c and d; compare with a and b) which exhibited a large base adherent to the lens (L) and contained a persistent hyaloid artery and vein (see also H, FIG. 12g). This structure was bilateral in the vast majority (~94%) of the affected homozygotes and was only exceptionally observed in their heterozygote and WT littermates (Table 2).

TABLE 2

Macroscopic Ocular Abnormalities in Adult RARβ2 and RARβ Mutants

| | RAR mutant genotypes | | | |
|---|---|---|---|---|
| | Aβ2 | Aβ+/− | Aβ | WT |
| Number of animals analyzed | 8 | 16 | 36 | 14 |
| Retrolenticular membrane or Persistent Hyperplastic Primary Vitreous (PHPV) | U:1/8 B:5/8 | B:1/16 | U:2/36 B:30/36 | U:1/14 |
| Cataract | 0 | 0 | B:3/36 | 0 |
| Persistence of Bermeister's papilla | | U:3/16 B:5/16 | | U:7/14 B:3/14 |
| Percentage of eyes with a PHPV | 68% | 6% | 86% | 3% |

Adult mice were 3 to 8 months old. WT, wildtype; U, unilateral; B, bilateral; ND, not determined.

A persistent and hyperplastic primary vitreous body (PHPV) represents the cause of the retrolenticular membrane (Traboulsi, E., "The Eye" in: *Human Malformations and Related Anomalies* 2:163–191, Eds. R. E. Stevenson et al., Oxford Univ. Press, N.Y. (1993)). The primary vitreous body is a transient embryonic structure consisting of fibroblastic cells stemming from the periocular mesenchyme and a capillary network given off by the hyaloid artery. By E13.5, the fibroblasts of the primary vitreous body (R, FIG. 12e) become dispersed within the rapidly expending secondary vitreous (SV, FIG. 12e), and are no longer identified at E15.5, except at the optic disk, forming the Bergmeister's papilla (or at least part of this structure; reviewed in Barishak, Y. R., *Embryology of the Eye and its Adnexae*, Karger, Basel (1992) and Traboulsi, E., "The Eye" in: *Human Malformations and Related Anomalies* 2:163–191, Eds. R. E. Stevenson et al., Oxford Univ. Press, N.Y. (1993)). About 70% of our WT adult mice displayed a persistent Bergmeister's papilla (Table 2) taking the appearance of a conic mass of pigmented cells covering the optic disk (B, FIG. 12b).

Figure 13A:
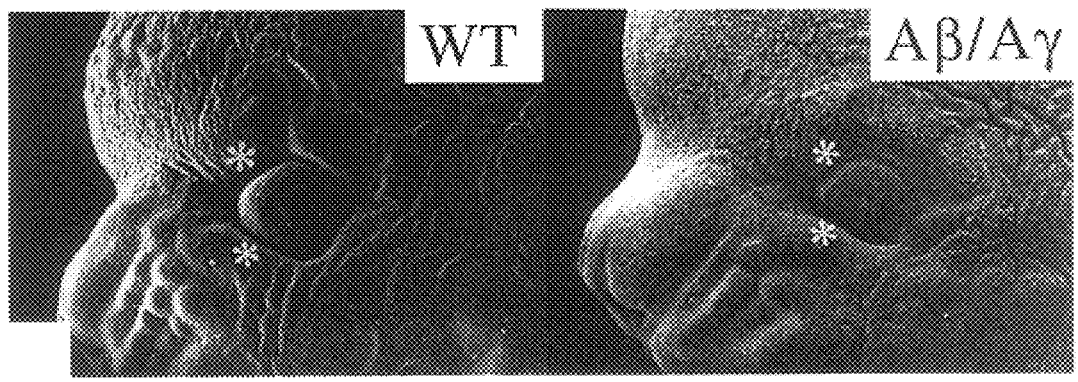
(FIG. 13A) Scanning electron micrograph of the eye region at E12.5; asterisks indicate the anlagen of the eyelids.
Figure 13B:
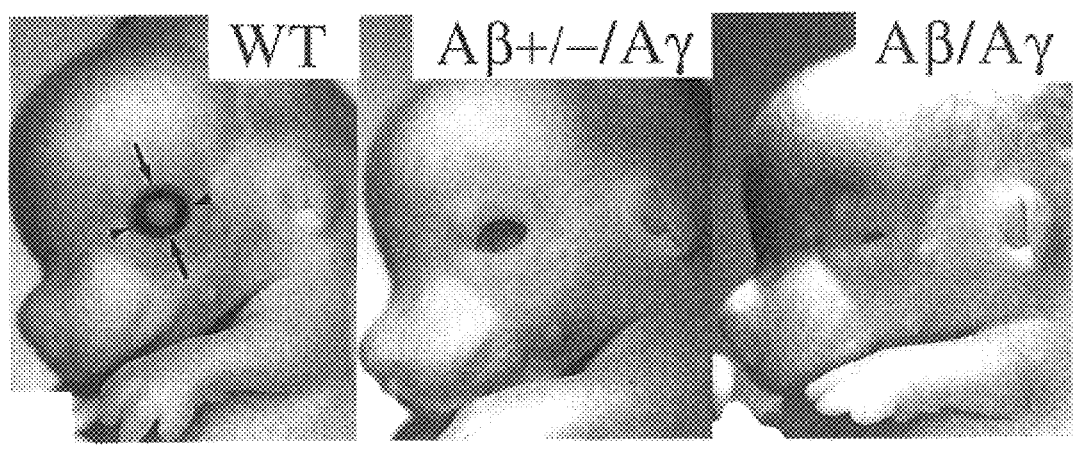
(FIG. 13B) The eye region at 14.5 dpc: note that in all Aβ/Aγ mutants the palpebral aperture is reduced to a narrow slit. The spacing between the two arrowheads and the two arrows correspond to the intercanthal distance and height of the palpebral aperture respectively, whose measurements permitted to calculate the surface of the palpebral aperture as represented in (FIG. 13C).
Figure 13C:
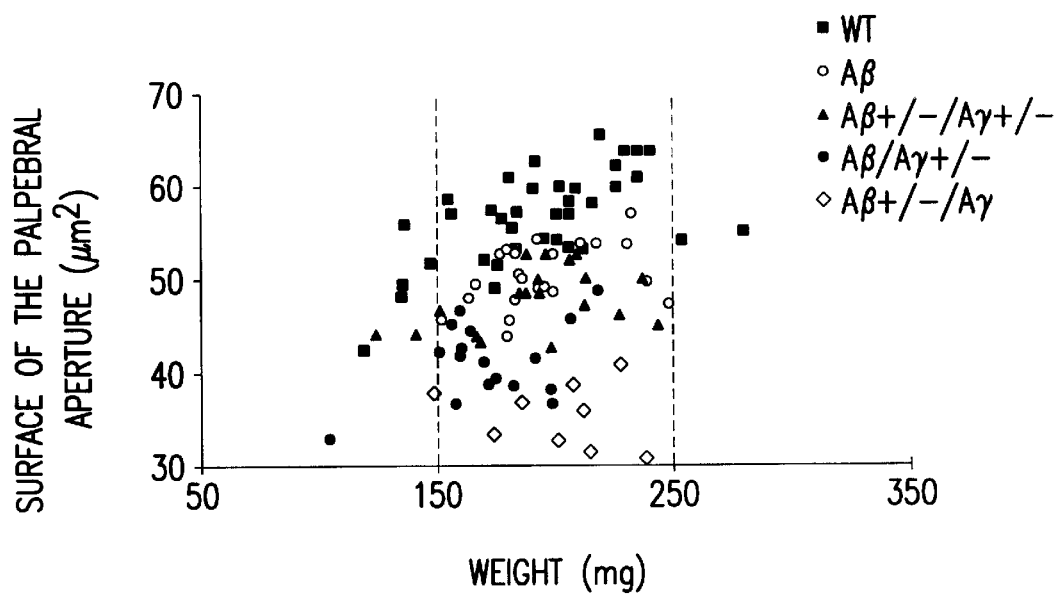
FIG. 13. Reduction of the palpebral aperture in RAR single and compound mutants (genotypes as indicated).
(FIG. 13D) Mean surfaces of the palpebral aperture are presented with standard errors (SEM). After testing for normality and variance homogeneity, results obtained for unpaired values were subjected to Student's t-test between group of mice for each genotype. The 0.05 level was selected as the point of minimal statistic significance. Asterisks indicate the level of significance for the observed differences between +/+ and −/− mice (NS, not significant; p<0.01 and *p<0.001).

Late E13.5 Aβ null and WT eyes were histologically indistinguishable. In particular, the closure of the optic fissure which suppresses the possibility of periocular cell migration into the optic cup, was achieved by this stage in both WT and Aβ mutants. However, in E14.5 Aβ fetuses the number of cell nuclei in the secondary vitreous was 4 to 6 times that of the WT (compare R, FIGS. 12*e* and *f* and five E18.5 Aβ mutants showed a well defined, bilateral mass of densely packed cells behind the lens (Table 3). The first pigmented retrolenticular cells (see R in FIG. 12*g*) appeared at P4 concomitantly with the onset of appearance of melanin granules in the choroidal fibroblasts of both WT and Aβ mutants. These observations indicate that the loss of RARβ results in the maintenance and overproliferation of the fibroblastic neural crest cell (NCC)-derived component of the primary vitreous body (Johnston, M. C., et al., *Exp. Eye Res.* 29:27–43 (1979)).

compared to their WT littermates (FIGS. 13*c* and *d*). A mild reduction of the palpebral aperture was also observed in E14.5 Aα, Aγ$^{+/-}$ and Aγ fetuses (FIGS. 13*c* and *d*). All 3 RARs are thus involved in the ontogenesis of the eyelids, probably through controlling the initial position of the origins of these structures (FIG. 13*a* and see below).

2. Axial Skeletal Defects

Homozygous RARβ mutants displayed some homeotic transformations and malformations of cervical vertebrae which were not previously observed in both RARβ2 (Mendelsohn, C., et al., *Dev. Biol.* 166:246–258 (1994)) and RARβ mutants (Luo, J., et al., *Mech. Dev.* 53:61–71 (1995)). Four per cent of the Aβ mutants displayed a ventral median

TABLE 3

Abnormalities of the Eye and Its Adnexae in RAR Mutant Fetuses

| | Aα/Aβ | | Aβ/Aγ | | Aβ+/–/Aγ+/– | Aβ+/–/Aγ | Aβ/Aγ+/– | Aα/Aβ+/– | Aβ | Aγ | |
|---|---|---|---|---|---|---|---|---|---|---|---|
| Age of the fetuses | 14.5 | 18.5 | 14.5 | 18.5 | 18.5 | 18.5 | 18.5 | 18.5 | 18.5 | 18.5 | |
| Number of fetuses examined | 3 | 6 | 5 | 7 | 6 | 8 | 6 | 5 | 5 | 10 | VAD |
| Small conjunctival sac | 0 | 0 | B:# | B:# | ND | ND | ND | ND | 0 | 0 | + |
| Lens abnormalities | | | | | | | | | | | |
| Corneal-lenticular stalk | 0 | 0 | B:1/5 | B:1/7 | 0 | 0 | 0 | 0 | 0 | 0 | NR |
| Lens degeneration | 0 | 0 | 0 | B:# | 0 | 0 | 0 | 0 | 0 | 0 | + |
| Mesenchymal defects | | | | | | | | | | | |
| Agenesis of the corneal stroma | 0 | 0 | B:# | B:# | 0 | 0 | 0 | 0 | 0 | 0 | + |
| Agenesis of the iris stroma | NA (1) | 0 | NA (1) | B:# | 0 | 0 | 0 | 0 | 0 | 0 | + |
| Agenesis of the anterior chamber | NA (1) | 0 | NA (1) | B:# | 0 | 0 | 0 | 0 | 0 | 0 | + |
| Agenesis of the sclera | NA (1) | 0 | NA (1) | B:# | 0 | 0 | 0 | 0 | 0 | 0 | NR |
| Retrolenticular membrane | | | | B:# | | B:# | | | | | |
| (PHPV) | B:# | B:# | B:# | Ch:# | B:5/6(*) | Ch:1/8 | B:5/6 | U:1/5(*) | B:5/5 | U:1/5(*) | + |
| Retinal defects | | | | | | | | | | | |
| Shortening of ventral retina | 0 | 0 | B:# | NA (2) | ND | ND | ND | ND | 0 | 0 | + |
| Eversion of neural retina | 0 | 0 | U:2/5 | U:2/7 | ND | ND | ND | ND | 0 | 0 | + |
| Retinal dysplasia | 0 | 0 | B:3/5 | B:# | ND | ND | ND | ND | 0 | 0 | + |
| Coloboma of the optic disk | | | | U:3/7 | | | | | | | |
| | 0 | 0 | B:2/5 | B:2/7 | ND | ND | ND | ND | 0 | 0 | + |
| Coloboma of the iris | 0 | 0 | U:1/5 | 0 | ND | ND | ND | ND | 0 | 0 | + |
| Agenesis of Harderian glands | | | | | | U:1/8 | | | | U:1/10 | |
| | NA (1) | 0 | NA (1) | B:# | 0 | B:6/8 | U:1/6 | 0 | 0 | B:2/10 | NR |
| Agenesis of naso-lacrimal duct | NA (1) | 0 | NA (1) | B:# | ND | ND | ND | ND | 0 | 0 | NR |

: these abnormalities are completely penetrant. U, unilateral; B, bilateral; NA, not applicable; (1) the corresponding structure is not yet formed at E14.5; (2) the relative lengths of the ventral and dorsal portions of the retina cannot be estimated at this stage due to extensive foldings; (*) very small retrolenticular membrane compared to that found in the other genotypes. ND, not deternnined; NR, not reported; Ch, chondrified; VAD, vitamin-A deficiency syndrome. For further details see textand Lohnes, D., et al., Development 120:2723–2748(1994).

Additional eye defects observed in Aβ null mice included congenital folds of the retina and cataracts, both of which are likely to be secondary to mechanical and/or metabolic stresses resulting from the presence of the PHPV. A single large fold of the neural retina was detected in 4 (out of 10) Aβ null eyes at E18.5 and was always confined to an area in contact with the retrolenticular membrane (F in FIG. 12*g*). Cataracts were observed in ~8% of the adult Aβ mutants (Table 2) and characterized by a disruption of the lens basement membrane and disorganisation of the lens fibres in contact with the PHPV (asterisk in FIG. 12*d*).

Figure 14A:
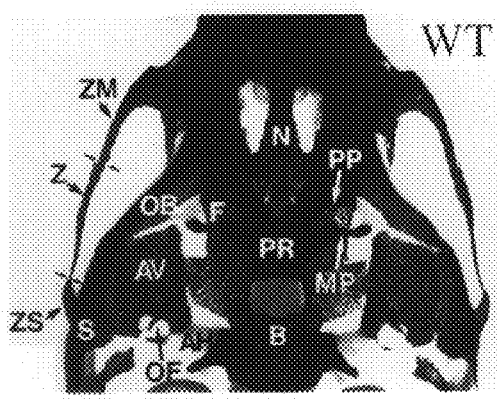
(FIGS. 14A–14C) Dorsal views.
Figure 14B:
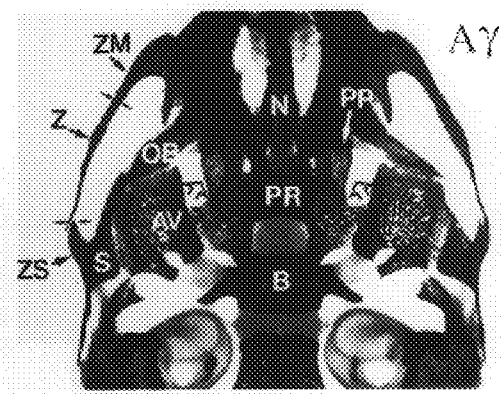
Figure 14C:
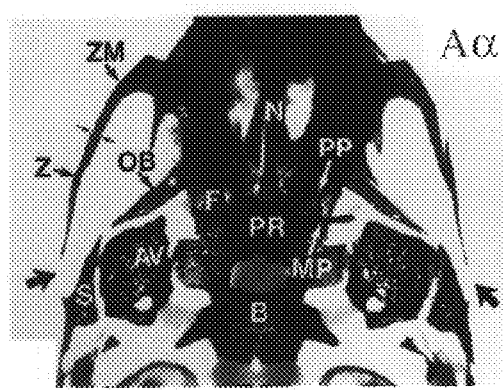
Figure 14D:
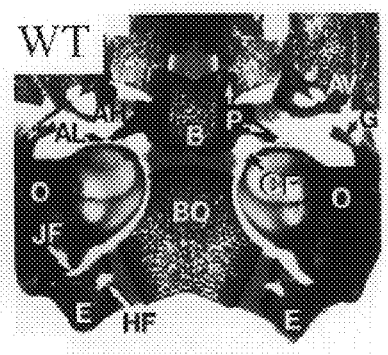
(FIGS. 14D–14G) Ventral views.
Figure 14E:
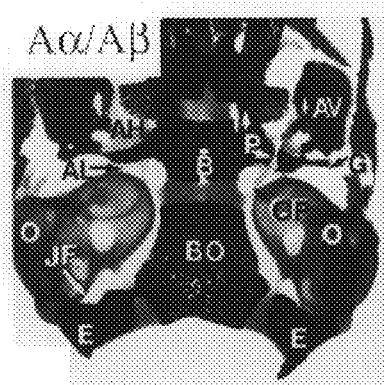
Figure 14F:
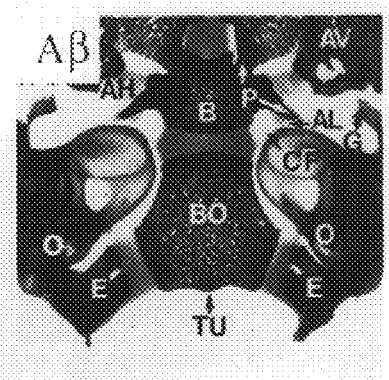
Figure 14G:
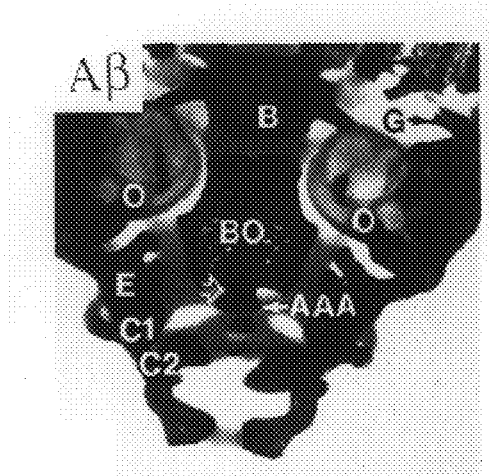

Eyelids first appear at E12.5 (asterisks in FIG. 13*a*) and unite between E15 and E16.5 (Harris, M. J., and McLeod, M. J., et al., *Anat Embryol.* 164:207–220 (1982)). Aβ$^{+/-}$ and Aβ mutants analyzed at E14.5, i.e. before the onset of eyelid closure, displayed a mild reduction of the palpebral aperture tubercle at the caudal edge of the basioccipital (BO) bone (TU, FIG. 14*f* compare with *d*), eventually fused with the anterior arch of the atlas (open white arrow in FIG. 14*g*). These features are indicative of a posterior homeotic transformation of the basioccipital bone (discussed in Lohnes, D., et al., *Development* 120:2723–2748 (1994)). Eleven per cent of the Aβ mutants displayed a posteriorization of the seventh cervical vertebra (posterior transformation of C7 to T1 in Table 4) characterized by the connection of this vertebra with a supernumerary rib fused ventrally to the first thoracic rib (Table 4). This transformation was usually unilateral and the ectopic C7 rib never contacted the sternum. Additionally, 10% of the Aβ mutants displayed malformations of the neural arches of the first three cervical vertebrae which were only exceptionally observed in WT fetuses (Table 4).

TABLE 4

Axial Skeletal and Cartilage Abnormalities in RAR Mutants

| | RAR mutant genotypes | | | | |
|---|---|---|---|---|---|
| | Aα | Aβ | Aγ | Aα/Aβ+/− | Aα/−/Aβ |
| Total number of skeletons examined | 15 | 75 | 12 | 15 | 15 |
| Number of malformed skeletons | 11 (73%) | 27 (36%) | 12 (100%) | 15 (100%) | 9 (60%) |
| Axial skeletal abnormalities | | | | | |
| *Transformations* | | | | | |
| *Anteriorizations* | | | | | |
| Anterior transformation of C2 to C1 | 1 (7%) | 0 | 1 (8%) | 3 (20%) | 0 |
| Anterior transformation of C6 to C5 | 0 | 0 | 0 | 0 | 0 |
| Anterior transformation of T8 to T17 | 3 (20%) | 1 (1%) | 5 (42%) | 0 | 0 |
| Anterior transformation of L1 to T14 | U:1 (7%) | | | U:1 (7%) | |
| | B:1 (7%) | 0 | 0 | B:5 (33%) | 0 |
| *Posteriorizations* | | | | | |
| Posterior tuberele on Bo | 0 | 2 (3%) | 2 (17%) | 0 | 0 |
| Fusion of Bo with C1-AA | 0 | 1 (1%) | 1 (8%) | 0 | 0 |
| Posterior transformation of C7 to T1 | 3 (20%) | 8 (11%) | 0 | 0 | 1 (7%) |
| *Malformations* | | | | | |
| Bo without hypoglossal nerve foramen | 0 | 0 | 0 | 0 | 0 |
| Fusion of C1-AA with C2 dens | 6 (40%) | 15 (20%) | 3 (25%) | 8 (53%) | 8 (53%) |
| C1 bifid | 0 | 2 (3%) | 1 (8%) | 3 (20%) | 0 |
| Dyssymphysis of C1 neural arch | 0 | 2 (3%) | 0 | 0 | 0 |
| C2 bifid | 0 | 5 (7%) | 5 (42%) | 5 (33%) | 2 (13%) |
| Fusions of neural arches of C2 and C3 | 1 (7%) | 2 (3%) | 1 (8%) | 2 (13%) | 0 |
| Sterum malformations | 0 | 0 | 0 | 0 | 1 (7%) |
| Xiphoid process malformation | 0 | 0 | 0 | 0 | 0 |
| Cartilage abnormalities | | | | | |
| *Larynegeal cartilages* | | | | | |
| Thyroid cartilage fused to hyoid bone | 1 (7%) | 0 | 0 | 1 (7%) | 0 |
| Misshapen thyroid cartilage | 0 | 0 | 0 | 0 | 0 |
| Misshapen arytenoid cartilage | 0 | 0 | 0 | 0 | 0 |
| Misshapen cricoid cartilage | 0 | 0 | 0 | 0 | 0 |
| Cricoid cartilage fused to traeheal rings | 0 | 0 | 0 | 0 | 0 |
| Tracheal cartilages | 1 (7%) | 0 | 11 (92%) | 3 (20%) | 0 |

| | RAR mutant genotypes | | | | |
|---|---|---|---|---|---|
| | Aα/Aβ | Aβ+/−/Aγ | Aβ/Aγ+/− | Aβ/Aγ | WT |
| Total number of skeletons examined | 8 | 14 | 13 | 13 | 80 |
| Number of malformed skeletons | 8 (100%) | 14 (100%) | 6 (46%) | 13 (100%) | 13 (16%) |
| Axial skeletal abnormalities | | | | | |
| *Transformations* | | | | | |
| *Anteriorizations* | | | | | |
| Anterior transformation of C2 to C1 | 3 (38%) | 2 (14%) | 0 | 5 (38%) | 0 |
| Anterior transformation of C6 to C5 | U:5 (63%) | 0 | 0 | 0 | 0 |
| | B:1 (13%) | | | | |
| Anterior transformation of T8 to T17 | 0 | 5 (36%) | 0 | 4 (31%) | 0 |
| Anterior transformation of L1 to T14 | U:3 (38%) | | | | |
| | B:2 (25%) | 0 | 0 | 0 | 0 |
| *Posteriorizations* | | | | | |
| Posterior tuberele on Bo | 0 | 2 (14%) | 1 (8%) | 5 (38%) | 0 |
| Fusion of Bo with C1-AA | 1 (13%) | 2 (14%) | 0 | 3 (23%) | 0 |
| Posterior transformation of C7 to T1 | 0 | 0 | 0 | 0 | 1 (1%) |
| *Malformations* | | | | | |
| Bo without hypoglossal nerve foramen | 8 (100%) | 0 | 0 | 0 | 0 |
| Fusion of C1-AA with C2 dens | 5 (63%) | 2 (14%) | 3 (23%) | 5 (38%) | 11 (14%) |
| C1 bifid | 1 (13%) | 9 (64%) | 0 | NA | 0 |
| Dyssymphysis of C1 neural arch | 7 (88%) | 0 | 13 (100%) | 0 | |
| C2 bifid | 2 (25%) | 12 (86%) | 2 (15%) | 13 (100%) | 1 (1%) |

TABLE 4-continued

Axial Skeletal and Cartilage Abnormalities in RAR Mutants

| | | | | | |
|---|---|---|---|---|---|
| Fusions of neural arches of C2 and C3 | 4 (50%) | 1 (7%) | 0 | 6 (46%) | 0 |
| Sterum malformations | 0 | 0 | 1 (8%) | 1 (8%) | 0 |
| Xiphoid process malformation | 8 (100%) | 0 | 0 | 0 | 0 |
| Cartilage abnormalities | | | | | |
| Larynegeal cartilages | | | | | |
| Thyroid cartilage fused to hyoid bone | 7 (88%) | 0 | 0 | 0 | 0 |
| Misshapen thyroid cartilage | 8 (100%) | 0 | 0 | 0 | 0 |
| Misshapen arytenoid cartilage | 8 (100%) | 0 | 0 | 0 | 0 |
| Misshapen cricoid cartilage | 8 (100%) | 0 | 0 | 0 | 0 |
| Cricoid cartilage fused to traeheal rings | 0 | 11 (79%) | 0 | 13 (100%) | 0 |
| Tracheal cartilages | 8 (100%) | 14 (100%) | 0 | 13 (100%) | 0 |

C1 to C7, first to seventh cervical vertebrae; T7 to T14, seventh to fourteenth thoracic vertebrae; L1, first lumbar vertebra; Bo, basioccipital; C1-AA, anterior arch of C1; U, unilateral; B, bilateral; NA, not applicable.

D. RARβ$^{-/-}$ (Aβ) Mice Have Normal Limbs

The present immunohistochemical data demonstrate the presence of the RARβ protein in the interdigital soft tissue and its apparent exclusion from the condensing precartilaginous blastema where the RARα and RARγ proteins are present (FIGS. 15a–c); in the fetal limb, the distribution of RARα protein is ubiquitous and those of RARβ and RARγ proteins are apparently non overlaping. The interdigital expression of RARβ transcripts has suggested that this receptor might be involved in digit separation (Dollé, P., et al., Nature 342:702–705 (1989)). It has also been proposed that RARβ2 could serve to prevent limb bud mesenchymal cells from expressing their chondrogenic bias in cultures (Jiang, H., et al., Int. J. Dev. Biol. 39:617–627 (1995)). None of the fifty adult Aβ mutants analyzed in the present study displayed interdigital webbing and none of the seventy five E18.5 Aβ skeletal preparation showed any limb defect, thus providing definitive evidence that the RARβ is dispensable for both interdigital cell death and normal chondrogenesis of the limbs.

E. The Nervous System of RARβ$^{-/-}$ (Aβ) Mice is Morphologically Normal

Between E12.5 and E18.5, RARβ transcripts are confined to specific regions of the central nervous system including the striatum (caudate-putamen and accumbens nucleus), the olfactory tubercle and the ventral column of the spinal cord (Ruberte et al., Development 118:267–282(1993)). At E18.5, all these structures strongly reacted with the anti-RARβ antibody, but not with the anti-RARα and anti-RARγ antibodies (A, CP and OT in FIGS. 15d–e). The same pattern of RARβ protein distribution was maintained in the adult brain and spinal cord (CP in FIG. 15f). However, histological analysis of E18.5 and adult Aβ mutant brains, which as expected were devoid of RARβ immunostaining (FIG. 15g), did not reveal any abnormality (e.g. FIGS. 16d and e).

Figure 16A:
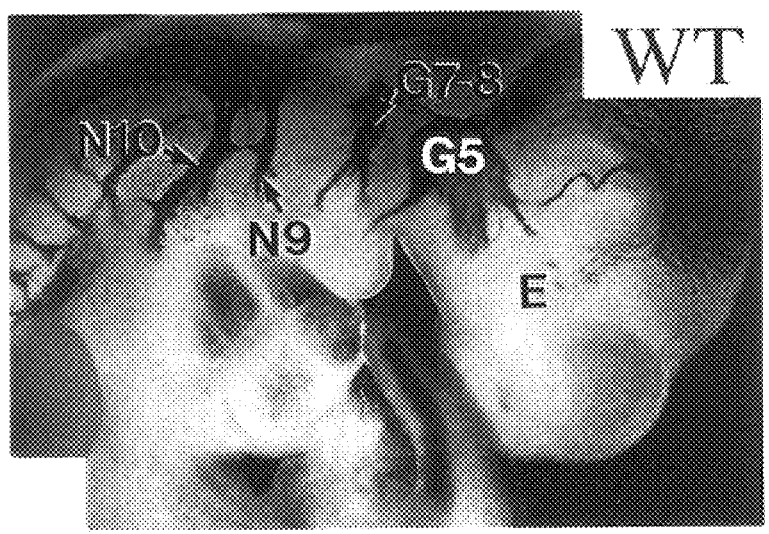
(FIGS. 16A–16C) E10.5 embryos immunolabelled with a monoclonal antibody (2H3) against a neurofilament protein.
Figure 16B:
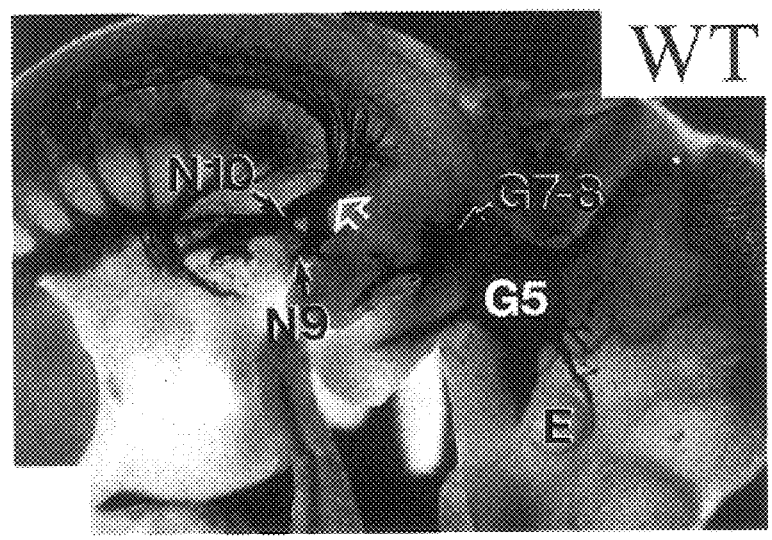
Figure 16C:
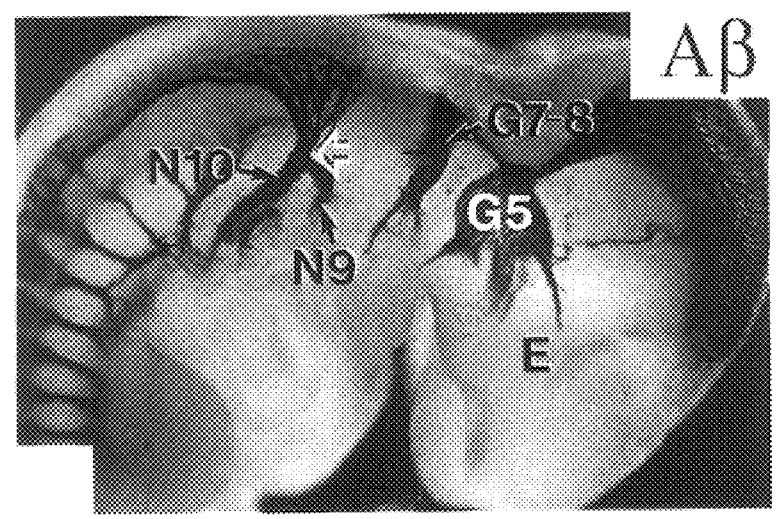
Figure 16D:
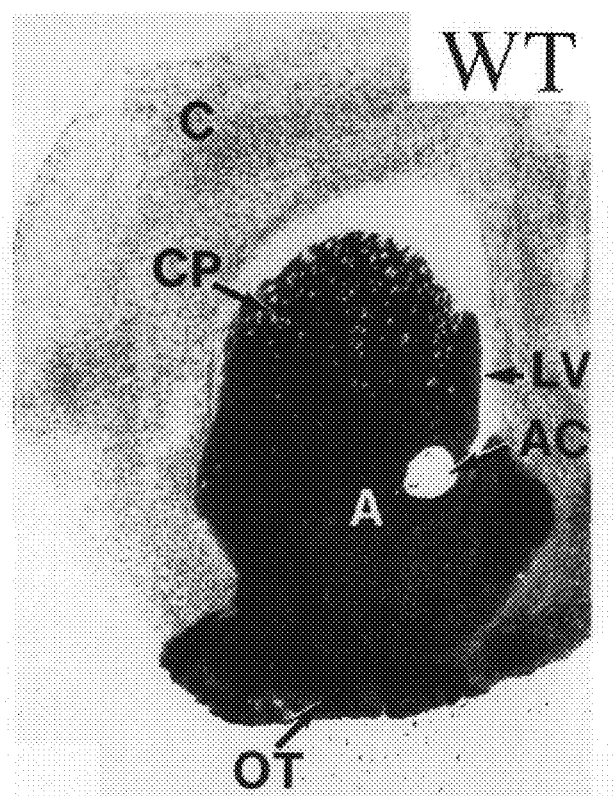
(FIGS. 16D and 16E) Frozen sections from adult brain stained for the demonstration of acetylcholinesterase activity (Paxinos and Watson, 1986). A, accubens nucleus; AC, anterior commissure; C, cerebral cortex; CP, caudate putamen; E, eye; G5 and G7-8, ganglion of cranial nerve V and facial-acoustic ganglia, respectively; LV, Lateral ventricule; N9 and N10, cranial nerves IX and X; OT, olfactory tubercle; the open arrow indicates the fusion between these two nerves. Magnification.
Figure 16E:
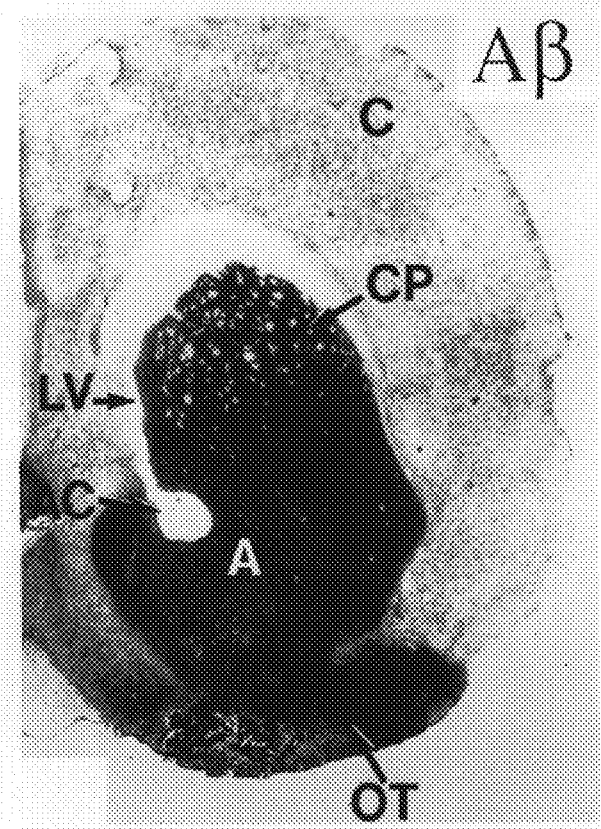

A bilateral fusion of the proximal portions of the glossopharyngeal and vagus nerves (cranial nerves IX and X respectively) represents the only malformation reported by Luo, J., et al., Mech. Dev. 53:61–71 (1995) in Aβ mutants. These authors therefore suggested that the loss of RARβ function might lead to localized disruption of the patterning of the hindbrain region corresponding to rhombomeres 6 and 7. To determine the actual penetrance of this nerve fusion, we performed whole-mount anti-neurofilament immunostaining on 91 Aβ homozygotes, 106 heterozygotes and 40 WT littermates at E10.5 (FIGS. 16a–c). Five (5.5%) Aβ, 4 (4.7%) Aβ$^{+/-}$ and 2 (5%) WT animals displayed an unilateral fusion (open arrow) of the proximal portion of the glossopharyngeal (N9) and vagus (N10) nerves. Therefore, in the genetic background of our mice, this nerve fusion occurs independently from the RARβ mutation.

F. Analysis of RARα$^{-/-}$/RARβ$^{-/-}$ (Aα/Aβ) and RARβ$^{-/-}$/RARγ$^{31}$ (Aβ/Aγ) Compound Mutants Compound RARα/RARβ and RARβ/RARγ null mutants were produced from intercrosses of RARβ$^{+/-}$/RARα$^{+/-}$ or RARβ$^{+/-}$/RAR$^{+/-}$ double heterozygotic mice, respectively. The Mendelian distribution of Aα$^{+/α}$/Aβ, Aα/Aβ$^{+/-}$, Aα/Aβ, Aβ$^{+/-}$/Aγ, Aβ/Aγ$^{+/-}$ and Aβ/Aγ double mutant offspring at E18.5 indicated that the loss of these receptors did not result in embryonic lethality. However, in contrast to all other single null mutants or compound mutants, the Aα/Aβ and Aβ/Aγ mutants invariably died within at most 12 h following cesarian delivery at E18.5.

1. Soft Tissue Defects in RAR α$^{-/-}$/RARβ$^{-/-}$ (A α/Aβ) Mutants

Each Aα/Aβ fetus displayed multiple visceral abnormalities (Tables 5, 6 and 7), most of which are incompatible with life after birth, affecting the respiratory tract (e.g. lung agenesis or hypoplasia, agenesis of the oesophagotracheal septum), the heart outflow tract (e.g. persistent truncus arteriosus, high ventricular septal defect), the arteries destined to the head and forelimbs (summarized in Table 7), the digestive tract (i.e. agenesis of the anal canal), the kidneys and ureters (kidney hypoplasia; hydronephrosis probably secondary to ectopic ureteral openings or involution of the caudal ureter), and the female genital tract (i.e. agenesis of the oviduct, uterus and cranial vagina). The majority of these abnormalities belong to the fetal VAD syndrome (see VAD in Tables 5 and 6).

With the exception of the retrolenticular membrane, the Aα/Aβ abnormalities were never observed in either Aα or Aβ single mutants. However, most of them have been previously found in Aα/Aβ2 mutants (Mendelsohn, C., et al., Development 120:2749–2771 (1994)), with the notable exceptions of agenesis of the stapedial artery, thymus agenesis or severe ectopias, absence of the spleen and defects of the inferior vena cava.

a. Agenesis of the Stapedial Artery

Figure 14H:
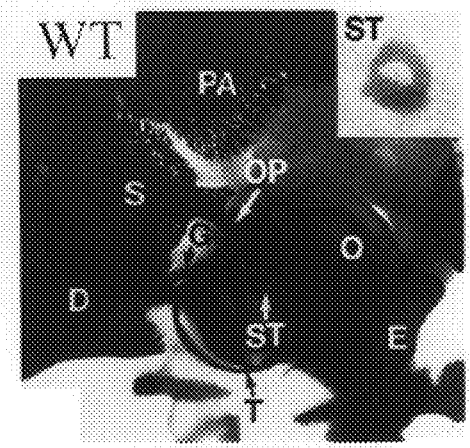
(FIGS. 14H–14K) Lateral views of the skull and nasal cavities.

This artery represents an important morphological landmark, since it corresponds to the remnant of the 2nd aortic arch; its passage through the precartilaginous blastema of the stapes determines the horseshoe shape of this middle ear ossicle (Diamond, M. K., J. Morphol. 200:71–86 (1989), and references therein). Unilateral and bilateral agenesis of the stapedial artery was observed on serial histological sections of some Aα/Aβ fetuses and was invariably associated with the absence of the intercrural foramen of the stapes (Table 5). Furthermore, this bony defect was bilaterally observed in some Aα/Aβ skeletons (ST, compare FIG. 14h and i; Table 8). It is noteworthy that these arterial and skeletal defects were not specific of one particular combination of disrupted RARs as they were also detected with lower frequencies in Aα1/Aγ, Aα/Aβ2, Aβ2/Aγ, and Aβ/Aγ mutants (Tables 5 and 8). That the stapedial artery is lacking in some RAR compound mutants extends our previous observations indicating that these nuclear receptors play an important role in the ontogenesis of NCC-derived arterial smooth muscle cells (Mendelsohn, C., et al., *Development* 120:2749–2771 (1994)).

TABLE 5

Abnormalities of the Respiratory System, Heart Outflow Tract, Blood Vessels and Glands in RAR Double Mutants

| | RAR mutant genotypes | | | | |
|---|---|---|---|---|---|
| | Aα/Aβ | | Aβ/γ | | |
| Age of the fetuses | 14.5 | 18.5 | 14.5 | 18.5 | |
| Number of fetuses examined | 3 | 6 | 5 | 7 | VAD |
| Respiratory system abnormalities | | | | | |
| Agenesis of left lung | # | 5/6 | 0 | 0 | + |
| Hypoplastic left lung | 0 | 1/6 | 0 | 0 | + |
| Hypoplastic right lung | # | # | 0 | 0 | + |
| Lack of oesophagotracheal septum | # | # | 0 | 0 | + |
| Diaphragmatic hernia | 0 | 3/6 | 0 | 0 | + |
| Heart outflow tract and vascular defects | | | | | |
| Persistent truncus-ateriosus (NCC) | # | # | 0 | 0 | + |
| Absence of cono-truncal septum (E14.5)/high VSD (E18.5) | # | # | 0 | 0 | + |
| Abnormal arteries derived from Ao.A. 3–6 (NCC) | # | # | 1/5 | 2/7 | + |
| Agenesis of the stapedial artery (NCC) | B:1/3 | U:2/6 | 0 | U:1/7 | NR |
| Double inferior vena cava | ND | 2/6 | 0 | 0 | NR |
| Absence of the inferior vena cava | ND | 1/6 | 0 | 0 | NR |
| Glandular abnormalities | | | | | |
| Persistent cervical thymus (NCC) | U:3/3 | U:4/6 B:1/6 | 0 | 0 | NR |
| Thymus genesis (NCC) | U:2/3 | U:1/6 B:1/6 | 0 | 0 | NR |
| Thyroid hypoplasia (NCC) | ND | U:1/6 | 0 | 0 | NR |
| Shortening of the sublingual duct | NA | U:1/6 B:1/6 | NA | B:# | NR |
| Shortening of the submandibular duct | NA | 0 | NA | 0 | NR |
| Spleen agenesis | 0 | 1/6 | 0 | 0 | NR |

: these abnormalities are completely penetrant. U, unilateral; B, bilateral; NA, not applicable: these ducts are not fully formed at E14.5; NR, not reported; ND, not determined; VAD, vitamin-A deficiency syndrome; high VSD, high ventricular septal defect: this abnormality represents the manifestation at E18.5 of the lack of formation of the cono-truncal septum observed in E14.5 mutants; Ao.A. 3–6: third,fourth and sixth aortic arches; NCC, these defects are likely caused by abnormal migration, proliferation, death or differentiation of neural crest cells. See Mendelsohn, C., et al., Development 120:2749-2771 (1994), for further details, and Table 3 for additional glandular abnormalities in the eye region.

TABLE 6

Abnormalities of the Urogenital and Digestive Tracts in RAR Double Mutants

| | RAR mutant genotypes | | | | |
|---|---|---|---|---|---|
| | Aα/Aβ | | Aβ/γ | | |
| Age of the fetuses | 14.5 | 18.5 | 14.5 | 18.5 | |
| Number of fetuses examined (males:females) | 3 | 1:5 | 5 | 5:2 | VAD |
| Kidney abnormalities | | | | | |
| Renal hypoplasia | B:# | B:# | 0 | 0 | + |
| Hydronephrosis | | U:2/6 | U:2/7 | | |
| | 0 | B:3/6 | 0 | B:#/7 | + |
| Ureter abnormalities | | | | | |
| Agenesis of caudal ureter | U:2/7 | | | | |
| | 0 | U:1/6 | 0 | B:1/7 | + |
| Ectopic urethral openings (a) | | U:2/6 | U:1/5 | U:1/7 | |
| | B:# | B:4/6 | B:2/5 | | + |
| Agenesis of the Müllerian duct (E14.5 fetuses) or of its derivatives (E18.5 females) (b) | | | | | |
| Complete | B:# | B:# | 0 | 0 | + |
| Partial (caudal portion missing) | | | U:1/5 | | |
| | NA | NA | B:2/5 | 0 | + |
| Agenesis of the anal canal | # | # | 0 | 1/7 | NR |

: these abnormalities are completely penetrant. U, unilateral; B, bilateral; NA, not applicable; NR, not reported; VAD, vitamin-A deficiency syndrome. (a): opening of the ureter in the terminal portion of the Wolfflan duct and/or common openings of the Wolfflan duct and ureter in the urogenital sinus (E14.5) or opening of the ureters in the urethra (E18.5); (b): absence of the oviducts, uterus and cranial vagina.

TABLE 7

Defects of Arteries in RAR Double Mutants

| | RAR mutant genotypes | |
|---|---|---|
| | Aα/Aβ | Aβ/Aγ |
| Number of fetuses examined | 9 | 12 |
| Arch of the aorta on the right side | 2/9 | 1/12 |
| Arch of the aorta on the right side; retrooesophageal left subclavian artery | 4/9 | 1/12 |
| Arch of the aorta on the right side and located in the cervical region; retrooesophageal left subclavian artery | 1/9 | 0 |
| Retrooesophageal right subclavian artery | 0 | 1/12 |
| Aberrant origin of the right pulmonary artery from ipsilateral arch of the aorta | 1/9 | 0 |
| Aberrant origin of the right pulmonary artery from ipsilateral common carotid; retrooesophageal right subclavian artery | 1/9 | 0 |

Defects of the arteries normally derived from the aortic arches 3 (i.e., common carotid), 4 (i.e., arch of the aorta, subclavian arteries) and 6 (i.e., pulmonary arteries) in RAR double mutants. For further details see Mendelsohn, C., et al., Development 120:2749-2771 (1994).

TABLE 8

Abnormalities of the Cranial Skeletons in RAR Mutants

| | RAR mutant genotypes | | | | | | | | | | | | |
|---|---|---|---|---|---|---|---|---|---|---|---|---|---|
| Number of skeletons examined | Aβ+/−  50 | Aβ  50 | Aγ+/−  7 | Aγ  15 | Aβ+/−  Aγ+/−  12 | Aβ+/−  Aγ  14 | Aβ  Aγ  13 | Aβ  Aγ+/−  14 | Aα  15 | Aα  Aβ+/−  14 | Aα  Aβ  6 | Aα+/−  Aβ  15 | WT  26 |
| Hypoplasia of ethmoturbinates | 0 | 0 | 0 | 0 | 0 | ND | # | ND | 0 | 0 | 0 | 0 | 0 |
| Agenesis of metoptic pillar | 7/50 | 15/50 | 0 | 11/15 | 4/12 | 11/14 | 12/13 | 10/14 | 1/15 | 1/14 | 0 | 2/15 | 4/26 |
| Partial | U:3/50  B:4/50 | U:8/50  B:7/50 | 0 | U:5/15  B:5/15 | U:2/12  B:2/12 | U:5/14  B:1/14 | U:1/13 | U:3/14  B:7/14 | U:1/15 | U:1/14 | 0 | U:2/15 | U:2/26  B:2/26 |
| Complete | 0 | 0 | 0 | U:1/25 | 0 | U:3/14  B:4/14 | B:11/13 | 0 | 0 | 0 | 0 | 0 | 0 |
| Pterygoquadrate element | 0 | 0 | 0 | 0 | 0 | 0 | 0 | U:2/15 | B:4/14 | U:3/14  B:1/6 | U:3/6  0 | 0 | |
| Abnormal gonial bone | 0 | 0 | 0 | 0 | 0 | 0 | 0 | 0 | 0 | 0 | U:1/6  B:2/6 | 0 | 0 |
| Squamosal malfoniied | 0 | 0 | 0 | 0 | 0 | 0 | 0 | 0 | B:4/15 | B:11/14 | B:# | 0 | 0 |
| Imperforated stapes | 0 | 0 | 0 | 0 | 0 | 0 | U:1/13 | 0 | 0 | 0 | B:2/6 | 0 | 0 |

Note that the abnormalities of the occipital bone have been listed in Table 4 since this bone represents, in ontogenic terms, a modified vertebra. #, this abnormalities is completely penetrant; U, unilateral; B, bilateral; ND, not determined.

b. Thymic Agenesis and Ectopia and Absence of the Spleen

The Aα/Aβ thymic phenotype represents the only obvious example of developmental defects whose severity is increased as compared to the Aα/Aβ2 situation (Table 5). A complete thymic lobe in the neck region (i.e. a persistent cervical thymus) and/or the absence of one or both thymic lobes were consistently observed in Aα/Aβ mutants, but not in Aα/Aβ2 mutants, which however displayed milder forms of thymic ectopias (i.e. accessory cervical thymus bodies and aberrant pharyngeal lymphoid tissue; Mendelsohn, C., et al., Development 120:2749–2771 (1994)). Thymic agenesis and ectopias generated in chicken by ablation of postotic rhombencephalic NCC are always associated with defects of the heart outflow tract or aortic arches and sometimes with thyroid agenesis or hypoplasia (Bockman, D. E. and Kirby, M. L., Science 223:498–500 (1984)). That this spectrum of malformations is completely recapitulated in some Aα/Aβ (as well as in some Aα/Aγ mutants; Mendelsohn, C., et al., Development 120:2749–2771 (1994)) is consistent with our previous hypothesis of a mesectodermal deficiency in mice lacking RARs Mendelsohn, C., et al., Development 120:2749–2771 (1994); Kastner, P., et al., Cell 83:859–869 (1995)).

Spleen agenesis was observed in only one (out of 9) Aα/Aβ mutants (Table 5). However, since this abnormality was absent in the dozens of WT and mutant fetuses that we have analyzed (including Aα/Aγ), it might reflect a specific developmental function of RARβ1/β3 isoforms in spleen.

c. Defects of the Inferior Vena Cava

Abnormal development of the embryonic venous system can result in absence of the hepatic and prerenal portions of the inferior vena cava (absence of the inferior vena cava; Table 5), or in the presence of both right (i.e. normal) and left (i.e. supernumerary) inferior vena cava below the renal veins (double inferior vena cava; Table 5). These two abnormalities were observed with the same low penetrance in Aα/Aβ mice (present data) and Aα/Aβ2 mice. It is noteworthy that in Aα/Aβ (Aα/Aβ2) mice as in human patients, absence of the inferior vena cava was always associated with, and thus might be secondary to a variety of congenital heart defects (Gray, S. W. and Skandalakis, J. E., Embryology for Surgeons. The Embryological Basis for the Treatment of Congenital Defects, Saunders Co., Philadelphia (1972)).

2. Soft Tissue Defects of RARβ$^{-/-}$/RARγ$^{-/-}$ (Aβ/Aγ) Mutants

As expected from our previous analysis of Aβ2/Aγ mutants, (Lohnes, D., et al., Development 120:2723–2748 (1994); Mendelsohn, C., et al., Development 120:2749–2771 (1994)), Aβ/Aγ mutants displayed severe ocular defects (Table 3), and a high frequency of hydronephrosis most likely caused by abnormalities of the caudal ureters (Table 6). Abnormalities of the great arteries derived from the 3rd, 4th and 6th aortic arches which were absent in the 3 previously analyzed Aβ2/Aγ were here observed in ~25% of the Aβ/Aγ mutants (Tables 5 and 7). Some of the ocular malformations which we previously overlooked in Aβ2/Aγ mutants, including defects in mesenchymal structures (sclera, iris and secondary vitreous), congenital cataracts, shortening of the ventral retina and pre-natal retinal dysplasia will be described here.

a. Defects of Ocular Structures Derived from the Mesectoderm

Figure 17A:
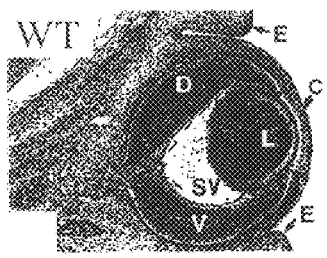
FIGS. 17A, 17B, 17E and 17F: ×43.
Figure 17B:
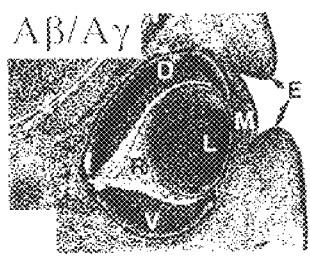
Figure 17C:
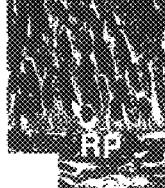
FIG. 17C, FIG. 17D: ×430.
Figure 17D:
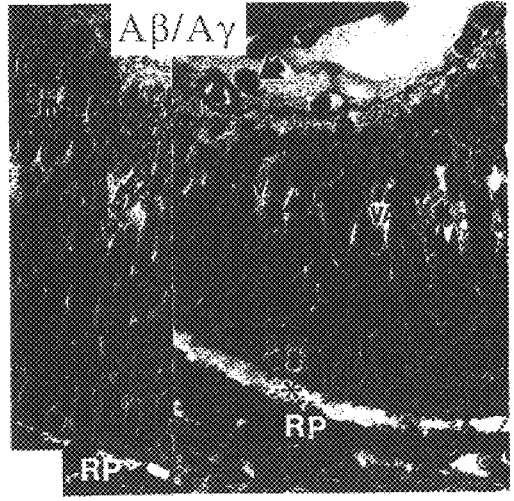
Figure 17E:
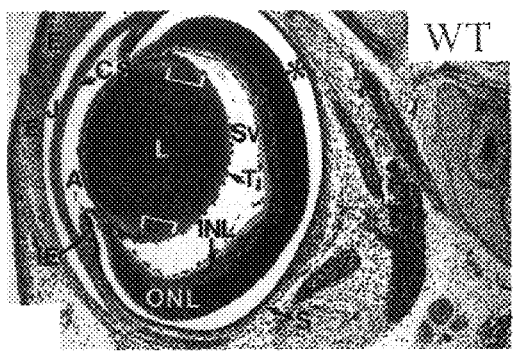
Figure 17F:
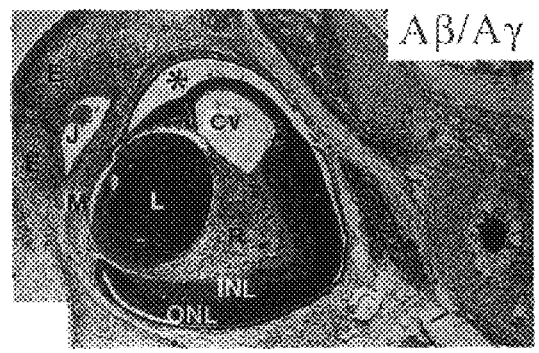
Figure 17G:
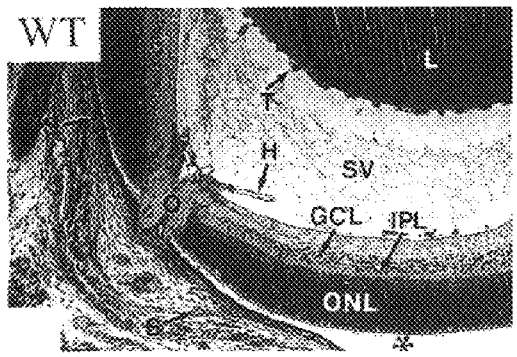
FIG. 17G, FIG. 17H: ×86.
Figure 17H:
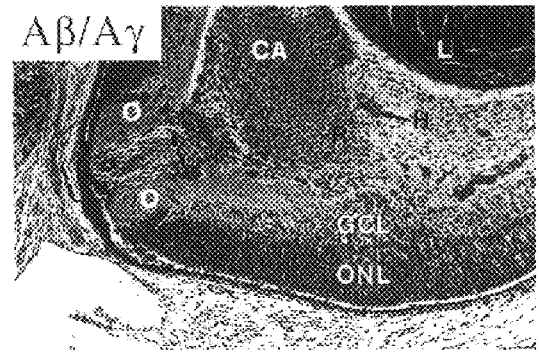
Figure 17I:
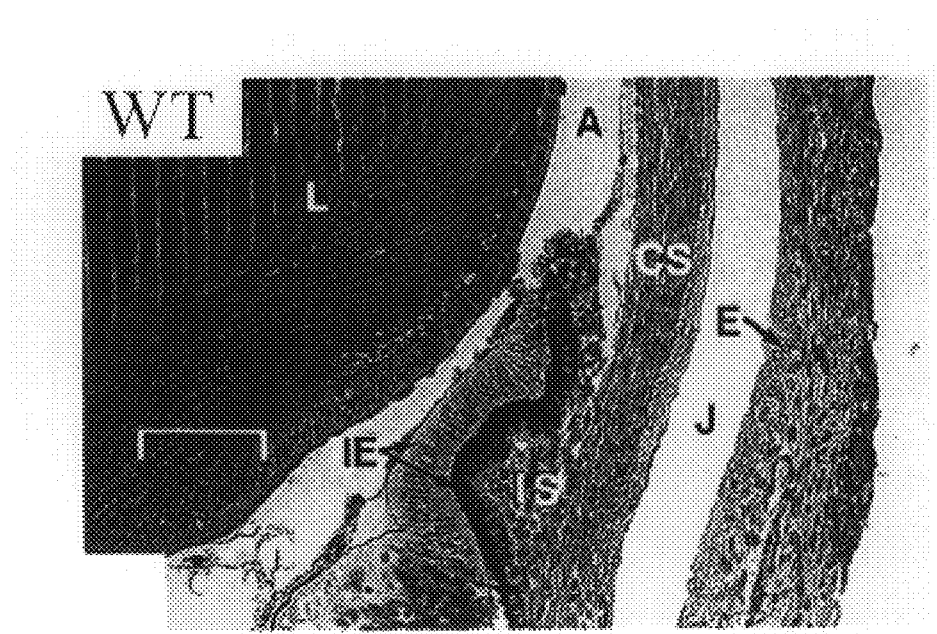
FIG. 17I, FIG. 17J: ×178.

In Aβ/Aγ mutants, the corneal stroma (CS, FIGS. 17e and i), that of the iris (IS, FIG. 17i) and the anterior chamber of the eye (A, FIGS. 17e and i) were consistently absent and replaced by a thick layer of loosely organised mesenchyme filling the space between the lens and the (small) conjunctival sac or the surface ectoderm (M, FIGS. 17b, f and j); the sclera was never identified (S in FIGS. 17e and g compare with f and h); the primary vitreous body filled completely the space between the retina and the lens due to extensive cell proliferation (demonstrated by the presence of numerous mitotic figures; and to the lack of formation of the secondary vitreous (see R, FIGS. 17b, f and h). Local aberrant differentiation of the ocular mesenchyme into cartilage was always observed within the vitreous body (CA, FIG. 17h).

b. Lens Abnormalities

Figure 17J:
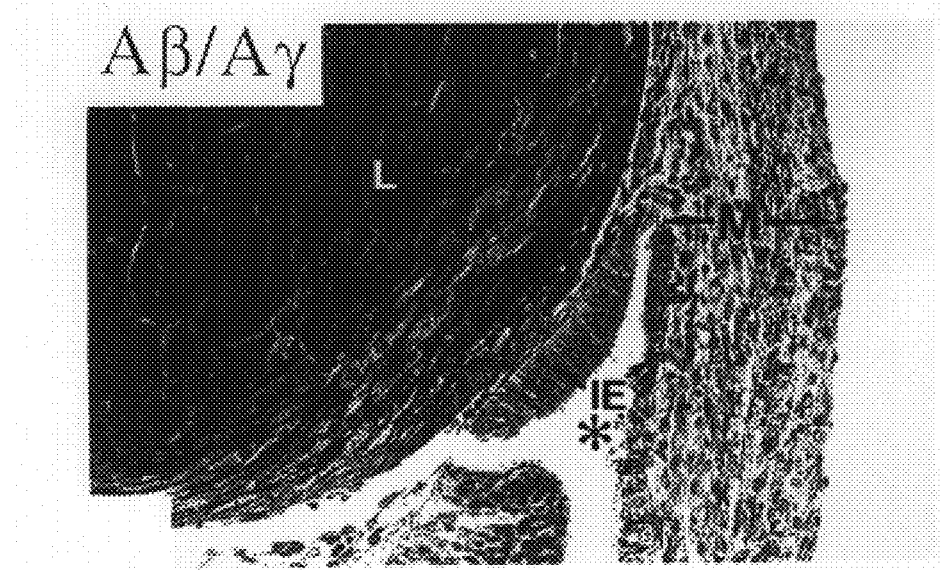

The histological structure of the Aβ/Aγ lenses was normal at E14.5 (compare L, FIGS. 17a and b). In contrast, in all Aβ/Aγ lenses seen at E16.5 and E18.5, the equatorial cells were missing (L, FIGS. 17f and j) and the secondary fibers displayed features of degeneration (i.e. swelling and vacuolation of their cytoplasm; L, FIG. 17j).

c. Retinal Defects

Shortening of the ventral retina and pre-natal retinal dysplasia represent the only two abnormalities of the fetal VAD syndrome not previously detected in RAR compound mutants. In all E14.5 Aβ/Aγ mutants, the ventral portion of the retina was bilaterally reduced in size with respect to its dorsal counterpart (compare V and D, FIGS. 17a, b). This defect was consistently associated with a ventral rotation of the lens (L, FIG. 17b), as it is also the case in RXRα null mutants where these two abnormalities were first described (Kastner, P., et al., Cell 78:987–1003 (1994)).

The normal E14.5 mouse neural retina shows two layers of nuclei, the outer and inner neuroblastic layers (ONL and INL respectively, FIG. 17c) which, at E16.5, become separated by a layer of cell processes, the primitive inner plexiform layer (IPL). Mitotic figures (arrow in FIG. 17c) are confined to the outermost ONL cells. In 3 out of 5 E14.5 Aβ/Aγ mutants, large extracellular pockets of empty space (vacuoles, VA in FIG. 17d) were observed between the neuroblasts located at the interface of the ONL and the INL. Cells with irregular outlines and excentrically-positioned nuclei, possibly corresponding to macrophages (large arrows FIG. 17d), were frequently observed within these vacuoles. As these macrophage-like cells often displayed mitotic figures (double arrows in FIG. 17d), the presence of ectopic cell division was a striking feature of the dysplastic phenotype at this developmental stage. In the eyes of the two Aβ/Aγ mutants analyzed at E16.5 and in all E18.5 Aβ/Aγ eyes, some vacuoles had apparently merged into larger cavities (CV, FIG. 17f). Moreover, at 18.5 dpc, the IPL was essentially lacking and the neural retina showed extensive foldings (compare FIGS. 17g and h). Interestingly, a similar retinal dysplasia is also observed in some RXRα null mutants at E14.5.

Figure 13D:
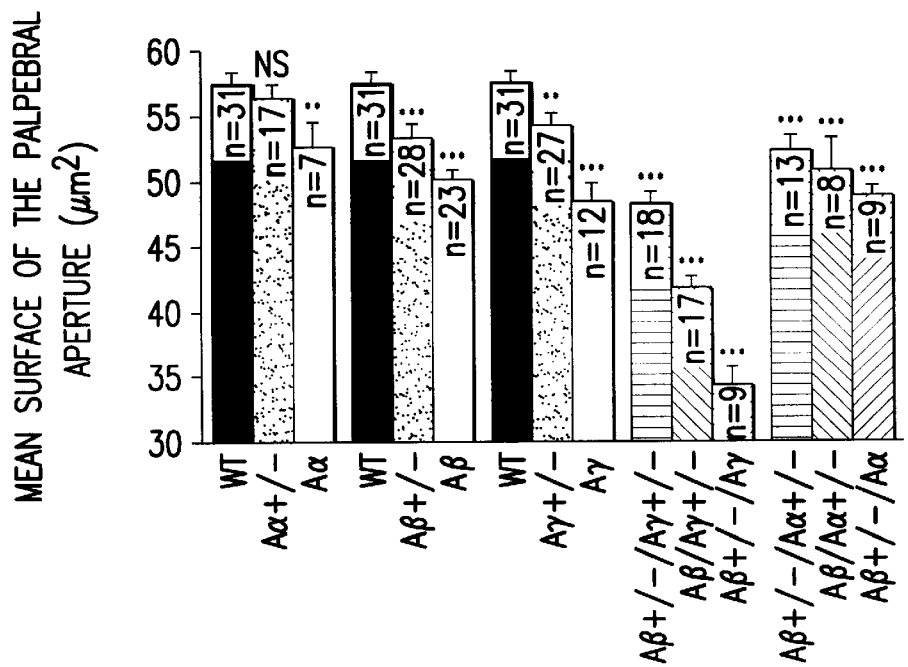

3. Ocular Defects of RARβ$^{-/-}$ (Aβ) Mutants are Increased in RARα$^{-/-}$/RARβ$^{-/-}$ (Aα/Aβ) and in RARβ$^{-/-}$/RARγ$^{-/-}$ (Aβ/Aγ) Compound Mutants The severity of the reduction of the palpebral aperture measured in E14.5 Aβ$^{+/-}$ and Aβ single mutants was increased in all compound mutants of RARβ and RARγ and also, albeit to a lesser extent, in all compound mutants of RARβ and RARα (FIGS. 13b–d). In Aβ/Aγ mutants the palpebral aperture was reduced to small narrow slit (FIG. 13b). The dorsal and ventral folds representing the origins of the eyelids at E12.5 were much closer to one another in Aβ/Aγ mutants than in WT embryos (asterisk in FIG. 13a). In severely affected viable, double mutants (i.e. Aβ/Aγ$^{+/-}$ and Aβ$^{+/-}$/Aγ, FIG. 13b–d), the outcome of this abnormality was a blepharophimosis, i.e. a severe reduction of the definitive palpebral aperture which can be diagnosed after eyelid opening by P14 (see also Grondona, J. M., et al., Development 122:2173–2188 (1996)).

Unexpectedly, a high frequency of PHPV was observed following disruption of only one allele of the RARβ gene in a Aγ and Aγ$^{+/-}$ genetic background (Table 3). In the case of E18.5 Aβ$^{+/-}$/Aγ$^{+/-}$ mutants, this PHPV was small and was not directly connected with the main hyaloid vessels at the optic disk; it was never observed in the twenty Aβ$^{+/-}$/Aγ$^{+/-}$ adult eye. A possible explanation for this discrepancy is that the Aβ$^{+/-}$/Aγ$^{+/-}$ PHPV is not large enough to elicit the maintenance of its own vascular supply and thus disappears together with the hyaloid system by P14.

4. Skeletal Defects of RAR α$^{-/-}$/RARβ$^{-/-}$ (Aα/Aβ) and of RARβ$^{-/-}$ RARγ$^{-/-}$ (Aβ/Aγ) Compound Mutants a. Homeotic Transformations and Other Vertebral Defects Aα/Aβ and Aβ/Aγ compound mutant mice exhibited homeotic transformations absent from the Aβ single mutants (Table 4). Malformations of the axial skeleton were also observed (Table 4). In particular, all Aα/Aβ mutant fetuses lacked the foramen of the hypoglossal nerve (HF in FIG. 14d, compare with FIG. 14e). Amongst vertebral defects, dyssymphysis of the neural arch of C1 represented the only obvious example of defect whose severity was increased in Aα/Aβ and Aβ/Aγ mutant as compared to the Aα/Aβ2 and Aβ2/Aγ situation (Lohnes, D., et al., Development 120:2723–2748 (1994)). The xiphoid process of all the Aα/Aβ mutants (Table 4), on which two supernumerary ossified horns were observed, displayed a delayed ossification.

b. Cranial Skeletal Defects

With the exception of the pterygoquadrate element, craniofacial skeletal defects have only been reported in Aα/Aγ and Aα1/Aα2$^{+/-}$/Aγ compound mutants (Lohnes, D., et al., Development 120:2723–2748 (1994)). In the course of the present study, we incidentally discovered discrete cranial skeletal abnormalities in Aα and Aγ single mutants as well as in compound mutants of either RAR, and RARα or RARβ and RARγ (Table 8). A pterygoquadrate element, previously shown to occur in various compound mutants of RARα1 and RARα (Lohnes, D., et al., Development 120:2723–2748 (1994)), was here observed in ~10% of the Aα mutants (Table 8). Agenesis or severe hypoplasia of the zygomatic process of the squamosal bone (ZS) was seen in about one third of the Aα mutants, resulting in a caudal gap of the zygomatic arch (compare FIGS. 14a and c). A complete absence of the metoptic pillar (MP, FIG. 14a), the caudal limit of the optic nerve foramen (F, FIG. 14a) was observed in some Aγ null fetuses (open arrows in FIG. 14b).

Figure 14I:
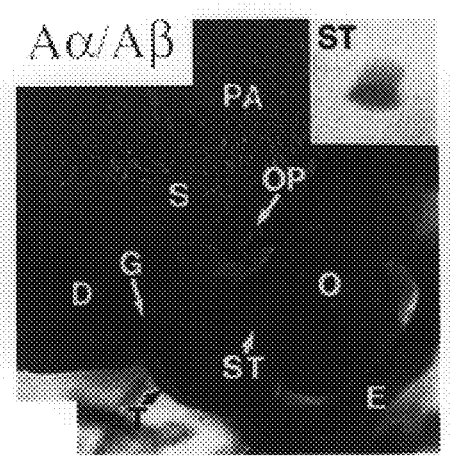
Figure 14J:
Figure 14K:
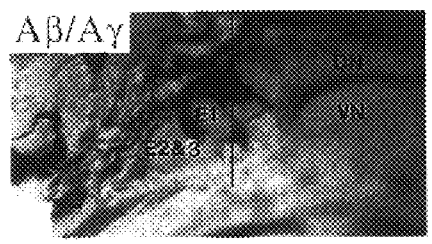
Figure 14L:
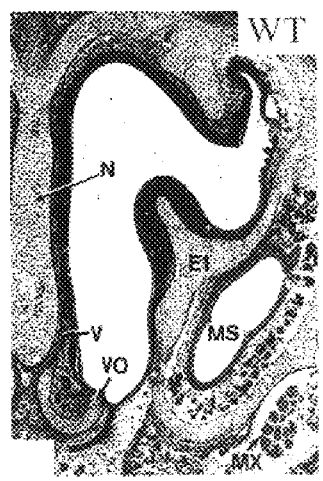
(FIGS. 14L and 14M) Frontal histological sections at comparable levels of the nasal cavities (materialized by the black lines in (FIG. 14J) and (FIG. 14K)). AH and AV, horizontal and vertical portions of the alisphenoid bone; AL, alicochlear commissure, partially masked by the horizontal portion of the pterygoid bone (P); AAA, anterior arch of the atlas; B, basisphenoid bone; BO, basioccipital bone; C1 and C2, first and second vertebrae (atlas and axis) respectively; CF, carotid foramen; D, dentary bone; DN, dorsal nasal concha; E, exoccipital bone; E1-E3, ethmoturbinates; F, optic (cranial nerve II) foramen; G, gonial; HF, hypoglossal nerve (cranial nerve XII) foramen; JF, jugular foramen for cranial nerves IX, X and the jugular vein; MP, metoptic pillar; MS, maxillary sinus; MX, maxillary nerve; N, nasal septum; O, otic capsule; OB, orbitosphenoid bone; OF, oval foramen for the mandibular branch of cranial nerve V; OP, occipital process of the squamosal bone; P, pterygoid bone; PA, parietal bone; PP, prooptic pillar; PR, presphenoid bone; S, squamosal bone; ST, stapes; T, tympanic bone; TU, median tubercle of the basioccipital bone; V, vomer; VN, ventral nasal concha; VO, vomeronasal cartilage; Z, zygomatic (or jugal) bone; ZM, zygomatic process of the maxillar bone; ZS, zygomatic process of the squamosal bone. The small arrows in (FIGS. 14A–14C) indicate the limits of the 3 components of the zygomatic arch; the black open arrows in (FIG. 14B), the large black arrows in (FIG. 14C) and the white open arrow in (FIG. 14G) indicate the absent MP, the absent ZS and the BO-AAA-fusion, respectively. The double arrow in (FIG. 14E) indicates a fusion of the gonial and pterygoid bones. Same magnifications.
Figure 14M:
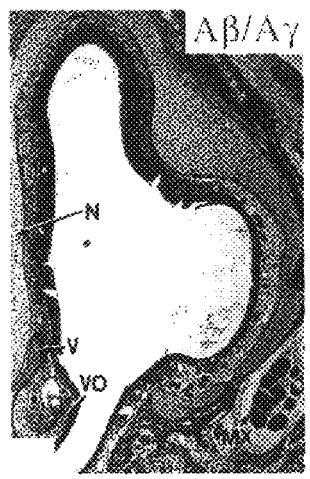

The penetrance of these 3 skeletal defects increased in a graded manner upon the inactivation of one and of both alleles of the RARβ gene from either the Aα null genetic background (i.e. pterygoquadrate element, agenesis of the zygomatic process) or the Aγ null genetic background (i.e. agenesis of the metoptic pillar). Additionally, in Aα/Aβ$^{+/-}$ and Aα/Aβ mutants the extent of the squamosal malformation was markedly increased (e.g. compare the normal occipital process of the squamosal, OP, in FIG. 14h with the misshappen OP in FIG. 14i). Cranial skeletal abnormalities observed only in the double null mutants included: (i) hypoplasia of the caudal ethmoturbinates (E2 and E3 in FIGS. 14j and k), partial agenesis of the rostral ethmoturbinate (E1, compare FIGS. 14j and l with FIGS. 14k and m) and absence of the maxillary sinus (MS compare FIG. 14l with m) in the nasal cavity of Aβ/Aγ mutants and (ii) abnormal shape of the gonial bone (G in FIGS. 14d–i), which corresponds to the anlage of the malleus anterior process, in Aα/Aβ mutants.

All Aα/Aβ and Aβ/Aγ compound mutants also showed laryngeal cartilage malformations (Table 4) identical to those described in Aα/Aβ2 and Aβ2/Aγ mutants by Mendelsohn, C., et al., Development 120:2749–2771 (1994).

5. Interdigital Webbing in RARβ$^{-/-}$/RARγ$^{-/-}$ (Aβ/Aγ) Mutants

In E13 WT embryos, the indentation of the handplate and footplate indicates the onset of digit separation (Wanek, N., et al., J. Exp. Zool. 249:41–49 (1989)) which is completed by E14 in the forelimb and by E15 in the hindlimb (e.g. FIG. 18e). Separation of the digits is followed by their reunion by epithelial fusion between E16 and E17 (Maconnachie, E., J. Embryol. Exp. Morphol. 49:259–276 (1979)), then digits stay fused for the first 4 days of post-natal life (Wanek, N., et al., J. Exp. Zool. 249:41–49 (1989)).

Figure 18A:
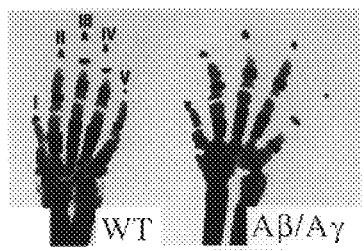
(FIG. 18A) Dorsal views of E18.5 forelimbs.
Figure 18B:
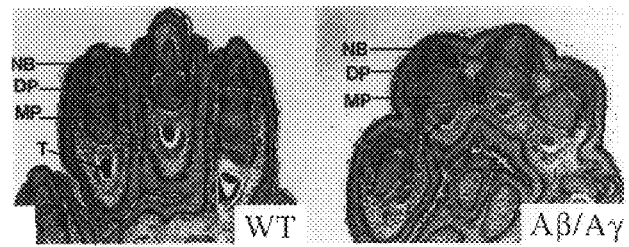
(FIG. 18B) Histological sections through E18.5 forelimbs.
Figure 18C:
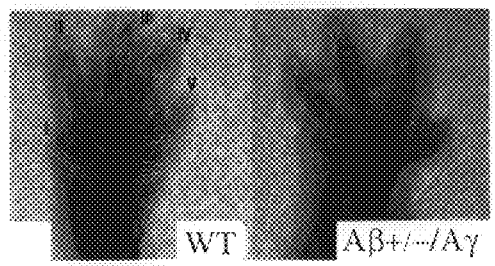
(FIG. 18C) Forelimbs and (FIG. 18D) hindlimb of 6 week-old mice.
Figure 18D:
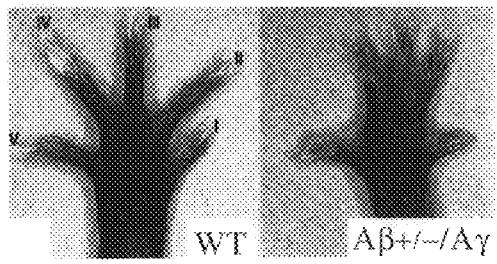
FIG. 18. Failure of digit separation and soft tissue syndactyly in compound mutants of RARβ and RARγ (genotypes as indicated).
(FIG. 18E) Scanning electron micrographs. I–V: digits; DP, distal phalanx; EL, epithelial lamina connecting the digits; ID, persistent interdigital mesenchyme; MP, medial phalanx; NB, nail bed; T, tendon; the small white arrow in (FIG. 18E) indicates an interdigital epithelial ridge. Magnifications.
Figure 18E:
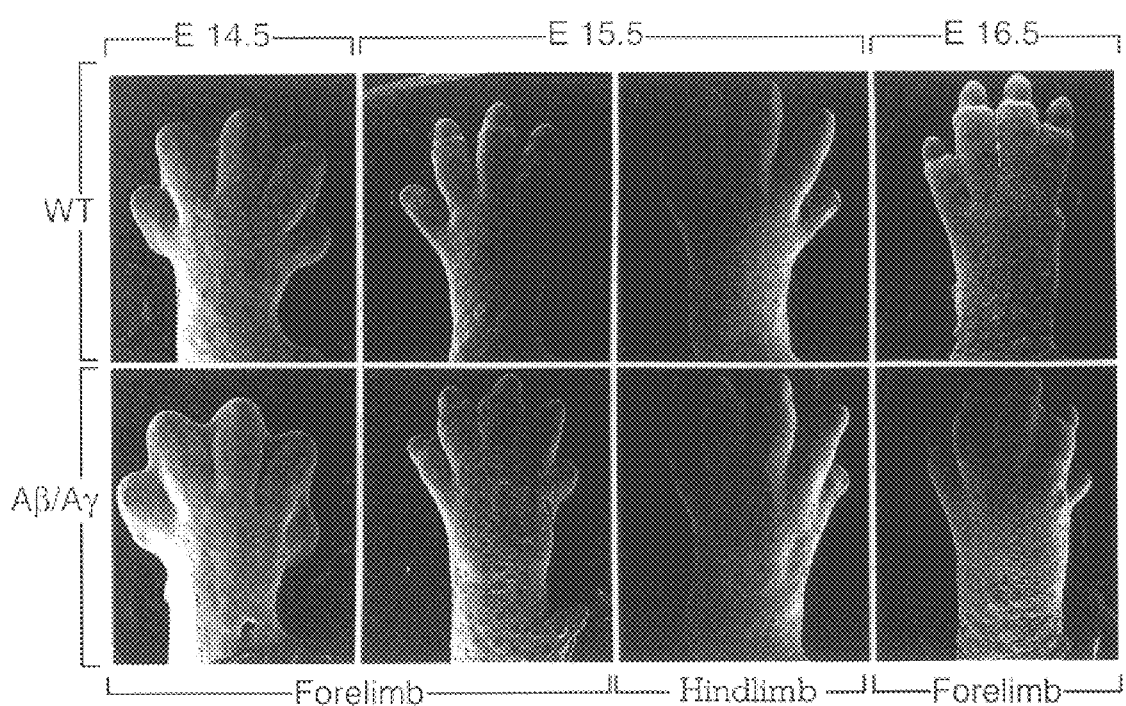

A striking feature of the E18.5 Aβ/Aγ skeleton was the claw shape of the fore—and hindlimb digits which were also divergent instead of being straight and nearly parallel to one another as in WT fetuses (FIG. 18a). Histological sections through these E18.5 mutant limbs showed an absence of the epithelial lamina normally connecting the digits (EL, FIG. 18b). To investigate the origin of these abnormalities, limbs of Aβ/Aγ fetuses were compared to those of weight-matched littermates on scanning electron micrographs (FIG. 18e). In E16.5 mutants, the interdigital epithelial ridges (white arrow, FIG. 18e) which are hallmarks of digital reunion were absent and at E15.5 the mutant digits were not separated. Moreover, at E14.5 and E16.5 the digits appeared broader than their WT counterparts. Taken together, these observations indicate that the skeletal abnormalities of the digits (FIG. 18a) and their absence of epithelial connection at birth (FIG. 18b) are likely to be caused by an absence of involution of the interdigital mesenchyme between E13.5 and E15.5. As already mentioned, Aβ/Aγ do not survive for more than a few hours after birth. However, the final outcome of the limb abnormalities could be seen in adult $Aβ^{+/-}/Aγ$ mutants which consistently displayed interdigital webbing affecting all digits of both hand and foot (FIGS. 18c and d). In contrast, this abnormality was not observed in E18.5 Aα/Aγ mutants nor in adult $Aβ/Aγ^{+/-}$ mutants, thus further indicating that RARγ is the main RAR involved in the involution of the interdigital mesenchyme.

Discussion

A. Functions of RARβ During Embryonic Development

A detailed morphological analysis allowed us to uncover abnormalities that we had previously overlooked in single and double mutants of RARα, RARβ2 and RARγ (Lufkin, T., et al., *Proc. Natl. Acad. Sci. USA* 90:7225–7229 (1993); Lohnes, D., et al., *Cell* 73:643–658 (1993); Lohnes, D., et al., *Development* 120:2723–2748 (1994); Mendelsohn, C., et al., *Dev. Biol.* 166:246–258 (1994); Mendelsohn, C., et al., *Development* 120:2749–2771(1994)) and to rule out the proposal that the patterning of cranial nerves IX and X could be critically dependent on RARβ (Luo, J., et al., *Mech. Dev.* 53:61–71(1995)). In addition, careful comparisons of the phenotypes of single or compound mutants of either RARβ2 (Mendelsohn, C., et al., *Dev. Biol.* 166:246–258 (1994); Mendelsohn, C., et al., *Development* 120:2749–2771(1994); Grondona J. M., et al., *Development* 122:2173–2188 (1996)) or RARβ did not reveal outstanding differences with the possible exceptions of spleen and thymus ageneses which were found only in Aα/Aβ mutants. However, it is noteworthy that thymus agenesis occurred with similar frequency in compound mutant fetuses lacking the RXRα gene and either all RARβ isoforms (RARβ 'total') or the RARβ2 isoform only (Kastner, P., et al., *Development* 124:313–326 (1997)). In contrast, the heart of RXRα/RARβ double mutants always lacked the cono-truncal septum, a defect which was only rarely observed in RARβ2/RXRα double mutants (Kastner, P., et al., *Development* 124:313–326 (1997)). Whether this difference between the occurrence of the thymus and cono-truncal septum defects reflects a specific role of RARβ1/β3 or merely a gene dosage effect will await the generation of RARβ1/β3 mutant mice.

1. Eye Development

RARβ is required for the normal involution of the fibroblastic component of the primary vitreous body. This function is largely fullfilled by the P2 isoform, as ~70% of the RARβ2 mutants also display a PHPV (Grondona J. M., et al., *Development* 122:2173–2188 (1996)). Interestingly, PHPV represents the most common abnormality of the rat fetal VAD syndrome (Warkany, J. and Shraffenberger, S., *Arch. Ophthalmol.* 35:150–169 (1946)). However, the rare occurrence of PHPV and high frequency of persistent Bergmeister's papilla (which might be assimilated to a partial PHPV) in our WT mice clearly indicate that RARβ is not the sole factor involved in the regression of the primary vitreous body. In this respect, we also note that PHPV has been observed in transgenic mice which overexpress TGFα in the eye globe (Renecker, L. W., et al., *Development* 121:1669–1680 (1995)) or in which ocular macrophages have been ablated by expression of the diphtheria toxin from a macrophage specific transgene (Lang, R. A. and Bishop, J. M., *Cell* 74:453–462 (1993)). The RARβ mutation may prevent cell death and/or elicit overproliferation of a subset of periocular mesenchymal cells. However, it has no apparent effect on cell differentiation, since the cells of the PHPV give rise to melanocytes, one of the two main overtly differentiated cell types (with scleral fibroblasts) found in the periocular envelopes. It has been shown that RARβ2 is transcriptionally upregulated in senescent human dermal fibroblasts and human mammary f epithelial cells (Si, S. P., et al., *Exp. Cell Res.* 223:102–111 (1996); and references therein). These latter data, combined with studies showing that certain tumor cell lines have lost the ability to express RARβ (reviewed in Lotan, 1993) and that RARβ (or RARβ2) plays a role in retinoic acid-induced apoptosis and/or growth arrest in HeLa cells and breast cancer cells (Si, S.P., et al., *Exp. Cell Res.* 223:102–111 (1996); Seewaldt, V. L., et al., *Cell Growth Differentiation* 6:1077–1088 (1995); Liu, Y., et al., *Mol Cell. Biol.* 16:1138–1149 (1996)), have suggested that RARβ could be involved in mechanisms preventing cell transformation. In this respect, our present finding that RARβ is involved in cell death and/or proliferation of a subset of embryonic fibroblasts is of interest, and further investigations on these cells in culture may provide insight into some aspects of retinoid action on cell fate.

Morphometric analysis of the palpebral aperture in E14.5 dpc fetuses reveals that all 3 RAR isotypes are involved in its formation. Interestingly, RARs are also required for eyelid fusion, as all Aα/Aγ mutants and about one third of the $Aα1/Aα2^{+/-}/Aγ$ mutants are born with open eyes (Lohnes, D., et al., *Development* 120:2723–2748 (1994)). The retinoic acid-dependence of both eyelid formation and fusion is further supported by the retinoic acid-rescue of lidgap mutations (i.e. mutations which cause the defect of open eye at birth): normal eyelid development can be restored in lidgap mouse mutants by maternal treatment with retinoic acid either at E11.5 (i.e. just prior to the onset of eyelid formation) or E14.5 (just prior to the onset of eyelid closure) (Juriloff, D. M. and Harris, M. J., *J. Exp. Zool.* 265:144–152 (1993)).

Eye development results from cell interactions between two epithelia, the ectoderm and neurectoderm, and a NCC-derived mesenchyme (Johnston, M. C., et al., *Exp. Eye Res.* 29:27–43 (1979); and references therein). All of these structures are affected to some extent in Aβ/Aγ mutants; therefore, as it is often the case when combination of multiple abnormalities exist within the same organ system, it is difficult to identify the primary and secondary target tissue(s) of this double mutation. The periocular mesenchyme might be a primary target, since it exhibits high levels of both RARβ and RARγ proteins and/or transcripts from E12.5 until after birth (Dollé, P., et al., *Nature* 342:702–705 (1989); Grondona J. M., et al., *Development* 122:2173–2188 (1996); see also PO in FIGS. 19a and c), and it also expresses high levels of RALDH2 (Niederrheither et al., *Mech. Dev.* 62:67–78 (1997)) a RA-generating dehydrogenase (Zhao, D., et al., *Eur. J. Biochem.* 240:15–22 (1996)). Thus, the periocular mesenchyme may be both a possible source of RA and a target for a RA autocrine action. In this respect, we note that all of its derivatives are consistently affected in the Aβ/Aγ mutants. It is more difficult to account for the occurrence of a shortening of the ventral retinal field and of a pre-natal retinal dysplasia in Aβ/Aγ mutants, since the possible role of the periocular mesenchyme in retinal patterning is not documented, and RARγ as well as RARβ are apparently absent from the pre-natal neural retina (see RE, ONL and GCL in FIGS. 19a and c). Interestingly, Aβ2/Aγ2 mutants develop post-natally a completely different form of retinal dysplasia probably secondary to RPE defects (Grondona J. M., et al., *Development* 122:2173–2188 (1996)).

2. Limb Development

Figure 15A:
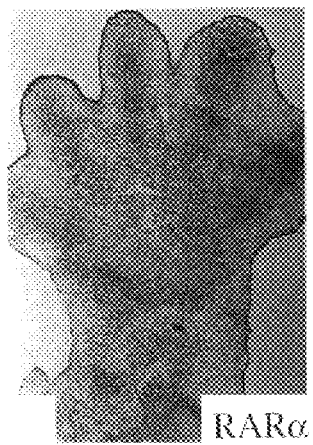
FIGS. 15A–15C: ×26.
Figure 15B:
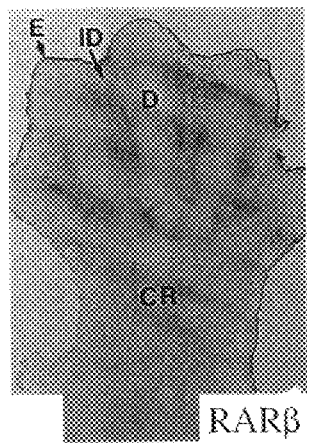
Figure 15C:
Figure 15D:
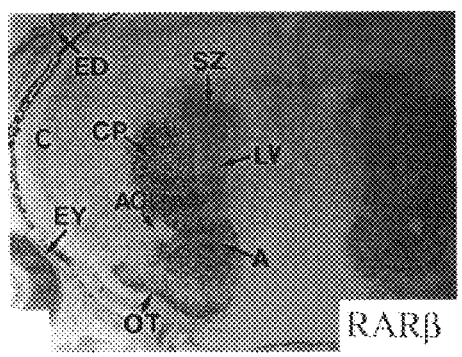
FIGS. 15D and 15E: ×16.
Figure 15E:
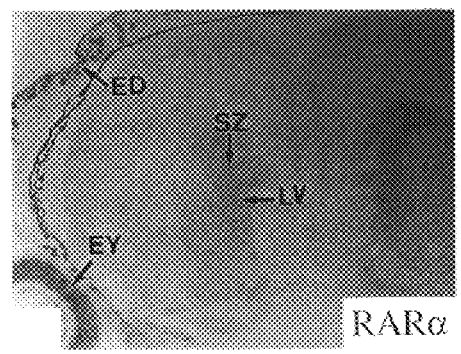
Figure 15F:
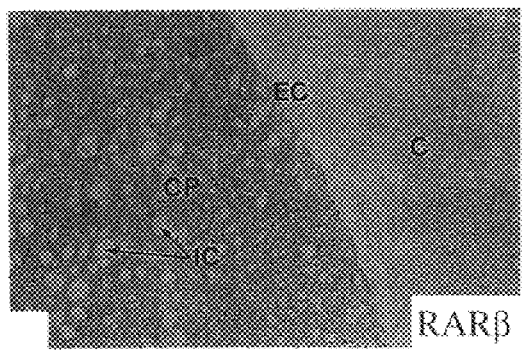
FIGS. 15F and 15G: ×41.
Figure 15G:
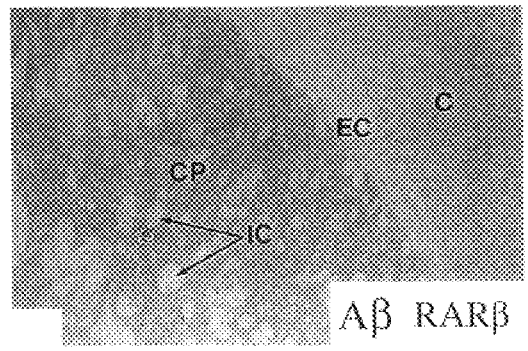

Three RARs are expressed in the interdigital mesenchyme during the period of morphogenetic cell death (Dollé, P., et al., *Nature* 342:702–705 (1989); Ruberte, E., et al., *Development* 108:213–222 (1990); FIGS. 15a–c) and RA has been shown to induce digit separation in cultured embryonic limbs (Lussier, M., et al., *Int. J. Dev. Biol.* 37:555–564 (1993)). The interdigital webbing observed in ~10% RARγ mice affects the interzones between digits 2–3 and/or 3–4 in the hindlimbs and is exceptional in forelimbs (Lohnes, D., et al., *Cell* 73:643–658 (1993); Kastner, P., et al., *Development* 124:313–326 (1997)). Interdigital webbing is also seen in some RARα mutants (Lufkin, T., et al., *Proc. Natl. Acad. Sci. USA* 90:7225–7229 (1993)) and is never found in RARβ mutants (present report). Our observation that Aβ/Aγ and Aβ$^{+/-}$/Aγ mutant mice display a severe and completely penetrant interdigital webbing strengthen the conclusion that RA plays a critical role in the separation of the digits. By an irony of fate, this role of RA was originally inferred from the distribution pattern of RARβ (Dollé, P., et al., *Nature* 342:702–705 (1989)) whose inactivation has no effect on interdigital tissues. Our data also demonstrate that the interdigital webbing induced by RAR inactivations is due to a lack of involvement of the fetal interdigital mesenchyme, not to a post-natal failure of breakdown of the epithelial lamina normally connecting the digits at birth. Interestingly, soft tissue syndactly was recently observed following inhibition of BMP (Bone Morphogenetic Protein) expression in the chick limb bud (Zou, H. and Niswander, L., *Science* 272:738–741 (1996)). Our compound mutants of RARβ and RARγ should represent usefull tools with which to investigate the relationships between the RA and BMP signaling pathways in controlling interdigital cell death.

3. Cranial Development and Atavistic Traits

Besides the dramatic craniofacial skeletal deficiencies seen in Aα/Aγ mutants (Lohnes, D., et al., *Development* 120:2723–2748 (1994)), more subtle defects which often alter the shape of a single skeletal piece are observed in Aα, Aγ, Aα1/Aγ, Aα/Aβ2, Aα/Aβ, Aβ2/Aγ and Aβ/Aγ mice, including: a cartilaginous or osseous connection between the incus middle ear bone and the alisphenoid bone (pterygoquadrate element); a medial cartilaginous wall for the cavum epipterycum (pila antotica); malformation of the squamosal bone; agenesis of the rostral ethmoturbinate and maxillary sinus; and absence of the metoptic pillar (Lohnes, D., et al., *Development* 120:2723–2748 (1994); and present report). The pterygoquadrate element and pila antotica, which were lost during evolution from reptiles to mammals, may represent atavistic features (discussed in Mark, M., et al., *Int. J. Dev. Biol.* 39:111–121 (1995)). Along the same lines, ethmoturbinate bones and paranasal sinuses (such as the maxillary sinus) are typical mammalian features not present in reptiles (Novacek, M. J., "Patterns of Diversity in the Mamalian Skull," in The Skull, Hanken, J. and Hall, B. K., eds., The University of Chicago Press, Chicago (1993), Vol. 2, pp. 438–548). Thus, their absence in Aβ/Aγ mutants could also mimic an atavistic condition. The pila metoptica is absent in monotremes and marsupials, but present in placental mammals, as well as in the reptilian ancestors of mammals. Therefore, the absence of this structure in Aγ null mutants and compound mutants of RARγ and RARβ cannot be interpreted as an atavism. However, it further suggests that changes in the temporal or spatial patterns of expression of RARs may have provided a general mechanism for modifying the number and morphology of individual cranial skeletal element during vertebrate evolution. Interestingly, such a function has also been assigned to members of the BMP family (reviewed by Kingsley, D. M., *Trends Genet.* 10:16–21 (1994); Hogan, B. L. M., *Genes & Dev.* 10:1580–1594 (1996)). Thus, BMPs which can elicit ectopic bone formation, possibly by promoting the entry of multipotent stem cells into the chondrogenic pathway, and whose loss-of-function mutations result in the disruption of specific subsets of skeletal elements could mediate the effects of RA on cranial skeletal patterning.

The PHPV, which is homologous to the reptilian pecten oculi, and the shortening of the ventral retina (Kastner, P., et al. *Cell* 78:987–1003 (1994)) may also represent atavistic traits.

4. Axial Specification

It was previously demonstrated that RARγ and (to a lesser extent) RARα are important for patterning of the body anteroposterior axis (Lohnes, D., et al., *Cell* 73:643–658 (1993); Lufkin, T., et al., *Proc. Natl. Acad. Sci. USA* 90:7225–7229 (1993)). RARβ also appears to be involved in this process, as RARβ single mutants and compound mutants of RARβ and either RARα or RARγ display homeotic transformations or malformations of vertebrae. The penetrance and expressivity of some of these defects increase in a graded manner with subsequent loss of the other RAR alleles from the RARβ null background, indicating that the specification of the affected segments could be particularly sensitive to RAR gene dosage effects. Most of the vertebral abnormalities observed in the RAR mutants probably arise through altered expression of some Hox genes (discussed in Lohnes, D., et al., *Development* 120:2723–2748 (1994); Kastner, P., et al., *Development* 124:313–326 (1997)). That RARβ transcripts were never detected during mouse development in presomitic mesoderm, somites or sclerotomes, while present in neurectoderm (Dollé, P., et al, *Development* 110:1133–1151 (1990); Ruberte, E., et al., *Development* 111:45–60 (1991)), suggests that the effect of RARβ on vertebral morphogenesis could involve RA-dependent diffusible signals emanating from the neural tube (Pourquié, O., et al., *Proc. Natl. Acad. Sci. USA* 90:5242–5246 (1993)).

B. Specificity and Functional Redundancy

In the early 90's, it was expected that systematic gene knock-out in the mouse would lead to defined abnormal phenotypes, and thus allow to uncover the functional domain of given genes. There are now numerous examples where this expectation was not fullfilled, either because the mutation resulted in a lethal phenotype, or because of genetic redundancies. Two genes are redundant whenever their respective products can perform equivalent functions. The possession of two fully redundant genes is, in an evolutionary sense, unlikely. Thus, the finding of apparently 'dispensable' genes (i.e. genes whose inactivation has no apparent phenotypic consequences) must correspond to the lack of precision of the phenotypic test by which mutants are deemed to be asymptomatic, and/or to the fact that the sample size might be too small to detect a small fitness reduction of the mutants, and/or to the fact that the fitness disadvantage might be manifested only in environments that are not duplicated in the laboratory (Brookfield, J., Current Biol. 2:553–554 (1992); Thomas, J. H., Trends Genet. 9:395–399 (1993); Gabor-Miklos, G. L. and Rubin, G. M., Cell 86:521–529 (1996)). Along these lines, it is noteworthy that the PHPV present in RARβ2 (Grondona J. M., et al., Development 122:2173–2188 (1996)) and RARβ (present report) null mutants was first overlooked due to its incomplete penetrance and lack of manifestation on the behaviour of the mutants in the animal facility (Mendelsohn, C., et al., Dev. Biol. 166:246–258 (1994); Luo, J., et al., Mech. Dev. 53:61–71 (1995)). However, it does result in a very poor vision (see Reese, A. B., Am. J. Ophthalmol. 40:317–331 (1955)) which, per se, is obviously sufficient to account for the evolutionary conservation of the RARβ2 isoform.

A classical genetic test for redundancy between two genes products in vivo is to determine whether compound loss-of-function mutants display novel abnormalities compared to single mutants or show an increase in the penetrance and/or expressivity of a phenotype already present in the single mutant(s) (Thomas, J. H., Trends Genet. 9:395–399 (1993)). However, the phenotypic redundancy observed in RAR/RAR compound mutants (and to a much lesser extent in RXRα/RAR compound mutants; Kastner, P., et al, Development 124:313–326 (1997)) should not be taken as an absolute proof of functional redundancy. Other explanations cannot be excluded, notably: 1) action of distinct RARs on specific subset of target genes within the same cell; 2) action of distinct RARs in different tissues whose reciprocal interactions are normally required for the making of a given structure. This second possibility is particularly appealing in structures which display developmental defects in Aβ/Aγ mutants, although showing clearly non-overlapping patterns of RARβ and RARγ expression such as the interdigital soft tissue and the ethmoturbinates. In this latter localization, RARγ is expressed in the maturing cartilage (e.g., E1 in FIG. 19b) whereas RARβ transcripts are confined to the perichondriurn (PC in FIG. 19b).

The phenomenon of functional redundancy observed in RAR knockout experiments might indicate that, in certain organ systems, all RARs (in the form of heterodimers with RXRα; Kastner, P., et al., Development 124:313–326 (1997)) are able to transactivate with similar efficiencies most of the RA target genes. The only requirement for normal development would be to reach a critical level of RXRα-RAR heterodimers in a given cell at a given time of its ontogeny. This possibility is discussed below in the case of the mesectodermal cells of the eyelid anlagen. Alternatively, the phenomenon of functional redundancy may not reflect a lack of functional specificity of RARs in the WT situation, but merely indicates the existence of compensatory mechanisms operating essentially, if not exclusively, in the artifactual context of the single null mutants. This second scenario might apply to the RA-mediated events which are required for the involution of the primary vitreous body and for the morphogenesis of the Harderian gland.

A mild reduction of the palpebral aperture is present in Aα, Aβ$^{+/-}$ and Aγ$^{+/-}$ single mutants; additive effects of RAR mutations on the size of the palpebral aperture are observed in compound heterozygotes (as well as Aα/Aβ$^{+/-}$ and Aα$^{+/-}$/Aβ mutants), and disrupting only one allele of either RARβ or RARγ in the Aγ or Aβ null genetic backgrounds leads to synergistic effects. As RARα, RARβ and RARγ are all strongly expressed in the mesenchymal component of the eyelid anlagen at the onset of their formation (E in FIG. 19a), a decrease in the total intracellular amount of RARs represents the simplest explanation to account for the appearance of a blepharophimosis in some mutants.

Figure 19A:
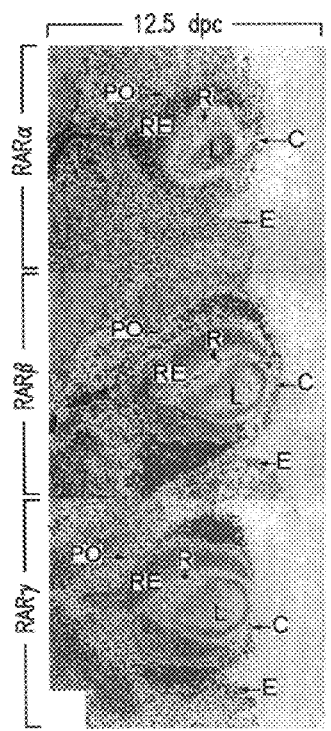
FIG. 19A: ×45.
Figure 19B:
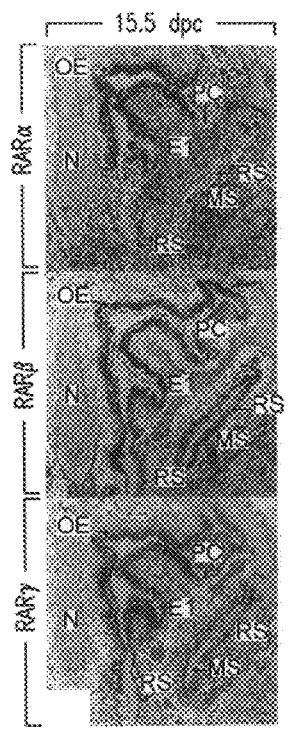
FIG. 19B, FIG. 19C: ×36.

On the other hand, several lines of evidence support the conclusion that, although the PHPV is completely penetrant in compound mutants only (e.g., Aα/Aβ and Aβ/Aγ mutants), RARβ is the receptor specifically involved in the disappearance of the primary vitreous body. Firstly, in the primary vitreous body RARβ transcripts are, by far, the most abundant; RARα and RARγ transcripts are not detected above background level in this structure (FIG. 19a). Secondly, a PHPV is observed with a high frequency only in RARβ (and RARβ2) null mutant mice; its presence in RARγ null mice is similar to that in WT mice and it is not detected in RARα null mice nor in Aα1/Aα2$^{+/-}$/Aγ mice (Lohnes, D., et al., Development 120:2723–2748 (1994)), Aα/Aγ1 or Aα/Aγ2 mice (V. Subbarayan, P. Kastner, M. M. P. Gorry). Note also that the PHPV in Aα/Aγ mice is most likely secondary to retinal colobomas (as discussed in Lohnes, D., et al., Development 120:2723–2748 (1994)). The third argument supporting a unique role of RARβ in the disappearance of the primary vitreous stems from the observation of mice in which half the RXRα/RAR heterodimers (the functional units of the retinoid signaling pathway) have been inactivated: ~50% of the Aβ$^{+/-}$/Xα$^{+/-}$ mice display a PHPV (Kastner, P., et al., Development 124:313–326 (1997)), whereas this abnormality is never observed in Aγ$^{+/-}$/Xα$^{+/-}$ mice (our personal observation). That the PHPV is not observed in ~15% of the RARβ null mutants is most easily explained by a functional compensation involving mainly (if not exclusively) RARγ: in Aβ$^{+/-}$/Aγ the PHPV is fully penetrant; in contrast Aα/Aβ$^{+/-}$ mice do not display this abnormality. Finally, that the PHPV is highly penetrant in compound mutants with only one allele of the RARβ gene disrupted (i.e. Aβ$^{+/-}$/Xα$^{+/-}$, Aβ$^{+/-}$/Aγ$^{+/-}$, Aβ$^{+/-}$/Aγ$^{-/-}$) supports the conclusion that, in 'real life' (the WT mice), a full complement of the RARβ gene is required for the involution of the primary vitreous.

Figure 19C:
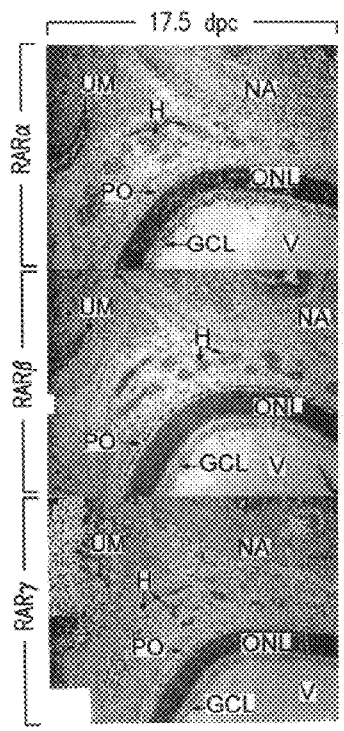

Along the same lines, RARγ is most probably the only RAR involved in the morphogenesis of the Harderian gland, despite the low penetrance of its agenesis in RARγ null mutants (Lohnes, D., et al., Cell 73:643–658 (1993); and present report). Firstly, this defect is fully penetrant in Aα1/Aγ, Aβ2/Aγ and Aμ/Aγ mutants but never observed in Aα/Aβ mutants (Lohnes, D., et al., Development 120:2723–2748(1994); and present results). Secondly, only RARγ transcripts are present at apparently high levels in the epithelial component of the developing Harderian gland (H in FIG. 19c); in contrast in situ hybridization failed to detect RARβ expression in both the Harderian gland epithelium and mesenchyme (FIG. 19c) and revealed only a weak expression of RARα (FIG. 19c). Thus, it appears that the absence of RARγ in the Harderian gland can be functionally compensated by RARα1 and RARβ2 (Lohnes, D., et al., Development 120:2723–2748 (1994)), but it is unlikely that RARα and RARβ are actually involved in the formation of this structure in WT animals. Note in addition that, although RARβ expression could not be detected in the Harderian gland, it can nevertheless partially compensate for the loss of RARγ in this structure. This emphasizes the lack of sensitivity of the available in situ detection techniques.

In any event, the present study, together with recent studies carried out with F9 cells (Taneja, R., et al., Proc. Natl. Acad. Sci. USA 93:6197–6202 (1996)) and RXRα/RAR compound mutant mice (Kastner, P., et al., Cell 78:987–1003 (1994); Kastner, P., et al., Development 124:313–326 (1997)) further support the possibility that the functional redundancies inferred from the morphological analysis of mice bearing mutations in the different RAR isotypes might reflect artefactual situations generated by the knock-out.

Materials and Methods

Targeting vector and homologous recombination

Genomic clones for the mouse RARβ (mRARβ) locus were obtained by screening a genomic library established in λEMBL3 from 129/Sv mouse DNA with a mRARβ cDNA probe (Zelent, A., et al., *EMBO J.* 10:71–81 (1991)). To construct the targeting vector, a 3.5 kb SalI-HindIII genomic fragment containing exons E9 to E11 was first inserted into pTZ18R plasmid (Pharmacia). Subsequently, the 1.3 kb BglII fragment containing E9 and most part of E10 was replaced with a PGK-Neo cassette (Adra, C. N., et al., *Gene* 60:65–74 (1987)). A 3.5 kb HindIII-SalI genomic fragment containing E8 was then introduced 5' to this construct and the resulting 7 kb HindIII DNA fragment was subsequently cloned into a Bluescript plasmid (pBSII-SK+, Stratagene) harboring an Herpes simplex virus thymidine kinase gene (HSV-TK; Lufkin, T., et al., *Cell* 66:1105–1119 (1991)). The linearized final plasmid was electroporated into D3 embryonic stem (ES) cells (Gossler, A., et al., *Proc. Natl. Acad. Sci. USA* 83:9056–9069 (1986); Lufkin, T., et al., *Cell* 66:1105–1119 (1991)). After selection, resistant clones were expanded. Genomic DNA was prepared from each clone and analysed by Southern blotting with probes A (FIG. 10*b*). The positive clone XW98 was injected into C57BL/6 blastocysts, and the resulting male chimeras tested for germline transmission.

Mice

All the mice used in the present study were on a mixed 129/SV-C57BL/6 genetic background. RARβ null mutants and RARβ/RARα or RARβ/RARγ double null mutants were produced from the intercrosses of RARβ$^{+/-}$ and RARβ/RARα or RARβ/RARγ double heterozygotic mice, respectively. Noon of the day of a vaginal plug was taken as 0.5 day post-coitum (E0.5). Embryos were collected by cesarian section and the yolk sacs were taken for DNA extraction. Genotypes were determined by Southern blotting. Genotyping conditions for RARα (disruption in the region encoding the B domain) and RARγ (disruption in the region encoding the DNA binding domain) mutant mice have been described previously (Lohnes, D., et al., *Cell* 73:643–658 (1993); Lufkin, T., et al., *Proc. Natl. Acad. Sci. USA* 90:7225–7229 (1993)).

RNAse protection analysis

Total RNA was prepared from E13.5 embryos (Chomczynski, P., and Sacchi, N., *Anal. Biochem.* 162:156–159 (1987)). Approximately 50 μg of total RNA was used per hybridization at 55° C. The conditions for the preparation of probes and hybridization reactions were essentially as described by Ausubel et al. (in *Current Protocols in Molecular Biology,* Green Pub. Assoc. and Wiley-Interscience. Wiley, N.Y. (1987)). Template for synthesis of the RARβ riboprobe was obtained by subcloning the EcoRV-EcoRI fragment of mRARβ cDNA containing most of the ligand binding domain (Zelent, A., et al., *EMBO J.* 10:71–81 (1991)). The RARα2 probe included the A2 region through the RARα C region to generate protected fragments of 382 nt for RARα2 and 179 nt for RARα1 (Lufkin, T., et al., *Proc. Natl. Acad. Sci. USA* 90:7225–7229 (1993)). The RARγ2 probe spanned the A2 region through the C region to generate protected fragments of 368 nt for RARγ2 and 162 nt for RARγ1 (Lohnes, D., et al., *Cell* 73:643–658 (1993)). The histone antisense riboprobe used as an internal control generates a 130 nt RNA fragment (a gift from R. Grosschedl, Howard Hughes Medical Institute, San Francisco, USA).

Protein Analysis

Cytoplasmic and nuclear protein extracts were prepared from E10.5 WT, heterozygous and homozygous RARβ mutant embryos according to Rochette-Egly, C., et al. *J. Cell Biol.* 115:535–545 (1991). Whole cell extracts from transfected Cos-1 cells were prepared as described (Gaub, M. P., et al., *Exp. Cell Res.* 201:335–346 (1992)). The proteins (20 μg for cytosolic extracts and 80 μg for nuclear extracts) were separated by SDS-PAGE and transferred to nitrocellulose membrane. Immunodectection procedures were as described previously (Rochette-Egly, C., et al., *J. Cell Biol.* 115:535–545 (1991)) using as antibody preparations rabbit polyclonal antisera specific for RARα [Rpα(F), Gaub, M. P., et al., *Exp. Cell Res.* 201:335–346 (1992)], RARβ [Rpβ(F)2, Rochette-Egly, C., et al., *Mol Endocrinol.* 6:2197–2209 (1992)] and RARγ [RPγ(mF), raised against synthetic peptide SP288 (amino acids 427–455)]. Monoclonal antibodies specific for CRABP-I (3CRA10F5) and CRABP-II (1CRA4C9) were also used (Lampron, C., et al., *Development* 121:539–548 (1995)). Immunoreactions were visualized using protein A or anti-mouse immunoglobulins coupled to horseradish peroxidase, followed by chemiluminescence according to the manufacturer's protocol (Amersham).

Histological and Skeletal Analyses

Serial histological sections were stained with Groat's hematoxylin and Mallory's trichrome and skeletons with alcian blue and alizarin red as previously described (Mark, M., et al., *Development* 119:319–338 (1993); Lufkin, T., et al., *Cell* 66:1105–1119 (1991)).

Histochemistry, Immunochemistry, and in Situ Hybridization

Acetylcholinesterase activity in brain section was detected according to Paxinos and Watson (Paxinos, G., and Watson, C. *The Rat Brain in Stereotaxic Coordinates.* Academic Press, San Diego (1986)). Whole-mount anti-neurofilament immunostaining and in situ hybridization on frozen tissue sections were performed as previously described (Mark, M., et al., *Development* 119:319–338 (1993); Décimo, D., "In situ hybridization of nucleic acid probes to cellular RNA," in *Gene Probes, a Practical Approach Book,* vol. II, pp. 183–210, Hames, B. D. and Higgins, S., eds., (1995)). For RAR immunolocalization studies, 10 μm thick frozen tissue sections were fixed in Zamboni's fluid (2% paraformaldehyde, 0.21% picric acid in 0.15M sodium phosphate buffer, pH 7.3), rinsed in PBS-0.05% Tween 20 (PBS-T) to block unspecific binding (30 min at 24° C). The sections were then incubated with the purified rabbit polyclonal antibodies diluted in PBS-T plus goat serum for 1 hr at 24° C. These antisera were purified by precipitation with ammonium sulfate and application onto sulfolink gel columns (Pierce, USA) coupled with the corresponding synthetic peptides. After rinsing in PBS-T (3×5 min) the bound antibodies were revealed using an ABC system (Vector) according to the manufacturer's instructions. Tissues from RARα, RARβ or RARγ null mutants were used as negative controls of the immunostaining procedure (e.g. in FIG. 15*f*).

EXAMPLE 4

Specific and Redundant Functions of Retinoid X Receptor/Retinoic Acid Receptor Heterodimers in Differentiation, Proliferation and Apoptosis of F9 Embryonal Carcinoma Cells Introduction Retinoids exert their pleiotropic effects on vertebrate development, cellular differentiation, proliferation and homeostasis through two classes of ligand-dependant transactivators: the retinoic acid receptors (RARs) and the retinoid X receptors (RXRs) (for reviews see De Luca, L. M., FASEB J. 5:2924–2933 (1991); Blomhoff, R, *Overview of Vitamin A metabolism and Function. In Vitamin A in Health and Disease,* Marcel Dekker, New York, Basel, Hong Kong, pp. 1–35 (1994); Chambon, P., *Semin. Cell Biol.* 5:115–125 (1994); Chambon, P., *FASEB J.* 10:940–954 (1996); Kastner, P., et al., *Cell* 83:859–869 (1995); Mangelsdorf, D. J., and Evans, R. M., *Cell* 83:841–850 (1995)). RARs are activated by all-trans retinoic acid (tRA) and its 9-cis isomer (9C-RA), whereas RXRs are activated by 9C-RA only. The various RAR (RARα, β and γ) and RXR (RXRα, β and γ) isotypes are encoded by different genes, and their isoforms, which differ in their $NH_2$-terminal regions, are generated by differential promoter usage and alternative splicing. The multiple RAR and RXR isotypes and isoforms are conserved in vertebrate evolution, and display distinct spatiotemporal expression patterns in developing embryos and adult tissues, suggesting that each receptor performs some unique functions (for reviews see Leid, M., et al., *Trends Biochem. Sci.* 17:427–433 (1992); Chambon, P., *Semin. Cell Biol.* 5:115–125 (1994); Kastner, P., et al., "The role of nuclear retinoic acid receptors in the regulation of gene expression," in *Vitamin A in Health and Disease, Blomhoff, R., ed., Marcel Dekker, New York.*(1994), pp. 189–238). RXR/RAR heterodimers bind much more efficiently to retinoic acid response elements (RAREs) than their respective homodimers in vitro (for reviews see Leid, M., et al., *Trends Biochem. Sci.* 17:427–433 (1992); Chambon, P., *Semin. Cell Biol.* 5:115–125 (1994); Chambon, P., *FASEB. J.* 10:940–954 (1996); Giguère, V., *Endocr. Rev.* 15:61–79 (1994); Glass, C. K., *Endocr. Rev.* 15:391–407 (1994); Kastner, P., et al., "The role of nuclear retinoic acid receptors in the regulation of gene expression," in *Vitamin A in Health and Disease,* Blomhoff, R., ed., Marcel Dekker, New York. (1994), pp. 189–238; Mangelsdorf, D. J., et al., "The Retinoid Receptors" in *The Retinoids: Biology, Chemistry and Medicine,* Sporn, M. B., et al., eds., Raven Press, New York.(1994), pp. 319–349; Gronemeyer, H., and Laudet, V., *Protein Profile.* 2:1173–1308 (1995); Keaveney, M., and Stunnenberg, H.G., "Retinoic Acid Receptors," in *Inducible Gene Expression,* vol. 2. Bauerle, P. A., ed., Birkhäeuser, Boston (1995), pp. 187–242; Mangelsdorf, D. J., and Evans, R. M., *Cell* 83:841–850 (1995)), and several lines of evidence support the idea that these heterodimers represent the f unctional units transducing the retinoid signal in vivo (Kastner, P., et al., *Cell* 83:859–869 (1995); Chambon, P., *FASEB. J.* 10:940–954 (1996)).

The F9 murine embryonal carcinoma (EC) cell line expresses all types of RARs and RXRs (Zelent, A., et al., *Nature* 339:714–717 (1989); Martin, C. A., et al., *Proc. Natl. Acad. Sci. USA* 87:4804–4808 (1990); Wan, Y-J., et al., *Exp. Cell Res.* 210:56–61 (1994)), and upon retinoic acid treatment, it differentiates into cells resembling three distinct extraembryonic endoderm (primitive, parietal, and visceral), depending on the culture conditions (for reviews see Strickland, S., *Cell* 24:277–278 (1981); Hogan, B. L. M., et al., *Cancer Surveys* 2:115–140 (1983); Gudas, L. J., et al., "Cellular biology and biochemistry of the retinoids," in *The Retinoids: Biology, Chemistry and Medicine,* Sporn, M. B., et al., eds., Raven Press, New York (1994), pp. 443–520). Retinoid-induced differentiation is accompanied by an apoptotic response and a dramatic decrease in the rate of proliferation (Sleigh, M. J., *BioEssays* 14:769–775(1992); Atencia,R., et al., *Exp. Cell Res.* 214:663–667 (1994); Clifford, J., et al., *EMBO J.* 15:4142–4155 (1996); and references therein). Thus, F9 cells provide an attractive system for the analysis of retinoid signaling in vivo.

In order to further investigate the roles of RXRs and RARs in differentiation, proliferation, and apoptosis, we have now generated F9 cells lacking either RXRα and RARα, or RXRα and RARγ, and then compared their phenotypes with those of wild-type (WT), $RXRα^{-/-}$ (Clifford, J., et al., *EMBO J.* 15:4142–4155 (1996)), $RARα^{-/-}$ (Boylan, J., et al., *Mol. Cell. Biol.* 15:843–851 (1995)) and $RARγ^{-/-}$ (Boylan, J., et al., *Proc. Natl. Acad. Sci. USA* 90:9601–9605 (1993); Taneja, R., et al., *Proc. Natl. Acad. Sci. USA* 92:7854–7858 (1995)) F9 cells. Multiple gene targeting in a given cell has been achieved by using a Cre/loxP system (Sauer, B., and Henderson, N., *New Biol.* 2:441–449 (1990); Metzger, D., et al., *Proc. Natl. Acad. Sci. USA* 92:6991–6995 (1995)), which allows removal of the antibiotic resistance gene from a targeted locus, and therefore subsequent mutagenesis of the second allele of a given gene with the same targeting construct, as well as the targeting of additional genes. We demonstrate that tRA-treated $RXRα^{-/-}/RARα^{-/-}$ cells differentiate poorly into primitive and parietal endodermlike cells and are impaired in both antiproliferative and apoptotic responses, whereas they fully differentiate into visceral endoderm (VE)-like cells, as previously observed for $RXRα^{-/-}$ cells (Clifford, J., et al., *EMBO J.* 15:4142–4155 (1996)). In contrast, $RXRα^{-/-}/RARγ^{-/-}$ cells are defective for all three types of endodermal differentiation, as well as for the antiproliferative and apoptotic responses, indicating that the absence of both RXRα and RARγ cannot be functionally compensated by the other retinoid receptors in these cells. Taken together with results obtained by treatment of WT and mutant F9 cells with panRXR- and RAR isotype-selective retinoids, our findings support the conclusion that RXR/RAR heterodimers are the functional units mediating the retinoid signal in vivo. Furthermore our results indicate that RXR/RAR heterodimers can exert both specific and redundant functions in differentiation, proliferation and apoptosis. We also show that functional redundancy between RXR isotypes and between RAR isotypes can be artifactually generated by gene knockouts.

Results

Targeted disruption of the RARα or RARγ genes in RXRα null F9 cells

Figure 20A:
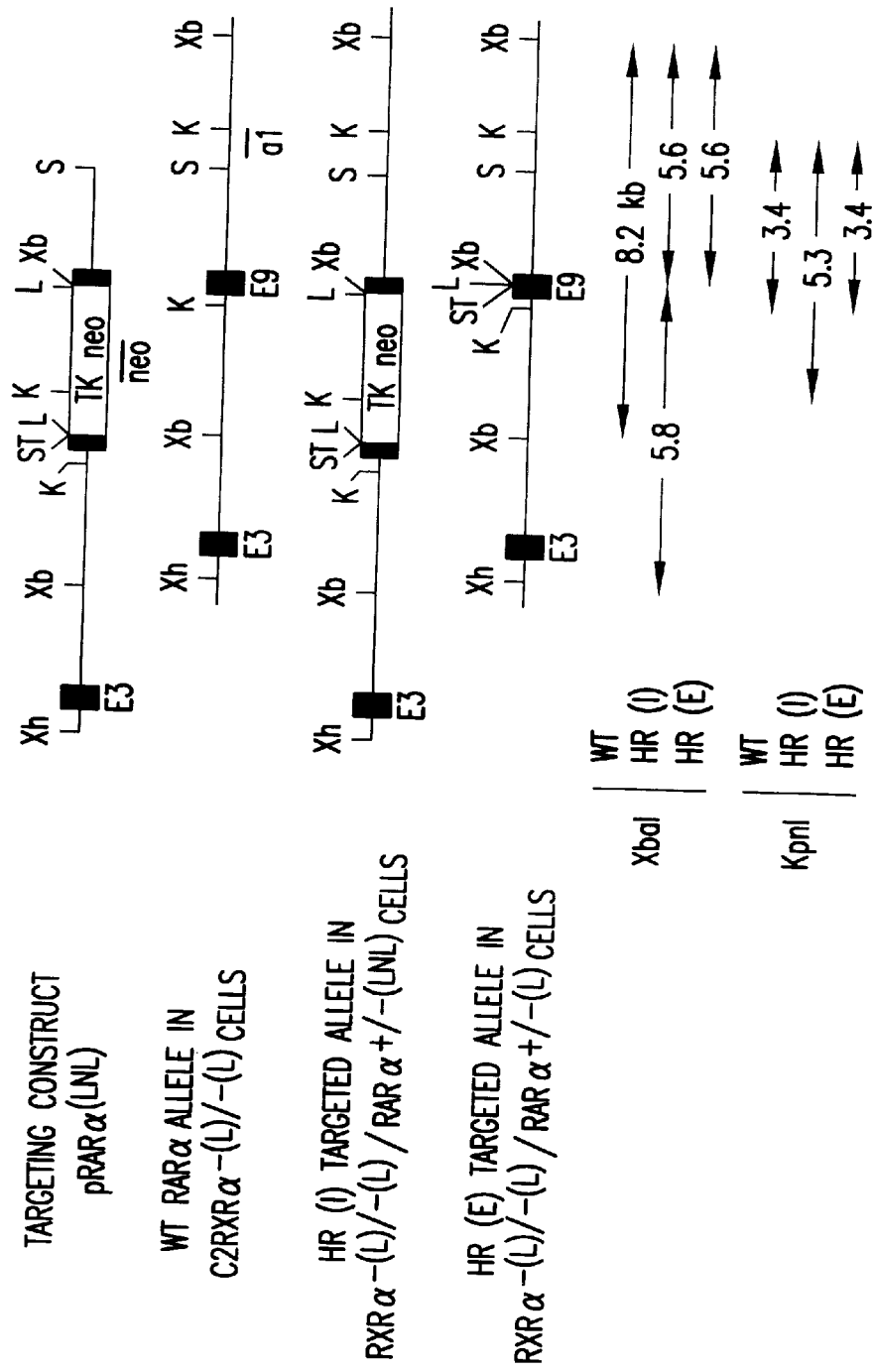
(FIG. 20A) Schematic diagram of the pRARα$^{(LNL)}$ targeting construct, the WT RARα locus, and the recombined locus after integration (HR[I]) and after Cre-mediated excision (HR[E]). Dark boxes indicate exons. The exons 4–8 encoding the NH2-terminal part of minor isoforns (RARα3–7) (Leroy, P., et al., *EMBO J.* 10:59–69 (1991)) are not represented. Restriction enzyme sites and the location of probes are indicated. The neo and a1 probes have been previously described (Metzger, D., et al., *Proc. Natl. Acad. Sci. USA* 92:6991–6995 (1995)). The numbers in the lower part of diagram are in kb. K, KpnI; L, loxP recombination site; S, SalI; ST, two translation stop codons; Xb, XbaI; Xh, XhoI.
Figure 21A:
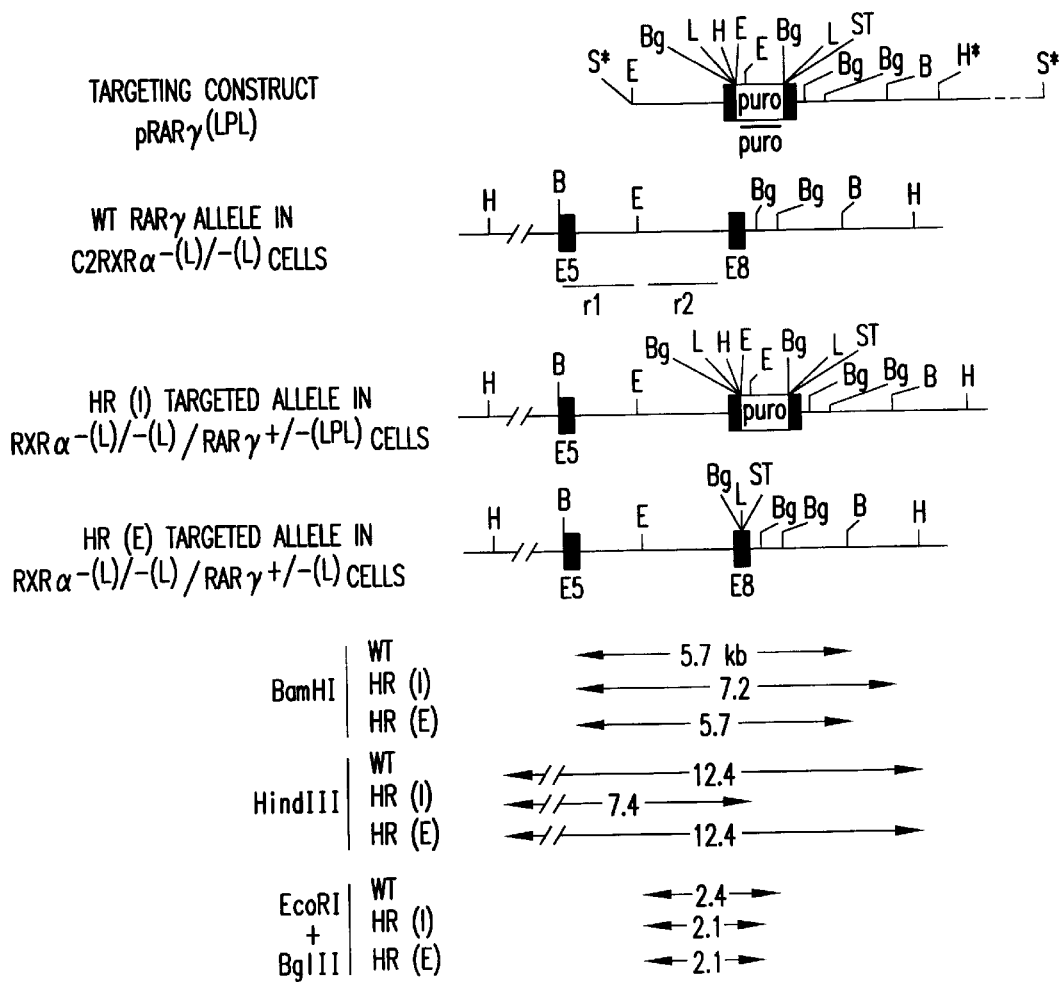
(FIG. 21A) Schematic diagram of the pRARγ$^{(LPL)}$ targeting construct, the WT RARγ locus, and the recombined locus after integration (HR[I]) and after Cre-mediated excision (HR[E]). Dark boxes indicate exons. The exons 6 and 7 encoding the NH2-terminal part of minor isoforms (RARγ4 and 6; Kastner, P., et al., *Proc. Natl. Acad. Sci. USA* 87:2700–2704 (1990)) are not represented. Restriction enzyme sites and the location of probes are indicated. The puro probe corresponds to a 0.7-kb EcoRI-XbaI fragment derived from pHRLpuro 1. The r1 probe corresponds to a 1.5-kb BamHI-EcoRI fragment derived from the RARγ genomic clone λG1mRARγ (Lohnes, D., et al., *Cell* 73:643–658 (1993)). The r2 probe corresponds to a 1.6–kb EcoRI-PstI fragment derived from pRARγ$^{(LPL)}$. The numbers in the lower part of the diagram are in kb. Abbreviations: B, BamHI; Bg, BglII; E, EcoRI; H, HindIII; L, loxP recombination site; S, SalI; ST, three translation stop codons inserted in all reading frames. Asterisk indicates that these sites are not present in the WT gene, and dashed line represents vector sequence.
Figures 21B, 21C:
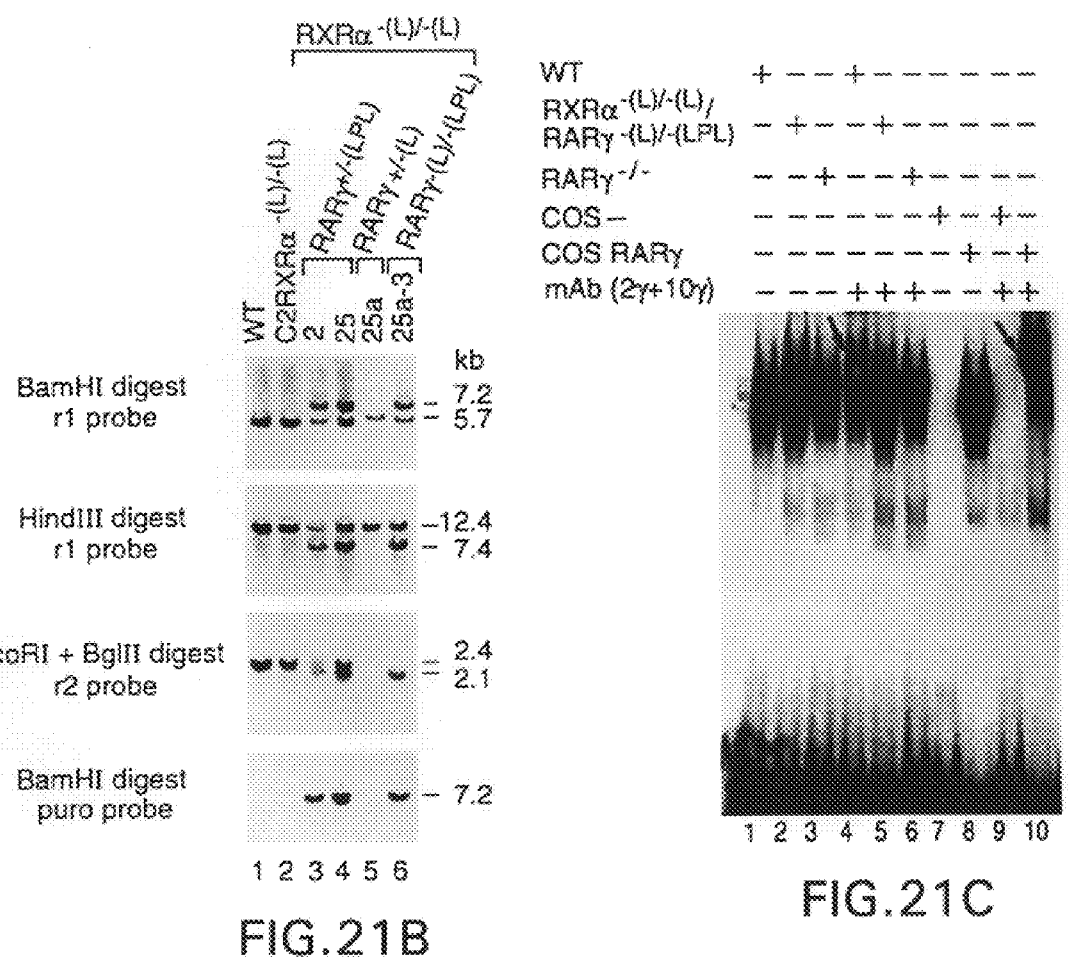
(FIG. 21B) Southern blot analysis indicating the disruption of the RARγ gene in a RXRα$^{-(L)/-(L)}$ cell line. The genotypes of different cell lines (e.g., 25) and their subclones (25a, etc.) are indicated at the top of each lane and correspond to all four panels.
(FIG. 21C) EMSA indicating the absence of RARγ protein in RXRα$^{-(L)/-(L)}$/RARγ$^{-(L)/-(LNL)}$ cells. A radiolabeled oligonucleotide corresponding to the Hoxa-1/RARβRARE was incubated with 20 μg of whole cell extracts from WT cells (lanes 1 and 4), RXRα$^{-(L)/-(L)}$/RARγ$^{-(L)/-(LNL)}$ cells (lanes 2 and 5) and RARγ$^{-/-}$ cells (lanes 3 and 6), or with 2 μg of whole cell extracts from COS cells transfected with either the pSG5 (lanes 7 and 9; Green, S., et al., *Nucl. Acids Res.* 16:369 (1988)) or mRARγø expression construct (lanes 8 and 10; Zelent, A., et al., *Nature* 339:714–717 (1989)), together with 0.5 μg of whole cell extracts from COS cells transfected with mRXRαø expression construct (Leid, M., et al., *Cell* 68:377–395 (1992)). The arrows indicate the shifted complex formed in the presence of mouse monoclonal antibodies Ab2γ(F) and Ab10γ(A2).

The RXRα-null F9 cell line, $C2RXRα^{-(L)/-(L)}$, which constitutively expresses a ligand-dependent chimeric Cre recombinase (Cre-ER; Metzger, D., et al., *Proc. Natl. Acad. Sci. USA* 92:6991–6995 (1995)), was electroporated with the targeting constructs $pRARα^{(LNL)}$ (FIG. 20A) or $pRARγ^{(LPL)}$ (FIG. 21A) to generate F9 cells disrupted in either the RXRα and RARα genes or the RXRα and RARγ genes. These targeting constructs contain translation stop codons and loxP site-flanked neomycin- or puromycin-resistance genes in exon 9 of the RARα gene or exon 8 of the RARγ gene, respectively (see Materials and Methods; FIG. 20A and FIG. 21A). Since these exons encode the B region, which is common to all isoforms of a given RAR isotype (see Kastner, P., et al., *Proc. Natl. Acad. Sci. USA* 87:2700–2704 (1990); Leroy, P., et al., *EMBO J.* 10:59–69 (1991); Chambon, P., *Semin. Cell Biol.* 5:115–125 (1994)), the expression of RARα and RARγ proteins is suppressed by these mutations. Homologous recombination (HR) and Cre-mediated excision of the resistance genes were verified by Southern blotting (FIG. 20B and FIG. 21B).

Southern blot analysis using a 3' probe (a1) located outside of the $pRARα^{(LNL)}$ targeting construct (FIG. 20A), indicated that, after electroporation, 5 out of 96 $C2RXRα^{-(L)/-(L)}$ neomycin-resistant clones had one targeted RARα allele (FIG. 20A, HR[I]; and FIG. 20B, compare lanes 3 and 4 with lanes 1 and 2). One $RXRα^{-(L)/-(L)}/RARα^{+/-(LNL)}$ cell line (clone nine) was treated with estradiol ($E_2$) to excise the loxP-flanked cassette (–[LNL] and –[L]) designate the targeted allele before and after Cre-mediated excision, respectively). Southern blot analysis using a1 and "neo" probes revealed that excision of the resistance gene occurred in two out of six subclones treated with $E_2$ (FIG. 20A, HR[E]; and FIG. 20B, compare lane 5 with lanes 3 and 4; see also Metzger, D., et al., *Proc. Natl. Acad. Sci. USA* 92:6991–6995 (1995)). The second allele of the RARα gene was targeted in the RXRα$^{-(L)/-(L)}$/RARα$^{+/-(L)}$ cell line (FIG. 20B, clone 9a) using the same targeting construct and strategy. Two of 96 neomycin-resistant clones were positive for the desired recombination event, resulting in RXRα$^{-(L)/-(L)}$/RARα$^{-(L)/-(LNL)}$ cell lines (FIG. 20B, clones 9a-10 and 9a-26; compare lanes 6 and 7 with lanes 1–5). No wild-type RARα transcripts were detected in RXRα$^{-(L)/-(L)}$/RARα$^{-(L)/-(LNL)}$ cells by semi-quantitative RT-PCR. Similarly, no RARα protein could be detected in RXRα$^{-(L)/-(L)}$/RARα$^{-(L)/-(LNL)}$ cells (called hereafter RXRα$^{-/-}$/RARα$^{-/-}$) by Western blotting using the polyclonal antibody RPα(F) (Gaub, M-P., et al., *Exp. Cell Res.* 201:335–346(1992)), directed against the F region of the RARα protein (FIG. 20C, compare lanes 3 and 4 with lanes 2, 5 and 6).

To establish F9 cells in which both RXRα and RARγ genes are inactivated, C2RXRα$^{-(L)/-(L)}$ cells were electroporated with the pRARγ$^{(LPL)}$ targeting construct (FIG. 21A). Southern blot analysis using the r1 probe, located 5' to the pRARγ$^{(LPL)}$ sequence (FIG. 21A), revealed that 3 out of 96 puromycin-resistant clones had one targeted RARγ allele (FIG. 21A, HR[I]; and FIG. 21B, compare lanes 3 and 4 with lanes 1 and 2). One RXRα$^{-(L)/-(L)}$/RARγ$^{+/-(LPL)}$ cell line (clone 25) was transiently transfected with a Cre recombinase expression construct (pPGK-Cre) (Clifford, J., et al., *EMBO J.* 15:4142–4155(1996), since for unknown reasons the loxP-flanked, puromycin-resistance gene was not excised by treatment of the cells with $E_2$ (–[LPL] and –[L] designate the targeted allele before and after Cre-mediated excision, respectively). The pattern obtained by Southern blot analysis, using r1, r2 and puro probes, clearly indicated that 2 out of 96 subclones had lost the puromycin-resistance cassette (FIG. 21A, HR[E]; and FIG. 21B, compare lane 5 with lane 4). The second allele of the RARγ gene was inactivated in one RXRα$^{-(L)/-(L)}$/RARγ$^{+/-(L)}$ cell line (FIG. 21B, clone 25a) using the same targeting construct and strategy, yielding a RXRα$^{-(L)/-(L)}$/RARγ$^{-(L)/-(LPL)}$ cell line (FIG. 21B, clone 25a-3, compare lane 6 with lanes 1–5). No wild-type RARγ RNA was detected in RXRα$^{-(L)/-(L)}$/RARγ$^{-(L)/-(LPL)}$ cells. The absence of RARγ protein was verified by EMSA using the monoclonal antibodies Ab2γ(F) and Ab10γ(A2) (Rochette-Egly et al., 1991), directed against the F and A2 regions of the RARγ protein, respectively. No antibody-shifted complex was observed in RXRα$^{-(L)/-(L)}$/RARγ$^{-(L)/-(LPL)}$ cells (called hereafter RXRα$^{-/-}$/RARγ$^{-/-}$) FIG. 21C, compare lane 5 with lanes 4, 6 and 10). Note that the RXRα loci, which contain loxP-sites, were not rearranged during excision of the resistance genes at the RARα A or RARγ loci. Note also that the knockout of a given receptor(s) did not result in major variations of those remaining (Chiba, H., et al., *Mol. Cell. Biol.* 17:3013–3020 (1997)).

Figure 22A:
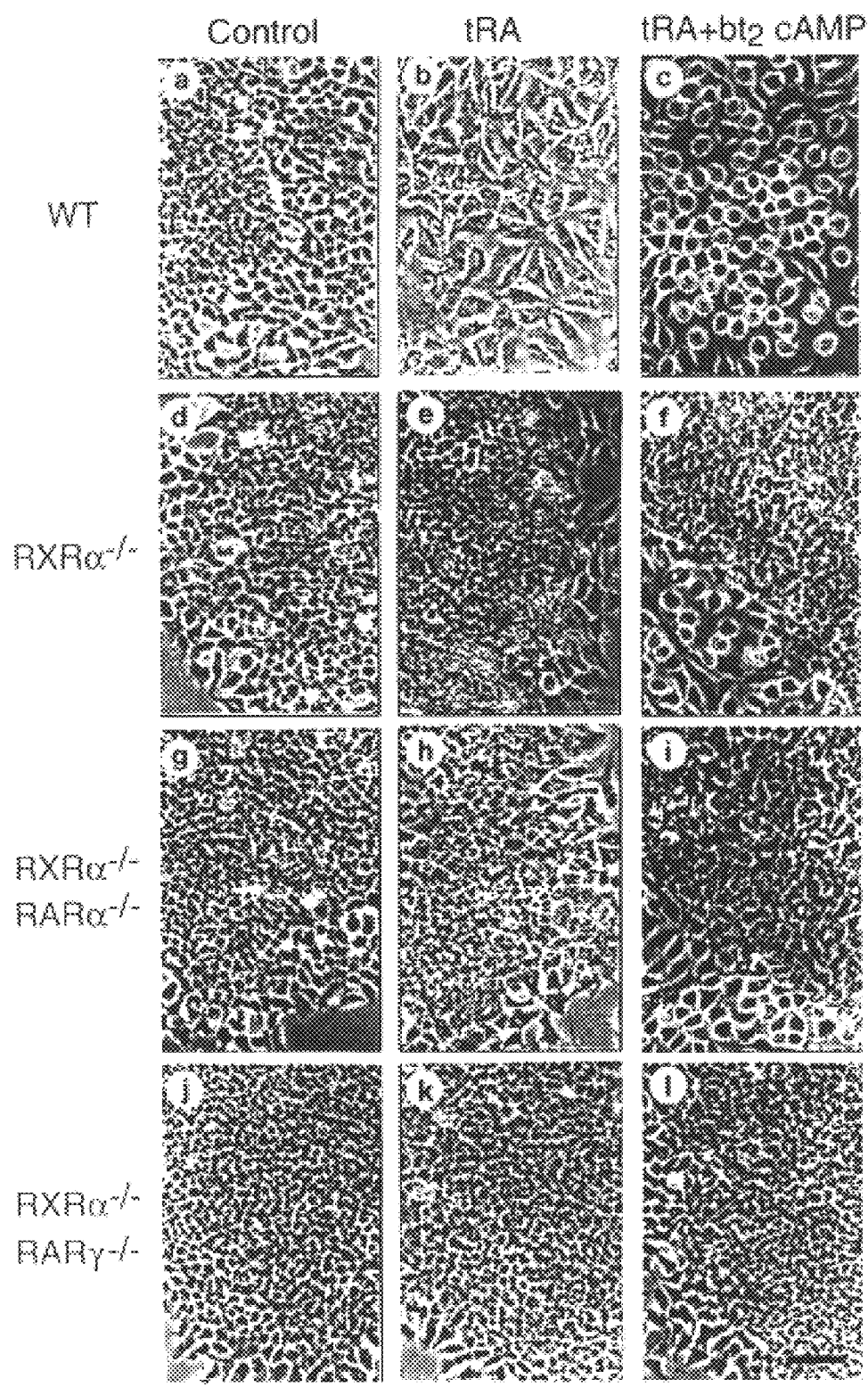
(FIG. 22A) WT (a–c), RXRα$^{-/-}$ (d–f), RXRα$^{-/-}$/RARα$^{-/-}$ (g–i) and RXRα$^{-/-}$/RARγ$^{-/-}$ (j–l) cells were treated with control vehicle (a, d, g and j), 1 μM tRA alone (b, e, h and k) or 1 μM tRA and 250 μM bt$_2$cAMP (c, f, i, and l) for 4 d. Cells were photographed under a phase-contrast microscope at ×125 magnification.

Function of RXRs and RARs in the retinoid-induced differentiation of F9 cells into primitive and parietal endodermlike cells WT F9 cells differentiate into primitive and parietal endoderm-like cells, when grown in monolayer culture in the presence of tRA alone and tRA in combination with dibutyryl cAMP (bt$_2$cAMP), respectively (Strickland, S., *Cell* 24:277–278 (1981); Hogan, B. L. M., et al., *Cancer Surveys* 2:115–140 (1983)). Previous studies have shown that these two types of differentiation are severely impaired in RARγ$^{-/-}$ and RXRα$^{-/-}$ cells (Boylan, J., et al., *Proc. Natl. Acad. Sci. USA* 90:9601–9605 (1993); Clifford, J., et al., *EMBO J.* 15:4142–4155 (1996)). The differentiation patterns of RXRα$^{-/-}$/RARα$^{-/-}$ and RXRα$^{-/-}$/RARγ$^{-/-}$ cells were compared with those of WT and single knockout cell lines. After 4 d of treatment, <10% of RXRα$^{-/-}$/RARα$^{-/-}$ cells became flatter and irregular in shape, or rounded with long cell processes, which are the morphological characteristics of primitive or parietal endodermal differentiation of WT F9 cells, respectively. The same results were obtained with 9a-10 and 9a-26 RXRα$^{-/-}$/RARα$^{-/-}$ cell lines (FIG. 22A, compare g-i with a-f). No morphological differentiation at all was observed in RXRα$^{-/-}$/RARγ$^{-/-}$ cells after 4 d of treatment, and <0.1% of the cells exhibited a differentiated morphology after 6 days of treatment (FIG. 22A, panels j–l). This undifferentiated phenotype persisted after 10 d of treatment.

Figure 22B:
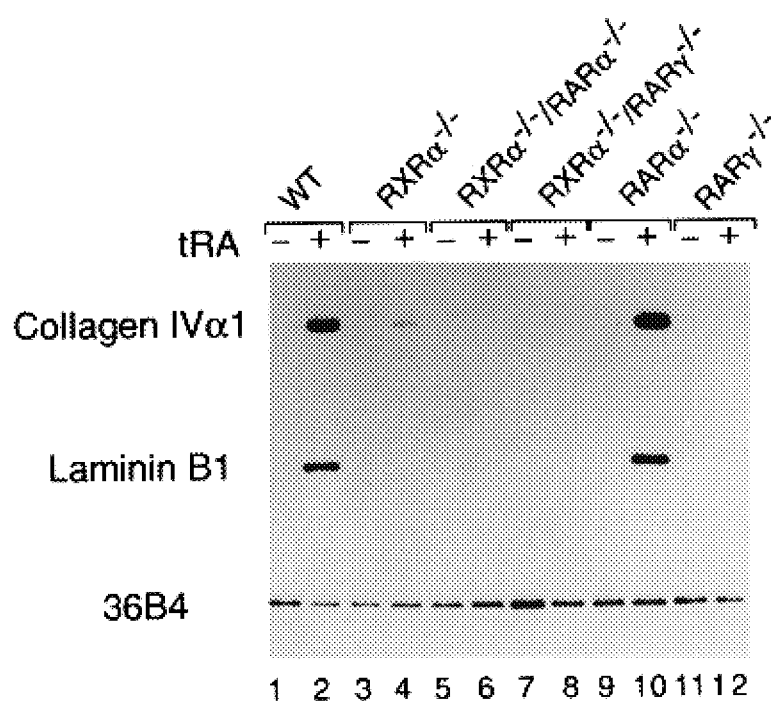
(FIG. 22B) Total RNA from WT and mutant cells, treated with control vehicle or 1 μM tRA for 48 h, was analyzed by RT-PCR analysis for collagen type IVβ1, laminin B1, and 36B4.
Figure 22C:
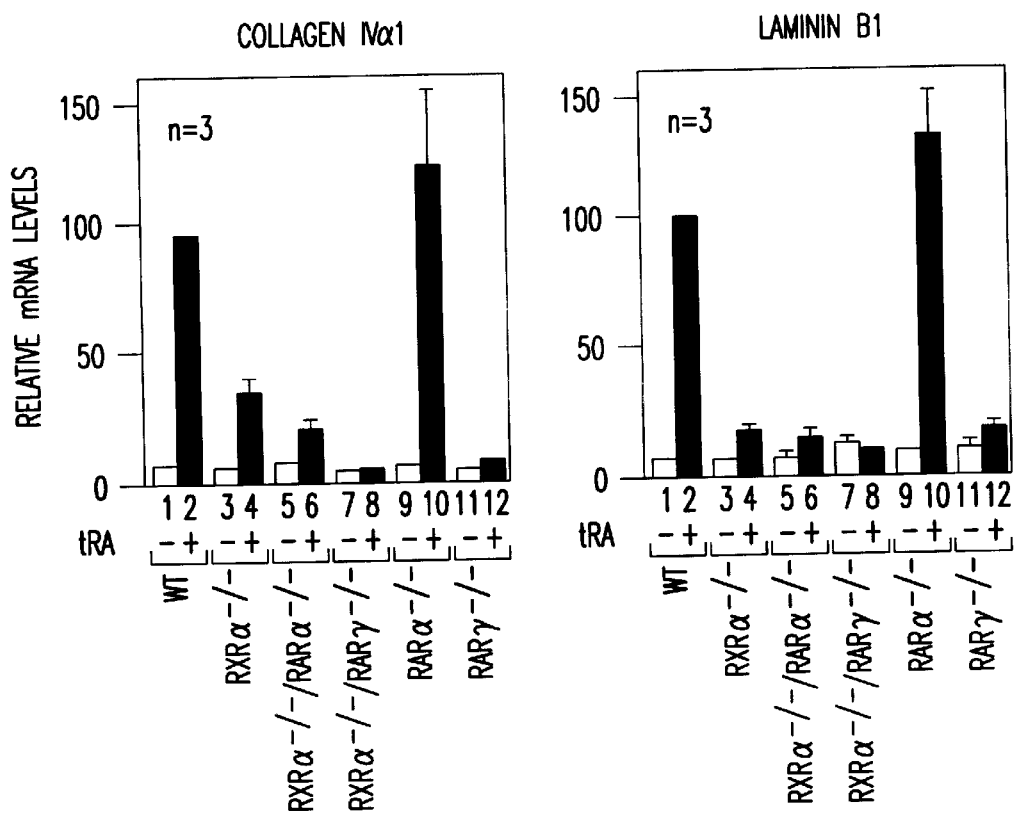
(FIG. 22C) RT-PCR analysis was performed as in (FIG. 22B), for three separate experiments. The levels of RNA transcripts were expressed relative to the amount present in tRA-treated WT cells, which was taken as 100 . The white and black bars correspond to transcript levels expressed in vehicle- and tRA-treated cells, respectively. Bar, 100 μM.

The extent of differentiation of WT and mutant F9 cells was further investigated biochemically by determining the mRNA levels of collagen type IVα1 and laminin B1, two markers of endodermal differentiation (FIG. 22B and 22C). After 48 h of 1 μM tRA treatment, the induction of collagen type IVα1 and laminin B1 was reduced in RARγ$^{-/-}$ cells (10-fold and 6-fold lower levels, respectively) and in RXRα$^{-/-}$ cells (3-fold and 6-fold lower levels, respectively) when compared to WT cells, whereas these inductions were not altered in RARα$^{-/-}$ cells (see also Boylan, J., et al., *Proc. Natl. Acad. Sci. USA* 90:9601–9605 (1993); Boylan, J., et al., *Mol. Cell. Biol.* 15:843–851 (1995); Clifford, J., et al., *EMBO J.* 15:4142–4155 (1996); Taneja, R., et al., *Proc. Natl. Acad. Sci. USA* 93:6197–6202 (1996)). The induction of both transcripts was also impaired in RXRα$^{-/-}$/RARα$^{-/-}$ cells (fivefold and sevenfold lower levels, respectively), whereas it was fully abrogated in RXRα$^{-/-}$/RARγ$^{-/-}$ cells. Thus, RA-induced primitive and parietal endodermal differentiation of WT F9 cells appears to be mainly mediated by the RXRα/RARγ pair, whereas it cannot be mediated by combinations of RXR(β+γ) with either RARα or RARβ (see also Table 12).

Figure 23A:
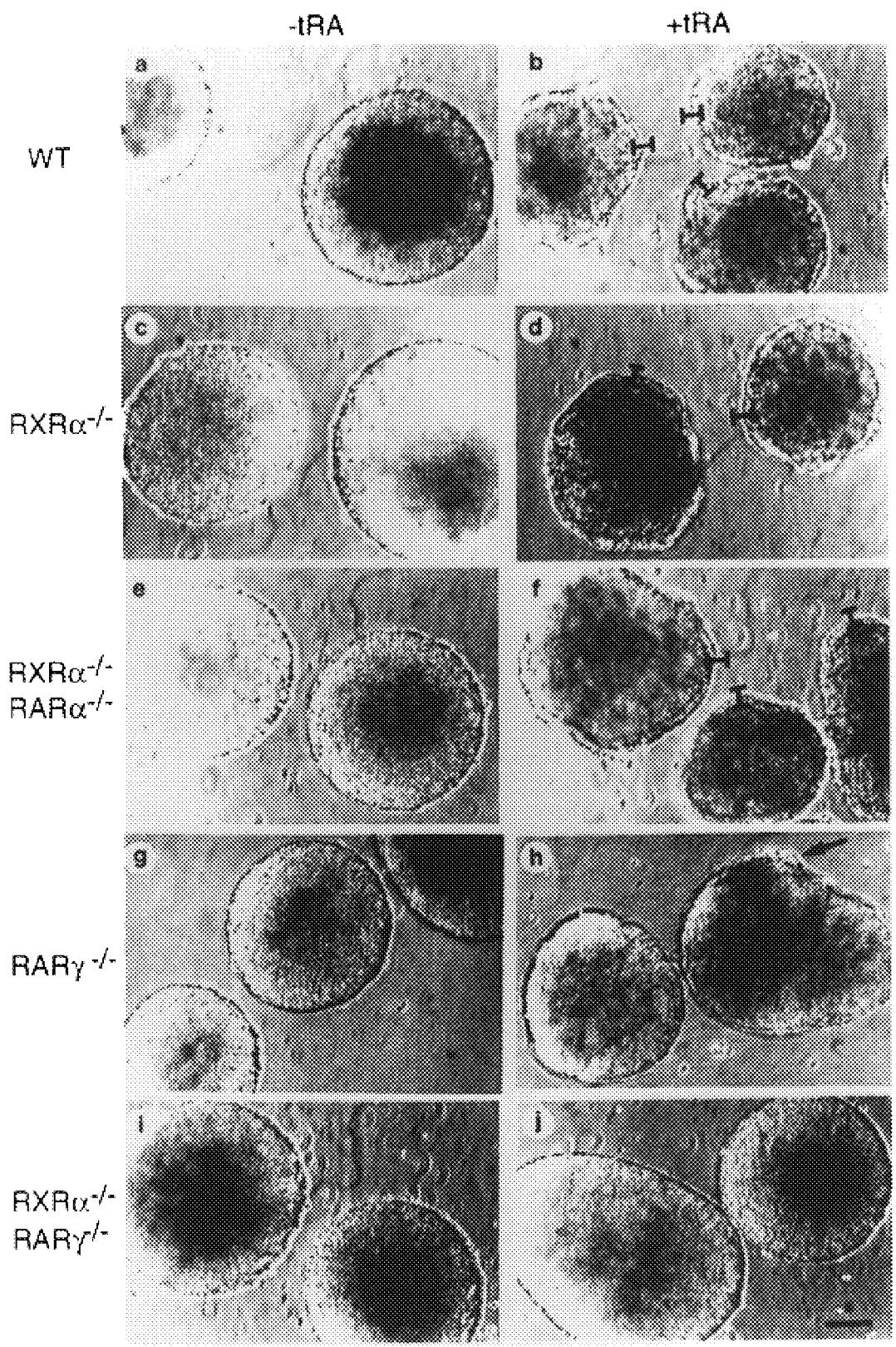
(FIG. 23A) WT (a and b), RXRα$^{-/-}$ (c and d), RXRα$^{-/-}$/RARα$^{-/-}$ (e and f), RARγ$^{-/-}$ (g and h), and RXRα$^{-/-}$/RARγ$^{-/-}$ (i and j) cells were grown in suspension in the absence (a, c, e, g and i) or presence (b, d, f, h and j) of 50 nM tRA for 10 d. The aggregates were photographed under a phase-contrast microscope at ×125 magnification. The arrows and brackets indicate VE morphology.

Function of RXRs and RARs in the retinoid-induced differentiation of F9 cells into VE-like cells When F9 cells are grown in suspension as aggregates, low levels of tRA induce a VE phenotype in the outermost layer of cells, which display an irregular surface (Strickland, S., *Cell* 24:277–278 (1981); Hogan, B. L. M., et al., *Cancer Surveys* 2:115–140 (1983); see also FIG. 23A, WT, a and b, brackets). We have previously shown that, in contrast to primitive and parietal endodermal differentiation, VE differentiation can be induced by tRA in RXRα$^{-/-}$ F9 cells (Clifford, J., et al., *EMBO J.* 15:4142–4155 (1996)). Similarly, after 10 d of treatment, >80% of the outer layer of RARα$^{-/-}$ and RXRα$^{-/-}$/RARα$^{-/-}$ cell aggregates differentiated into VE-like cells, which were indistinguishable from those of WT and RXRα$^{-/-}$ cells (FIG. 23A, compare f with panels b and d; and Table 9). In contrast, <10% of the outer layer of RARγ$^{-/-}$ cells exhibited VE conversion after 10 d of treatment, whereas full VE differentiation was eventually achieved after 14 d of treatment (FIG. 23A, compare h with g and b; and Table 9). In RXRα$^{-/-}$/RARγ$^{-/-}$ cells, the surface of the aggregates was as smooth after 10 days of treatment as in untreated controls (FIG. 23A, compare j with a and i), and <10% of the aggregates displayed only a spotty VE conversion after 12 or 18 d of treatment (Table 9). To exclude the possibility that this very poor differentiation of the RXRα$^{-/-}$/RARγ$^{-/-}$ cells could be due to some clonal variation, rather than the presence of the RXRα-null mutation in the RARγ-null background, we expressed the RXRα cDNA in RXRα$^{-/-}$/RARγ$^{-/-}$ cells. As expected, cells expressing the RXRα cDNA exhibited a phenotype identical to that of RARγ$^{-/-}$ cells, i.e., the RA-induced VE differentiation was restored at late time (14 d) of RA treatment.

Figure 23B:
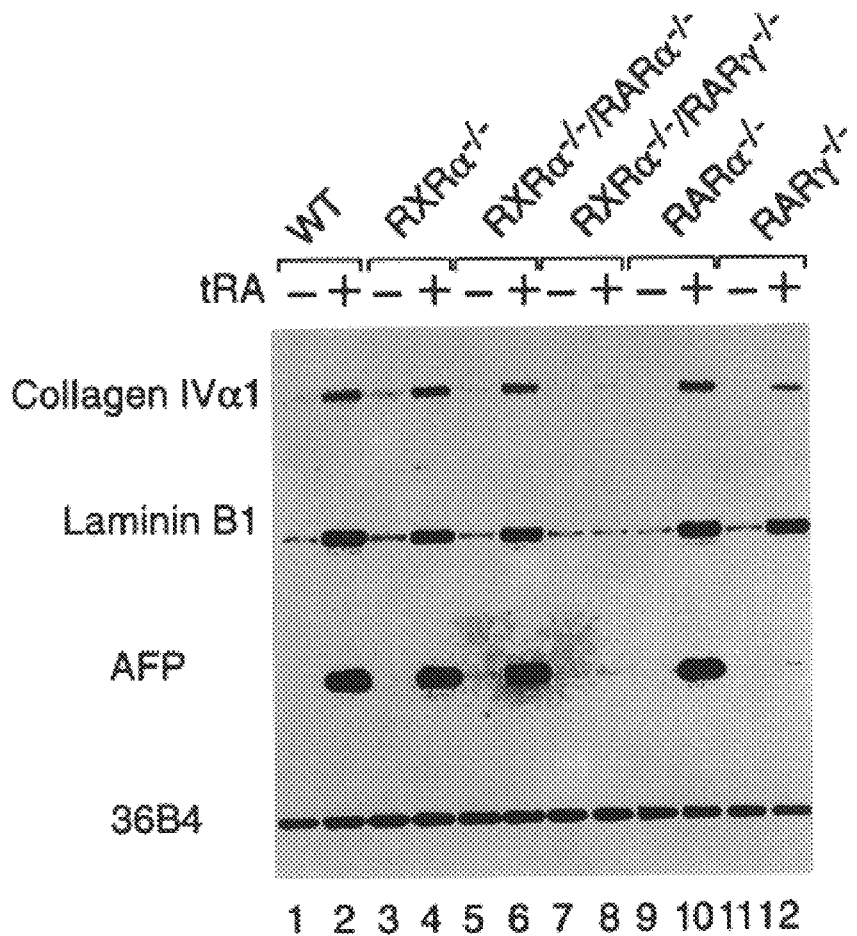
(FIG. 23B) Total RNA from WT and mutant aggregates, treated with control vehicle or 50 nM tRA for 10 days, was subjected to RT-PCR analysis for collagen IVα1, laminin B1, AFP and 36B4. Similar results were obtained for three independent experiments. Bar, 100 μM.

We also analyzed the mRNA levels of collagen type IVα1, laminin B1 and AFP in WT and mutant F9 cells (FIG. 23B). After 10 d of aggregate culture in the presence of 50 nM tRA, the three markers were similarly induced in WT, RXRα$^{-/-}$/RARα$^{-/-}$ and RXRα$^{-/-}$/RARα$^{-/-}$ cells. In RARγ$^{-/-}$ cells, the induction of laminin B1 was similar to that of WT cells, whereas the induction of collagen IVα1 was slightly reduced (two-fold lower than in WT cells). In contrast, the induction of AFP, a specific marker of VE differentiation, was hardly detectable in RARγ$^{-/-}$ cells after 10 d of RA treatment (FIG. 23B). There was no induction of either collagen IVα1, laminin B1 or AFP in RXRα$^{-/-}$/RARγ$^{-/-}$ cells, in agreement with their lack of morphological differentiation into VE. Thus, RXRα and RARγ play an essential role in VE differentiation of WT F9 cells.

To further investigate the functions of RARs and RXRs in VE differentiation, WT and mutant F9 cells were treated for 10–18 d with tRA or synthetic retinoid agonist selective for RARα (BMS 188,753 (BMS753); Taneja, R., et al., *Proc. Natl. Acad. Sci. USA* 93:6197–6202 (1996)), RARβ (BMS 189,453 (BMS453); Chen, J-Y., et al., *EMBO J.* 14:1187–1197 (1995)), RARγ (BMS188,961 (BMS961); Taneja, R., et al., *Proc. Natl. Acad Sci. USA* 93:6197–6202 (1996)) and all three RXRs (panRXR, BMS188,649 (BMS649); also known as SR11237; Lehmann, J. M., et al., *Science* 258:1944–1946 (1992); see Roy, B., et al., *Mol. Cell. Biol.* 15:6481–6487 (1995)) (Table 9). In WT cells, VE differentiation was triggered by 100 nM of the RARγ agonist as effectively as by 50 nM tRA, and it was synergistically induced by a combination of 10 nM RARγ and 1 μM panRXR agonists (Table 9). In contrast, VE differentiation of RARα$^{-/-}$ cells was triggered by 10 nM RARγ agonist as efficiently as by 50 nM tRA, and it was even synergistically induced by 1 nM of the RARγ agonist in combination with 1 μM panRXR agonist, indicating that RARα partially hinders the RARγ function in WT cells. The RARγ agonist alone, or together with the panRXR agonist, was more efficient in RXRα$^{-/-}$ and RXRα$^{-/-}$/RARα$^{-/-}$ cells than in WT cells, but weaker than in RARα$^{-/-}$ cells, demonstrating that RXRα prevents an efficient synergism between RXR (β+γ) and RARγ (Table 9; see also Table 12). As expected, no VE differentiation was observed in RARγ$^{-/-}$ and RXRα$^{-/-}$/RARγ$^{-/-}$ cells treated with the RARγ/panRXR agonist combination.

The RARα agonist, BMS753, on its own did not trigger VE differentiation of WT and RXRα$^{-/-}$ cells, whereas the combination of 100 nM RARα and 1 μM panRXR agonists was much less efficient than the RARγ/panRXR agonist combination. As expected, no VE differentiation was seen in RARα$^{-/-}$ and RXRα$^{-/-}$/RARα$^{-/-}$ cells upon treatment with the RARα /panRXR agonist combination. In contrast, RARγ$^{-/-}$ cells weakly differentiated into VE-like cells upon treatment with 100 nM RARα agonist alone, and this differentiation was markedly enhanced by addition of 1 μM panRXR agonist. This synergistic stimulation was almost abrogated in RXRα$^{-/-}$/RARγ$^{-/-}$ cells.

A combination of RARβ (BMS453) and panRXR agonists did not trigger VE differentiation in WT, RXRα$^{-/-}$, RARα$^{-/-}$, and RXRα$^{-/-}$/RARα$^{-/-}$ cells. Interestingly, this combination synergistically induced VE differentiation of RARγ$^{-/-}$ cells, and this effect was almost absent in RXRα$^{-/-}$/RARγ$^{-/-}$cells, as in the case of the RARα/ panRXR agonist combination (Table 9). Thus, RARγ strongly prevents RARα and RARβ to synergize with RXRα, and mutation of RARγ artefactually generates functional redundancy between RARs for VE differentiation of F9 cells (see also Table 12).

Function of RXRs and RARs in the retinoid-induced antiproliferative response of F9 cells and retinoid-induced proliferation of RXR α/RAR γ null F9 cells The effect of tRA on proliferation of WT, RXRα$^{-/-}$, RXRα$^{-/-}$/RARα$^{-/-}$, and RXRα$^{-/-}$/RARγ$^{-/-}$ F9 cells was investigated (FIG. 24A). After 6 d of 1 μM tRA treatment, the inhibition of growth as determined by cell counting, was lower for RXRα$^{-/-}$than for WT cells (58% and 79% inhibition relative to untreated control cells, respectively) (Clifford, J., et al., *EMBO J.* 15:4142–4155 (1996)). The anti-proliferative effect of tRA was decreased to the same extent for RXRα$^{-/-}$/RARα$^{-/-}$ cells (54% inhibition) and RXRα$^{-/-}$ cells. On the other hand, tRA did not reduce, but slightly increased the number of RXRα$^{-/-}$/RARγ$^{-/-}$ cells. The rate of DNA synthesis was also compared for WT and mutant cell lines by measuring [$^3$H]thymidine incorporation during the anti-proliferative response to tRA (FIG. 24B). After 4 d of 1 μM tRA treatment, [$^3$H]-thymidine incorporation was reduced by 54% in WT cells relative to vehicle-treated control cells, and only by 20% in RXRα$^{-/-}$ and RXRα$^{-/-}$/RARα$^{-/-}$ cells. In contrast, there was no inhibition of [$^3$H]thymidine incorporation in RXRα$^{-/-}$/RARγ$^{-/-}$ cells.

FACS® analysis has previously shown that tRA treatment of WT F9 cells results in an accumulation of cells in the G0 and G1 phases of the cell cycle, and that this accumulation was decreased in RXRα$^{-/-}$ cells (Clifford, J., et al., *EMBO J.* 15:4142–4155 (1996) (FIG. 24C). The cell cycle profile of untreated RXRα$^{-/-}$/RARα$^{-/-}$ and RXRα$^{-/-}$/RARγ$^{-/-}$ cells was the same as that of WT and RXRα$^{-/-}$ cells. After 5 d of 1 μM tRA treatment, the proportion of cells in the G0 and G1 phases, was 71% for WT cells, whereas it was lower for RXRα$^{-/-}$ and RXRα$^{-/-}$/RARα$^{-/-}$ cells (38 and 40%, respectively; FIG. 24C, compare b, d and f). Interestingly, the cell cycle profile of RXRα$^{-/-}$/RARγ$^{-/-}$ cells was not significantly affected by tRA treatment, and was almost identical to that of untreated WT cells (FIG. 24C, compare h with g and a).

To further dissect the roles of RARs and RXRs in the control of proliferation, WT and mutant F9 cells were treated for 6 d with tRA or receptor-selective retinoids, and cell numbers were counted (Table 10). In WT cells, 100 nM RARγ agonist efficiently reduced the proliferation, and 10 nM of the same agonist, which had no effect on its own, synergized with 1 μM panRXR agonist. The effect of these retinoids on proliferation was reduced, while not abolished, in RXRα$^{-/-}$ and RXRα$^{-/-}$/RARα$^{-/-}$ cells, indicating that RXRα can be partially replaced by RXR(β+γ) for synergizing with RARγ (see Table 12). Interestingly, the RARγ/ panRXR agonist combination was more efficient in RARα$^{-/-}$ cells than in WT cells, revealing that RARα partially hinders the anti-proliferative effect of RARγ in WT cells (Table 10; see Table 12). As expected, this combination did not inhibit the proliferation of RARγ$^{-/-}$ and RXRα$^{-/-}$/RARγ$^{-/-}$ cells. The combination of 100 nM RARα and 1 μM panRXR agonists, which reduced the proliferation of WT cells less efficiently than the RARγ/panRXR agonist combination, was more efficient in RARγ$^{-/-}$ cells than in WT cells (Table 10), indicating that RARγ partially hinders the anti-proliferative effect of RARα in WT cells (see Table 12). The RARα/panRXR agonist combination had no effect on the proliferation of RXRα$^{-/-}$ cells, showing that RARα can only synergize with RXRα to inhibit proliferation (see Table 12).

Surprisingly, a treatment with 10 and 100 nM RARα agonist increased the number of RXRα$^{-/-}$/RARγ$^{-/-}$ cells, indicating that RARα can mediate a proliferative effect in the absence of both RXRα and RARγ. As expected, the RARα/panRXR agonist combination did not affect proliferation of RARα$^{-/-}$ and RXRα$^{-/-}$/RARα$^{-/-}$ cells. Neither the RARβ agonist alone nor in combination with the panRXR agonist affected the proliferation of WT, RXRα$^{-/-}$, RARα$^{-/-}$ and RXRα$^{-/-}$/RARα$^{-/-}$ cells, whereas this combination synergistically reduced the proliferation of RARγ$^{-/-}$ cells. Note that 500 nM RARβ agonist alone increased the cell number of RXRα$^{-/-}$/RARγ$^{-/-}$ cells, and that this effect was enhanced by addition of 1 μM panRXR agonist. Thus, the presence of RARγ not only hinders the anti-proliferative effect of the RXRα/RARβ pair, but also the proliferation-promoting effects of the combinations of RXR(β+γ) with RARβ, showing again that knockouts generate artifactual effects not observed under WT conditions, as already seen above in the case of F9 cell differentiation (see Table 12).

Figure 25:
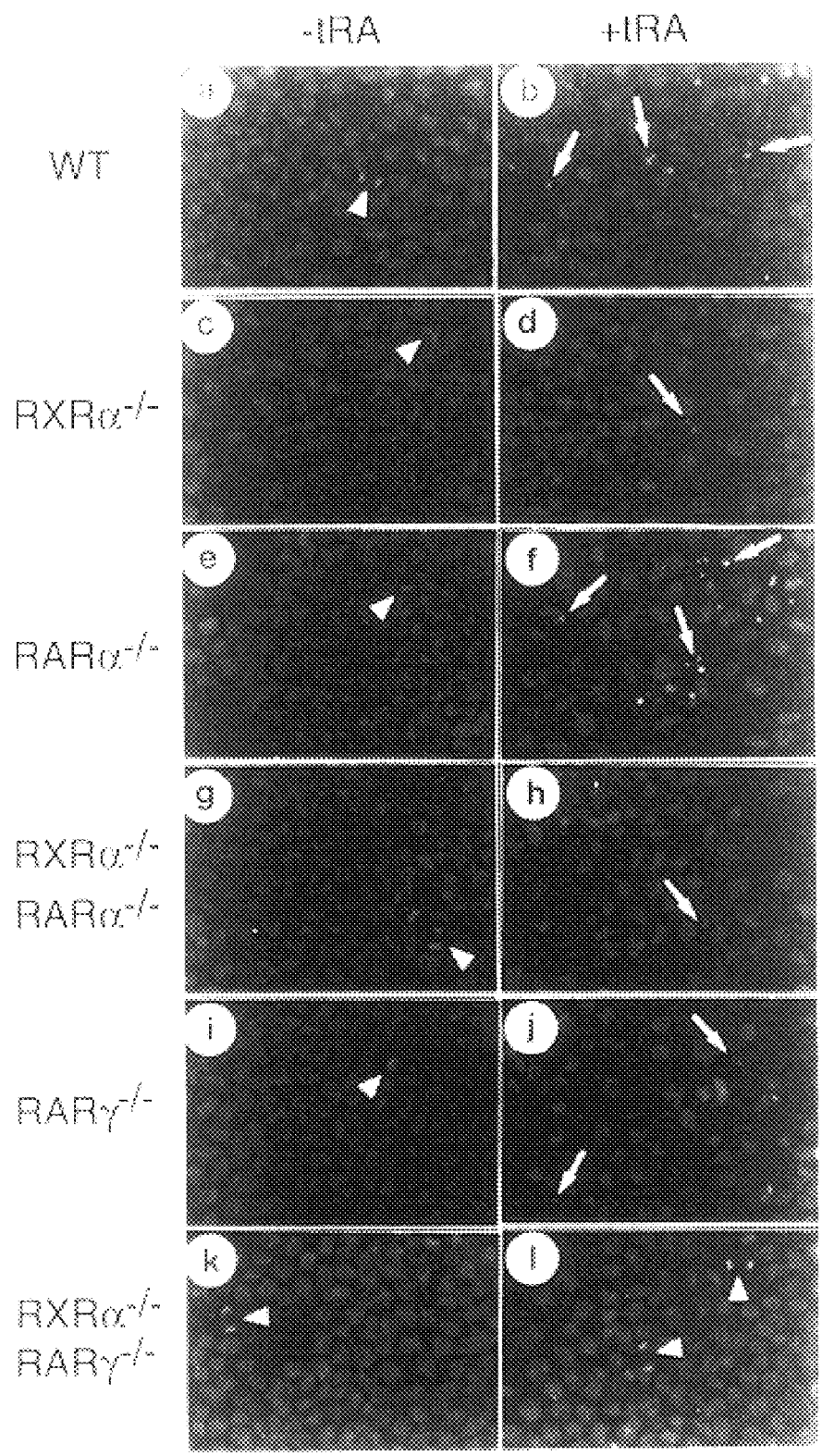

Function of RXRs and RARs for the retinoid-induced apoptotic response of F9 cells Since retinoids can induce apoptosis, which also contributes to the decrease in cell number in retinoid-treated F9 cells (Atencia, R., et al., *Exp. Cell Res.* 214:663–667 (1994)), we determined the extent of the tRA-induced apoptotic response of WT and mutant F9 cells by FACS® analysis. Sub-2N size, DNA-containing particles corresponding to 'apoptotic bodies' appeared in WT cells after 5 d of tRA treatment, whereas they were not detected in tRA-treated RXRα$^{-/-}$ (see also Clifford, J., et al., *EMBO J.* 15:4142–4155 (1996)), RXRα$^{-/-}$/RARα$^{-/-}$ and RXRα$^{-/-}$/RARγ$^{-/-}$ cells (FIG. 24C, compare d, f and h with b (arrow)). Apoptosis was confirmed by staining with the DNA-binding fluorochrome Hoechst 33258. Apoptotic particles and condensed chromatin were similarly observed in tRA-treated WT and RARα$^{-/-}$ cells (FIG. 25, a, b, e and f; Table 11). In contrast, tRA-induced apoptosis was reduced in RARγ$^{-/-}$ cells, rarely seen in RXRα$^{-/-}$ (see also Clifford, J., et al., *EMBO J.* 15:4142–4155 (1996)) and RXRα$^{-/-}$/RARα$^{-/-}$ cells, and abolished in RXRα$^{-/-}$/RARγ$^{-/-}$ cells (FIG. 25, c, d and g–l; and Table 11). Note that a background level of apoptosis occurred at high cell density even in the absence of tRA, as previously mentioned (Clifford, J., et al, *EMBO J.* 15:4142–4155 (1996)).

To further investigate the role played by the different RAR and RXR isotypes in apoptosis, WT and mutant F9 cells were treated for 6 d with receptor-selective retinoids, and stained with Hoechst dye (Table 11). In WT cells, 100 nM RARγ agonist triggered apoptosis, and the addition of 1 μM panRXR agonist resulted in a synergistic effect. The effect of the se retinoids was markedly reduced in RXRα$^{-/-}$ and RXRα$^{-/-}$/RARα$^{-/-}$ cells, indicating that RXRα can only poorly be replaced by RXR(β+γ) for this response (Table 12). In contrast, the RARγ/panRXR agonist combination was more efficient in RARα$^{-/-}$ cells than in WT cells, indicating that RARα partially prevents the apoptotic response mediated by RARγ in WT cells (Table 12). As expected, this combination had no effect on the apoptosis of RARγ$^{-/-}$ and RXRα$^{-/-}$/RARγ$^{-/-}$ cells. Neither the RARα/panRXR nor the RARβ/panRXR agonist combination induced the apoptosis of WT, RXRα$^{-/-}$, RARα$^{-/-}$, RXRα$^{-/-}$/RARα$^{-/-}$, and RXRα$^{-/-}$/RARγ$^{-/-}$ cells. cells, whereas they weakly triggered apoptosis of RARγ$^{-/-}$ cells (Table 11). 100 nM Am80, which acts as pan-RAR agonist at this concentration (Hashimoto, Y., et al., *Biochem. Biophys. Res. Commun.* 166:1300–1307(1990)), was as efficient as 100 nM RARγ agonist for WT, RXRα$^{-/-}$, RARα$^{-/-}$, and RXRα$^{-/-}$/RARα$^{-/-}$ cells. The panRAR /panRXR combination was more effective than either the RARα/panRXR or the RARβ/panRXR combination in RARγ$^{-/-}$ cells, whereas these retinoids had no effects on the apoptosis of RXRα$^{-/-}$/RARγ$^{-/-}$ cells (Table 11). Thus, RARγ fully prevents the weak apoptotic response that can be mediated by the RXRα/RARα and RXRα/RARβ pairs, and mutation of RARγ artifactually generates some functional redundancy (Table 12).

Discussion

In vitro studies using either cell-free systems or cultured cells co-transfected with vectors overexpressing the various retinoid receptors and cognate recombinant reporter genes, have suggested that RXR/RAR heterodimers could be the functional units transducing the retinoid signal in vivo. These studies have also indicated that the various RXR/RAR heterodimers, resulting from the combination of either one of three RXRs (α, β, or γ) with either one of the three RARs (α, β, or γ), could be differentially involved in the numerous physiological events that are controlled by retinoids in vivo (Chambon, P., Semin. *Cell Biol.* 5:115–125 (1994); Chambon, P., *FASEB. J.* 10:940–954 (1996)). The results of RAR and RXR gene knock-out studies in the mouse have supported these suggestions, but their interpretation remains equivocal, in particular because cell-autonomous and non cell-autonomous effects cannot be distinguished in the intact animal (Kastner, P., et al., *Cell* 83:859–869 (1995); Kastner, P., et al., *Development* 124:313–326 (1997)).

The aim of the present study was to determine the actual role of the various RXR/RAR combinations as retinoid transducers in a well-established, cell-autonomous system, namely that provided by the retinoid-responsive F9 EC cells. To this end, differentiation into primitive, parietal, and visceral endoderms, as well as antiproliferative and apoptotic responses have been studied in RXR and RAR single or compound mutant F9 EC cells cultured in the presence of either tRA or selective panRXR- and/or RAR isotype-selective synthetic retinoids. Our present results are summarized in Table 12 with relevant data from previous reports (Roy, B., et al., *Mol. Cell. Biol.* 15:6481–6487 (1995); Clifford, J., et al., *EMBO J.* 15:4142–4155 (1996); Taneja, R., et al., *Proc. Natl. Acad. Sci. USA* 93:6197–6202 (1996)), and lead to several important conclusions, which are in keeping with those recently drawn from a study of the expression of RA-responsive genes in the same mutant F9 EC cells (Chiba, H., et al., *Mol. Cell. Biol.* 17:3013–3020 (1997)).

Taken together, our genetic data and those obtained with selective retinoids in WT or mutated cells establish that RXR/RAR pairs are always involved in the transduction of the retinoid signal, irrespective of the nature of the retinoid-induced event examined (differentiation, antiproliferative, or apoptotic effects). This is obvious from both the comparison of single and double mutants, and the combined use of the panRXR ligand with suboptimal concentrations of either one of the RAR isotype-specific, synthetic retinoids. Thus, since the pan-RXR-specific agonist is never active of its own, all cellular events induced by retinoids in F9 EC cells appear to be mediated by RXR/RAR heterodimers. Note that the "subordination" of RXRs to RARs (i.e., that a RXR cannot be transcriptionally activated unless its heterodimer RAR partner is liganded), which has been repeatedly observed in different cell systems (Roy, B., et al., *Mol. Cell. Biol.*

15:6481–6487 (1995); Chen, J-Y., et al., *Nature* 382:819–822 (1996); Horn, V., et al., *FASEB J.* 10:1071–1077 (1996); Taneja, R., et al., *Proc. Natl. Acad. Sci. USA* 93:6197–6202 (1996)), as well as in some in vitro studies (Durand, B., et al., *EMBO J.* 13:5370–5382 (1994); Apfel, C., et al., *J. Biol. Chem.* 270:30765–30772 (1995); Forman, B. M., et al., *Cell* 81:541–550 (1995)), may be important to prevent the promiscuous activation of the retinoid and other signaling pathways (e.g., those of thyroid hormones and vitamin D3) by RXR ligands (Mangelsdorf, D. J., and Evans, R. M., *Cell* 83:841–850 (1995); Chambon, P., *FASEB. J.* 10:940–954 (1996)). The dispensability of the RXR ligand that can be observed in some instances when a saturating amount of a RAR-selective ligand (notably in the case of RARγ) is used, has been previously noted (Roy, B., et al., *Mol. Cell. Biol.* 15:6481–6487 (1995)). This dispensability most probably reflects the fact that the RAR activation functions of RXR/RAR heterodimers alone are sufficient to trigger the expression of the genes involved in the cellular event considered, whereas the synergistic effect of the activation functions of the RXR heterodimeric partner becomes indispensable at lower concentrations of the RAR ligand which are probably closer to physiological retinoic acid concentrations.

The second important conclusion of the present study is that the various RXR/RAR heterodimers that can be formed in F9 EC cells exhibit some functional specificity. Indeed, each of the cellular events that are RA-induced in F9 cells appears to preferentially involve a specific RXR/RAR isotype combination (or set of combinations) (Table 12). It appears that in all cases the RA signal is transduced by RXRα/RARγ heterodimers in WT F9 cells. However, both the RXRα/RARγ and RXRα/RARα heterodimers can mediate the RA-induced inhibition of WT F9 cell proliferation. Thus, in WT F9 cells, depending on the cellular event considered, different RXR/RAR isotype heterodimers possess both specific functions and redundant functions shared with other heterodimers. Interestingly, additional redundant functions, not seen in WT cells, are revealed when either RXRα or RARγ are not expressed. The presence of RARγ often hinders or blocks the activity of RARα and RARβ, where the presence of RXRα can hinder the activity of RXR(β+γ) (Table 12). In several instances, the retinoid-induced cellular events mediated by RXRα/RARγ in WT cells can be mediated by RXR(β+γ)/RARγ heterodimers in the absence of RXRα, and by RXRα/RAR(α and/or β) heterodimers in the absence of RARγ (Table 12). Again, these redundancies vary according to the cellular event examined, further supporting the conclusion that the different RXR/RAR isotype heterodimers possess some functional specificity.

The third conclusion is that gene knockouts generate artifactual conditions unmasking potential functional redundancies, which actually do not occur in the WT situation (Table 12). For instance, in the case of visceral endoderm differentiation, RXR(β+γ)/RARγ heterodimers can efficiently substitute for RXRα/RARγ heterodimers in the absence of RXRα; in addition, either RXRα/RARα or RXRα/RARβ heterodimers can efficiently substitute for RXRα/RARγ heterodimers in the absence of RARγ, even though RXRα/RARγ heterodimers essentially mediate this differentiation in WT F9 EC cells. How the presence of RXRα/RARγ heterodimers prevent potentially functionally redundant heterodimers from transducing the RA signal is unknown, but it could be related to their differential affinities for the RAREs of the target genes involved in the cellular processes induced by RA in F9 cells. In any event, it is clear that the functional redundancies that are revealed by gene knockout cannot be taken as evidence for a lack of functional specificity of the knocked out gene product under WT physiological conditions. It is not unlikely that many of the functional redundancies that have been so far revealed by mouse gene knockouts are similarly artifactually generated.

Interestingly, our present study also reveals that different RXR/RAR heterodimers can have opposite effects on cell proliferation of F9 cells. RXRα/RARγ or RARα heterodimers are involved in the transduction of the antiproliferative effect of RA, but in the absence of RXRα and RARγ, both RXR(β+γ)/RARα and RARβ heterodimers can mediate a proliferative effect of RA (Tables 10 and 12). Note that induction of proliferation of certain cell types by retinoids has been previously reported (Amos, B., and Lotan, R., *Methods Enzymol.* 190:217–225 (1990); Koshimizu, U., et al., *Dev. Biol.* 168:683–685 (1995)). Our present observations on retinoid-induced cell antiproliferative and proliferative effects, strengthen the conclusion that different RXR/RAR heterodimers can exert specific functions. These observations also suggest that the actual set of retinoid receptors present in a given cell may have a profound influence on the effects generated by a retinoid treatment.

It is interesting to note that morphological differentiation of WT F9 EC cells can be efficiently triggered by a combination of panRXR/RARγ-specific (BMS961) agonists, but not by a combination of panRXR/RARα-specific (BMS753) agonists, nor by a combination of a panRXR/RARβ-specific (BMS453) agonists. In contrast, P19 EC cell differentiation can be triggered by either a panRXR/RARγ or a panRXR/RARα agonist combination, but not by a panRXR/RARβ agonist combination (Taneja, R., et al., *Proc. Natl. Acad. Sci. USA* 93:6197–6202 (1996)), whereas the differentiation of the NB4 acute promyelocytic leukemia cells, and HL60 myeloblastic leukemia cells can be triggered by a combination of a panRXR/RARα or a panRXR/RARβ agonists, but not by a panRXR/RARγ agonist combination (Chen, J-Y., et al., *Nature* 382:819–822 (1996)). Similarly, the apoptosis of NB4 cells can be induced by a panRXR/RARβ agonist combination (Chen, J-Y., et al., *Nature* 382:819–822 (1996)), which on the other hand is inefficient in the case of F9 cells (Table 11). Thus, different RAR isotype-specific agonists acting synergistically with a panRXR agonist are not only more restricted than tRA in their effects on various cellular events in a given cell type (e.g., differentiation and apoptosis), but also affect differentially these events in a cell-specific manner. These cell type-specific effects of synthetic retinoids may extend their potential for therapeutical use.

Finally, to our best knowledge, this study is the first report of multiple gene targeting (two alleles of two genes) in a mammalian cell-autonomous system. Similar approaches will allow the inactivation of any set of genes in a given cell, which will undoubtedly and particularly useful to elucidate the molecular mechanisms underlying complex biological events.

Materials and Methods

Cell culture

F9 cells were cultured and induced to differentiate into primitive, parietal and visceral endoderm-like cells as previously described (Boylan, J., et al., *Proc. Natl. Acad. Sci. USA* 90:9601–9605 (1993); Clifford, J., et al., *EMBO J.* 15:4142–4155 (1996)). The retinoids (tRA, Am80, BMS753, BMS453, BMS961, and BMS649) were dissolved in ethanol.

Targeting of the RARα or RARγ genes in RXR α-null F9 cells

The RARα targeting vector, pRARα$^{(LNL)}$, was previously described (Metzger, D., et al., *Proc. Natl. Acad. Sci. USA* 92:6991–6995 (1995)). The RARγ targeting vector pRARγ $^{(LPL)}$, was derived from pDγ6.5A (a gift from D. Lohnes, IGBMC, CNRS/INSERM/ULP, Illkirch, France), which contains a 6-kb genomic fragment including exons 5 and 8. A unique SmaI site, followed by stop codons in all three reading frames, was introduced into pDγ6.5A at the Kpnl site located in exon 8 RARγ by inserting the oligonucleotides 5'-CCCCGGGTAGGTAGATAGCGTAC-3' (SEQ ID NO:7) and 5'-GCTATCTACCTACCCGGGGGTAC-3' (SEQ ID NO:8), yielding the pRARγT4 construct. An XhoI-BAMHI fragment containing the phosphoglycerate kinase (PGK) promoter-driven, puromycin-resistance (puro) gene, flanked by loxP sites, was isolated from pHRLpuro1, and bluntended with T4 DNA polymerase, followed by ligation into the SmaI site of pRARγT4. pHRLpuro1 was constructed from VS-1, a plasmid containing a loxP site-flanked PGKpuroA+ cassette, by mutating the SalI site. The PGKpuroA+cassette was obtained by ligating the PGK promoter (a 500-bp EcoRI-PstI fragment isolated from pKJ-1 (Adra, C. N., et al., *Gene* 60:65–74 (1987)) to the coding sequence of the puro gene (a 600-bp HindIII-ClaI fragment isolated from pLXPB (Imler, J. L., et al, *Gene Therapy* 3:75–84 (1996)), and by inserting the SV-40 polyadenylation signal (a 160-bp BglII-XbaI fragment isolated from pSG5 (Green, S., et al., *Nucl. Acids Res.* 16:369 (1988)) using synthetic oligonucleotides. This cloning resulted in the loss of the PstI, HindIII and ClaI restriction sites, and the introduction of HindIII and EcoRI sites at 5' and 3' ends of the PGK promoter, respectively. KpnI, ApaI, XhoI and BglII restriction sites, and BamHI and SacI sites are located at 5' and 3' ends of the loxP-flanked cassette, respectively.

Electroporation, selection of neomycin-resistant clones, Cre-mediated excision of the resistance genes, and Southern blot analysis were performed as previously described (Metzger, D., et al., *Proc. Natl. Acad. Sci. USA* 92:6991–6995 (1995); Clifford, J., et al., *EMBO J.* 15:4142–4155 (1996)). Puromycin selection (500 ng/ml) was carried out for 10 d.

Western blotting and Electrophoretic Mobility Shift Assays (EMSA)

Isolation of whole cell extracts from F9 cells and transfected COS-1 cells, Western blot analysis, and electrophoretic mobilityshift assays were performed as previously described (Rochette-Egly, C., et al ., *J. Cell Biol.* 115:535–545 (1991); Gaub, M-P., et al., *Exp. Cell Res.* 201:335–346 (1992); Boylan, J., et al., *Proc. Natl. Acad. Sci. USA* 90:9601–9605 (1993)).

Reverse Transcription (R7)-PCR

RNA preparation, RT-PCR, and Southern blotting were performed as previously described (Bouillet, P., et al., *Dev. Biol.* 170:420–433 (1995); Roy, B., et al., Mol. Cell. Biol. 15:6481–6487 (1995)). The PCR primers and end-labeled oligonucleotide probes for collagen IVα1, laminin B1, α-fetoprotein (AFP), and 36B4 were described previously (Clifford, J., et al ., *EMBO J.* 15:4142–4155 (1996)). Transcript levels were quantified using a BAS 2000 bioimaging analyzer (Fuji Ltd., Tokyo, Japan), and were normalized to the corresponding 36B4 signals.

Analysis of cellular growth

Cells were plated in triplicate 3-cm culture wells (5×10$^2$ cells per well), and cell counting experiments were performed as previously described (Clifford, J., et al., *EMBO J.* 15:4142–4155 (1996)). [$^3$H]Thymidine incorporation assays were performed essentially as described (Clifford, J., et al., *EMBO J.* 15:4142–4155 (1996)), with the following modifications. Cells were cultured for 4 d in six replicate 3 -cm wells, in the presence or absence of 1 µM tRA, and three of the six wells were treated with 8 µCi/well [$^3$H] methylthymidine (20.0 Ci/mmol; Dupont-NEN, Boston, Mass.) for 2 h before harvesting. The cell cycle profile of WT and mutant cells was determined as previously described (Clifford, J., et al. *EMBO J.* 15:4142–4155 (1996)).

Analysis of apoptosis

Apoptosis was analyzed by both Hoechst staining of nuclei and FACS® analysis, as previously described (Clifford, J., et al., *EMBO J.* 15:4142–4155 (1996)).

TABLE 9

Effect of Various Retinoids on Morphological Differentiation of WT and Mutant F9 Cells into Visceral Endoderm (VE)-like Cells

| Treatment | | WT | RXRα$^{-/-}$ | RARα$^{-/-}$ | RXRα$^{-/-}$ RARα$^{-/-}$ | RARγ$^{-/-}$ | RXRα$^{-/-}$ RARγ$^{-/-}$ |
|---|---|---|---|---|---|---|---|
| Ethanol | | (−) | (−) | (−) | (−) | (−) | (−) |
| 50 nM | tRA | +++ | +++ | +++ | +++ | ±(+++*) | (−)(−$^‡$) |
| 1 µM | panRXR agonist | (−) | (−) | (−) | (−) | (−) | (−) |
| 10 nM | RARα agonist | (−) | (−) | ND | ND | (−) | ND |
| 100 nM | RARα agonist | (−) | (−) | (−) | (−) | ± | (−) |
| 500 nM | RARβ agonist | (−) | (−) | (−) | (−) | ± | (−) |
| 1 nM | RARγ agonist | (−) | (−) | (−) | (−) | (−) | ND |
| 10 nM | RARγ agonist | ± | + | +++ | + | (−) | ND |
| 100 nM | RARγ agonist | +++ | +++ | +++ | +++ | (−) | (−) |
| 10 nM | RARα + 1 µM panRXR agonists | (−) | (−) | ND | ND | (−) | ND |
| 100 nM | RARα + 1 µM panRXR agonists | ± | ± | (−) | (−) | ++ | (−)($^§$) |
| 500 nM | RARβ + 1 µM panRXR agonists | (−) | (−) | (−) | (−) | ++ | (−)(±$^§$) |
| 1 nM | RARγ + 1 µM panRXR agonists | (−) | (−) | + | (−) | (−) | ND |

TABLE 9-continued

Effect of Various Retinoids on Morphological Differentiation of WT and Mutant F9 Cells into Visceral Endoderm (VE)-like Cells

| Treatment | | WT | RXRα$^{-/-}$ | RARα$^{-/-}$ | RXRα$^{-/-}$ RARα$^{-/-}$ | RARγ$^{-/-}$ | RXRα$^{-/-}$ RARγ$^{-/-}$ |
|---|---|---|---|---|---|---|---|
| 10 nM | RARγ + 1 μM panRXR agonists | + | +++ | +++ | +++ | (−) | (−) |
| 100 nM | RARγ + 1 μM panRXR agonists | +++ | +++ | +++ | +++ | (−) | (−) |

WT and mutant F9 cell aggregates were treated for 10 d with the indicated retinoids, and their differentiation was scored according to the proportion of outer layer of cells displaying VE morphology. +++, more than 80%; ++, 50–80%; +, 10–50%; ±, not more than 10%; (−), no visible effect; ND, not determined. * After 14 d of treatment. ‡ After 12 or 18 d of treatment, < 10% of the aggregates exhibited a spotty VE morphology only. The RARα, RARβ, RARγ,and panRXR agonists were BMS753, BMS453, BMS961, and BMS649, respectively (see text). § After 12 or 18 d of treatment. Note that this visual scoring correlated well with the determination of the relative level of induction of α-fetoprotein RNA using semi-quantitative RT-PCR (FIG. 23B).

TABLE 10

Effect of Various Retinoids on Proliferation of WT and Mutant F9 Cells

| Treatment | | WT | RXRα$^{-/-}$ | RSRα$^{-/-}$ | RXRα$^{-/-}$ RARα$^{-/-}$ | RARγ$^{-/-}$ | RXRα$^{-/-}$ RARγ$^{-/-}$ |
|---|---|---|---|---|---|---|---|
| Ethanol | | 100 | 100 | 100 | 100 | 100 | 100 |
| 1 μM | tRA | 21 | 42 | 22 | 46 | 28 | 112 |
| 1 μM | panRXR agonist | 100 | 100 | 100 | 100 | 100 | 100 |
| 10 nM | RARα agonist | 100 | 100 | 100 | 100 | 100 | 124 |
| 100 nM | RARα agonist | 100 | 100 | 100 | 100 | 100 | 143 |
| 50 nM | RARβ agonist | 100 | 100 | ND | ND | 100 | ND |
| 500 nM | RARβ agonist | 100 | 100 | 100 | 100 | 100 | 120 |
| 10 nM | RARγ agonist | 100 | 100 | 100 | 100 | 100 | 100 |
| 100 nM | RARγ agonist | 37 | 51 | 30 | 49 | 100 | 100 |
| 10 nM | RARα + 1 μM panRXR agonists | 100 | 100 | 100 | 100 | 100 | 130 |
| 100 nM | RARα + 1 μM panRXR agonists | 56 | 100 | 100 | 100 | 40 | 146 |
| 50 nM | RARβ + 1 μM panRXR agonists | 100 | 100 | ND | ND | 53 | ND |
| 500 nM | RARγ + 1 μM panRXR agonists | 100 | 100 | 100 | 100 | 47 | 154 |
| 10 nM | RARγ + 1 μM panRXR agonists | 60 | 81 | 42 | 77 | 100 | 100 |
| 100 nM | RARγ + 1 μM panRXR agonists | 31 | 44 | ND | ND | 100 | ND |

WT and mutant F9 cell were treated for 6 d in monolyaer culture with the indicated retinoids. In each case, the number of cells was expressed in percent relative to the number of cells grown in 0.1% ethnaol, which was taken as 100%. ND, not determined. These values correspond to the average of at least three experiments (±10%). RARα, RARβ, RARγ, and panRXR specific agonists were as in Table 9.

TABLE 11

Effect of Various Retinoids on Apoptosis of WT and Mutant F9 Cells

| Treatment | | WT | RXRα$^{-/-}$ | RARα$^{-/-}$ | RXRα$^{-/-}$ RARα$^{-/-}$ | RARγ$^{-/-}$ | RXRα$^{-/-}$ RARγ$^{-/-}$ |
|---|---|---|---|---|---|---|---|
| Ethanol | | (−) | (−) | (−) | (−) | (−) | (−) |
| 1 μM | tRA | ++ | ± | ++ | ± | + | (−) |
| 1 μM | panRXR agonist | (−) | (−) | (−) | (−) | (−) | (−) |
| 100 nM | RARα agonist | (−) | (−) | (−) | (−) | (−) | (−) |
| 500 nM | RARβ agonist | (−) | (−) | (−) | (−) | (−) | (−) |
| 10 nM | RARγ agonist | (−) | ND | (−) | ND | ND | ND |
| 100 nM | RARγ agonist | + | ±* | + | ±* | (−) | (−) |
| 100 nM | panRAR agonist | + | ±* | + | ±* | ± | (−) |
| 100 nM | RARα + 1 μM panRXR agonists | (−) | (−) | (−) | (−) | ± | (−) |
| 500 nM | RARβ + 1 μM panRXR agonists | (−) | (−) | (−) | (−) | ± | (−) |
| 10 nM | RARγ + 1 μM panRXR agonists | ± | (−) | + | (−) | ND | ND |

TABLE 11-continued

Effect of Various Retinoids on Apoptosis of WT and Mutant F9 Cells

| Treatment | | WT | RXRα$^{-/-}$ | RARα$^{-/-}$ | RXRα$^{-/-}$ RARα$^{-/-}$ | RARγ$^{-/-}$ | RXRα$^{-/-}$ RARγ$^{-/-}$ |
|---|---|---|---|---|---|---|---|
| 100 nM | RARγ + 1 μM panRXR agonists | ++ | ± | ++ | ± | (−) | (−) |
| 10 nM | panRAR + 1 μM panRXR agonists | ++ | ± | ++ | ± | + | (−) |

Wt and mutant R9 cells were treated for 6 d in monolayer culture with the indicated retoinds, and their apoptosis was scored according to the proportion of apoptotic nuclei and subcellular fragments upon staining of fixed cells with Hoechst 33258, as shown in FIG. 25. ++, >10%; +, >1–10%, ±, <1%; (−), no visible effect, asterisks less than that in combination with 1 μM panRXR agonist; ND, not determined. RARα, RARβ, RARγ, and panRXR agonists were as in Table 9.The panRAR agonist was AM80.

TABLE 12

Summary of the Involvement of the Various RARs and RXRs in the Transduction of the Retinoid Signal in F9 Cells, as Deduced from the Present and Previous Studies of RAR and RXR Mutant Cells and the Use of Receptor-specific Retinoids

| Retinoid-induced events and RXR/RAR pairs capable transducing the signal | Roles of RXRs | Role of RARs |
|---|---|---|
| Primitive endodermal differentiation | | |
| | RXR ligand inactive on its own (Roy. B., et al., Mol. Cell Biol. 15:6481–6487 (1995)) | RARγ<br>RARγ ligand active on its own at saturating concentration (Taneja, R., et al., Proc. Natl. Acad. Sci. USA 93:6197–6202 (1996))<br>RARγ−/− cells differentiate very poorly (Boylan, J., et al., Proc. Natl. Acad. Sci. USA 90:9601–9605 (1993) |
| RXRα/RARγ in all instances | RXRα−/− cells differentiate very poorly (Clifford, J., et al., EMBO J. 15:4142–4155 (1996))<br><br>RXR ligand is required at suboptional concentration of RARγ ligand (Roy, B., et al., Mol. Cell. Biol. 15:6481–6487 (1995); Taneja, R., et al., Proc. Natl. Acad. Sci. USA 93:6197–6202 (1996))<br><br>RXRα can be poorly replaced by RXR(β + γ) provided that RARγ is present | synergizes with RXRα at suboptimal ligand concentration (Clifford, J., et al., EMBO J. 15:4142–4155 (1996))<br>weakly hindered by RARα in WT cells (Taneja, R., et al., Proc. Natl. Acad. Sci. USA 93:6197–6202 (1996))<br>RARα<br>RARα ligand inactive on its own (Taneja, R., et al., Proc. Natl. Acad. Sci. USA 93:6197–6202 (1996))<br>RARα−/− cells differentiate normally (Boylan, J., et al. Mol. Cell. Biol. 15:843–851 (1995))<br>can poorly replace RARγ provided RXRα is activated<br>RARβ<br>inactive or very poorly active (Taneja, R., et al., Proc. Natl. Acad. Sci. USA 93:6197–6202 (1996)) |
| Visceral endodermal differentiation | | |
| RXRα/RARγ in WT cells | RXR ligand inactive on its own<br>RXR ligand is required at suboptimal concentration of a RAR ligand | RARγ<br>indispensable in WT cells<br>RARγ ligand active on its own at saturating concentration<br>synergizes with RXRs at suboptimal ligand concentration hindered by RARα in WT cells<br>RARα |
| RXR(β + γ)/RARγ in absence of RXRα (efficiently) | RXRα can be efficiently replaced by RXR(β + γ) provided that RARγ is present | RARα ligand inactive on its own or very poorly active<br>RARα−/− cells differentiate normally |
| RXRα/RARα or RARβ in absence of RARγ (efficiently) | hindered by RARγ in WT cells<br>RXRα prevent efficient synergism between RXR(β + γ) and RARγ | synergies with RXRα in the absence of RARγ<br>RARβ<br>RARβ ligand inactive on its own or very poorly active synergizes with RXRα in the absence of RARγ blocked by RARγ in WT cells |
| Inhibition of proliferation | | |
| RXRα/RARγ or RARα in WT cells | RXR ligand inactive on its own | RARγ<br>not indispensable in WT cells<br>RARγ ligand active on its own at saturating concentration synergizes with RXPs at suboptimal ligand concentration partially hindered by RARα in WT cells |

TABLE 12-continued

Summmary of the Involvement of the Various RARs and RXRs in the Transduction of the Retinoid Signal in F9 Cells, as Deduced from the Present and Previous Studies of RAR and RXR Mutant Cells and the Use of Receptor-specific Retinoids

| Retinoid-induced events and RXR/RAR pairs capable transducing the signal | Roles of RXRs | Role of RARs |
|---|---|---|
| RXRα/RARβ in absence of RARγ | RXR ligand is required at limiting concentration of RAR ligand | RARα<br>RARα ligand inactive on its own<br>synergizes with RXRα in WT cells<br>partially hindered by RARγ in WT cells<br>RARβ<br>RARβ ligand inactive on its own<br>synergizes with RXRα in the absence of RARγ<br>blocked by RARγ in WT cells |
| RXR(β + γ)/RARγ in absence of RXRα | RXRα can be partially replaced by RXR(β +γ) provided that RARγ is present | RARα<br>RARα ligand active on its own<br>RARβ<br>RARβ ligand active on its own<br>synergizes with RXR(β + γ) |
| Induction of proliferation in RXRα−/−/RARγ−/− cells | | |
| RXR(β + γ)/RARα<br>RXR(β + γ)/RARβ | RXR ligand inactive on its own | RARγ<br>indispensible in WT cells |
| Apoptosis | | |
| RARα/RXRγ in WT cells | RXR ligand inactive on its own | RARα ligand active on its own at saturating ligand concentration |
| RXR(β + γ)/RARγ in absence of RXRα, but very inefficiently | RXRα ligand is required at suboptimal ligand concentration of RAR ligand | synergizes with RXRα at suboptimal ligand concentration hindered by RARα in WT cells<br>RARα<br>RARα ligand inactive on its own<br>weakly synergizes with RXRα in the absencc of RARγ<br>blocked by RARγ in WT cells<br>RARβ<br>RARβ ligand inactive on its own<br>weakly synergizes with RXRα in the absence of RARγ<br>blocked by RARγ in WT cells |
| RXRα/RARα or RARβ in absence of RARγ, but inefficiently | RXRα can be poorly replaced by RXR(β + γ) provided that RARγ is present | |

All documents, e.g., scientific publications, patents and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A transgenic mouse embryo whose genome comprises a disruption in the gene encoding RARβ, wherein said disruption is in the region encoding the ligand binding domain, said disruption prevents said gene from producing all isoforms of RARβ in active form, and said mouse embryo at embryonic stage day 14.5 has a reduction of the palpebral aperture compared to a wild-type mouse embryo.

2. The transgenic mouse embryo of claim 1, wherein said disruption is heterozygous.

3. The transgenic mouse embryo of claim 1, wherein said disruption is homozygous.

4. The transgenic mouse embryo of claim 3, wherein said mouse embryo at embryonic stage day 14.5 has excess of fibroblasts between the lens and the retina compared to a wild-type mouse embryo.

5. A cell isolated from the transgenic mouse embryo of claim 1, wherein the genome of said cell comprises a disruption in the gene encoding RARβ, wherein said cell is prevented from producing all isoforms of RARβ in active form.

6. A method of identifying an agent which is an antagonist or agonist of a subtype or isoform of a retinoic acid or retinoid X receptor, said method comprising:

(a) administering said agent to the transgenic mouse embryo of any one of claims 1, 2, 3, and 5;

(b) determining the effect of said agent on said transgenic mouse embryo deficient in normal expression of said receptor subtype or isoform; and (c) comparing said effect to the effect of said agent on a mouse embryo without said disruption and exhibiting normal expression of said receptor subtype or isoform, thereby identifying the agent which is an antagonist or agonist of the subtype or isoform of the retinoic acid or retinoid X receptor.

7. The method of claim 6, wherein said effect of said agent in (b) is an effect on the development of said transgenic mouse embryo.

8. A method of identifying an agent which is an antagonist or agonist of a subtype or isoform of a retinoic acid or retinoid X receptor, said method comprising:

(a) administering said agent to the transgenic mouse embryo of any one of claims 1, 2, 3, and 5;

(b) determining the effect said agent has on the expression of a retinoic acid inducible gene sequence in said transgenic mouse embryo deficient in normal expression of said receptor subtype or isoform; and (c) comparing said effect to effect of said agent on the expression of a retinoic acid inducible gene sequence in a mouse embryo without said disruption and exhibiting normal expression of said receptor subtype or isoform, thereby identifying an agent which is an antagonist or agonist of a subtype or isoform of a retinoic acid or retinoid X receptor.

9. A mouse cell, wherein the genome of the cell comprises a disruption the gene encoding RARβ, wherein said disruption is in the region encoding the ligand binding domain and said disruption prevents said gene from producing all isoforms of RARβ in active form.

10. The cell of claim 9, wherein said disruption is heterozygous.

11. The cell of claim 9, wherein said disruption is homozygous.

12. A mouse cell line comprising the cell of claim 9.

13. The mouse cell line of claim 12, wherein said cell line is generated using a pluripotent cell line.

14. The mammalian cell line of claim 13, wherein said pluripotent cell line has the American Type Culture Collection designation CRL 11632.

15. A method of identifying an agent which is an antagonist or agonist of a subtype or isoform of a retinoic acid or retinoid X receptor, said method comprising:

(a) incubating said agent with a cell line of any one of claims 12, 9, 10, and 11;

(b) determining the amount of agent bound by cells of said cell line; and (c) comparing said amount to the amount of said agent bound by cells of a cell line without said disruption, thereby identifying the subtype or isoform of the receptor bound by said agent.

16. A transgenic mouse embryo whose genome comprises a disruption in each of the genes encoding a combination of two receptors selected from the group consisting of:

(a) RARβ/RARα and
(b) RARβ/RARγ, wherein each said disruption prevents said gene from producing all isoforms of said receptor in active form and said mouse embryo at embryonic stage day 14.5 has a reduction of the palpebral aperture compared to a wild-type mouse embryo.

17. The transgenic mouse embryo of claim 16, wherein said combination of two receptors is RARβ/RARα.

18. The transgenic mouse embryo of claim 17, wherein both of said disruptions are homozygous and said mouse embryo has persistent truncus arteriosus.

19. The transgenic mouse embryo of claim 17, wherein said disruption of RARβ is in the region encoding the ligand binding domain and said disruption of RARα is in the region encoding the B domain.

20. The transgenic mouse embryo of claim 16, wherein said combination of two receptors is RARβ/RARγ.

21. The transgenic mouse embryo of claim 20, wherein both of said disruptions are homozygous and said mouse embryo has shortened ventral retina compared to a wild-type mouse embryo.

22. The transgenic mouse embryo of claim 20, wherein said disruption of RARβ is in the region encoding the ligand binding domain and said disruption of RARγ is in the region encoding the DNA binding domain.

23. The transgenic mouse embryo of claim 16, wherein both of said disruptions are homozygous.

24. The transgenic mouse embryo of claim 16, wherein both of said disruptions are heterozygous.

25. The transgenic mouse embryo of claim 16, wherein one said disruption is homozygous and other said disruption is heterozygous.

26. A cell isolated from the transgenic mouse embryo of claim 16, wherein the genome comprises a disruption in each of the genes encoding a combination of two receptors, either (a) RARβ/RARα or (b) RARβ/ RARγ wherein said cell is prevented from providing all isoforms of said combination of two receptors in active form.

27. A mouse cell, wherein the genome of the cell comprises a disruption in each of the genes encoding a combination of two receptors selected from the group consisting of:

(a) RARβ/RARα and
(b) RARβ/RARγ, wherein each said disruption prevents said gene from producing all isoforms of said receptors in active form.

28. The cell of claim 27, wherein said combination of two receptors is RARα/RARβ.

29. The cell of claim 28, wherein said disruption of RARα is in the region encoding the B domain and said disruption of RARβ is in the region encoding the ligand binding domain.

30. The cell of claim 27, wherein said combination of two receptors is RARβ/RARγ.

31. The cell of claim 30, wherein said disruption of RARβ is in the region encoding the ligand binding domain and said disruption of RARγ is in the region encoding the DNA binding domain.

32. The cell of claim 27, wherein both of said disruptions are homozygous.

33. The cell of claim 27, wherein both of said disruptions are heterozygous.

34. The cell of claim 27, wherein one said disruption is homozygous and other said disruption is heterozygous.

35. A mouse cell line comprising the cell of claim 27.

36. The mouse cell line of claim 35, wherein said cell line is generated using a pluripotent cell line.

37. The mouse cell line of claim 36, wherein said pluripotent cell line has the American Type Culture Collection designation CRL 11632.

38. A transgenic mouse embryo whose genome comprises a disruption in each of the genes encoding a combination of two receptors selected from the group consisting of:

(a) RARβ/RXRβ and
(b) RARβ/RXRγ, wherein each said disruption prevents said gene from producing said receptor in active form and said mouse embryo at embryonic stage day 14.5 has a reduction of the palpebral aperture compared to a wild-type mouse embryo.

39. The transgenic mouse embryo of claim 38, wherein said combination of two receptors is RARβ/RARβ.

40. The transgenic mouse embryo of claim 39, wherein said disruption of RARβ is in the region encoding the ligand binding domain and said disruption of RARβ is in the region encoding the DNA binding domain.

41. The transgenic mouse embryo of claim 39, wherein both said disruptions are homozygous and said mouse embryo has a reduction in forward locomotion compared to a wild type mouse embryo.

42. The transgenic mouse embryo of claim 38, wherein said combination of two receptors is RARβ/RXRγ.

43. The transgenic mouse embryo of claim 42, wherein said disruption of RARβ is in the region encoding the ligand binding domain and said disruption of RXRγ is in the region encoding the DNA binding domain.

44. The transgenic mouse embryo of claim 42, wherein both said disruptions are homozygous and said mouse embryo has a decrease in striatal dopamina D2 receptor (D2R) expression compared to a wild type mouse embryo.

45. The transgenic mouse embryo of claim 38, wherein both of said disruptions are homozygous.

46. The transgenic mouse embryo of claim 38, wherein both of said disruptions are heterozygous.

47. The transgenic mouse embryo of claim 38, wherein one said disruption is homozygous and other said disruption is heterozygous.

48. A cell isolated from the transgenic mouse embryo of claim 38.

49. A mouse cell, wherein the genome of the cell comprises a disruption in each of the genes encoding a combination of two receptors selected from the group consisting of:
   (a) RARβ/RXRβ and
   (b) RARβ/RXRγ,
wherein each said disruption prevents said gene from producing said receptor in active form.

50. The cell of claim 49, wherein said combination of two receptors is RARβ/RARβ.

51. The cell of claim 50, wherein said disruption of RARβ is in the region encoding the ligand binding domain and said disruption of RXRβ is in the region encoding the DNA binding domain.

52. The cell of claim 49, wherein said combination of two receptors is RARβ/RXRγ.

53. The cell of claim 52, wherein said disruption of RARβ is in the region encoding the ligand binding domain and said disruption of RXRγ is in the region encoding the DNA binding domain.

54. The cell of claim 49, wherein both of said disruptions are homozygous.

55. The cell of claim 49, wherein both of said disruptions are heterozygous.

56. The cell of claim 49, wherein one said disruption is homozygous and other said disruption is heterozygous.

57. A mouse cell line comprising the cell of claim 49.

58. The mouse cell line of claim 57, wherein said cell line is generated using a pluripotent cell line.

59. The mouse cell line of claim 58, wherein said pluripotent cell line has the American Type Culture Collection designation CRL 11632.

60. A transgenic mouse embryo whose genome comprises a disruption in each of the genes encoding a combination of two receptors RARα/RXRγ, wherein said disruptions prevent said genes from producing said receptors in active form and said mouse embryo has reduced striatal D2 dopamine receptor expression compared to a wild-type mouse embryo when said disruptions are homozygous disruptions.

61. The transgenic mouse embryo of claim 60, wherein both said disruptions are homozygous.

62. The transgenic mouse embryo of claim 60, wherein both said disruptions are heterozygous.

63. The transgenic mouse embryo of claim 60, wherein one said disruption is homozygous and other said disruption is heterozygous.

64. A cell isolated from the transgenic mouse embryo of claim 60, wherein the genome comprises a disruption in each of the genes encoding a combination of two receptors RARα/RARγ, wherein said cell is prevented from producing said combination of receptors in active form, and wherein said disruptions are homozygous disruptions.

65. The transgenic mouse embryo of claim 60, wherein said disruption of RARα is in the region encoding the B domain and said disruption of RXRγ is in the region encoding the DNA binding domain.

66. A mouse cell whose genome comprises a disruption in each of the genes encoding a combination of two receptors RARα/RXRγ, wherein said disruptions prevent said genes from producing said receptors in active form.

67. The cell of claim 66, wherein both said disruptions are homozygous.

68. The cell of claim 66, wherein both said disruptions are heterozygous.

69. The cell of claim 66, wherein one said disruption is homozygous and other said disruption is heterozygous.

70. A mouse cell line comprising the cell of claim 66.

71. The mouse cell line of claim 70, wherein said cell line is generated using a pluripotent cell line.

72. The mouse cell line of claim 71, wherein said pluripotent cell line has the American Type Culture Collection designation CRL 11632.

73. The cell of claim 66, wherein said disruption of RARα is in the region encoding the B domain and said disruption of RXRγ is in the region encoding the DNA binding domain.

* * * * *

UNITED STATES PATENT AND TRADEMARK OFFICE
CERTIFICATE OF CORRECTION

PATENT NO. : 6,521,814 B1
DATED : February 18, 2003
INVENTOR(S) : Chambon et al.

It is certified that error appears in the above-identified patent and that said Letters Patent is hereby corrected as shown below:

<u>Title page,</u>
Item [75], please delete "Morchwiller" and insert therein -- Morschwiller --.
Item [73], please delete "Santa" and insert -- Santé --.

<u>Column 95, line 60, to Column 100, line 38,</u>
Please delete Claims 6 to 73 and insert:
-- 6. A mouse cell, wherein the genome of the cell comprises a disruption the gene encoding RARβ, wherein said disruption is in the region encoding the ligand binding domain and said disruption prevents said gene from producing all isoforms of RARβ in active form.

7. The cell of claim 6, wherein said disruption is heterozygous.

8. The cell of claim 6, wherein said disruption is homozygous.

9. A mouse cell line comprising the cell of claim 6.

10. The mouse cell line of claim 9, wherein said cell line is generated using a pluripotent cell line.

11. The mouse cell line of claim 10, wherein said pluripotent cell line has the American Type Culture Collection designation CRL 11632.

12. A transgenic mouse embryo whose genome comprises a disruption in each of the genes encoding a combination of two receptors selected from the group consisting of:
    (a) RARβ/RARα and
    (b) RARβ/RARγ,
wherein each said disruption prevents said gene from producing all isoforms of said receptor in active form and said mouse embryo at embryonic stage day 14.5 has a reduction of the palpebral aperture compared to a wild-type mouse embryo.

13. The transgenic mouse embryo of claim 12, wherein said combination of two receptors is RARβ/RARα.

UNITED STATES PATENT AND TRADEMARK OFFICE
CERTIFICATE OF CORRECTION

PATENT NO. : 6,521,814 B1
DATED : February 18, 2003
INVENTOR(S) : Chambon et al.

It is certified that error appears in the above-identified patent and that said Letters Patent is hereby corrected as shown below:

14. The transgenic mouse embryo of claim 13, wherein both of said disruptions are homozygous and said mouse embryo has persistent truncus arteriosus.

15. The transgenic mouse embryo of claim 13, wherein said disruption of RARβ is in the region encoding the ligand binding domain and said disruption of RARα is in the region encoding the B domain.

16. The transgenic mouse embryo of claim 12, wherein said combination of two receptors is RARβ/RARγ.

17. The transgenic mouse embryo of claim 16, wherein both of said disruptions are homozygous and said mouse embryo has shortened ventral retina compared to a wild-type mouse embryo.

18. The transgenic mouse embryo of claim 16, wherein said disruption of RARβ is in the region encoding the ligand binding domain and said disruption of RARγ is in the region encoding the DNA binding domain.

19. The transgenic mouse embryo of claim 12, wherein both of said disruptions are homozygous.

20. The transgenic mouse embryo of claim 12, wherein both of said disruptions are heterozygous.

21. The transgenic mouse embryo of claim 12, wherein one said disruption is homozygous and other said disruption is heterozygous.

22. A cell isolated from the transgenic mouse embryo of claim 12, wherein the genome comprises a disruption in each of the genes encoding a combination of two receptors, either (a) RARβ/RARα or (b) RARβ/ RARγ wherein said cell is prevented from providing all isoforms of said combination of two receptors in active form.

UNITED STATES PATENT AND TRADEMARK OFFICE
CERTIFICATE OF CORRECTION

PATENT NO.   : 6,521,814 B1
DATED        : February 18, 2003
INVENTOR(S)  : Chambon et al.

It is certified that error appears in the above-identified patent and that said Letters Patent is hereby corrected as shown below:

23. A mouse cell, wherein the genome of the cell comprises a disruption in each of the genes encoding a combination of two receptors selected from the group consisting of:
   (a) RARβ/RARα and
   (b) RARβ/RARγ,
wherein each said disruption prevents said gene from producing all isoforms of said receptors in active form.

24. The cell of claim 23, wherein said combination of two receptors is RARα/RARβ.

25. The cell of claim 24, wherein said disruption of RARα is in the region encoding the B domain and said disruption of RARβ is in the region encoding the ligand binding domain.

26. The cell of claim 23, wherein said combination of two receptors is RARβ/RARγ.

27. The cell of claim 26, wherein said disruption of RARβ is in the region encoding the ligand binding domain and said disruption of RARγ is in the region encoding the DNA binding domain.

28. The cell of claim 23, wherein both of said disruptions are homozygous.

29. The cell of claim 23, wherein both of said disruptions are heterozygous.

30. The cell of claim 23, wherein one said disruption is homozygous and other said disruption is heterozygous.

31. A mouse cell line comprising the cell of claim 23.

32. The mouse cell line of claim 31, wherein said cell line is generated using a pluripotent cell line.

33. The mouse cell line of claim 32, wherein said pluripotent cell line has the American Type Culture Collection designation CRL 11632.

UNITED STATES PATENT AND TRADEMARK OFFICE
CERTIFICATE OF CORRECTION

PATENT NO. : 6,521,814 B1
DATED : February 18, 2003
INVENTOR(S) : Chambon et al.

It is certified that error appears in the above-identified patent and that said Letters Patent is hereby corrected as shown below:

34. A transgenic mouse embryo whose genome comprises a disruption in each of the genes encoding a combination of two receptors selected from the group consisting of:
  (a) RARβ/RXRβ and
  (b) RARβ/RXRγ,
wherein each said disruption prevents said gene from producing said receptor in active form and said mouse embryo at embryonic stage day 14.5 has a reduction of the palpebral aperture compared to a wild-type mouse embryo.

35. The transgenic mouse embryo of claim 34, wherein said combination of two receptors is RARβ/RXRβ.

36. The transgenic mouse embryo of claim 35, wherein said disruption of RARβ is in the region encoding the ligand binding domain and said disruption of RXRβ is in the region encoding the DNA binding domain.

37. The transgenic mouse embryo of claim 35, wherein both said disruptions are homozygous and said mouse embryo has a reduction in forward locomotion compared to a wild type mouse embryo.

38. The transgenic mouse embryo of claim 34, wherein said combination of two receptors is RARβ/RXRγ.

39. The transgenic mouse embryo of claim 38, wherein said disruption of RARβ is in the region encoding the ligand binding domain and said disruption of RXRγ is in the region encoding the DNA binding domain.

40. The transgenic mouse embryo of claim 38, wherein both said disruptions are homozygous and said mouse embryo has a decrease in striatal dopamine D2 receptor (D2R) expression compared to a wild type mouse embryo.

41. The transgenic mouse embryo of claim 34, wherein both of said disruptions are homozygous.

UNITED STATES PATENT AND TRADEMARK OFFICE
CERTIFICATE OF CORRECTION

PATENT NO. : 6,521,814 B1
DATED : February 18, 2003
INVENTOR(S) : Chambon et al.

It is certified that error appears in the above-identified patent and that said Letters Patent is hereby corrected as shown below:

42. The transgenic mouse embryo of claim 34, wherein both of said disruptions are heterozygous.

43. The transgenic mouse embryo of claim 34, wherein one said disruption is homozygous and other said disruption is heterozygous.

44. A cell isolated from the transgenic mouse embryo of claim 34.

45. A mouse cell, wherein the genome of the cell comprises a disruption in each of the genes encoding a combination of two receptors selected from the group consisting of:
    (a) RARβ/RXRβ and
    (b) RARβ/RXRγ,
wherein each said disruption prevents said gene from producing said receptor in active form.

46. The cell of claim 45, wherein said combination of two receptors is RARβ/RXRβ.

47. The cell of claim 46, wherein said disruption of RARβ is in the region encoding the ligand binding domain and said disruption of RXRβ is in the region encoding the DNA binding domain.

48. The cell of claim 45, wherein said combination of two receptors is RARβ/RXRγ.

49. The cell of claim 48, wherein said disruption of RARβ is in the region encoding the ligand binding domain and said disruption of RXRγ is in the region encoding the DNA binding domain.

50. The cell of claim 45, wherein both of said disruptions are homozygous.

51. The cell of claim 45, wherein both of said disruptions are heterozygous.

52. The cell of claim 45, wherein one said disruption is homozygous and other said disruption is heterozygous.

53. A mouse cell line comprising the cell of claim 45.

UNITED STATES PATENT AND TRADEMARK OFFICE
CERTIFICATE OF CORRECTION

PATENT NO. : 6,521,814 B1
DATED : February 18, 2003
INVENTOR(S) : Chambon et al.

It is certified that error appears in the above-identified patent and that said Letters Patent is hereby corrected as shown below:

54. The mouse cell line of claim 53, wherein said cell line is generated using a pluripotent cell line.

55. The mouse cell line of claim 54, wherein said pluripotent cell line has the American Type Culture Collection designation CRL 11632.

56. A transgenic mouse embryo whose genome comprises a disruption in each of the genes encoding a combination of two receptors RARα/RXRγ, wherein said disruptions prevent said genes from producing said receptors in active form and said mouse embryo has reduced striatal D2 dopamine receptor expression compared to a wild-type mouse embryo when said disruptions are homozygous disruptions.

57. The transgenic mouse embryo of claim 56, wherein both said disruptions are homozygous.

58. The transgenic mouse embryo of claim 56, wherein both said disruptions are heterozygous.

59. The transgenic mouse embryo of claim 56, wherein one said disruption is homozygous and other said disruption is heterozygous.

60. The transgenic mouse embryo of claim 56, wherein said disruption of RARα is in the region encoding the B domain and said disruption of RXRγ is in the region encoding the DNA binding domain.

61. A cell isolated from the transgenic mouse embryo of claim 56, wherein the genome comprises a disruption in each of the genes encoding a combination of two receptors RARα/ RARγ, wherein said cell is prevented from producing said combination of receptors in active form, and wherein said disruptions are homozygous disruptions.

UNITED STATES PATENT AND TRADEMARK OFFICE
CERTIFICATE OF CORRECTION

PATENT NO.    : 6,521,814 B1
29DATED       : February 18, 2003
INVENTOR(S)   : Chambon et al.

It is certified that error appears in the above-identified patent and that said Letters Patent is hereby corrected as shown below:

62. A method of identifying an agent which is an antagonist or agonist of a subtype or isoform of a retinoic acid or retinoid X receptor, said method comprising:

(a) administering said agent to the transgenic mouse embryo of any one of claims 1, 12, 34, and 56;

(b) determining the effect of said agent on said transgenic mouse embryo deficient in normal expression of said receptor subtype or isoform; and (c) comparing said effect to the effect of said agent on a mouse embryo without said disruption and exhibiting normal expression of said receptor subtype or isoform,
thereby identifying the agent which is an antagonist or agonist of the subtype or isoform of the retinoic acid or retinoid X receptor.

63. The method of claim 62, wherein said effect of said agent in (b) is an effect on the development of said transgenic mouse embryo.

64. A method of identifying an agent which is an antagonist or agonist of a subtype or isoform of a retinoic acid or retinoid X receptor, said method comprising:

(a) administering said agent to the transgenic mouse embryo of any one of claims 1, 12, 34, and 56;

(b) determining the effect said agent has on the expression of a retinoic acid inducible gene sequence in said transgenic mouse embryo deficient in normal expression of said receptor subtype or isoform; and (c) comparing said effect to effect of said agent on the expression of a retinoic acid inducible gene sequence in a mouse embryo without said disruption and exhibiting normal expression of said receptor subtype or isoform,
thereby identifying an agent which is an antagonist or agonist of a subtype or isoform of a retinoic acid or retinoid X receptor.

65. A mouse cell whose genome comprises a disruption in each of the genes encoding a combination of two receptors RAR$\alpha$/RXR$\gamma$, wherein said disruptions prevent said genes from producing said receptors in active form.

UNITED STATES PATENT AND TRADEMARK OFFICE
CERTIFICATE OF CORRECTION

PATENT NO.    : 6,521,814 B1
DATED         : February 18, 2003
INVENTOR(S)   : Chambon et al.

It is certified that error appears in the above-identified patent and that said Letters Patent is hereby corrected as shown below:

66. The cell of claim 65, wherein both said disruptions are homozygous.

67. The cell of claim 65, wherein both said disruptions are heterozygous.

68. The cell of claim 65, wherein one said disruption is homozygous and other said disruption is heterozygous.

69. The cell of claim 65, wherein said disruption of RARα is in the region encoding the B domain and said disruption of RXRγ is in the region encoding the DNA binding domain.

70. A mouse cell line comprising the cell of claim 65.

71. The mouse cell line of claim 70, wherein said cell line is generated using a pluripotent cell line.

72. The mouse cell line of claim 71, wherein said pluripotent cell line has the American Type Culture Collection designation CRL 11632.

UNITED STATES PATENT AND TRADEMARK OFFICE
CERTIFICATE OF CORRECTION

PATENT NO. : 6,521,814 B1
29DATED : February 18, 2003
INVENTOR(S) : Chambon et al.

It is certified that error appears in the above-identified patent and that said Letters Patent is hereby corrected as shown below:

73. A method of identifying an agent which is an antagonist or agonist of a subtype or isoform of a retinoic acid or retinoid X receptor, said method comprising:

(a) incubating said agent with a cell line of any one of claims 9, 31, 53 and 71;

(b) determining the amount of agent bound by cells of said cell line; and (c) comparing said amount to the amount of said agent bound by cells of a cell line without said disruption, thereby identifying the subtype or isoform of the receptor bound by said agent.--

Signed and Sealed this

Eleventh Day of May, 2004

JON W. DUDAS
*Acting Director of the United States Patent and Trademark Office*